US012629453B2

(12) United States Patent
Schilling et al.

(10) Patent No.: US 12,629,453 B2
(45) Date of Patent: *May 19, 2026

(54) ACELLULAR SOFT TISSUE-DERIVED MATRICES AND METHODS FOR PREPARING SAME

(71) Applicant: Musculoskeletal Transplant Foundation, Edison, NJ (US)

(72) Inventors: Benjamin Schilling, Jersey City, NJ (US); Andrew Madans, Jersey City, NJ (US); Abigail Phipps, East Brunswick, NJ (US); Thomas Tylutki, Rahway, NJ (US); Todd Nilsen, Howell, NJ (US); Yen-Chen Huang, East Brunswick, NJ (US); Evangelia Chnari, Scotch Plains, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 811 days.

This patent is subject to a terminal disclaimer.

(21) Appl. No.: 17/985,183

(22) Filed: Nov. 11, 2022

(65) Prior Publication Data

US 2023/0072250 A1 Mar. 9, 2023

Related U.S. Application Data

(60) Division of application No. 17/130,137, filed on Dec. 22, 2020, now Pat. No. 11,524,093, which is a division of application No. 16/428,505, filed on May 31, 2019, now Pat. No. 10,912,864, which is a continuation-in-part of application No. 15/217,409, filed on Jul. 22, 2016, now abandoned.

(60) Provisional application No. 62/347,944, filed on Jun. 9, 2016, provisional application No. 62/196,522, filed on Jul. 24, 2015.

(51) Int. Cl.
 *A61L 27/38* (2006.01)

(52) U.S. Cl.
 CPC ....... *A61L 27/3886* (2013.01); *A61L 27/3839* (2013.01); *A61L 27/3895* (2013.01); *A61L 2430/40* (2013.01)

(58) Field of Classification Search
 CPC ............. A61L 27/3886; A61L 27/3839; A61L 27/3895; A61L 2430/40; A61L 27/3687; A61L 27/3834; A61L 2430/34; A61L 27/54; A61L 27/3604; A61K 35/35; C12N 5/0667
 See application file for complete search history.

(56) References Cited

U.S. PATENT DOCUMENTS

| | | | |
|---|---|---|---|
| 919,002 A | 4/1909 | Griseri | |
| 923,800 A | 6/1909 | Thompson et al. | |
| 4,707,369 A | 11/1987 | Suresky | |
| 4,767,746 A | 8/1988 | Catsimpoolas | |
| 4,776,853 A | 10/1988 | Klement | |
| 4,801,299 A | 1/1989 | Brendel | |
| 4,820,626 A | 4/1989 | Williams | |
| 5,035,708 A | 7/1991 | Alchas | |
| 5,073,373 A | 12/1991 | O'Leary et al. | |
| 5,079,160 A | 1/1992 | Lacy | |
| 5,131,907 A | 7/1992 | Williams | |
| 5,230,693 A | 7/1993 | Williams | |
| 5,277,555 A | 1/1994 | Robinson | |
| 5,284,655 A | 2/1994 | Bogdansky et al. | |
| 5,316,247 A | 5/1994 | Wodka | |
| 5,336,616 A | 8/1994 | Livesey | |
| 5,436,135 A | 7/1995 | Tayot | |
| 5,484,601 A | 1/1996 | O'Leary et al. | |

(Continued)

FOREIGN PATENT DOCUMENTS

| | | |
|---|---|---|
| AU | 2014296259 | 8/2017 |
| CA | 2919374 | 12/2019 |

(Continued)

OTHER PUBLICATIONS

Issue Notification issued on Nov. 22, 2022 for U.S. Appl. No. 17/130,137, now U.S. Pat. No. 11,524,093.
Notice of Allowance issued on Aug. 8, 2022 for U.S. Appl. No. 17/130,137.
Non-Final Office Action issued on May 11, 2022, for U.S. Appl. No. 17/130,137.
Requirement for Restriction issued on Feb. 4, 2022 for U.S. Appl. No. 17/130,137.

(Continued)

*Primary Examiner* — Aaron J Kosar
*Assistant Examiner* — Jennifer Lynn Cain
(74) *Attorney, Agent, or Firm* — Cole Schotz P.C.; Marcella M. Bodner, Esq.

(57) ABSTRACT

Compositions including a first soft tissue-derived matrix and a second soft tissue-derived matrix are provided, as well as methods of making such compositions. In some embodiments, the composition comprises delipidated, decellularized adipose tissue-derived matrix and delipidated, decellularized fascial tissue-derived matrix, which may be combined in various proportions. Such adipose-fascia matrix compositions provide improved volume retention when implanted into a patient. The composition may further include exogenous cells or other substances, and/or a carrier. The composition is suitable for use in plastic surgery procedures, including reconstructive or cosmetic surgery procedures, as well as procedures for wound treatment and tissue regeneration. The methods for making the compositions may involve separation of first and second soft tissues from one another, followed by performing one or more treatments on the separated soft tissues, then combining the treated soft tissues and, optionally, performing one or more additional treatments on the combined soft tissues.

23 Claims, 3 Drawing Sheets

(56)     References Cited

U.S. PATENT DOCUMENTS

| | | | |
|---|---|---|---|
| 5,628,781 A | 5/1997 | Williams |
| 5,632,778 A | 5/1997 | Goldstein |
| 5,744,360 A | 4/1998 | Hu |
| 5,800,537 A | 9/1998 | Bell |
| 5,804,366 A | 9/1998 | Hu |
| 5,837,235 A | 11/1998 | Mueller |
| 5,843,182 A | 12/1998 | Goldstein |
| 5,869,037 A | 2/1999 | Crystal |
| 5,893,888 A | 4/1999 | Bell |
| 5,899,936 A | 5/1999 | Goldstein |
| 5,993,844 A | 11/1999 | Abraham |
| 6,020,196 A | 2/2000 | Hu |
| 6,099,567 A | 8/2000 | Badylak |
| 6,127,143 A | 10/2000 | Gunasekaran |
| 6,149,906 A | 11/2000 | Mosca |
| 6,277,555 B1 | 8/2001 | Duran et al. |
| 6,284,284 B1 | 9/2001 | Naughton |
| 6,316,247 B1 | 11/2001 | Katz |
| 6,326,029 B1 | 12/2001 | Geistlich |
| 6,348,069 B1 | 2/2002 | Vacanti |
| 6,355,239 B1 | 3/2002 | Bruder |
| 6,371,992 B1 | 4/2002 | Tanagho |
| 6,387,693 B2 | 5/2002 | Reiser |
| 6,391,297 B1 | 5/2002 | Halvorsen |
| 6,398,819 B1 | 6/2002 | Bell |
| 6,429,013 B1 | 8/2002 | Halvorsen |
| 6,596,274 B1 | 7/2003 | Abatangelo |
| 6,652,872 B2 | 11/2003 | Nevo |
| 6,676,969 B2 | 1/2004 | Geistlich |
| 6,696,074 B2 | 2/2004 | Oai |
| 6,734,018 B2 | 5/2004 | Wolfinbarger |
| 6,777,231 B1 | 8/2004 | Katz |
| 6,841,150 B2 | 1/2005 | Halvorsen |
| 6,866,686 B2 | 3/2005 | Ollerenshaw |
| 6,893,653 B2 | 5/2005 | Abraham |
| 6,942,961 B1 | 9/2005 | Baumgartner |
| 6,991,652 B2 | 1/2006 | Burg |
| 7,001,430 B2 | 2/2006 | Mills |
| 7,004,977 B2 | 2/2006 | Ashman |
| 7,008,591 B2 | 3/2006 | Kafesjian |
| 7,029,666 B2 | 4/2006 | Bruder |
| 7,029,689 B2 | 4/2006 | Berglund |
| 7,029,838 B2 | 4/2006 | Williams |
| 7,030,157 B2 | 4/2006 | HuaZhu |
| 7,033,587 B2 | 4/2006 | Halvorsen |
| 7,052,829 B2 | 5/2006 | Williams |
| 7,052,856 B2 | 5/2006 | Ting |
| 7,060,022 B2 | 6/2006 | Chen |
| 7,078,230 B2 | 7/2006 | Wilkison |
| 7,078,232 B2 | 7/2006 | Konkle |
| 7,131,994 B2 | 11/2006 | Mills |
| 7,186,557 B2 | 3/2007 | Marki |
| 7,201,917 B2 | 4/2007 | Malaviya |
| 7,208,177 B2 | 4/2007 | Geistlich |
| 7,294,509 B2 | 11/2007 | Oarimont |
| 7,297,540 B2 | 11/2007 | Mitrani |
| 7,323,190 B2 | 1/2008 | Chu |
| 7,338,757 B2 | 3/2008 | Wolfinbarger |
| 7,354,702 B2 | 4/2008 | Dai |
| 7,354,749 B2 | 4/2008 | Fisher |
| 7,390,484 B2 | 6/2008 | Fraser |
| 7,402,319 B2 | 7/2008 | Schmidt |
| 7,429,488 B2 | 9/2008 | Fraser |
| 7,445,793 B2 | 11/2008 | Niwa |
| 7,470,537 B2 | 12/2008 | Hedrick |
| 7,473,420 B2 | 1/2009 | Fraser |
| 7,476,257 B2 | 1/2009 | Sah |
| 7,498,040 B2 | 3/2009 | Masinaei |
| 7,498,041 B2 | 3/2009 | Masinaei |
| 7,501,115 B2 | 3/2009 | Fraser |
| 7,514,075 B2 | 4/2009 | Hedrick |
| 7,520,888 B2 | 4/2009 | Trieu |
| 7,531,355 B2 | 5/2009 | Rodriguez |
| 7,544,486 B2 | 6/2009 | Ting et al. |
| 7,550,152 B2 | 6/2009 | Pandit |
| 7,582,292 B2 | 9/2009 | Wilkison |
| 7,585,670 B2 | 9/2009 | Hedrick |
| 7,592,174 B2 | 9/2009 | Sylvester |
| 7,595,043 B2 | 9/2009 | Hedrick |
| 7,595,062 B2 | 9/2009 | Pedrozo |
| 7,621,963 B2 | 11/2009 | Simon |
| 7,625,581 B2 | 12/2009 | Laredo |
| 7,648,676 B2 | 1/2010 | Mills |
| 7,651,684 B2 | 1/2010 | Hedrick |
| 7,682,822 B2 | 3/2010 | Noll |
| 7,687,059 B2 | 3/2010 | Fraser |
| 7,687,462 B2 | 3/2010 | Ting et al. |
| 7,691,607 B2 | 4/2010 | Ting et al. |
| 7,709,442 B2 | 5/2010 | Mao |
| 7,723,108 B2 | 5/2010 | Truncale et al. |
| 7,732,126 B2 | 6/2010 | Zhang |
| 7,763,081 B2 | 7/2010 | Ollerenshaw |
| 7,767,452 B2 | 8/2010 | Kleinsek |
| 7,771,716 B2 | 8/2010 | Hedrick |
| 7,775,965 B2 | 8/2010 | McFetridge |
| 7,776,361 B2 | 8/2010 | Ting |
| 7,776,596 B2 | 8/2010 | Badylak |
| 7,785,582 B2 | 8/2010 | Johnson |
| 7,795,022 B2 | 9/2010 | Badylak |
| 7,807,461 B2 | 10/2010 | Kang |
| 7,807,787 B2 | 10/2010 | Ting et al. |
| 7,815,686 B2 | 10/2010 | Badylak |
| 7,824,609 B2 | 11/2010 | Konertz |
| 7,824,701 B2 | 11/2010 | Binette |
| 7,833,968 B2 | 11/2010 | Soo et al. |
| 7,846,728 B2 | 12/2010 | Brooks |
| 7,871,605 B2 | 1/2011 | Hampson |
| 7,875,296 B2 | 1/2011 | Binette |
| 7,883,541 B2 | 2/2011 | Mills |
| 7,883,968 B2 | 2/2011 | Nihei |
| 7,884,066 B2 | 2/2011 | Ting |
| 7,887,795 B2 | 2/2011 | Fraser |
| 7,892,724 B2 | 2/2011 | Shimko |
| 7,901,672 B2 | 3/2011 | Fraser |
| 7,906,110 B2 | 3/2011 | Chancellor |
| 7,915,039 B2 | 3/2011 | Teplyashin |
| 7,931,687 B2 | 4/2011 | Masuda |
| 7,932,084 B2 | 4/2011 | Katz |
| 7,947,266 B2 | 5/2011 | Gronthos |
| 7,960,098 B2 | 6/2011 | Roy |
| 7,968,329 B2 | 6/2011 | Dancu |
| 7,977,094 B2 | 7/2011 | Masinaei |
| 7,993,679 B2 | 8/2011 | Ingram |
| 7,998,472 B2 | 8/2011 | Huss |
| 7,998,735 B2 | 8/2011 | Morrison |
| 8,017,389 B2 | 9/2011 | Phillips |
| 8,017,390 B2 | 9/2011 | Park |
| 8,021,869 B2 | 9/2011 | Chu |
| 8,067,149 B2 | 11/2011 | Livesey |
| 8,067,234 B2 | 11/2011 | March |
| 8,071,083 B2 | 12/2011 | De Brujin |
| 8,093,047 B2 | 1/2012 | Takakura |
| 8,105,580 B2 | 1/2012 | Fraser |
| 8,106,251 B2 | 1/2012 | Ayares |
| 8,114,668 B2 | 2/2012 | Stolen |
| 8,119,121 B2 | 2/2012 | Fraser |
| 8,119,398 B2 | 2/2012 | Sayre |
| 8,137,703 B2 | 3/2012 | Binette |
| 8,163,018 B2 | 4/2012 | Trieu |
| 8,163,276 B2 | 4/2012 | Hedrick |
| 8,163,495 B2 | 4/2012 | Buhring |
| 8,187,619 B2 | 5/2012 | Johnson |
| 8,192,348 B2 | 6/2012 | Tranquillo |
| 8,192,763 B2 | 6/2012 | Johnson |
| 8,202,493 B2 | 6/2012 | Buss |
| 8,214,902 B2 | 7/2012 | Khosravi et al. |
| 8,226,715 B2 | 7/2012 | Hwang |
| 8,246,947 B2 | 8/2012 | Hedrick |
| 8,263,359 B2 | 9/2012 | Reschiglian |
| 8,273,253 B2 | 9/2012 | Curran |
| 8,292,799 B2 | 10/2012 | Xu |
| 8,308,814 B2 | 11/2012 | Sengun |
| 8,309,106 B2 | 11/2012 | Masinaei |
| 8,309,342 B2 | 11/2012 | Subbers |

(56)  References Cited

U.S. PATENT DOCUMENTS

| | | | |
|---|---|---|---|
| 8,334,135 | B2 | 12/2012 | Rodriguez |
| 8,337,711 | B2 | 12/2012 | Dorian |
| 8,337,834 | B2 | 12/2012 | Fraser |
| 8,354,221 | B2 | 1/2013 | Roy |
| 8,361,503 | B2 | 1/2013 | Badylak |
| 8,367,405 | B2 | 2/2013 | Gronthos |
| 8,377,143 | B2 | 2/2013 | Hamby |
| 8,394,141 | B2 | 3/2013 | Mills |
| 8,394,631 | B2 | 3/2013 | Hampson |
| 8,404,229 | B2 | 3/2013 | Fraser |
| 8,425,600 | B2 | 4/2013 | Maxwell |
| 8,446,586 | B2 | 5/2013 | Wu |
| 8,455,008 | B2 | 6/2013 | Johnson |
| 8,470,520 | B2 | 6/2013 | Ott |
| 8,470,595 | B2 | 6/2013 | Torhihashi |
| 8,475,827 | B2 | 7/2013 | Hamby |
| 8,481,253 | B2 | 7/2013 | Wouters |
| 8,491,885 | B2 | 7/2013 | Oh |
| 8,512,695 | B2 | 8/2013 | Austen |
| 8,530,415 | B2 | 9/2013 | Naughton |
| 8,541,372 | B2 | 9/2013 | Shah et al. |
| 8,545,855 | B2 | 10/2013 | Boyden |
| 8,557,581 | B2 | 10/2013 | Ngo |
| 8,574,614 | B2 | 11/2013 | Liu |
| 8,574,826 | B2 | 11/2013 | Wolfinbarger |
| 8,592,209 | B2 | 11/2013 | Khurgel |
| 8,603,819 | B2 | 12/2013 | Allon |
| 8,637,066 | B2 | 1/2014 | Binnette |
| 8,641,372 | B2 | 2/2014 | Stein et al. |
| 8,641,775 | B2 | 2/2014 | Harmon |
| 8,652,872 | B2 | 2/2014 | Chang |
| 8,679,809 | B2 | 3/2014 | Chan |
| 8,691,542 | B2 | 4/2014 | Guilak |
| 8,691,946 | B2 | 4/2014 | Sanford |
| 8,693,653 | B1 | 4/2014 | Abraham |
| 8,715,733 | B2 | 5/2014 | Kadiyala |
| 8,735,054 | B1 | 5/2014 | Sun |
| 8,747,467 | B2 | 6/2014 | Mills |
| 8,758,781 | B2 | 6/2014 | Ward |
| 8,779,089 | B2 | 7/2014 | Sanford |
| 8,784,890 | B2 | 7/2014 | Farrell |
| 8,802,081 | B2 | 8/2014 | Wang et al. |
| 8,828,724 | B2 | 9/2014 | Blanc-Brude |
| 8,835,170 | B2 | 9/2014 | Katz |
| 8,841,150 | B2 | 9/2014 | Kim et al. |
| 8,865,199 | B2 | 10/2014 | Coleman |
| 8,883,408 | B2 | 11/2014 | Hamby |
| 8,927,202 | B2 | 1/2015 | Shimko |
| 8,936,651 | B2 | 1/2015 | Yang |
| 8,945,920 | B2 | 2/2015 | Casteilla |
| 8,962,044 | B2 | 2/2015 | Anderson |
| 8,962,324 | B2 | 2/2015 | Matheny |
| 8,986,377 | B2 | 3/2015 | Richter |
| 8,986,378 | B2 | 3/2015 | Koob |
| 8,999,709 | B2 | 4/2015 | Fernandez |
| 9,005,646 | B2 | 4/2015 | Masinaei |
| 9,011,985 | B2 | 4/2015 | Masegawa et al. |
| 9,034,386 | B2 | 5/2015 | Flynn |
| 9,034,644 | B2 | 5/2015 | Masinaei |
| 9,044,455 | B2 | 6/2015 | Shaf |
| 9,056,084 | B2 | 6/2015 | Yilkomi |
| 9,057,052 | B2 | 6/2015 | Kobayashi |
| 9,074,190 | B2 | 7/2015 | Yoshimura |
| 9,089,117 | B2 | 7/2015 | Grande et al. |
| 9,089,523 | B2 | 7/2015 | Xu |
| 9,090,678 | B2 | 7/2015 | Gronthos |
| 9,102,913 | B2 | 8/2015 | Roach |
| 9,115,176 | B2 | 8/2015 | Hocquax |
| 9,125,971 | B2 | 9/2015 | Wolfinbarger |
| 9,132,208 | B2 | 9/2015 | Chen |
| 9,133,431 | B2 | 9/2015 | Peterson |
| 9,162,011 | B2 | 10/2015 | Stilwell |
| 9,173,903 | B2 | 11/2015 | Singh |
| 9,192,695 | B2 | 11/2015 | Shi |
| 9,199,002 | B2 | 12/2015 | Mao |
| 9,200,255 | B2 | 12/2015 | Halvorsen |
| 9,205,172 | B2 | 12/2015 | Neethling |
| 9,206,442 | B2 | 12/2015 | Chen |
| 9,211,307 | B2 | 12/2015 | McDevitt |
| 9,216,236 | B2 | 12/2015 | Machluf |
| 9,238,090 | B1 | 1/2016 | Fette |
| 9,238,793 | B2 | 1/2016 | Chen |
| 9,249,393 | B2 | 2/2016 | Gimble |
| 9,271,821 | B2 | 3/2016 | Roock |
| 9,278,165 | B2 | 3/2016 | Park |
| 9,296,781 | B2 | 3/2016 | Schendel |
| 9,310,975 | B2 | 4/2016 | Rouy |
| 9,358,327 | B1 | 6/2016 | Venturi |
| 9,370,536 | B2 | 6/2016 | Sun |
| 9,370,606 | B2 | 6/2016 | Nakamura |
| 9,375,513 | B2 | 6/2016 | Sun |
| 9,381,273 | B2 | 7/2016 | Gazil |
| 9,382,422 | B2 | 7/2016 | Owens |
| 9,382,514 | B2 | 7/2016 | Hantash |
| 9,408,875 | B2 | 8/2016 | Masinaei |
| 9,441,200 | B2 | 9/2016 | Rosson |
| 9,446,077 | B2 | 9/2016 | Southard |
| 9,504,770 | B2 | 11/2016 | Xu |
| 9,828,724 | B2 | 11/2017 | Kindstrand |
| 10,022,472 | B2 | 7/2018 | Mills et al. |
| 10,092,600 | B2 | 10/2018 | Huang |
| 10,092,677 | B2 | 10/2018 | Xu et al. |
| 10,478,587 | B2 | 11/2019 | Tremolada |
| 10,500,308 | B2 | 12/2019 | Flynn |
| 10,549,010 | B2 | 2/2020 | Lee et al. |
| 10,596,201 | B2 | 3/2020 | Huang et al. |
| 10,709,810 | B2 | 7/2020 | Sun et al. |
| 10,792,395 | B2 | 10/2020 | Mazza et al. |
| 10,912,684 | B2 | 2/2021 | Munakata et al. |
| 10,912,864 | B2 | 2/2021 | Schilling |
| 11,524,093 | B2 | 12/2022 | Schilling et al. |
| 11,779,610 | B2 | 10/2023 | Huang |
| 2002/0076400 | A1 | 6/2002 | Katz |
| 2003/0054331 | A1 | 3/2003 | Fraser |
| 2003/0065017 | A1 | 4/2003 | HuaZhu et al. |
| 2003/0082152 | A1 | 5/2003 | Hedrick |
| 2003/0152558 | A1 | 8/2003 | Luft |
| 2003/0161816 | A1 | 8/2003 | Fraser |
| 2003/0162707 | A1 | 8/2003 | Fraser |
| 2003/0181978 | A1 | 9/2003 | Brown |
| 2004/0030406 | A1 | 2/2004 | Ochi |
| 2004/0048375 | A1 | 3/2004 | Alt |
| 2004/0052768 | A1 | 3/2004 | Morrison |
| 2004/0052830 | A1 | 3/2004 | Konertz |
| 2004/0067218 | A1 | 4/2004 | Castiella |
| 2004/0082063 | A1 | 4/2004 | Desphpande |
| 2004/0092011 | A1 | 5/2004 | Wilkison |
| 2004/0171146 | A1 | 9/2004 | Katz |
| 2004/0191226 | A1 | 9/2004 | Badylak |
| 2004/0197367 | A1 | 10/2004 | Rezania |
| 2004/0241146 | A1 | 12/2004 | Biscup |
| 2004/0265971 | A1 | 12/2004 | Sato |
| 2005/0008626 | A1 | 1/2005 | Fraser et al. |
| 2005/0009000 | A1 | 1/2005 | Wilhelm |
| 2005/0013870 | A1 | 1/2005 | Freyman |
| 2005/0033449 | A1 | 2/2005 | Ashman |
| 2005/0048035 | A1 | 3/2005 | Fraser |
| 2005/0048036 | A1 | 3/2005 | Fraser |
| 2005/0076396 | A1 | 4/2005 | Katz |
| 2005/0095228 | A1 | 5/2005 | Fraser |
| 2005/0118228 | A1 | 6/2005 | Trieu |
| 2005/0136042 | A1 | 6/2005 | Betz |
| 2005/0152941 | A1 | 7/2005 | Hunter |
| 2005/0152944 | A1 | 7/2005 | Hunter |
| 2005/0152945 | A1 | 7/2005 | Hunter |
| 2005/0152947 | A1 | 7/2005 | Hunter |
| 2005/0152948 | A1 | 7/2005 | Hunter |
| 2005/0153442 | A1 | 7/2005 | Katz |
| 2005/0171616 | A1 | 8/2005 | Sung |
| 2005/0182463 | A1 | 8/2005 | Hunter |
| 2005/0182496 | A1 | 8/2005 | Hunter |
| 2005/0186286 | A1 | 8/2005 | Takami |
| 2005/0187639 | A1 | 8/2005 | Hunter |
| 2005/0203635 | A1 | 9/2005 | Hunter |

(56)        References Cited

U.S. PATENT DOCUMENTS

| | | |
|---|---|---|
| 2005/0209705 A1 | 9/2005 | Niederauer |
| 2005/0250202 A1 | 11/2005 | March |
| 2005/0256588 A1 | 11/2005 | Sawa |
| 2005/0260748 A1 | 11/2005 | Odorico et al. |
| 2005/0260749 A1 | 11/2005 | Chang |
| 2005/0266390 A1 | 12/2005 | Ueda |
| 2005/0282275 A1 | 12/2005 | Katz |
| 2006/0045872 A1 | 3/2006 | Miguel |
| 2006/0051865 A1 | 3/2006 | Higgins |
| 2006/0073124 A1 | 4/2006 | Castro |
| 2006/0078993 A1 | 4/2006 | Phan |
| 2006/0083720 A1 | 4/2006 | Fraser |
| 2006/0153797 A1 | 7/2006 | Bortolotto |
| 2006/0159664 A1 | 7/2006 | Pandit et al. |
| 2006/0171932 A1 | 8/2006 | Hendricks |
| 2006/0203636 A1 | 9/2006 | Ko |
| 2006/0204556 A1 | 9/2006 | Daniels |
| 2006/0228796 A1 | 10/2006 | Kolkin |
| 2006/0282173 A1 | 12/2006 | McFetridge |
| 2007/0026518 A1 | 2/2007 | Healy |
| 2007/0027543 A1 | 2/2007 | Gimble |
| 2007/0036768 A1 | 2/2007 | Fraser |
| 2007/0077649 A1 | 4/2007 | Sammak |
| 2007/0104692 A1 | 5/2007 | Quijano |
| 2007/0104693 A1 | 5/2007 | Quijano |
| 2007/0148766 A1 | 6/2007 | Yoshimura |
| 2007/0172812 A1 | 7/2007 | Ochi |
| 2007/0185585 A1 | 8/2007 | Bracy |
| 2007/0196421 A1 | 8/2007 | Hunter |
| 2007/0202592 A1 | 8/2007 | Kitagawa |
| 2007/0207125 A1 | 9/2007 | Bothwell |
| 2007/0212336 A1 | 9/2007 | Fulkerson |
| 2007/0212396 A1 | 9/2007 | Zheng |
| 2007/0213822 A1 | 9/2007 | Trieu |
| 2007/0244568 A1 | 10/2007 | Matsuda |
| 2007/0248580 A1 | 10/2007 | Garcia Castro |
| 2007/0249044 A1 | 10/2007 | Desai |
| 2007/0258956 A1 | 11/2007 | Higgins |
| 2007/0264239 A1 | 11/2007 | Huard |
| 2007/0269791 A1 | 11/2007 | Takami |
| 2007/0282456 A1 | 12/2007 | Geng |
| 2007/0292401 A1 | 12/2007 | Harmon |
| 2007/0299508 A1 | 12/2007 | Morrison |
| 2008/0014179 A1 | 1/2008 | Ferree |
| 2008/0026461 A1 | 1/2008 | Deshpande |
| 2008/0077251 A1 | 3/2008 | Chen |
| 2008/0097601 A1 | 4/2008 | Codori-Hurff |
| 2008/0160085 A1 | 7/2008 | Boland |
| 2008/0187518 A1 | 8/2008 | Ogle |
| 2008/0195229 A1 | 8/2008 | Quijano |
| 2008/0206208 A1 | 8/2008 | Casteilla |
| 2008/0213235 A1 | 9/2008 | Katz |
| 2008/0269762 A1 | 10/2008 | Simon |
| 2008/0274184 A1 | 11/2008 | Hunt |
| 2008/0274185 A1 | 11/2008 | Mao |
| 2008/0279939 A1 | 11/2008 | Firestone |
| 2008/0286241 A1 | 11/2008 | Lee |
| 2008/0286268 A1 | 11/2008 | Johnson |
| 2008/0306610 A1 | 12/2008 | Wang |
| 2008/0318317 A1 | 12/2008 | Roche |
| 2009/0012629 A1 | 1/2009 | Yao |
| 2009/0024224 A1 | 1/2009 | Chen |
| 2009/0041729 A1 | 2/2009 | Wolfinbarger |
| 2009/0041825 A1 | 2/2009 | Kolov |
| 2009/0053277 A1 | 2/2009 | Nagaya |
| 2009/0054983 A1 | 2/2009 | Ignatius |
| 2009/0068154 A1 | 3/2009 | Ueda |
| 2009/0130067 A1 | 5/2009 | Buscher |
| 2009/0130756 A1 | 5/2009 | Klann |
| 2009/0142409 A1 | 6/2009 | Firestone |
| 2009/0163900 A1 | 6/2009 | Yang |
| 2009/0169642 A1 | 7/2009 | Fradette |
| 2009/0181104 A1 | 7/2009 | Rigotti |
| 2009/0181456 A1 | 7/2009 | Hedrick |
| 2009/0209020 A1 | 8/2009 | Park |
| 2009/0220569 A1 | 9/2009 | Williams |
| 2009/0252711 A1 | 10/2009 | Boquest |
| 2009/0269315 A1 | 10/2009 | Fraser |
| 2009/0269769 A1 | 10/2009 | Panja |
| 2009/0292311 A1 | 11/2009 | Olmo |
| 2009/0297488 A1 | 12/2009 | Fraser |
| 2009/0304644 A1 | 12/2009 | Hedrick |
| 2009/0304646 A1 | 12/2009 | Sakurada |
| 2009/0304654 A1 | 12/2009 | Lue |
| 2010/0015104 A1 | 1/2010 | Fraser |
| 2010/0015204 A1 | 1/2010 | Hedrick |
| 2010/0040687 A1 | 2/2010 | Pedrozo |
| 2010/0047213 A1 | 2/2010 | Zeitlin |
| 2010/0082113 A1 | 4/2010 | Gingras |
| 2010/0098739 A1 | 4/2010 | Katz |
| 2010/0105100 A1 | 4/2010 | Sakurada |
| 2010/0112031 A1 | 5/2010 | Katz |
| 2010/0112084 A1 | 5/2010 | Wu et al. |
| 2010/0112543 A1 | 5/2010 | Ngo |
| 2010/0112695 A1 | 5/2010 | Min |
| 2010/0112696 A1 | 5/2010 | Min |
| 2010/0119492 A1 | 5/2010 | Hans |
| 2010/0119496 A1 | 5/2010 | Wilkison |
| 2010/0120069 A1 | 5/2010 | Sakurada |
| 2010/0129330 A1 | 5/2010 | Wilkison |
| 2010/0136114 A1 | 6/2010 | Mao |
| 2010/0143879 A1 | 6/2010 | Curran |
| 2010/0145473 A1 | 6/2010 | Yannas |
| 2010/0151435 A1 | 6/2010 | Thatte |
| 2010/0151574 A1 | 6/2010 | Matsuyama |
| 2010/0158876 A1 | 6/2010 | Alessndri |
| 2010/0166824 A1 | 7/2010 | Naughton |
| 2010/0173411 A1 | 7/2010 | Katz |
| 2010/0178681 A1 | 7/2010 | Lee |
| 2010/0179639 A1 | 7/2010 | Bloor |
| 2010/0183568 A1 | 7/2010 | Matsuyama |
| 2010/0196439 A1 | 8/2010 | Beck |
| 2010/0203023 A1 | 8/2010 | Johnson |
| 2010/0223954 A1 | 9/2010 | Brinchmann |
| 2010/0227399 A1 | 9/2010 | Funaki |
| 2010/0233131 A1 | 9/2010 | Kang |
| 2010/0239540 A1 | 9/2010 | Brinchman |
| 2010/0239542 A1 | 9/2010 | Young |
| 2010/0239543 A1 | 9/2010 | Young |
| 2010/0267107 A1 | 10/2010 | Zuba-Surma |
| 2010/0285521 A1 | 11/2010 | Vossman |
| 2010/0285580 A1 | 11/2010 | Evans |
| 2010/0291219 A1 | 11/2010 | Karp |
| 2010/0303766 A1 | 12/2010 | Miyaji |
| 2010/0303774 A1 | 12/2010 | Hedrick |
| 2010/0304477 A1 | 12/2010 | Buscher |
| 2010/0310527 A1 | 12/2010 | Alt |
| 2010/0311667 A1 | 12/2010 | Hocquax et al. |
| 2010/0330047 A1 | 12/2010 | Valorani |
| 2011/0014701 A1 | 1/2011 | Ghosh |
| 2011/0027879 A1 | 2/2011 | Katz |
| 2011/0035004 A1 | 2/2011 | Maxwell |
| 2011/0039332 A1 | 2/2011 | Sakurada |
| 2011/0064701 A1 | 3/2011 | Young |
| 2011/0064782 A1 | 3/2011 | Bloor |
| 2011/0070647 A1 | 3/2011 | Dezawa |
| 2011/0086426 A1 | 4/2011 | Freund |
| 2011/0087338 A1 | 4/2011 | Siemionow |
| 2011/0091517 A1 | 4/2011 | Binette et al. |
| 2011/0098826 A1 | 4/2011 | Mauck |
| 2011/0104133 A1 | 5/2011 | Tseng |
| 2011/0104735 A1 | 5/2011 | Buehrer |
| 2011/0110898 A1 | 5/2011 | Kleinsek |
| 2011/0111497 A1 | 5/2011 | Tamai |
| 2011/0117171 A1 | 5/2011 | Melican |
| 2011/0117650 A1 | 5/2011 | Riordan |
| 2011/0129447 A1 | 6/2011 | Meretzki |
| 2011/0143429 A1 | 6/2011 | Chun |
| 2011/0150845 A1 | 6/2011 | Perekkadan |
| 2011/0150846 A1 | 6/2011 | Van Epps |
| 2011/0151005 A1 | 6/2011 | Yikomi et al. |
| 2011/0151011 A1 | 6/2011 | Flynn |
| 2011/0152196 A1 | 6/2011 | Shah et al. |
| 2011/0158959 A1 | 6/2011 | McIntosh et al. |

(56) References Cited

U.S. PATENT DOCUMENTS

| | | |
|---|---|---|
| 2011/0171726 A1 | 7/2011 | Kang |
| 2011/0177593 A1 | 7/2011 | Funaki |
| 2011/0183001 A1 | 7/2011 | Rosson et al. |
| 2011/0189140 A1 | 8/2011 | Christman |
| 2011/0293667 A1 | 12/2011 | Baksh |
| 2012/0010728 A1 | 1/2012 | Sun |
| 2012/0034191 A1 | 2/2012 | Matheny |
| 2012/0037436 A1 | 2/2012 | Kwon |
| 2012/0087958 A1 | 4/2012 | Oufrane |
| 2012/0164116 A1 | 6/2012 | Van Epps |
| 2012/0189588 A1 | 7/2012 | Nahas |
| 2012/0208556 A1 | 8/2012 | Jung et al. |
| 2012/0221118 A1 | 8/2012 | Barlee |
| 2012/0263763 A1 | 10/2012 | Sun et al. |
| 2012/0264190 A1 | 10/2012 | Christman |
| 2012/0282226 A1 | 11/2012 | Ayares |
| 2012/0310367 A1 | 12/2012 | Connor |
| 2012/0329034 A1 | 12/2012 | Chun |
| 2013/0013068 A1 | 1/2013 | Forsell |
| 2013/0028981 A1 | 1/2013 | Gratzer |
| 2013/0158658 A1 | 6/2013 | Hayzlett |
| 2013/0202563 A1 | 8/2013 | Badylak |
| 2013/0231288 A1 | 9/2013 | Bhatia |
| 2013/0251687 A1 | 9/2013 | Christman |
| 2013/0310322 A1 | 11/2013 | Shah et al. |
| 2014/0004549 A1 | 1/2014 | Chen et al. |
| 2014/0017206 A1 | 1/2014 | Barere |
| 2014/0056865 A1 | 2/2014 | Samaniego |
| 2014/0088701 A1 | 3/2014 | Sun et al. |
| 2014/0178450 A1 | 6/2014 | Christman |
| 2014/0341871 A1 | 11/2014 | Morris |
| 2014/0377833 A1 | 12/2014 | Chen |
| 2015/0017140 A1 | 1/2015 | Bhatra |
| 2015/0037436 A1* | 2/2015 | Huang ............... A61L 27/3604 424/574 |
| 2015/0110753 A1 | 4/2015 | Wang |
| 2015/0112089 A1 | 4/2015 | Finch |
| 2015/0202348 A1 | 7/2015 | Ovir |
| 2016/0008511 A1 | 1/2016 | Stilwell |
| 2016/0008512 A1 | 1/2016 | Stilwell |
| 2016/0008515 A1 | 1/2016 | Stilwell |
| 2016/0030487 A1 | 2/2016 | Bachrach |
| 2016/0030635 A1 | 2/2016 | Bhatia et al. |
| 2016/0030636 A1 | 2/2016 | Muir |
| 2016/0051728 A1 | 2/2016 | Flynn |
| 2016/0066563 A1 | 3/2016 | Moscatello |
| 2016/0113863 A1 | 4/2016 | Kolle |
| 2016/0135940 A1 | 5/2016 | Roock |
| 2016/0144086 A1 | 5/2016 | Park |
| 2016/0159884 A1 | 6/2016 | Schendel |
| 2016/0160172 A1 | 6/2016 | Ciminio |
| 2016/0184479 A1 | 6/2016 | Fette |
| 2016/0186125 A1 | 6/2016 | Bertoni |
| 2016/0192640 A1 | 7/2016 | Bertoni |
| 2016/0193382 A1 | 7/2016 | Levenberg |
| 2016/0317708 A1 | 11/2016 | Mills |
| 2017/0021058 A1 | 1/2017 | Huang |
| 2017/0119826 A1 | 5/2017 | Huang |
| 2018/0193459 A1 | 7/2018 | Govil |
| 2018/0325830 A1 | 11/2018 | Ganey et al. |
| 2018/0326122 A1 | 11/2018 | Ganey et al. |
| 2019/0008903 A1 | 1/2019 | Huang |
| 2019/0009003 A1 | 1/2019 | Xu et al. |
| 2019/0024043 A1 | 1/2019 | Roach et al. |
| 2019/0076582 A1 | 3/2019 | Connor |
| 2019/0099520 A1 | 4/2019 | Jessop et al. |
| 2019/0111183 A1 | 4/2019 | Xu et al. |
| 2019/0134265 A1 | 5/2019 | Semler |
| 2019/0142572 A1 | 5/2019 | Locarno et al. |
| 2019/0142575 A1 | 5/2019 | Locarno |
| 2019/0298885 A1 | 10/2019 | Schilling et al. |
| 2019/0374683 A1 | 12/2019 | Badylak et al. |
| 2020/0000855 A1 | 1/2020 | Xu et al. |
| 2020/0000968 A1 | 1/2020 | Pollock et al. |
| 2020/0171094 A1 | 6/2020 | Huang et al. |
| 2021/0106725 A1 | 4/2021 | Schilling et al. |
| 2022/0079994 A1 | 3/2022 | Huang et al. |

FOREIGN PATENT DOCUMENTS

| | | |
|---|---|---|
| EP | 0518389 | 12/1992 |
| EP | 3027235 | 6/2016 |
| EP | 3744356 | 12/2020 |
| VC | 20090292311 | 11/2009 |
| WO | 2007037572 | 4/2007 |
| WO | 2008154623 | 12/2008 |
| WO | 2009102452 | 8/2009 |
| WO | 2011019822 | 2/2011 |
| WO | 2011087743 | 7/2011 |
| WO | 2012002986 | 1/2012 |
| WO | 2012166784 | 12/2012 |
| WO | 2014052376 | 4/2014 |
| WO | 2015017500 | 2/2015 |

OTHER PUBLICATIONS

Hsieh A. H., et al., "Cellular mechanobiology of the intervertable disc: New directions and approaches", J. Biomech., 2010, 43(1): 137-156.

Huang Y. et al. Compsosite of Decellular Adipose Tissue with Chitosan Based Scaffold for Tissue Engineering with Adipose Derived Stem Cells. Biomaterials and Tissue Engineering 5(1)56-63 Jan. 2015 (Year: 2015).

Hubbell, J., Materials as morphogenic guides in tissue engineering, Current Opinion in Biotechnology, 14, pp. 551-558, (2003).

Int'Anker, P. et al., "Isolation of mesenchymal stem cells of fetal or maternal origin from human placenta", Stem Cells, 2004, 22: 1338-1345.

International Search Report and Written Opinion for International (PCT) Application No. PCT/US2014/025619, mailed Jun. 30, 2014.

International Search Report and Written Opinion of the International Searching Authority in regard to International Application No. PCT/US2014/048797, mailed Oct. 9, 2014.

Issue Fee Payment Transmittal on Jan. 4, 2020, for U.S. Appl. No. 16/428,505.

Issue Notification for U.S. Appl. No. 15/388,428, issued on Sep. 19, 2018.

Issue Notification for U.S. Appl. No. 16/428,505, issued on Jan. 20, 2021.

Issue Notification for U.S. Appl. No. 16/782,653, issued on Nov. 17, 2021.

Issue Notification for U.S. Appl. No. 16/121,969, issued on Mar. 4, 2020.

Kajstura, J. et al., Evidence for human lung stem cells, 2011, New Engl. J. Med., 364(19):1795-1806.

Karlsson et al., Identification of a stem cell niche in the zone of ranvier within the knee joint, 2009, J. Anat. 215(3): 355-63.

Kilroy et. al., Cytokine profile of human adipose-derived stem cells: Expression of angiogenic, hematopoietic, and pro-inflammatory factors 2007, J. Cell. Physiol. 212: 702-709.

Kinnaird et al, "Local delivery of marrow-derived stromal cells augments collateral perfusion through paracrine mechanisms", Circulation 109: 1543-49 (2004).

Koga et al., "Comparison of mesenchymal tissues-derived stem cells for in vivo chondrogenesis: suitable conditions for cell therapy of cartilage defects in rabbit" 2008, Cell Tissue Res., 333: 207-215.

Kropp, BP., et al., Experimental assessment of small intestinal submucosa as a bladder wall substitute, Urology, vol. 46, Iss. 3, pp. 396-400, (Sep. 1995).

Kropp, BP., et al., Regenerative urinary bladder augmentation using small intestinal submucosa: urodynamic and histopathologic assessment in long-term canine bladder augmentations, J. Ural., vol. 155, Iss. 6, pp. 2098-2104 (Jun. 1996).

Kurth et al., "Functional mesenchymal stem cell niches in adult mouse knee joing synovium in vivo", Arthritis Rheum., 2011, 63(5): 1289-1300.

(56)            References Cited

OTHER PUBLICATIONS

LaBarge, 2007, "Of microenvironments and mammary stem cells", Stem Cell Rev., 3(2): 137-146.

Lee, et al., Mesenchymal progenitor cells derived from synovium and infrapatellar fat pad as a source for superficial zone cartilage tissue engineering: Analysis of superficial zone protein/lubricin expression, 2010, Tissue Eng. A, 16(1): 317-325.

Li, et al., "Human treated dentin matrix as a natural scaffold for complete human dentin tissue regeneration", 2011, Biomaterials, doi:10:1016/j.biomaterials. 2011.03.008.

Majumdar, et al., "Phenotypic and functional comparison of cultures of marrow-derived mesenchymal stem cells (MSCs) and stromal cells" J. Cell Physiol. 176: 57-66 (1998).

Mariman et al., "Adipocyte extracellular matrix composition, dynamics and role in obesity", 2010, Cell. Mcg. Life Sci., 67:1277-1292.

Mazhari R., et al., "Mechanisms of action of mesenchymal stem cells in cardiac repair: potential influences on the cardiac stem cell niche", 2007, Nat. Clin. Pract. Cardiovasc. Med., 4(S1): S21-S26.

Melero-Martin J.M., et al., "Concise review: Vascular stem cells and tumor angiogenesi", Stem Cells, 2011, pp. 163-168, vol. 29.

Mercuri et al., "Novel tissue-derived biomimetic scaffold for regenerating the human nucleus pulpous", J. Biomed. Mater. Res. A., 96(2): 433-435.

Mihu, C. et al., "Isolation and characterization of stem cells from the placenta and the umbilical cord", 2008, Romanian Journal of Morphology and Embryology, 2008, 49(4):441-446.

Miki T., et al., "Amnion-derived pluripotent/multipotent stem cells", Stem Cells, 2006, 2: p. 133-142.

Miki T., et al., "Stem cell characteristics of amnniotice epitelial cells", Stem Cells, 2005, pp. 1549-1559.

Miyamoto, et al., "Indtradiscal transplantation of synovial mesenchymal stem cells prevents intervertebral disc degeneration through suppression of matrix metalloproteinase-related genes in nucleus pulpous cells in rabbits", 2010, Arthritis Res. Ther., 12: R206-218.

Munn, D. et al., "Inhibition of T cell proliferation by macrophage tryptophan catabolism", J Exp Med, 1999, 189: 1363-1372.

Munn, D. et al., "Prevention of allogenic fetal rejection by tryptophan catabolism", Science, 1998, 281: 1191-1193.

Murakami et al., "Quantitative differences in intervertebral disc-matrix composition with age-related degeneration", 2010, Med. Biol. Eng. Comput. 48: 469-474.

Non-Final Office Action for U.S. Appl. No. 15/217,409, issued on Dec. 1, 2017.

Non-Final Office Action for U.S. Appl. No. 15/236,975, issued on Sep. 7, 2018.

Non-Final Office Action for U.S. Appl. No. 15/388,428, issued on Sep. 15, 2017.

Non-Final Office Action for U.S. Appl. No. 16/428,505, issued on Jun. 12, 2020.

Non-Final Office Action issued for U.S. Appl. No. 16/782,653, on Apr. 14, 2021.

Non-Final Office Action issued Sep. 22, 2016 by the USPTO regarding U.S. Appl. No. 14/446,629.

Notice of Allowance for U.S. Appl. No. 15/388,428, issued on Jun. 4, 2018.

Notice of Allowance for U.S. Appl. No. 16/121,969, issued on Nov. 15, 2019.

Notice of Allowance for U.S. Appl. No. 16/428,505, issued on Oct. 20, 2020.

Office Action for European Patent Application No. 14750917.8, issued on Dec. 5, 2019.

Office Action response submitted on Sep. 22, 2020 for Non-Final Office Action issued on Jun. 12, 2020 for U.S. Appl. No. 16/428,505.

Oliver, et al., "Reconstruction of Full-Thickness Loss Skin Wounds Using Skin Collagen Allografts", British Journal of Plastic Surgery, 32 (1979), pp. 87-90.

PACE Request for European Patent Application No. 19179105, filed May 14, 2021.

Parolini O., et al., "Consise review: Isolation and characterization of cells from human term placenta: Outcome of the first international workshop on placenta derived stem cells", Stem Cells, 2008, pp. 300-311, vol. 26.

Parolini, 0. et al., "Concise review: Isolation and characterization of cells from human term placenta: Outcome of the first international workshop on placenta derived stem cells", 2008, Stem Cell, 2008, 26:300-311.

Pacilli et al., "Vascular wall resident progenitor cells a review", 2008, Exp. Cell Res., 315: 901-914.

Alvarez-Buyalla A., et al., "For the long run: Maintaining germinal niches in the adult brain", Neuron, 2004, pp. 683-686, vol. 41.

Alviano, F. et al., "Term amniotic membrane is a high throughout source form multipotent mesenchymal stem cells with the ability to differentiate into endothelial cells in vitro", BMC Dev Biol, 2007, 7: 11.

Amendment (Response) for European Patent Application No. 19179105, filed May 14, 2021.

Asalameh et al., "Identification of mesenchymal progenitor cells in normal and osteoarthritic human articular cartilage", Arthritis & Rheumatism, 2004, 50(5): 1522-1532.

Australian Patent Examination Report No. 1, regarding Australian Patent Application No. 2014296259, issued Jun. 2, 2016.

Baban, B. et al., "Indoleamine 2,3-dioxygenase expression is restricted to fetal trophoblast giant cells during murine gestation and is maternal genome specific", J Reprod Immunol, 2004, 61: 67-77.

Bailo M., et al., "Engraftment potential of human amnion and chorion cells derived from term placenta", Transplantation, 2004, pp. 1439-1449, vol. 10, Lippincott Williams & Wilkins.

Baksh, et al., "Adult mesenchymal stem cells: characterization differentiation, and application in cell and gene therapy", J. Cell. Mol. Med. 8(3): 301-16, 305 (2004).

Benirschke, K., et al., "Pathology of the human placenta". New York, Springer-Verlag, 2000, 42-46, 116, 281-297.

Bi et al., "Identification of tendon stem/progenitor cells and the role of the extracellular matrix in their niche", 2007, Nat. Med., 13(10): 1219-1227.

Blanpain C., "Skin regeneration and repair", 2010, Nature, 464: 686-687.

Blanpain C., et al., "Epidermal homeostasis: a balancing act of stem cells in the skin" 2009, Nat. Rev. Mol. Cell. Biol., 10(3): 207-217.

Blanpain, C., "Skin regeneration and repair", Nature, 2010, pp. 686-687, vol. 464, Macmillian Publishers.

Brochhausen et al., "Signaling molecules and growth factors for tissue engineering of cartilage—what can we learn from the growth plate?" J. 10 Tissue Eng. Regen. Med. 2009, 3: 416-429.

Brown et al., "Comparison of three methods for the derivation of a biologic scaffold composed of adipose tissue extracellular matrix", Tssue Engg. C., 17(4): 411-421.

Brown et. al., "Basic science review on adipose tissue for clinicians" 2010, Plast. Reconstr. Surg., 126(6): 1936-1946.

Butler et al., Dentin extracellular matrix (ECM) proteins: comparison to done ECM and contribution to dynamics of dentinogenesis 2003, Connective Tissue Research, 44(S1): 171-178.

Casey, M. et al., Interstitial synthesis and processing in human amnione: A propert of the mesenchymal cells, Biol Reprod, 1996, 55: 1253-1260).

Choi , J. et al., Human extracellular matrix (ECM) powders for injectable cell delivery and adipose tissue engineering, Control Release, 139, 1, (2009), p. 2-7.

Cheng et al., "Chondrogenic differentiation of adipose-derived adult stem cells by a porous scaffold derived from native articular cartilage extracellular matrix", 2009, Tissue Engg. A, 15(2): 231-241.

Cheng et al., Comparison of potentials between stem cells isolated from human anterior cruciate ligament and bone marrow for ligament tissue engineering, 2010, Tissue Engg. A, 16(7):2237-2253.

Cheng, H. et al., Osteogenic activity of the fourteen types of human bone morphogenetic proteins (BMPs),J. Bone & Joint Surgery 85: 1544-52 (2003).

Choi et al., "Fabrication of porous extracellular matrix scaffolds from human adipose tissue", Tissue Engg. C., 16(3): 387-396.

(56) References Cited

OTHER PUBLICATIONS

Clarke, KM, et al., Intestine submucosa and Polypropylene Mesh for Abdominal Wall Repair in Dogs, Journal of Surgical Research, vol. 60, Iss. 1, pp. 107-114, (Jan. 1996).

Coleman III, W. et al., Autologous Collagen? Lipocytic Dermal Augmentation A Histopathologic Study, J. Dermatol. Burg. Oneal., vol. 19, pp. 1032-1040, (1993).

Colombian Office Action regarding Colombian Patent Application No. 16-049.384, mailed Mar. 22, 2016.

Election filed on May 7, 2020, in response to Restriction Requirement issued on Mar. 11, 2020 for U.S. Appl. No. 16/428,505.

Erdag, et al., Fibroblasts Improve Performance of Cul Tu Red Composite Skin Substitutes on Athymic Mice, Burns, 30 (2004) pp. 322-328.

European Search Report for corresponding European Patent Application No. EP 19179105, issued on Nov. 25, 2019.

Examination Report No. 2, for corresponding Australian Application No. 2019204031, issued on Apr. 12, 2021.

Feng et al., "Exracellular matrix in disc degeneration", 2006, J.Bone Joint Surg. Am. 88: 25-29).

Final Office Action for U.S. Appl. No. 15/217,409, issued on Feb. 22, 2019.

Final Office Action for U.S. Appl. No. 15/236,975, issued on May 15, 2019.

First Examination Report for Australian Patent Application No. 2019204031, issued on Mar. 2, 2021.

Flynn et al., "Adipose tissue engineering with cells in engineered matrices", 2208 Organogenesis, 4(4): 228-235.

Flynn L., et al., "Adipose engineering with cells in engineered matrices", Organogenesis, 2008, pp. 228-235, vol. 4.

Fong et al., "The crowning achievement: Getting to the root of the problem" 2005, J. Dent. Educ., 69(5): 555-570.

Gaissmaier et al., "Growth and differentiation factors for cartilage healing and repair", 2008, Int. J. Care Injured, 39S1: S88-S96.

Gopinath et al.,"Stem cell review series: Aging of the skeletal muscle stem cell niche", 2008, Aging Cell, 7: 590-598.

Grauss, R.W. et al., Decellularization of Rat Aortic Valve Allografts Reduces Leaflet Destruction and Extracellular Matrix Remodeling, Journal Thoracic and Cardiovascular Surgery, 126, 2003-2010, (2003).

Gregoire et al., "Understanding adipocyte differentiation", 1998, Physiol. Rev. 78(3): 783-809.

Grogan et al.,"Mesenchymal progenitor cell markers in human articular cartilage; normal distribution and changes in osteoarthritis" Arthritis Res. Ther. 2009, 11(3): R85-R97.

Halberg et. al., "The adipocyte as an endocrine cell", 2008, Endocrinol. Metab. Clin. North Am., 37(3): 753-767.

Hara, A. et al., Lipid extraction of tissues with a low-toxicity solvent, Analytical Biochemistry, 90, 1, (1978), p. 420-426.

Henriksson et al., "Identification of cell proliferation zones, progenitor cells and a potential stem cell niche in the intervertebral disc region", 2009, Spine, 34(21): 2278-2287.

Hiraoka et al.,"Mesenchymal progenitor cells in adult human articular cartilage", Biorheology, 2006, 43: 447-454.

Hirschi K.K., et al., "Smooth muscle stem cells", 2004, The Anatomical Record, Part A, 276A: 22-33.

Hodde J.P., et al., "Extracellular matrix as a strategy for treating chronic wounds", 2007, Am. J. Clin. Dermatol. 8(2): 61-66.

Holmberg et al., "Activation of neural and pluripotent stem cell signatures correlates with increased malignancy in human glioma", 2011, PLoS One., 6(3): e18454.

Hombach-Klonisch et al., "Adult stem cells and their trans-differentiation potential-perspectives and therapeutic applications", 2008, J. Mol. Med. 86(12): 1301-1314.

Peng et al., "Comparative analysis of mesenchymal stem cells from bone marrow, cartilage, and adipose tissue", 2008, Stems Cells and Development, 17: 761-774.

Pittenger, M.F. et al., "Multilineage potential of adult human mesenchymal stem cells", Science 284: 143-47 (1999).

Poon C.. et al, "Preparation of an adipogenic hydrogel from subcutaneous adipose tissue", 2013, Acta Biomaterials, vol. 9, pp. 5609-5620.

Portmann-Lanz, C. et al, "Placental mesenchymal stem cells as potential autologous graft for pre- and perinatal neurogeneration" Am J Obstet Gynecol, 2006, 194: 664-673.

Porzionatoe A., et al., "Decellularized omentum as novel biologic scaffold for reconstructive surgery and regenerative medicine", 2013, European Journal of Histochemistry, vol. 57, pp. 24-30.

Prevel, CD., et al., Small intestinal submucosa: utilization for repair of rodent abdominal wall defects, Ann. Plast. Burg., vol. 35, Iss. 4, pp. 374-380, (Oct. 1995).

Response to Exam Report No. 1 in Australian Patent Application No. 2019204031, filed Mar. 25, 2021.

Restriction Requirement for U.S. Appl. No. 15/217,409, filed Sep. 1, 2017.

Restriction Requirement for U.S. Appl. No. 15/236,975 on Jun. 13, 2018.

Restriction Requirement for U.S. Appl. No. 15/388,428, issued on Jul. 18, 2017.

Restriction Requirement for U.S. Appl. No. 16/782,653, issued on Mar. 11, 2021.

Restriction Requirement for U.S. Appl. No. 16/428,505.

Restriction Requirement issued for U.S. Appl. No. 16/121,969, on Oct. 8, 2019.

Sandjeu Y., et al., "Desmosealin and other components of the epdidermal extracellular matrix", 2009, J. Physiol. Pharmacol. 60 (S4): 20 23-30.

Schmidt, C. et al., Acellular vascular tissues: natural biomaterials for tissue repair and tissue engineering, Biomaterials, 21, (2000), p. 2215-2231.

Sekiya S. et al., Bioengineered cardiac cell sheet grafts have intrinsic angiogenic potential, Biochemical and Biophysical Research Communications, 341, pp. 573-582, (2006).

Shamji et al., "Proinflammatory cytokine expression profile in degenerated and herniated human intervertebral disc issues", 2010, Arthritis & Rheumatism, 62(7): 1974-1982.

Shoulders M.D., et al., "Collagen structure and stability", Annu. Rev. Biochem, 2010, pp. 929-958, vol. 78.

Smith L.J., "Degeneration and regeneration of the intervertebral disc: lessons from development", 2011, Disease Models & Mechanisms, pp. 31-41, vol. 4.

Soncini, M. et al., "Isolation and characterization of mesenchymal cells from human fetal membranes", J Tissue Eng Regen Med, 2007, 1:296-305.

Takasaki, S. et al., Human type VI collagen: purification from human subcutaneous fat tissue and an Immunohistochemical study of morphea and systemic sclerosis, J Dermatol, 22, 7, (Jul. 1995), p. 480-485.

Tilki et al., "Emerging biology of vascular wall progenitor cells in health and disease", 2009, Trends Mol. Med. 15(11): 501-509.

Truillo, M.E., et al., "Adipose tissue-derived factors: Impact on health and disease", Endocrine Rev. 2006, 27(7): 762-778.

U.S. Appl. No. 14/446,629, filed Jul. 30, 2014.

U.S. Appl. No. 15/217,409, filed Jul. 22, 2016.

U.S. Appl. No. 15/388,428, filed Dec. 22, 2016.

U.S. Appl. No. 16/428,505, filed May 31, 2019.

U.S. Appl. No. 61/860,043, filed Jul. 30, 2013.

U.S. Appl. No. 62/196,522, filed Jul. 24, 2015.

U.S. Appl. No. 62/347,944, filed Jun. 9, 2016.

Ueda, Y. et al., Antigen clearing from porcine heart valves with preservation of structural integrity, The International Journal of Artificial Organs, vol. 29, No. 8, pp. 781-789, (2006).

Ulmer et al., "Stem cells-prospects in dentistry", 2010, Schweiz Monatsschr Zahnmed, 120:860-872.

Wang L. et al. Decellularized Musculafascial Extracellular Matrix for Tissue Engineering. Biomaterials 34(11) 2641-2654 Apr. 2013. Year: 2013).

Wang, L. et al., Combining decellularized human adipose tissue extracellular matrix and adipose-derived stem cells for adipose tissue engineering, Acta Biomater, 9, 11, (2013), p. 8921-8931.

(56) References Cited

OTHER PUBLICATIONS

Wei J. et al., "Human amnion-isolated cells normalize blood glucose in streptozocin-induced diabetic mice", Cell Transplant, 2003, 12: 545-552.

Wellisz, T. et al., Ostene, a new water-soluble bone hemostasis agent, J. Craniofac. Surg., vol. 17, Iss. 3, pp. 420-425, (May 2006).

Wilshaw S et alProduction of an Acellular Amniotic Membrane Matrix for Use in Tissue Engineering, Tissue Engineering, vol. 12, No. 8, pp. 2117-2129, (2006).

Wilson et al., "Proteomic analysis of cartilage proteins", 2008, Methods, 48: 22-31.

Wolbank, S. et al., "Dose-dependent immunomodulatory effect of human stem cells from amniotic membrane: A comparison with human mesenchymal stem cells from adipose tissue", Tissue Eng, 2007, 13: 1173-1183.

Wu et al., "Muscle-derived stem cells: isolation, characterization, differentiation, and application in cell and gene therapy", 2010, Cell Tissue Res., 340: 549-567.

Young, D.A., et al., "Injectable hydrogel scaffold from decullularized human lipoaspirate", Acta Biomater, 2011, pp. 1040-1049, vol. 7.

Yun et al., "Transcriptional regulatory networks associated with self-renewal and differentiation of neural stem cells", 2010, J. Cell. Physiol. 225: 337-347.

Zhang et al., "Periosteal stem cells are essential for bone revitalization and repair", 2005, J. Musculoskelet. Neuronal. Interact. 5(4):25 360-362.

Zhang et al., "Successful immortalization of mesenchymal progenitor cells derived from human placenta and the differentiation abilities of immortalized cells", Biochem Biophys Res Commun, 2006, 351: 853-859).

Zhang, X., et al., "Mesenchymal progenitor cells derived from chorionic villi of + human placenta for cartilage tissue engineering", Biochem Biophys Res Commun, 2006, 340: 944-952.

Zhao, P. et al, "Human amniotic mesenchymal cells have some characteristics of cardiomyocytes" Transplantation, 2005, 79: 528-535.

Zouboulis et al., "Human skin stem cells and the ageing process" 2008, Exp. Gerontol., 43: 986-997.

Notice of Allowance for U.S. Appl. No. 15/388,428, issued on Jun. 1, 2018 [Cited in U.S. Appl. No. 17/130,137, filed Dec. 22, 2020].

Non-Final Office Action for U.S. Appl. No. 15/237,975, issued on Sep. 7, 2018. [Cited in U.S. Appl. No. 17/130,137, filed Dec. 22, 2020].

Restriction Requirement for U.S. Appl. No. 16/428,505, issued on Mar. 11, 2020. [Cited in U.S. Appl. No. 17/130,137, filed Dec. 22, 2020].

Office Action response submitted on Sep. 22, 2020 for Non-Final Office Action issued on Jun. 12, 2020, for U.S. Appl. No. 16/244,190. [Cited in U.S. Appl. No. 17/130,137, filed Dec. 22, 2020].

Wang, L. et al. "Combining Decellularized Human Adipose Tissue Extracellular Matrix and Adipose Derived Stem Cells for Adipose Tissue Engineering" Acta Bio materials, Nov. 2013, 9(11), 8921-8931; doi: 10.1016/j.actbio.2013.06.035. (Year: 2013) [Cited in U.S. Appl. No. 18/143,316, filed May 4, 2023].

* cited by examiner

ACELLULAR SOFT TISSUE-DERIVED MATRICES AND METHODS FOR PREPARING SAME

CROSS-REFERENCE TO RELATED APPLICATIONS

The present application is a divisional of U.S. patent application Ser. No. 17/130,137, filed Dec. 22, 2020, now pending and which is a divisional of U.S. patent application Ser. No. 16/428,505, filed May 31, 2019, now issued as U.S. Pat. No. 10,912,864 on Feb. 9, 2021, which is a continuation-in-part of co-pending U.S. patent application Ser. No. 15/217,409, filed Jul. 22, 2016 and now abandoned, which claims the benefit of U.S. Provisional Application No. 62/347,944, filed Jun. 9, 2016, and U.S. Provisional Application No. 62/196,522, filed Jul. 24, 2015, the entire disclosures of all of which are hereby incorporated by reference herein.

FIELD OF THE INVENTION

The present invention relates generally to matrices made from decellularized soft tissues, including adipose, dermis, fascia, muscle, pericardium, and other connective or membranous tissues, and in particular, to such matrices as are suitable for implantation into a living body in plastic surgery procedures, including reconstructive or cosmetic surgery procedures, wound care procedures or other procedures of regenerative medicine.

BACKGROUND OF THE INVENTION

Techniques for restoring structure and function to damaged tissue are used routinely in the fields of plastic surgery, including reconstructive and cosmetic surgery, wound care procedures or other procedures of regenerative medicine. Tissue transplantation is one way of restoring structure and function by replacing or rebuilding the damaged tissue. The transfer of biological material from one individual to another can raise significant risks. One such risk is tissue rejection, which can occur even in cases where there is a good histocompatibility match. The risk of tissue rejection can be reduced by processing tissues so that they become essentially free of cell components (e.g., cellular membranes, nucleic acids, lipids, and cytoplasmic components) that cause immunogenic responses. Such tissues are sometimes referred to as decellularized, cell-free, or acellular matrices. It is also desirable to retain the growth factors that are required to promote cellular ingrowth into the acellular matrix, eventually replacing the acellular matrix with the patient's native tissue.

In particular, injectable soft tissue fillers have expanded the non-surgical options available for volume replacement, facial defect filling and rejuvenation in the aging face. Injectable soft tissue fillers are widely used for both superficial and deep aesthetic applications, including lip augmentation or rejuvenation of the aging lip to restore shape and contour, fine line filling to reduce the appearance of wrinkles around the eyes or mouth, improvement of nasolabial folds, correction of eyelid deformities, volume filling for the cheek and jawline, and for deep wrinkle or scar filling.

There are many soft tissue fillers that are commercially available for these applications, and in general, fall within the following categories: autologous implant materials, collagens, hyaluronic acid (HA), and biosynthetic polymers.

Durability of these materials varies from several weeks to years, or is considered permanent.

SUMMARY OF THE INVENTION

Embodiments of the present invention relate generally to decellularized soft tissue-derived matrices (also referred to as "acellular matrices") suitable for use in plastic surgery procedures, including reconstructive and cosmetic procedures, wound care procedures or other procedures of regenerative medicine. The matrices may be derived from a number of types of mammalian tissues, including human tissues. Such types of tissues include, but are not limited to, adipose, dermis, fascia, muscle, pericardium, other connective or membranous tissues, and combinations thereof. In some embodiments, the matrices may include two or more types of tissue. In some embodiments of the present invention, the matrices are in the form of lyophilized (i.e., freeze-dried) particles. According to some embodiments of the present invention, the particles are rehydrated in a carrier for injection into a patient. According to some embodiments of the present invention, the matrices are autologous to the patient. In other embodiments, the tissues are allografts. In yet other embodiments, the matrices are xenografts. According to some embodiments of the present invention, the matrices are in the form of sheets or strips. In other embodiments of the present invention, the matrices are in a particulate form. In yet other embodiments of the present invention, the matrices are in the form of an injectable paste, gel, suspension, or slurry. According to some embodiments of the present invention, the matrices are in a lyophilized (i.e., freeze-dried) form. In other embodiments of the present invention, the matrices are in pre-hydrated (undried or only partially dried) form. In still other embodiments of the present invention, the matrices are in a rehydrated (partially or substantially dried, then combined with a carrier or other fluid) form. According to some embodiments, the matrices have been reseeded with cells. According to some embodiments of the present invention, factors for promoting and directing tissue ingrowth and differentiation (e.g., growth factors, such as VEGF or bFGF) have been added to the matrices.

Other embodiments of the present invention relate to a process for preparing acellular matrices from soft tissues. Some embodiments of the process include the steps of: (1) isolating a desired soft tissue obtained from a donor; (2) decellularizing the tissue by a process which includes soaking the isolated tissue in a hypertonic solution, soaking the isolated tissue in a surfactant, and soaking or rinsing the processed tissue in sterile water; (3) disinfecting the decellularized tissue; and (4) post-processing the tissue into a desired form. The post-processing step typically (4) involves at least partially drying, or substantially drying, and milling the tissue, among other things as discussed below. In some embodiments, the desired soft tissue of the isolating step (1) comprises a first soft tissue and a second soft tissue, which are different types of tissue and may be attached to each other or may be separated from each other before being subjected to one or more process steps and recombined after being subjected to one or more process steps. According to some embodiments of the process, the process further includes a step of removing lipids from the isolated tissue (i.e., delipidizing/delipidating the tissue), which may be performed before decellularizing the isolated tissue. According to some embodiments of the process, the delipidization step is performed by agitating the isolated tissue in an alcohol.

In embodiments where the soft tissue is substantially dried, the foregoing process produces dry acellular soft tissue-derived matrices which are useful as grafts or implants and may be rehydrated prior to such use. In embodiments where the soft tissue is partially dried, or not subjected to a drying process, the foregoing process produces pre-hydrated acellular soft tissue-derived matrices which are useful as grafts or implants and may or may not be hydrated prior to such use.

BRIEF DESCRIPTION OF THE DRAWINGS

The present invention will be further explained with reference to the attached drawings, wherein.

DETAILED DESCRIPTION OF THE INVENTION

Figure 1:
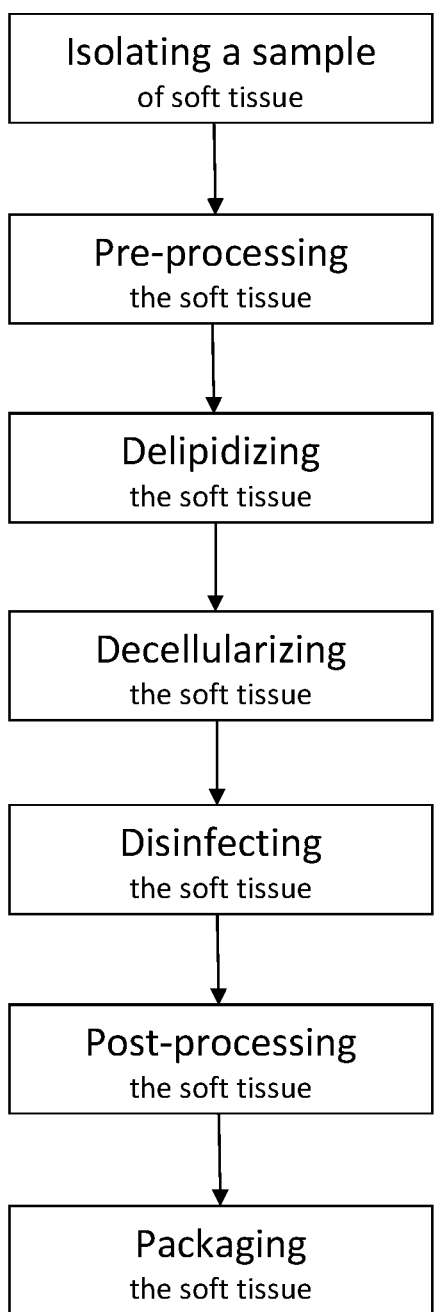
FIG. 1 is a schematic flowchart illustrating a process of preparing an acellular soft tissue-derived matrix according to an exemplary embodiment of the present invention.

Detailed embodiments of the present invention are disclosed herein. It should be understood that the disclosed embodiments are merely illustrative of the invention that may be embodied in various forms. In addition, each of the examples given in connection with the various embodiments of the invention is intended to be illustrative, and not restrictive.

The present invention relates generally to matrices made from decellularized soft tissues, including, but not limited to, adipose, dermis, fascia, muscle, pericardia, other connective or membranous tissues, and combinations thereof. Decellularized soft tissues, and methods of making same, are also disclosed in the co-owned U.S. Pat. No. 7,723,108, issued May 25, 2010, which is incorporated herein by reference. Acellular matrices of the present invention in a particulate or slurry form may be used as bulking agents in reconstructive or cosmetic surgery procedures (e.g., for filling voids in tissue or smoothing wrinkles), and as scaffolds for tissue repair and regeneration. In strip or sheet form, acellular matrices according to the present invention may be used to provide structural support to other tissues, and also to provide scaffolds for tissue repair and regeneration. Examples of procedures in which acellular matrices may be used include, but are not limited to, volume replacement, facial defect filling and rejuvenation in the aging face. Injectable acellular matrices may also be used for both superficial and deep aesthetic applications, including lip augmentation or rejuvenation of the aging lip to restore shape and contour, fine line filling to reduce the appearance of wrinkles around the eyes or mouth, improvement of nasolabial folds, correction of eyelid deformities, volume filling for the cheek and jawline, and for deep wrinkle or scar filling.

As used herein, the term "soft tissues" refers generally to non-calcified tissues from the mammalian body. For the purposes of the present disclosure, such tissues include an adipose tissue, an amnion tissue, an artery tissue, a demineralized bone tissue, a cartilage tissue, a connective tissue, a chorion tissue, a colon tissue, a non-calcified dental tissue, a dermal tissue, a duodenal tissue, an endothelial tissue, an epithelial tissue, a fascial tissue, a gastrointestinal tissue, a gingival tissue, a growth plate tissue, an intervertebral disc tissue, an intestinal mucosal tissue, an intestinal serosal tissue, a ligament tissue, a liver tissue, a lung tissue, a mammary tissue, a membranous tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and other non-calcified tissues.

Tissue and Cell Types

Tissues from which the acellular matrices of the present invention may be formed, as well as tissues which may be augmented or repaired using such acellular matrices are described more fully hereinbelow.

1. Tissue Compartments

In multicellular organisms, cells that are specialized to perform common functions are usually organized into cooperative assemblies embedded in a complex network of secreted extracellular macromolecules (i.e., the extracellular matrix (ECM)), to form specialized tissue compartments. Individual cells in such tissue compartments are in contact with ECM macromolecules. The ECM helps hold the cells and compartments together and provides an organized lattice or scaffold within which cells can migrate and interact with one another. In many cases, cells in a compartment can be held in place by direct cell-cell adhesions. In vertebrates, such compartments may be of four major types, a connective tissue (CT) compartment, an epithelial tissue (ET) compartment, a muscle tissue (MT) compartment and a nervous tissue (NT) compartment, which are derived from three embryonic germ layers: ectoderm, mesoderm and endoderm. The NT and portions of the ET compartments are differentiated from the ectoderm; the CT, MT and certain portions of the ET compartments are derived from the mesoderm; and further portions of the ET compartment are derived from the endoderm.

1.1. Extracellular Matrix

The ECM is an intricate network of secreted extracellular macromolecules that largely fills the extracellular space in the tissue compartments and comprises large polymeric complexes of glycosaminoglycans (GAGs) and proteoglycans. GAGs are negatively charged unbranched polysaccharide chains comprising repeating disaccharide units. Each repeating disaccharide unit of a GAG chain contains an amino sugar (e.g., N-acetyl glucosamine), which in most cases is sulfated, and an -uronic acid (e.g., glucuronic or iduronic acid). Four main types of GAG molecules are distinguished based on sugar residues, type of linkage, number and location of sulfate groups: (1) hyaluronan; (2) chondroitan sulfate and dermatan sulfate; (3) heparan sulfate and heparin; and (4) keratin sulfate.

GAG chains are inflexible and tend to adopt extended conformations occupying a huge volume relative to their mass, forming gels even at low concentrations. Their high density of negative charges attracts cations, such as Nat, that are effective in osmotic absorption of large amounts of water into the matrix. This creates high turgor enabling the ECM to withstand compressive forces.

Hyaluronan (also termed hyaluronic acid or hyaluronate) (HA), which comprises a regular repeating sequence of up to 25,000 nonsulfated disaccharide units, serves many functions, many of which depend on the binding of HA-binding proteins and proteoglycans, which are either themselves constituents of the ECM or are integral constituents of cell surfaces. For example, HA resists compressive forces in joints as a major constituent of joint fluid serving as a lubricant; serves as a space filler during embryonic development; creates a cell-free space in the epithelial compartment to allow cell migration during the formation of heart, cornea and other organs; and plays a role in wound repair. Excess HA is usually degraded by hyaluronidase.

All GAGs, except for HA, are covalently linked to proteins in the form of proteoglycans. During their synthesis, the polypeptide chain of proteoglycans is synthesized on membrane-bound ribosomes and threaded into the lumen of endoplasmic reticulum, from which they are sorted in the Golgi apparatus, and assembled with polysaccharide chains. While still in the Golgi, proteoglycans undergo a series of sequential and coordinated sulfation and epimerization reactions to produce sulfated proteoglycans. Sulfated and non-sulfated proteoglycans then travel through the Golgi network and are ultimately secreted into the ECM by exocytosis with the help of secretory vesicles.

Proteoglycans are heterogenous molecules, with core proteins ranging in molecular weight from 10 kD to about 600 kD and with attached GAG chains varying in number and type, further modified by a complex variable pattern of sulfate groups. At least one of the proteoglycan sugar side chains is a GAG; the core protein is usually a glycoprotein, but may comprise up to 95% carbohydrate by weight, mostly as long unbranched GAG chains up to at least 80 sugar residues long.

Proteoglycans along with their attached GAG chains regulate the activities of secreted macromolecules. They can serve as selective molecular sieves regulating a size-based trafficking of molecules and cells, and play a role in cell-cell signaling. Proteoglycans modulate the activities of secreted factors, such as growth factors and cytokines, by binding to them For example, binding of fibroblast growth factor (FGF) to heparan sulfate chains of proteoglycans is required for FGF activation of its cell surface receptors. On the other hand, for example, binding of a ubiquitous growth regulatory factor, such as transforming growth factor β (TGF-β) to core proteins of several ECM proteoglycans, such as decorin, results in inhibition of TGF-β activity. Proteoglycans also bind and regulate the activities of other types of secreted proteins, such as proteases and protease inhibitors. Cell-surface proteoglycans also may act as co-receptors: for example, syndecan binds to FGF and presents it to the FGF-receptor. Similarly, betaglycan binds to TGF-β and presents it to TGF-β receptors.

Collagens and elastin are the major fibrous proteins of the ECM. Collagens comprise a family of highly characteristic fibrous proteins and are a major component of skin and bone. Collagen fibers consist of globular units of the collagen subunit tropocollagen. Each tropocollagen subunit molecule comprises three polypeptide chains, called a chains, each exhibiting a left-handed helical conformation that are wrapped around each other in a right-handed coiled coil structure, also called a triple helix or super helix. A characteristic feature of collagen is a repeating tripeptide unit comprising Glycine-Proline-X or Glycine-X-Hydroxyproline, where X may be any amino acid. The presence of glycine at every third position in a collagen unit is critical for maintaining the coiled coil structure, since each repeating glycine residue sits on the interior axis of the helix, which sterically hinders bulkier side chains. Prolines and hydroxyprolines help stabilize the triple helix. Collagen is secreted as procollagen molecules, which undergo proteolytic processing and subsequent assembly to form collagenous fibrils. Collagens are highly glycosylated during protein trafficking through intracellular secretory pathways.

Collagens are classified into various types depending on the nature of their a chains. Table 1 lists types of collagen, composition, class and distribution. (Reproduced from Shoulders and Raines, Annu. Rev. Biochem. 2009, 78:929-958 and Bailey's Textbook of Microscopic Anatomy, Kelly et al., Williams and Wilkins, 18$^{th}$ edition, 1984).

TABLE 1

| Collagen Type, Class and Distribution | | | |
|---|---|---|---|
| Collagen Type | Composition | Class | Distribution |
| I | $\alpha_1[I]_2\alpha_2[I]$ | Fibrillar | Dermis, tendon, ligament, bone, cornea |
| II | $\alpha_1[II]_3$ | Fibrillar | Cartilage, intervertebral disc, vitreous body |
| III | $\alpha_1[III]_3$ | Fibrillar | Fetal skin, cardiovascular system, basal lamina, intestine. |
| IV | $\alpha_1[IV]_2\alpha_2[IV]$; $\alpha_3[IV]\alpha_4[IV]\alpha_5[IV]$; $\alpha_5[IV]_2\alpha_6[IV]$ | Network | Basal lamina, external lamina |
| V | $\alpha_1[V]_3$; $\alpha_1[V]_2\alpha_2[V]$; $A_1[V]\alpha_2[V]\alpha_3[V]$ | Fibrillar | Bone, dermis, cornea, placenta |
| VI | $\alpha_1[VI]\alpha_2[VI]\alpha_3[VI]$; $\alpha_1[VI]\alpha_2[VI]\alpha_4[VI]$ | Network | Bone, cartilage, cornea, dermis |
| VII | $\alpha_1[VII]_2\alpha_2[VII]$ | Anchoring fibril | Dermis, bladder |
| VIII | $\alpha_1[VIII]_3$; $\alpha_2[VIII]_3$; $\alpha_1[VIII]_2\alpha_2[VIII]$ | Network | Dermis, brain, heart, kidney |
| IX | $\alpha_1[IX]\alpha_2[IX]\alpha_3[IX]$ | FACIT$^a$ | Cartilage, cornea, vitreous |
| X | $\alpha_1[X]_3$ | Network | Cartilage |
| XI | $\alpha_1[XI]\alpha_2[XI]\alpha_3[XI]$ | Fibrillar | Cartilage, intervertebral disc |
| XII | $\alpha_1[XII]_3$ | FACIT | Dermis, tendon |
| XIII | $\alpha_1[XIII]_3$ | MACIT$^a$ | Endothelial cells, dermis, eye, heart |
| XIV | $\alpha_1[XIV]_3$ | FACIT | Bone, dermis, cartilage |
| XV | | MULTIPLEXIN$^a$ | Capillaries, testis, kidney, heart, bone |
| XVI | | FACIT | Dermis, kidney |
| XVII | $\alpha_1[XVII]_3$ | MACIT | Hemidesmosomes in epithelia |
| XVIII | | MULTIPLEXIN | Basal lamina, liver |
| XIX | | FACIT | Basal lamina |
| XX | | FACIT | Cornea |
| XXI | | FACIT | Stomach, kidney |
| XXII | | FACIT | Tissue junctions |
| XXIII | | MACIT | Heart, retina |
| XXIV | | Fibrillar | Bone, cornea |
| XXV | | MACIT | Brain, heart, testis |
| XXVI | | FACIT | Testis, ovary |
| XXVII | | | Dermis, sciatic nerve |
| XXIX | | | Dermis |

$^a$Abbreviations: FACIT, fibril-associated collagen with interrupted triple helices; MACIT, membrane-associated collagen with interrupted triple helices; MULTIPLEXIN, multiple triple helix domains.

A network of elastic fibers in the ECM offers resilience and elasticity so that organs are able to recoil following transient stretch. Elastic fibers primarily comprise the fibrous protein elastin, a highly hydrophobic protein about 750 amino acids in length that is rich in proline and glycine, is not glycosylated and is low in hydroxyproline and hyroxylysine. Elastin molecules are secreted into the ECM and assemble into elastic fibers close to the plasma membrane. Upon secretion, elastin molecules become highly cross-linked to form an extensive network of fibers and sheets.

The ECM also comprises many non-collagen adhesive proteins, usually with multiple domains containing binding sites of other macromolecules and for cell-surface receptors. One such adhesive protein, fibronectin, is a large glycoprotein comprising two subunits joined by a pair of disulfide bonds near the carboxy termini. Each subunit is folded into a series of rod-like domains interspersed by regions of flexible polypeptide chains. Each domain further comprises repeating modules of various types. One major type of fibronectin repeating module, called type III fibronectin repeat, is about 90 amino acids in length and occurs at least 15 times in each subunit. Fibronectin type Ill repeats have characteristic Arg-Gly-Asp (RGD) tripeptide repeats that function as binding sites for other proteins such as collagen, heparin or cell surface receptors. Fibronectin not only plays an important role in cell adhesion to the ECM, but also in guiding cell migration in vertebrate embryos.

Laminin, another adhesive glycoprotein of the ECM, is a major constituent (along with type IV collagen and another glycoprotein, nidogen/entactin) of the basal lamina, a tough sheet of ECM formed at the base of epithelial cells. Laminin is a large flexible complex, about 850 kD in molecular weight, with three very long polypeptide chains arranged in the form of an asymmetric cross held together with disulfide bonds. Laminin contains numerous functional domains, e.g., one binds to type IV collagen, one to heparan sulfate, one to entactin, and two or more to laminin receptor proteins on the cell surface.

1.2 Stem Cells

The term "stem cells" as used herein refers to undifferentiated cells having high proliferative potential with the ability to self-renew that can generate daughter cells that can undergo terminal differentiation into more than one distinct cell phenotype. Stem cells are distinguished from other cell types by two characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

Embryonic stem cells (EmSC) are stem cells derived from an embryo that are pluripotent (i.e., they are able to differentiate in vitro into endodermal, mesodermal and ectodermal cell types).

Adult (somatic) stem cells are undifferentiated cells found among differentiated cells in a tissue or organ. Their primary role in vivo is to maintain and repair the tissue in which they are found. Adult stem cells have been identified in many organs and tissues, including brain, bone marrow, peripheral blood, blood vessels, skeletal muscles, skin, teeth, gastrointestinal tract, liver, ovarian epithelium, and testis. Adult stem cells are thought to reside in a specific area of each tissue, known as a stem cell niche, where they may remain quiescent (non-dividing) for long periods of time until they are activated by a normal need for more cells to maintain tissue, or by disease or tissue injury. Examples of adult stem cells include, but not limited to, hematopoietic stem cells, mesenchymal stem cells, neural stem cells, epithelial stem cells, and skin stem cells.

Hematopoietic Stem Cells (HSCs)

Hematopoietic stem cells (also known as the colony-forming unit of the myeloid and lymphoid cells (CFU-M,L), or CD34+ cells) are rare pluripotential cells within the blood-forming organs that are responsible for the continued production of blood cells during life. While there is no single cell surface marker exclusively expressed by hematopoietic stem cells, it generally has been accepted that human HSCs have the following antigenic profile: CD34+, CD59+, Thy1+ (CD90), CD38low/−, C-kit-/low and, Lin−. CD45 is also a common marker of HSCs, except platelets and red blood cells. HSCs can generate a variety of cell types, including erythrocytes, neutrophils, basophils, eosinophils, platelets, mast cells, monocytes, tissue macrophages, osteoclasts, and the T and B lymphocytes. The regulation of hematopoietic stem cells is a complex process involving self-renewal, survival and proliferation, lineage commitment and differentiation and is coordinated by diverse mechanisms including intrinsic cellular programming and external stimuli, such as adhesive interactions with the micro-environmental stroma and the actions of cytokines.

Different paracrine factors are important in causing hematopoietic stem cells to differentiate along particular pathways. Paracrine factors involved in blood cell and lymphocyte formation are called cytokines. Cytokines can be made by several cell types, but they are collected and concentrated by the extracellular matrix of the stromal (mesenchymal) cells at the sites of hematopoiesis. For example, granulocyte-macrophage colony-stimulating factor (GM-CSF) and the multilineage growth factor IL-3 both bind to the heparan sulfate glycosaminoglycan of the bone marrow stroma. The extracellular matrix then presents these factors to the stem cells in concentrations high enough to bind to their receptors.

Mesenchymal Stem Cells (MSCs)

Mesenchymal stem cells (MSCs) (also known as bone marrow stromal stem cells or skeletal stem cells) are non-blood adult stem cells found in a variety of tissues. They are characterized by their spindle-shape morphologically; by the expression of specific markers on their cell surface; and by their ability, under appropriate conditions, to differentiates along a minimum of three lineages (osteogenic, chondrogenic, and adipogenic).

No single marker that definitely delineates MSCs in vivo has been identified due to the lack of consensus regarding the MSC phenotype, but it generally is considered that MSCs are positive for cell surface markers CD105, CD166, CD90, and CD44 and that MSCs are negative for typical hematopoietic antigens, such as CD45, CD34, and CD14. As for the differentiation potential of MSCs, studies have reported that populations of bone marrow-derived MSCs have the capacity to develop into terminally differentiated mesenchymal phenotypes both in vitro and in vivo, including bone, cartilage, tendon, muscle, adipose tissue, and hematopoietic-supporting stroma. Studies using transgenic and knockout mice and human musculoskeletal disorders have reported that MSC differentiate into multiple lineages during embryonic development and adult homeostasis.

Analyses of the in vitro differentiation of MSCs under appropriate conditions that recapitulate the in vivo process have led to the identification of various factors essential for stem cell commitment. Among them, secreted molecules and their receptors (e.g., transforming growth factor-β), extracellular matrix molecules (e.g., collagens and proteogly-cans), the actin cytoskeleton, and intracellular transcription factors (e.g., Cbfa1/Runx2, PPARγ, Sox9, and MEF2) have been shown to play important roles in driving the commitment of multipotent MSCs into specific lineages, and maintaining their differentiated phenotypes.

For example, it has been shown that osteogenesis of MSCs, both in vitro and in vivo, involves multiple steps and the expression of various regulatory factors. During osteogenesis, multipotent MSCs undergo asymmetric division and generate osteoprecursors, which then progress to form osteoprogenitors, preosteoblasts, functional osteoblasts, and eventually osteocytes. This progression from one differentiation stage to the next is accompanied by the activation and subsequent inactivation of transcription factors, i.e., Cbfa1/Runx2, Msx2, Dlx5, Osx, and expression of bone-related marker genes, (i.e., osteopontin, collagen type I, alkaline phosphatase, bone sialoprotein, and osteocalcin).

Members of the Wnt family also have been shown to impact MSC osteogenesis. Wnts are a family of secreted cysteine-rich glycoproteins that have been implicated in the regulation of stem cell maintenance, proliferation, and differentiation during embryonic development. Canonical Wnt signaling increases the stability of cytoplasmic β-catenin by receptor-mediated inactivation of GSK-3 kinase activity and promotes β-catenin translocation into the nucleus. The active β-catenin/TCF/LEF complex then regulates the transcription of genes involved in cell proliferation. In humans, mutations in the Wnt co-receptor LRP5 lead to defective bone formation. "Gain of function" mutation results in high bone mass, whereas "loss of function" causes an overall loss of bone mass and strength, indicating that Wnt signaling is positively involved in embryonic osteogenesis. Canonical Wnt signaling pathway also functions as a stem cell mitogen via stabilization of intracellular β-catenin and activation of the β-catenin/TCF/LEF transcription complex, resulting in activated expression of cell cycle regulatory genes, such as Myc, cyclin D1, and Msx1. When MSCs are exposed to Wnt3a, a prototypic canonical Wnt signal, under standard growth medium conditions, they show markedly increased cell proliferation and a decrease in apoptosis, consistent with the mitogenic role of Wnts in hematopoietic stem cells. However, exposure of MSCs to Wnt3a conditioned medium or overexpression of ectopic Wnt3a during osteogenic differentiation inhibits osteogenesis in vitro through β-catenin mediated down-regulation of TCF activity. The expression of several osteoblast specific genes, (e.g., alkaline phosphatase, bone sialoprotein, and osteocalcin), is dramatically reduced, while the expression of Cbfa1/Runx2, an early osteo-inductive transcription factor is not altered, implying that Wnt3a-mediated canonical signaling pathway is necessary, but not sufficient, to completely block MSC osteogenesis. On the other hand, Wnt5a, a typical non-canonical Wnt member, has been shown to promote osteogenesis in vitro. Since Wnt3a promotes MSC proliferation during early osteogenesis, it is thought likely that canonical Wnt signaling functions in the initiation of early osteogenic commitment by increasing the number of osteoprecursors in the stem cell compartment, while non-canonical Wnt drives the progression of osteoprecursors to mature functional osteoblasts.

Epithelial Stem Cells.

An epithelial membrane is a continuous multicellular sheet composed of an epithelium adhered to underlying connective tissue. Epithelial membranes can be cutaneous (e.g. skin), mucous (e.g., gastrointestinal lining), and or serous (e.g. pleural lining, pericardial lining and peritoneal lining).

Epithelial stem cells line the gastrointestinal tract in deep crypts and give rise to absorptive cells, goblet cells, paneth cells, and enteroendocrine cells.

Components of the Human Gastrointestinal Tract

The gastrointestinal tract is a continuous tube that extends from the mouth to the anus. On a gross level, the gastrointestinal tract is composed of the following organs: the mouth, most of the pharynx, the esophagus, the stomach, the small intestine (duodenum, jejunum and ileum), and the large intestine. Each segment of the gastrointestinal tract participates in the absorptive processes essential to digestion by producing chemical substances that facilitate digestion of orally-taken foods, liquids, and other substances such as therapeutic agents.

Within the gastrointestinal tract, the small intestine, the site of most digestion and absorption, is structured specifically for these important functions. The small intestine is divided into three segments: the duodenum, the jejunum, and the ileum. The absorptive cells of the small intestine produce several digestive enzymes called the "brush-border" enzymes. Together with pancreatic and intestinal juices, these enzymes facilitate the absorption of substances from the chyme in the small intestine. The large intestine, the terminal portion of the gastrointestinal tract, contributes to the completion of absorption, the production of certain vitamins, and the formation and expulsion of feces.

At the cellular level, the epithelium is a purely cellular avascular tissue layer that covers all free surfaces (cutaneous, mucous, and serous) of the body including the glands and other structures derived from it. It lines both the exterior of the body, as skin, and the interior cavities and lumen of the body. While the outermost layer of human skin is composed of dead stratified squamous, keratinized epithelial cells, mucous membranes lining the inside of the mouth, the esophagus, and parts of the rectum are themselves lined by nonkeratinized stratified squamous epithelium. Epithelial cell lines are present inside of the lungs, the gastrointestinal tract, and the reproductive and urinary tracts, and form the exocrine and endocrine glands.

Epithelial cells are involved in secretion, absorption, protection, transcellular transport, sensation detection and selective permeability. There are variations in the cellular structures and functions in the epithelium throughout the gastrointestinal tract. The epithelium in the mouth, pharynx, esophagus and anal canal is mainly a protective, nonkeratinized, squamous epithelium. The epithelium of the stomach is composed of (i) simple columnar cells that participate in nutrient and fluid absorption and secretion, (ii) mucus-producing goblet cells that participate in protective and mechanical functions, and (iii) enteroendocrine cells that participate in the secretion of gastrointestinal hormones. Additionally, within the intestine, the epithelial lining provides an important defense barrier against microbial pathogens.

The development of intestinal epithelium involves three major phases: 1) an early phase of epithelial proliferation and morphogenesis; 2) an intermediate period of cellular differentiation in which the distinctive cell type's characteristic of intestinal epithelium appear; and 3) a final phase of biochemical and functional maturation. Intestinal crypts, located at the base of villi, contain stem cells which supply the entire epithelial cell surface with a variety of epithelial cell subtypes. These specialized cells provide for an external environment-internal environment interface, ion and fluid secretion and reabsorption, antigen recognition, hormone secretion, and surface protection. The exposure of epithelial cells on the surfaces of the intestinal lumen subjects them to a wide range of assaults, including microbial, chemical, and physical forces; thus they also may contribute to patho-physiologic impairment in diseases. Additionally, these cells are targets for inflammation, infection, and malignant trans-formation.

Within the intestinal tract, the epithelium forms upon stem cell differentiation.

Molecular Markers of Gastrointestinal Epithelial Stem Cells

As disclosed in U.S. Published Application No. 2009/0269769, which is incorporated herein by reference in its entirety, there are no universally accepted molecular mark-ers that identify gastrointestinal stem cells. However, several markers have been used to identify stem cells in small and large intestinal tissues. These include: β-1-integrin, mush-ashi-1, CD45, and cytokeratin.

CD45, also called the common leukocyte antigen, T220 and B220 in mice, is a transmembrane protein with cyto-plasmic protein tyrosine phosphatase (PTP) activity. CD45 is found in hematopoietic cells except erythrocytes and platelets. CD45 has several isoforms that can be seen in the various stages of differentiation of normal hematopoietic cells.

Mushashi-1 is an early developmental antigenic marker of stem cells and glial/neuronal cell precursor cells.

β-1-integrin (CD29, fibronectin receptor), is a β-subunit of a heterodimer protein member of the integrin family of proteins; integrins are membrane receptors involved in cell adhesion and recognition.

Cytokeratins are intermediate filament proteins found in the intracytoplasmic cystoskeleton of the cells that comprise epithelial tissue.

There are four main epithelial cell lineages: (i) columnar epithelial cells, (ii) goblet cells, (iii) enteroendocrine chro-maffin cells, and (iv) Paneth cells. Several molecular mark-ers have been used to identify each of these lineages.

The markers used to identify columnar epithelial cells include: intestinal alkaline phosphatase (ALP1), sucrase isomaltase (SI), sodium/glucose cotransporter (SLGT1), dipeptidyl-peptidase 4 (DPP4), and CD26. Intestinal alka-line phosphatase (E.C. 3.1.3.1) is a membrane-bound enzyme localized in the brush border of enterocytes in the human intestinal epithelium. Sucrase-isomaltase (SI, EC 3.2.1.48) is an enterocyte-specific small intestine brush-border membrane disaccharidase. Dipeptidyl-peptidase 4 (E.C. 3.4.14.5) is a membrane bound serine-type peptidase. Sodium/glucose transporter (SGLT) mediates transport of glucose into epithelial cells. SGLT belongs to the sodium/glucose cotransporter family SLCA5. Two different SGLT isoforms, SGLT1 and SGLT2, mediate renal tubular glucose reabsorption in humans. Both of them are characterized by their different substrate affinity. SGLT1 transports glucose as well as galactose, and is expressed both in the kidney and in the intestine. SGLT2 transports glucose and is believed to be responsible for 98% of glucose reabsorption; SGLT2 is generally found in the S1 and S2 segments of the proximal tubule of the nephron. CD26 is a multifunctional protein of 110 KDa strongly expressed on epithelial cells (kidney proximal tubules, intestine, and bile duct) and on several types of endothelial cells and fibroblasts and on leukocyte subsets.

The markers used to identify goblet cells include mucin 2 (MUC2) and trefoil factor 3 (TFF3). Mucin-2, a secreted gel-forming mucin, is the major gel-forming mucin secreted by goblet cells of the small and large intestines and is the main structural component of the mucus gel. Intestinal trefoil factor 3 is a nonmucin protein and a product of fully differentiated goblet cells.

The markers used to identify enteroendocrine chromaffin cells include chromogranin A (CHGA) and synaptophysin (SYP). Chromogranin A (CHGA) and its derived peptides, which are stored and released from dense-core secretory granules of neuroendocrine cells, have been implicated as playing multiple roles in the endocrine, cardiovascular, and nervous systems. Synaptophysin I (SYP) is a synaptic vesicle membrane protein that is ubiquitously expressed throughout the brain without a definite synaptic function.

The markers used to identify Paneth cells include lysozyme (LYZ), defensin (DEFA1), and matrix metallo-peptidase 7 (MMP7). Lysozyme (LYZ or muramidase) (E.C. 3.2.1.17) catalyzes the hydrolysis of 1,4-beta-linkages between N-acetylmuramic acid and N-acetyl-D-glu-cosamine residues in a peptidoglycan and between N-acetyl-D-glucosamine residues in chitodextrins. Defensins (DEFA1) are small peptides that are produced by leukocytes and epithelial cells. Human defensin α-1 is a 3.5-kDa, 30-amino-acid peptide that has shown effector functions in host innate immunity against some microorganisms. Matrix metalloproteinases (MMPs) are a family of metal-dependant enzymes that are responsible for the degradation of extra-cellular matrix components. MMPs are involved in various physiologic processes, such as embryogenesis and tissue remodeling and also play a role in invasion and metastasis of tumor cells, which require proteolysis of basal mem-branes and extracellular matrix.

Neural Stem Cells

The adult mammalian brain contains multipotent neural stem cells (NSCs) that have the capacity to self-renew and are responsible for neurogenesis and maintenance of specific regions of the adult brain. Neural stem cells can generate astrocytes, oligodendrocytes, and neurons. Self-renewal and differentiation of neural stem cells are directed by interac-tions within a complex network of intrinsic regulators and extrinsic factors. Recent proteomic analyses have identified a horde of transcription factors belonging to the Wnt/β-catenin, Notch and Sonic Hedgehog (shh) pathways, in addition to epigenetic modifications, microRNA networks and extrinsic growth factor networks, including but not limited to the FGFs and BMPs. (Yun et al., 2010, J. Cell. Physiol. 225:337-347).

With the advent of high throughput microarray and pro-teomic technologies, a number of different molecular sig-natures of neural stem cells have been identified, including but not limited to CD133/promini, nestin, NCAM, the HMG-box transcription factor, Sox2 and the bHLH protein, Olig2. (Holmberg et al., 2011, PLOS One., 6 (3): e18454; Hombach-Klonisch et al., 2008, J. Mol. Med. 86 (12): 1301-1314).

Skin Stem Cells.

Several different adult stem cell populations with distinct molecular signatures are responsible for maintaining skin homeostasis. These include, but are not limited to, epidermal stem cells of the interfollicular region, epidermal stem cells of the hair follicle (also known as the bulge stem cells), dermal stem cells, dermal papilla stem cells, and sebaceous gland stems. The epidermal stem cells are ectodermal in origin while the dermal stem cells originate from the meso-derm and are mesenchymal in nature. (Zouboulis et al., 2008, Exp. Gerontol., 43:986-997).

The interfollicular epidermal stem cells reside in the basal layer of the epidermis and give rise to keratinocytes, which migrate to the surface of the skin and form a protective layer.

A diverse range of molecular signatures has been described for such epidermal stem cells including but not limited to high a6-integrin, low CD71, high Delta 1 (Notch signaling ligand) and high CD200 expression levels. The follicular stem cells located at the base of hair follicles give rise to both hair follicle and to the epidermis. These are characterized by Cytokeratin 15 (K15) immunostaining and high levels of 1-integrin. Dermal stem cell marker proteins include but are not limited to nestin, fibronectin and vimentin, the surface markers for dermal papilla stem cells include mesenchymal stem cell markers such as for example CD44, CD73 and CD90 and sebaceous stem cells express keratin 14. (Zouboulis et al., 2008, Exp. Gerontol., 43:986-997).

In addition, adult somatic cells can be reprogrammed to enter an embryonic stem cell-like state by being forced to express a set of transcription factors, for example, Oct-3/4 (or Pou5f1, the Octamer transcription factor-3/4), the Sox family of transcription factors (e.g., Sox-1, Sox-2, Sox-3, and Sox-15), the Klf family transcription factors (Klf-1, Klf-2, Klf-4, and Klf-5), and the Myc family of transcription factors (e.g., c-Myc, N-Myc, and L-Myc). For example, human inducible Pluripotent Stem cells (iPSCs) are cells reprogrammed to express transcription factors that express stem cell markers and are capable of generating cells characteristic of all three germ layers (i.e., ectoderm, mesoderm, and endoderm).

1.3. Stem Cell Niches

Adult tissue compartments contain endogenous niches of adult stem cells that are capable of differentiating into diverse cell lineages of determined endodermal, mesodermal or ectodermal fate depending on their location in the body. For example, in the presence of an appropriate set of internal and external signals, bone marrow-derived adult hematopoietic stem cells (HSCs) have the potential to differentiate into blood, endothelial, hepatic and muscle cells; brain-derived neural stem cells (NSCs) have the potential to differentiate into neurons, astrocytes, oligodendrocytes and blood cells; gut- and epidermis-derived adult epithelial stem cells (EpSCs) have the potential to give rise to cells of the epithelial crypts and epidermal layers; adipose-derived stem cells (ASCs) have the potential to give rise to fat, muscle, cartilage, endothelial cells, neuron-like cells and osteoblasts; and bone-marrow-derived adult mesenchymal stem cells (MSCs) have the potential to give rise to bone, cartilage, tendon, adipose, muscle, marrow stroma and neural cells.

Endogenous adult stem cells are embedded within the ECM component of a given tissue compartment, which, along with support cells, form the cellular niche. Such cellular niches within the ECM scaffold together with the surrounding microenvironment contribute important biochemical and physical signals, including growth factors and transcription factors required to initiate stem cell differentiation into committed precursors cells and subsequent precursor cell maturation to form adult tissue cells with specialized phenotypic and functional characteristics.

Stem Cell Markers

Coating the surface of every cell in the body are specialized proteins ("receptors") capable of selectively binding or adhering to other "signaling" molecules. Normally, cells use these receptors and the molecules that bind to them as a way of communicating with other cells and to carry out their proper functions in the body. These cell surface receptors are the stem cell markers. Each cell type has a certain combination of receptors on their surface that makes them distinguishable from other kinds of cells.

The cluster of differentiation (CD) system is a protocol used for the identification of cell surface molecules. CD molecules can act in numerous ways, often acting as receptors or ligands; by which a signal cascade is initiated, altering the behavior of the cell. Some CD proteins do not play a role in cell signaling, but have other functions, such as cell adhesion. Generally, a proposed surface molecule is assigned a CD number once two specific monoclonal antibodies (mAb) are shown to bind to the molecule. If the molecule has not been well-characterized, or has only one mAb, the molecule usually is given the provisional indicator "w."

The CD system nomenclature commonly used to identify cell markers thus allows cells to be defined based on what molecules are present on their surface. These markers often are used to associate cells with certain functions. While using one CD molecule to define populations is uncommon, combining markers has allowed for cell types with very specific definitions. More than 350 CD molecules have been identified for humans.

CD molecules are utilized in cell sorting using various methods, including flow cytometry. Cell populations usually are defined using a "+" or a "−" symbol to indicate whether a certain cell fraction expresses or lacks a particular CD molecule.

Table 2 identifies markers commonly used to identify stem cells and to characterize differentiated cell types:

TABLE 2

| Commonly-Used Stem Cell Surface Markers and Corresponding Differentiated Cell Types | | |
|---|---|---|
| Marker Name | Cell Type | Significance |
| Blood Vessel | | |
| Fetal liver kinase-1 (Flk1) | Endothelial | Cell-surface receptor protein that identifies endothelial cell progenitor; marker of cell-cell contacts |
| Smooth muscle cell-specific myosin heavy chain | Smooth muscle | Identifies smooth muscle cells in the wall of blood vessels |
| Vascular endothelial cell cadherin | Smooth muscle | Identifies smooth muscle cells in the wall of blood vessels |
| Bone | | |
| Bone-specific alkaline phosphatase (BAP) | Osteoblast | Enzyme expressed in osteoblast; activity indicates bone formation |

TABLE 2-continued

Commonly-Used Stem Cell Surface Markers and
Corresponding Differentiated Cell Types

| Marker Name | Cell Type | Significance |
| --- | --- | --- |
| Hydroxyapatite | Osteoblast | Mineralized bone matrix that provides structural integrity; marker of bone formation |
| Osteocalcin (OC) | Osteoblast | Mineral-binding protein synthesized by osteoblast; marker of bone formation |
| | | Bone Marrow and Blood |
| Bone morphogenetic protein receptor (BMPR) | Mesenchymal stem and progenitor cells | Important for the differentiation of committed mesenchymal cell types from mesenchymal stem and progenitor cells; BMPR identifies early mesenchymal lineages (stem and progenitor cells) |
| CD4 and CD8 | White blood cell (WBC) | Cell-surface protein markers specific for mature T lymphocyte (WBC subtype) |
| CD34 | Hematopoietic stem cell (HSC), satellite, endothelial progenitor | Cell-surface protein on bone marrow cell, indicative of a HSC and endothelial progenitor; CD34 also identifies muscle satellite, a muscle stem cell |
| CD34$^+$Sca1$^+$ Lin$^-$ profile | Mesenchymal stem cell (MSC) | Identifies MSCs, which can differentiate into adipocyte, osteocyte, chondrocyte, and myocyte |
| CD38 | Absent on HSC Present on WBC lineages | Cell-surface molecule that identifies WBC lineages. Selection of CD34$^+$/CD38$^-$ cells allows for purification of HSC populations |
| CD44 | Mesenchymal | A type of cell-adhesion molecule used to identify specific types of mesenchymal cells |
| c-Kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Colony-forming unit (CFU) | HSC, MSC progenitor | CFU assay detects the ability of a single stem cell or progenitor cell to give rise to one or more cell lineages, such as red blood cell (RBC) and/or white blood cell (WBC) lineages |
| Fibroblast colony-forming unit (CFU-F) | Bone marrow fibroblast | An individual bone marrow cell that has given rise to a colony of multipotent fibroblastic cells; such identified cells are precursors of differentiated mesenchymal lineages |
| Hoechst dye | Absent on HSC | Fluorescent dye that binds DNA; HSC extrudes the dye and stains lightly compared with other cell types |
| Leukocyte common antigen (CD45) | WBC | Cell-surface protein on WBC progenitor |
| Lineage surface antigen (Lin) | HSC, MSC Differentiated RBC and WBC lineages | Thirteen to 14 different cell-surface proteins that are markers of mature blood cell lineages; detection of Lin-negative cells assists in the purification of HSC and hematopoietic progenitor populations |
| Mac-1 | WBC | Cell-surface protein specific for mature granulocyte and macrophage (WBC subtypes) |
| Muc-18 (CD146) | Bone marrow fibroblasts, endothelial | Cell-surface protein (immunoglobulin superfamily) found on bone marrow fibroblasts, which may be important in hematopoiesis; a subpopulation of Muc-18+ cells are mesenchymal precursors |
| Stem cell antigen (Sca-1) | HSC, MSC | Cell-surface protein on bone marrow (BM) cell, indicative of HSC and MSC Bone Marrow and Blood cont. |
| Stro-1 antigen | Stromal (mesenchymal) precursor cells, hematopoietic cells | Cell-surface glycoprotein on subsets of bone marrow stromal (mesenchymal) cells; selection of Stro-1+ cells assists in isolating mesenchymal precursor cells, which are multipotent cells that give rise to adipocytes, osteocytes, smooth myocytes, fibroblasts, chondrocytes, and blood cells |
| Thy-1 | HSC, MSC | Cell-surface protein; negative or low detection is suggestive of HSC |
| | | Cartilage |
| Collagen types II and IV | Chondrocyte | Structural proteins produced specifically by chondrocyte |
| Keratin | Keratinocyte | Principal protein of skin; identifies differentiated keratinocyte |
| Sulfated proteoglycan | Chondrocyte | Molecule found in connective tissues; synthesized by chondrocyte |
| | | Fat |
| Adipocyte lipid-binding protein (ALBP) | Adipocyte | Lipid-binding protein located specifically in adipocyte |

TABLE 2-continued

| | Commonly-Used Stem Cell Surface Markers and Corresponding Differentiated Cell Types | |
|---|---|---|
| Marker Name | Cell Type | Significance |
| Fatty acid transporter (FAT) | Adipocyte | Transport molecule located specifically in adipocyte |
| Adipocyte lipid-binding protein (ALBP) | Adipocyte | Lipid-binding protein located specifically in adipocyte |
| Perilipin A | Adipocyte | Protein associated with mature adipocytes |
| | Liver | |
| Albumin | Hepatocyte | Principal protein produced by the liver; indicates functioning of maturing and fully differentiated hepatocytes |
| B-1 integrin | Hepatocyte | Cell-adhesion molecule important in cell-cell interactions; marker expressed during development of liver |
| | Nervous System | |
| CD133 | Neural stem cell, HSC | Cell-surface protein that identifies neural stem cells, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligodendrocyte | Protein produced by mature oligodendrocytes; located in the myelin sheath surrounding neuronal structures |
| Nestin | Neural progenitor | Intermediate filament structural protein expressed in primitive neural tissue |
| Neural tubulin | Neuron | Important structural protein for neuron; identifies differentiated neuron |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligodendrocyte | Cell-surface marker on immature, developing oligodendrocyte |
| O1 | Oligodendrocyte | Cell-surface marker that characterizes mature oligodendrocyte |
| Synaptophysin | Neuron | Neuronal protein located in synapses; indicates connections between neurons |
| Tau | Neuron | Type of MAP; helps maintain structure of the axon |
| | Pancreas | |
| Cytokeratin 19 (CK19) | Pancreatic epithelium | CK19 identifies specific pancreatic epithelial cells that are progenitors for islet cells and ductal cells |
| Glucagon | Pancreatic islet | Expressed by alpha-islet cell of pancreas |
| Insulin | Pancreatic islet | Expressed by beta-islet cell of pancreas |
| Insulin-promoting factor-1 (PDX-1) | Pancreatic islet | Transcription factor expressed by beta-islet cell of pancreas |
| Nestin | Pancreatic progenitor | Structural filament protein indicative of progenitor cell lines including pancreatic |
| Pancreatic polypeptide | Pancreatic islet | Expressed by gamma-islet cell of pancreas |
| Somatostatin | Pancreatic islet | Expressed by delta-islet cell of pancreas |
| | Pluripotent Stem Cells | |
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation Pluripotent Stem Cells |
| Bone morphogenetic protein-4 | Mesoderm | Growth and differentiation factor expressed during early mesoderm formation and differentiation |
| Brachyury | Mesoderm | Transcription factor important in the earliest phases of mesoderm formation and differentiation; used as the earliest indicator of mesoderm formation |
| Cluster designation 30 (CD30) | ES, EC | Surface receptor molecule found specifically on PSC |

TABLE 2-continued

Commonly-Used Stem Cell Surface Markers and
Corresponding Differentiated Cell Types

| Marker Name | Cell Type | Significance |
|---|---|---|
| Cripto (TDGF-1) | ES cardiomyocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| OCT4/POU5F1 | ES, EC | Transcription factor unique to PSCs; essential for establishment and maintenance of undifferentiated PSCs |
| Pax6 | Ectoderm | Transcription factor expressed as ES cell differentiates into neuroepithelium |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extracellular matrix molecule normally synthesized by undifferentiated PSCs |
| Vimentin | Ectoderm, neural and pancreatic progenitor | Intermediate filaments within cells; characteristic of primitive neuroectoderm formation |
| Skeletal Muscle/Cardiac/Smooth Muscle | | |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardiomyocyte | A component of structural and contractile protein found in cardiomyocyte |
| Myosin light chain | Skeletal myocyte | A component of structural and contractile protein found in skeletal myocyte |

Table 3 shows commonly used markers employed by skilled artisans to identify and characterize differentiated white blood cell types:

TABLE 3

List of Surface Markers on White Blood Cell Types

| Type of Cell | CD Markers |
|---|---|
| Stem cells | CD34+, CD31− |
| All leukocyte groups | CD45+ |
| Granulocyte | CD45+, CD15+ |
| Monocyte | CD45+, CD14+ |
| T lymphocyte | CD45+, CD3+ |
| T helper cell | CD45+, CD3+, CD4+ |
| Cytotoxic T cell | CD45+, CD3+, CD8+ |

TABLE 3-continued

List of Surface Markers on White Blood Cell Types

| Type of Cell | CD Markers |
|---|---|
| B lymphocyte | CD45+, CD19+ or CD45+, CD20+ |
| Thrombocyte | CD45+, CD61+ |
| Natural killer cell | CD16+, CD56+, CD3− |

Table 4 correlates the exemplary protein expression profile of adipose derived stem cells (ASCs) with the corresponding surface markers (Flynn et. al., 2208 Organogenesis, 4 (4): 228-235; Gronthos et. al., 2011, J. Coll. Physiol., 189:54-63).

TABLE 4

Adipose-derived Stem Cell Protein
Expression and Surface Marker Profile

| Class | Protein | Marker |
|---|---|---|
| Cell | Integrin β1 | CD29 |
| Adhesion | Integrin α4 | $CD49_d$ |
| | Integrin $a_a$ | $CD49_e$ |
| | Vascular Cell Adhesion Molecule | VCAM; CD106 |
| | Intracellular Adhesion Molecule-1 | ICAM; CD54 |
| | Activated Leukocyte Cell Adhesion Molecule | ALCAM; CD166 |
| | Tetraspan | CD9 |
| | Endoglin | CD105 |
| | Muc18 | CD146 |
| Receptors | Hyaluronate receptor | CD44 |
| | Transferrin receptor | CD71 |
| | Insulin receptor | |
| | Glucocorticoid receptor | |
| | Triiodothyronine (T3) receptor | |
| | Retinoic acid receptor | |
| ECM | Collagen type I | |
| | Collagen type III | |
| | Collagen type IV | |
| | Collagen type VI | CD68 |
| | Osteopontin | |
| | Osteonectin | |
| | Laminin | |
| | Elastin | |
| | Fibronectin | |
| | Heparan sulfate proteoglycan | |
| Cytoskeletal | A-smooth muscle actin | |
| | Vimentin | |
| Other | HLA-ABC | Major histocompatibility complex class I antigen |
| | DAF | CD55 |
| | Complement protectin | CD59 |

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

Integrins are receptors that mediate attachment between a cell and the tissues surrounding it and are involved in cell-cell and cell-matrix interactions. In mammals, 18 α and 8 β subunits have been characterized. Both a and B subunits contain two separate tails, both of which penetrate the plasma membrane and possess small cytoplasmic domains.

Integrin αM (ITGAM; CD11b; macrophage-1 antigen (Mac-1); complement receptor 3 (CR3)) is a protein subunit of the heterodimeric integrin αMβ2 molecule. The second chain of αMβ2 is the common integrin β2 subunit (CD18). αMβ2 is expressed on the surface of many leukocytes including monocytes, granulocytes, macrophages and natural killer cells. It generally is believed that αMβ2 mediates inflammation by regulating leukocyte adhesion and migration. Further, αMβ2 is thought to have a role in phagocytosis, cell-mediated cytotoxicity, chemotaxis and cellular activation, as well as being involved in the complement system due to its capacity to bind inactivated complement component 3b (iC3b). The ITGAM subunit of integrin αMβ2 is involved directly in causing the adhesion and spreading of cells, but cannot mediate cellular migration without the presence of the β2 (CD18) subunit.

CD14 is a cell surface protein expressed mainly by macrophages and, to a lesser extent, neutrophil granulocytes. CD14+ cells are monocytes that can differentiate into a host of different cells; for example, differentiation to dendritic cells is promoted by cytokines such as GM-CSF and IL-4. CD14 acts as a co-receptor (along with toll-like receptor (TLR) 4 and lymphocyte antigen 96 (MD-2)) for the detection of bacterial lipopolysaccharide (LPS). CD14 only can bind LPS in the presence of lipopolysaccharide binding protein (LBP).

CD15 (3-fucosyl-N-acetyl-lactosamine; stage specific embryonic antigen 1 (SSEA-1)) is a carbohydrate adhesion molecule that can be expressed on glycoproteins, glycolipids and proteoglycans. CD15 commonly is found on neutrophils and mediates phagocytosis and chemotaxis.

CD16 is an Fc receptor (FcγRIIIa and FcγRIIIb) found on the surface of natural killer cells, neutrophil polymorphonuclear leukocytes, monocytes and macrophages. Fc receptors bind to the Fc portion of IgG antibodies.

CD19 is a human protein expressed on follicular dendritic cells and B cells. This cell surface molecule assembles with the antigen receptor of B lymphocytes in order to decrease the threshold for antigen receptor-dependent stimulation. It generally is believed that, upon activation, the cytoplasmic tail of CD19 becomes phosphorylated, which allows binding by Src-family kinases and recruitment of phosphoinositide 3 (PI-3) kinases.

CD20 is a non-glycosylated phosphoprotein expressed on the surface of all mature B-cells. Studies suggest that CD20 plays a role in the development and differentiation of B-cells into plasma cells. CD20 is encoded by a member of the membrane-spanning 4A gene family (MS4A). Members of this protein family are characterized by common structural features and display unique expression patterns among hematopoietic cells and nonlymphoid tissues.

CD31 (platelet/endothelial cell adhesion molecule; PECAM1) normally is found on endothelial cells, platelets, macrophages and Kupffer cells, granulocytes, T cells, natural killer cells, lymphocytes, megakaryocytes, osteoclasts and neutrophils. CD31 has a key role in tissue regeneration and in safely removing neutrophils from the body. Upon contact, the CD31 molecules of macrophages and neutrophils are used to communicate the health status of the neutrophil to the macrophage.

CD34 is a monomeric cell surface glycoprotein normally found on hematopoietic cells, endothelial progenitor cells, endothelial cells of blood vessels, and mast cells. The CD34 protein is a member of a family of single-pass transmembrane sialomucin proteins and functions as a cell-cell adhesion factor. Studies suggest that CD34 also may mediate the attachment of stem cells to bone marrow extracellular matrix or directly to stromal cells.

CD44 (the "hyaluronan receptor"), a cell-surface glycoprotein involved in cell-cell interactions, cell adhesion and migration, is used to identify specific types of mesenchymal cells.

CD45 (protein tyrosine phosphatase, receptor type, C; PTPRC) cell surface molecule is expressed specifically in hematopoietic cells. CD45 is a protein tyrosine phosphatase (PTP) with an extracellular domain, a single transmembrane segment, and two tandem intracytoplasmic catalytic domains, and thus belongs to receptor type PTP. Studies suggest it is an essential regulator of T-cell and B-cell antigen receptor signaling that functions by direct interaction with components of the antigen receptor complexes, or by activating various Src family kinases required for antigen receptor signaling. CD45 also suppresses JAK kinases, and thus functions as a regulator of cytokine receptor signaling. The CD45 family consists of multiple members that are all products of a single complex gene. Various known isoforms of CD45 include: CD45RA, CD45RB, CD45RC, CD45RAB, CD45RAC, CD45RBC, CD45RO, and CD45R (ABC). Different isoforms may be found on different cells. For example, CD45RA is found on naïve T cells and CD45RO is found on memory T cells.

CD56 (neural cell adhesion molecule, NCAM) is a homophilic binding glycoprotein expressed on the surface of neurons, glia, skeletal muscle and natural killer cells. It generally is believed that NCAM has a role in cell-cell adhesion, neurite outgrowth, and synaptic plasticity. There are three known main isoforms of NCAM, each varying only in their cytoplasmic domains: NCAM-120 kDA (glyco-sylphopharidylinositol (GPI) anchored); NCAM-140 kDa (short cytoplasmic domain); and NCAM (long cytoplasmic domain). The different domains of NCAM have different roles, with the Ig domains being involved in homophilic binding to NCAM, and the fibronectin type III (FNIII) domains being involved in signaling leading to neurite outgrowth.

CD59 refers to a glycosylphosphatidylinositol (GPI)-linked membrane glycoprotein which protects human cells from complement-mediated lysis.

The CD66 antigen family identifies a neutrophil-specific epitope within the hematopoietic system that is expressed by members of the carcinoembryonic antigen family of adhesion molecules, which belong within the immunoglobulin gene superfamily. The extracellular portions of all CD66 (a-f) molecules possess a N-terminal V-set IgSF domain which, lacks the canonical inter-b-sheet disulfide of the CD-2 family. CD66a is heavily glycosylated type 1 glyco-protein with more than 60% of the mass contributed by N-linked glycans, which bear sialylated Lex (sLe x, CD15s) structures. In CD66a they are spaced further apart, VxYxxLx211xYxxV, and resemble motifs which bind tyro-sine phosphatases such as SHIP-1 and -2. Activation of neutrophils leads to phosphorylation of tyrosine residues in the CD66a cytoplasmic domain. CD66a is expressed on granulocytes and epithelial cells. Products of 4 of the 7 functional carcinoembryonic antigen (CEA) family genes, CD66a-d, are known to be expressed on hematopoietic cells. The expression of these molecules on hematopoietic cells is generally restricted to the myeloid lineage. These molecules are present at low levels on resting mature granulocytes but expression increases rapidly following activation with inflammatory agonists, probably as a result of exocytosis from storage granules. CD66a is detected on some macro-phages in tissue sections and has been reported on T cells and a subpopulation of activated NK cells.

CD66b ((CGM1); CD67, CGM6, NCA-95) is a glyco-sylphosphatidylinositol (GPI)-linked protein that is a mem-ber of the immunoglobulin superfamily and carcinoembry-onic antigen (CEA)-like subfamily. CD66b, expressed on granulocytes, generally is believed to be involved in regu-lating adhesion and activation of human eosinophils.

CD90 or Thy-1 is a 25-37 kDa heavily N-glycosylated, glycophosphatidylinositol (GPI) anchored conserved cell surface protein with a single V-like immunoglobulin domain, originally discovered as a thymocyte antigen. It belongs to the immunoglobulin gene superfamily. The com-plex carbohydrate side chains vary in composition between tissues and species. Generally, CD90 is expressed on hema-topoietic stem cells and neurons. CD90 is highly expressed in connective tissue, on various fibroblast and stromal cell lines and is expressed on all thymocytes and peripheral T cells in mice. In humans, CD90 is expressed only on a small number of fetal thymocytes, 10%-40% of blood CD34+ cells in bone marrow, and <1% of CD3+CD4+ lymphocytes in peripheral circulation. CD90 also is expressed in the human lymph node HEV endothelium but not on other endothelia and lastly, is expressed on a limited number of lymphoblas-toid and leukemic cell lines.

CD105 (endoglin) is a homodimeric integral membrane glycoprotein composed of disulfide-linked subunits of 90-95 kDa. In humans, it is expressed at high levels on vascular endothelial cells and on syncytiotrophoblast of term pla-centa. During human heart development, it is expressed at high levels on endocardial cushion tissue mesenchyme dur-ing heart septation and valve formation; subsequently expression drops as the valves mature. It also is expressed by a population of pre-erythroblasts, leukemic cells of lym-phoid and myeloid lineages, and bone marrow stromal fibroblasts. Endoglin is an accessory protein of multiple kinase receptor complexes of the TGF-β superfamily. The TGF-β1 superfamily of structurally related peptides includes the TGF-β isoforms, β1, β2, β3, and β5, the activins and the bone morphogenetic proteins (BMPs). TGF-β-like factors are a multifunctional set of conserved growth and differentiation factors that control biological processes such as embryogenesis, organogenesis, morphogenesis of tissues like bone and cartilage, vasculogenesis, wound repair and angiogenesis, hematopoiesis, and immune regulation. Signaling by ligands of the TGF-β superfamily is mediated by a high affinity, ligand-induced, heteromeric complex consisting of related Ser/Thr kinase receptors divided into two subfamilies, type I and type II. The type II receptor transphosphorylates and activates the type I receptor in a Gly/Ser-rich region. The type I receptor in turn phosphory-lates and transduces signals to a novel family of recently identified downstream targets, termed Smads. Endoglin binds transforming growth factor (TGF) TGF-β1 and -β3 by associating with the TGF-β type II receptor, interacts with activin-A, interacts with bone morphogenic protein (BMP)-7 via activin type II receptors, ActRII and ActRIIB, and binds BMP-2 by interacting with the ligand binding type I receptors ALK3 and ALK6.

CD166 antigen (ALCAM), a 556 amino acid glycoprotein belonging to the immunoglobulin gene superfamily, is encoded by the activated leukocyte-cell adhesion molecule (ALCAM) gene in humans. It contains a secretory signal sequence, an extracellular domain which contains 3 Ig-like C2-type domains, 2 Ig-like V-type domains and 9 potential N-linked glycosylation sites, a hydrophobic transmembrane spanning domain and a 32 amino acid cytoplasmic domain with no known motifs. The N-terminal Ig domain is the binding site for both homophilic and CD166-CD6 interac-tions. CD166 is anchored to the actin cytoskeleton via the cytoplasmic domain but the receptors involved in this inter-action are unknown. The soluble CD166 is produced by proteolytic cleavage of extracellular domains or by alterna-tive splicing. It is expressed on mesenchymal stem cells and progenitor cells and on cortical thymic epithelial cells and medullary thymic epithelial cells, neurons, activated T cells, B cells, monocytes, fibroblasts, endothelium, epithelium, primitive subsets of hematopoietic cells including pluripo-tent stem cells, blastocysts and endometrium.

1.4. Growth Factors

Growth factors are extracellular polypeptide molecules that bind to a cell-surface receptor triggering an intracellular signaling pathway, leading to proliferation, differentiation, or other cellular response. These pathways stimulate the accumulation of proteins and other macromolecules, and they do so by both increasing their rate of synthesis and decreasing their rate of degradation. One intracellular signaling pathway activated by growth factor receptors involves the enzyme PI 3-kinase, which adds a phosphate from ATP to the 3 position of inositol phospholipids in the plasma membrane. The activation of PI 3-kinase leads to the activation of several protein kinases, including S6 kinase. The S6 kinase phosphorylates ribosomal protein S6, increasing the ability of ribosomes to translate a subset of mRNAs, most of which encode ribosomal components, as a result of which, protein synthesis increases. When the gene encoding S6 kinase is inactivated in *Drosophila*, cell numbers are normal, but cell size is abnormally small, and the mutant flies are small. Growth factors also activate a translation initiation factor called eIF4E, further increasing protein synthesis and cell growth.

Growth factor stimulation also leads to increased production of the gene regulatory protein Myc, which plays a part in signaling by mitogens. Myc increases the transcription of a number of genes that encode proteins involved in cell metabolism and macromolecular synthesis. In this way, it stimulates both cell metabolism and cell growth.

Some extracellular signal proteins, including platelet-derived growth factor (PDGF), can act as both growth factors and mitogens, stimulating both cell growth and cell-cycle progression. This functional overlap is achieved in part by overlaps in the intracellular signaling pathways that control these two processes. The signaling protein Ras, for example, is activated by both growth factors and mitogens. It can stimulate the PI3-kinase pathway to promote cell growth and the MAP-kinase pathway to trigger cell-cycle progression. Similarly, Myc stimulates both cell growth and cell-cycle progression. Extracellular factors that act as both growth factors and mitogens help ensure that cells maintain their appropriate size as they proliferate.

Since many mitogens, growth factors, and survival factors are positive regulators of cell-cycle progression, cell growth, and cell survival, they tend to increase the size of organs and organisms. In some tissues, however, cell and tissue size also is influenced by inhibitory extracellular signal proteins that oppose the positive regulators and thereby inhibit organ growth. The best-understood inhibitory signal proteins are TGF-β and its relatives. TGF-β inhibits the proliferation of several cell types, either by blocking cell-cycle progression in G1 or by stimulating apoptosis. TGF-β binds to cell-surface receptors and initiates an intracellular signaling pathway that leads to changes in the activities of gene regulatory proteins called Smads. This results in complex changes in the transcription of genes encoding regulators of cell division and cell death.

Bone morphogenetic protein (BMP), a TGF-β family member, helps trigger the apoptosis that removes the tissue between the developing digits in the mouse paw. Like TGF-β, BMP stimulates changes in the transcription of genes that regulate cell death.

Fibroblast Growth Factor (FGF)

The fibroblast growth factor (FGF) family currently has over a dozen structurally related members. FGF1 is also known as acidic FGF; FGF2 is sometimes called basic FGF (bFGF); and FGF7 sometimes goes by the name keratinocyte growth factor. Over a dozen distinct FGF genes are known in vertebrates; they can generate hundreds of protein isoforms by varying their RNA splicing or initiation codons in different tissues. FGFs can activate a set of receptor tyrosine kinases called the fibroblast growth factor receptors (FGFRs). Receptor tyrosine kinases are proteins that extend through the cell membrane. The portion of the protein that binds the paracrine factor is on the extracellular side, while a dormant tyrosine kinase (i.e., a protein that can phosphorylate another protein by splitting ATP) is on the intracellular side. When the FGF receptor binds an FGF (and only when it binds an FGF), the dormant kinase is activated, and phosphorylates certain proteins within the responding cell, activating those proteins.

FGFs are associated with several developmental functions, including angiogenesis (blood vessel formation), mesoderm formation, and axon extension. While FGFs often can substitute for one another, their expression patterns give them separate functions. FGF2 is especially important in angiogenesis, whereas FGF8 is involved in the development of the midbrain and limbs.

The expression levels of angiogenic factors, such as VEGF, IGF, PDGF, HGF, FGF, TGFm Angiopoeitin-1, and stem cell factor (SCF) have been found to differ amongst bone-derived-, cartilage-derived-, and adipose-derived MSCs. (Peng et al., 2008, Stems Cells and Development, 17:761-774).

Insulin-Like Growth Factor (IGF-1)

IGF-1, a hormone similar in molecular structure to insulin, has growth-promoting effects on almost every cell in the body, especially skeletal muscle, cartilage, bone, liver, kidney, nerves, skin, hematopoietic cell, and lungs. It plays an important role in childhood growth and continues to have anabolic effects in adults. IGF-1 is produced primarily by the liver as an endocrine hormone as well as in target tissues in a paracrine/autocrine fashion. Production is stimulated by growth hormone (GH) and can be retarded by undernutrition, growth hormone insensitivity, lack of growth hormone receptors, or failures of the downstream signaling molecules, including SHP2 and STAT5B. Its primary action is mediated by binding to its specific receptor, the Insulin-like growth factor 1 receptor (IGF1R), present on many cell types in many tissues. Binding to the IGF1R, a receptor tyrosine kinase, initiates intracellular signaling; IGF-1 is one of the most potent natural activators of the AKT signaling pathway, a stimulator of cell growth and proliferation, and a potent inhibitor of programmed cell death. IGF-1 is a primary mediator of the effects of growth hormone (GH). Growth hormone is made in the pituitary gland, released into the blood stream, and then stimulates the liver to produce IGF-1. IGF-1 then stimulates systemic body growth. In addition to its insulin-like effects, IGF-1 also can regulate cell growth and development, especially in nerve cells, as well as cellular DNA synthesis.

Transforming Growth Factor Beta (TGF-β)

There are over 30 structurally related members of the TGF-β superfamily, and they regulate some of the most important interactions in development. The proteins encoded by TGF-β superfamily genes are processed such that the carboxy-terminal region contains the mature peptide. These peptides are dimerized into homodimers (with themselves) or heterodimers (with other TGF-β peptides) and are secreted from the cell. The TGF-β superfamily includes the TGF-β family, the activin family, the bone morphogenetic proteins (BMPs), the Vg-1 family, and other proteins, including glial-derived neurotrophic factor (GDNF, necessary for kidney and enteric neuron differentiation) and Müllerian inhibitory factor, which is involved in mammalian sex determination. TGF-β family members TGF-β1, 2, 3, and 5 are important in regulating the formation of the extracellular matrix between cells and for regulating cell division (both positively and negatively). TGF-β1 increases the amount of extracellular matrix epithelial cells make both by stimulating collagen and fibronectin synthesis and by inhibiting matrix degradation. TGF-βs may be critical in controlling where and when epithelia can branch to form the ducts of kidneys, lungs, and salivary glands.

The members of the BMP family were originally discovered by their ability to induce bone formation. Bone formation, however, is only one of their many functions, and they have been found to regulate cell division, apoptosis (programmed cell death), cell migration, and differentiation. BMPs can be distinguished from other members of the TGF-β superfamily by their having seven, rather than nine, conserved cysteines in the mature polypeptide. The BMPs include proteins such as Nodal (responsible for left-right axis formation) and BMP4 (important in neural tube polarity, eye development, and cell death).

Neural Epidermal Growth-Factor-Like 1 (NELL1)

Neural epidermal growth-factor-like 1 (NEL-like 1, NELL1) is a gene that encodes an 810-amino acid polypeptide, which trimerizes to form a mature protein involved in the regulation of cell growth and differentiation. The neural epidermal growth-factor-like (nel) gene first was detected in neural tissue from an embryonic chicken cDNA library, and its human orthologue NELL1 was discovered later in B-cells. Studies have reported the presence of NELL in various fetal and adult organs, including, but not limited to, the brain, kidneys, colon, thymus, lung, and small intestine.

NELL1—General Structure

Generally, the arrangement of the functional domains of the 810 amino acid NELL1 protein bears resemblance to thrombospondin-1 ("THBS1") and consists of a thrombospondin N-terminal domain ("TSPN") and several von Willebrand factor, type C ("VWC"), and epidermal growth-factor ("EGF") domains.

Additional studies have shown that there are two transcript variants encoding different isoforms. The nel-like 1 isoform 1 precursor transcript variant represents the longer transcript and encodes the longer isoform 1.

The conserved domains of the nel-like 1 isoform 1 precursor transcript reside in seven regions of the isoform 1 peptide and include: (1) a TSPN domain/Laminin G superfamily domain; (2) a VWC domain; (3) an EGF-like domain; (4) an EGF-like domain; (5) an EGF-like domain; (6) an EGF-like domain and (7) a VWC domain.

The first conserved domain region comprises amino acids (amino acids 29 to 213) that are most similar to a thrombospondin N-terminal-like domain. Thrombospondins are a family of related, adhesive glycoproteins, which are synthesized, secreted and incorporated into the extracellular matrix of a variety of cells, including alpha granules of platelets following thrombin activation and endothelial cells. They interact with a number of blood coagulation factors and anticoagulant factors, and are involved in cell adhesion, platelet aggregation, cell proliferation, angiogenesis, tumor metastasis, vascular smooth muscle growth and tissue repair. The first conserved domain also comprises amino acids (amino acids 82 to 206; amino acids 98 to 209) that are similar to a Laminin G-like domain. Laminin G-like (LamG) domains usually are $Ca^{2+}$ mediated receptors that can have binding sites for steroids, β1-integrins, heparin, sulfatides, fibulin-1, and α-dystroglycans. Proteins that contain LamG domains serve a variety of purposes, including signal transduction via cell-surface steroid receptors, adhesion, migration and differentiation through mediation of cell adhesion molecules.

Much of what is known about NELL1 concerns its role in bone development. See, e.g., U.S. Pat. Nos. 7,884,066, 7,833,968, 7,807,787, 7,776,361, 7,691,607, 7,687,462, 7,544,486, and 7,052,856, the entire contents of which are incorporated herein by reference. It generally is believed that during osteogenic differentiation, NELL1 signaling may involve an integrin-related molecule and tyrosine kinases that are triggered by NELL1 binding to a NELL1 specific receptor and a subsequent formation of an extracellular complex. As thus far understood, in human NELL1 (hNELL1), the laminin G domain comprises about 128 amino acid residues that show a high degree of similarity to the laminin G domain of extracellular matrix ("ECM") proteins, such as human laminin α3 chain (hLAMA3), mouse laminin α3 chain (mLAMA3), human collagen 11 α3 chain (hCOLA1), and human thrombospondin-1 (hTSP1). This complex facilitates either activation of Tyr-kinases, inactivation of Tyr phosphatases, or intracellular recruitment of Tyr-phosphorylated proteins. The ligand bound integrin (cell surface receptors that interact with ECM proteins such as, for example, laminin 5, fibronectin, vitronectin, TSP1/2) transduces the signals through activation of the focal adhesion kinase (FAK) followed by indirect activation of the Ras-MAPK cascade, and then leads to osteogenic differentiation through Runx2; the laminin G domain is believed to play a role in the interaction between integrins and a 67 kDa laminin receptor.

The second conserved domain (amino acids 273 to 331) and seventh conserved domain (amino acids 701 to 749; amino acids 703 to 749) are similar to von Willebrand factor type C (VWC) domains, also known as chordin-like repeats. VWC domains occur in numerous proteins of diverse functions. It is thought that these domains may be involved in protein oligomerization.

The third conserved domain (amino acids 434 to 471; amino acids 434 to 466), fourth conserved domain (amino acids 478 to 512), fifth conserved domain (amino acids 549 to 586; amino acids 549 to 582), and sixth conserved domain (amino acids 596 to 627; amino acids 596 to 634) are similar to a calcium-binding EGF-like domain. Calcium-binding EGF-like domains are present in a large number of membrane-bound and extracellular (mostly animal) proteins. Many of these proteins require calcium for their biological function. Calcium-binding sites have been found to be located at the N-terminus of particular EGF-like domains, suggesting that calcium-binding may be crucial for numerous protein-protein interactions. Six conserved core cysteines form three disulfide bridges as in non-calcium-binding EGF domains whose structures are very similar.

The nel-like 1 isoform 2 precursor transcript variant lacks an alternate in-frame exon compared to variant 1. The resulting isoform 2, which has the same N- and C-termini as isoform 1 but is shorter compared to isoform 1, has six conserved regions including a TSPN domain/LamG superfamily domain (amino acids 29 to 313); VWC domains (amino acids 273 to 331; amino acids 654 to 702); and calcium-binding EGF-like domains (amino acids 478 to 512; amino acids 434 to 471; amino acids 549 to 580).

NELL1 and its orthologs are found across several species including *Homo sapiens* (man), *Mus musculus* (mouse), *Rattus norvegicus* (rat), Pan troglodytes (chimpanzee), *Xenopus* (Silurana) *tropicalis* (frog), *Canis lupus familiaris* (dog), *Culex quinquefasciatus* (mosquito) *Pediculus humanus* corporis (head louse), *Aedes aegypti* (mosquito), *Ixodes scapularis* (tick), Strongylocentrotus purpuratus (purple sea urchin), and *Acyrthosiphon pisum* (pea aphid).

NELL1 is Variable

NELL1 comprises several regions susceptible to increased recombination. Studies have indicated that susceptibilities to certain diseases may be associated with genetic variations within these regions, suggesting the existence of more than one causal variant in the NELL1 gene. For example, in patients suffering irritable bowel syndrome ("IBS"), six different single nucleotide polymorphisms (SNPs) within NELL1 have been identified, with most of these SNPs near the 5' end of the gene and fewer at the 3' end. These include R136S and A153T (which reside in the TSPN) and R354W (which resides in a VWC domain). Additional studies have identified at least 26 variants comprising some of at least 263 SNPs within the NELL1 region.

NELL1-Function

The NELL1 protein is a secreted cytoplasmic heterotrimeric protein. The complete role NELL1 plays in vivo remains unknown.

Several studies have indicated that NELL1 may play a role in bone formation, inflammatory bowel disease, and esophageal adenocarcinoma, among others.

NELL1 in Osteogenesis

It generally is believed that NELL1 induces osteogenic differentiation and bone formation of osteoblastic cells during development. Studies have shown that the NELL1 protein (1) transiently activates the mitogen-activated protein kinase ("MAPK") signaling cascade (which is involved in various cellular activities such as gene expression, mitosis, differentiation, proliferation and apotosis); and (2) induces phosphorylation of Runx2 (a transcription factor associated with osteoblast differentiation). Consequently, it generally is believed that upon binding to a specific receptor, NELL1 transduces an osteogenic signal through activation of certain Tyr-kinases associated with the Ras-MAPK cascade, which ultimately leads to osteogenic differentiation. Studies have shown that bone development is severely disturbed in transgenic mice where over-expression of NELL1 has been shown to lead to craniosynotosis (premature ossification of the skull and closure of the sutures) and NELL1 deficiency manifests in skeletal defects due to reduced chondrogenesis and osteogenesis.

Additional studies have supported a role for NELL-1 as a craniosynostosis-related gene. For example, three regions within the NELL-1 promoter have been identified that are directly bound and transactivated by Runx2. Further, studies in rat skullcaps have indicated that forced expression of Runx2 induces NELL-1 expression (which is suggestive that Nell-1 is a downstream target of Runx2).

2. Cells of the Connective Tissue Compartment

The connective tissue compartment contains cells that primarily function to elaborate and maintain ECM structure. The character of the extracellular matrix is region-specific and is determined by the amount of the extracellular materials.

Common cell types of connective tissue compartments include: fibroblasts, macrophages, mast cells, and plasma cells. Specialized connective tissue compartments, such as cartilage, bone, and the vasculature, and those with special properties, such as adipose, tendons, ligaments, etc., have specialized cells to perform specialized functions.

2.1. Adipose Tissue Compartment

Adipose tissue compartments are dynamic, multifunctional, ubiquitous and loose connective tissue compartments. Adipose comprises fibroblasts, smooth muscle cells, endothelial cells, leukocytes, macrophages, and closely packed mature lipid-filled fat cells, termed adipocytes, with characteristic nuclei pushed to one side, embedded within an areolar matrix that are located in subcutaneous layers of skin and muscle (panniculus adiposus), in the kidney region, cornea, breasts, mesenteries, mediastinium, and in the cervical, axillary and inguinal regions. Adipocytes play a primary role in energy storage and in providing insulation and protection. As sites of energy storage, adipocytes regulate the accumulation or mobilization of triacylglycerol in response to the body's energy requirements and store energy in the form of a single fat droplet of triglycerides, included among the more general class of lipids.

Adipocyte Matrix

Each adipocyte is surrounded by a thick ECM called the basal lamina. The strong adipocyte ECM scaffold lowers mechanical stress by spreading forces over a large surface area of the adipose tissue compartments. The ECM composition of adipocytes is similar to that of other cell types, but it is the relative quantity of individual components that impart cell specificity. Adipocyte ECM is particularly enriched in collagen VI, a coiled coil comprising $\alpha 1$ (VI), $\alpha 2$ (VI) and $\alpha 3$ (VI) subunits. Collagen VI binds to collagen IV and also to other matrix proteins such as proteoglycans and fibronectin. Table 5 lists core proteins that have been annotated to the adipocyte ECM with current proteomic techniques. (Mariman et al., 2010, *Cell. Mol. Life Sci.*, 67:1277-1292).

TABLE 5

| Core Proteins of Human Adipocyte ECM | |
|---|---|
| Protein | Symbol |
| Basement membrane-specific heparan sulfate proteoglycan core protein (HSPG) (perlecan) | HSPG2 |
| Calreticulin | CALR |
| Chitinase-3-like protein 1 | CHI311 |
| Coiled coil domain containing protein 80 | CCDC80 |
| Collagen a 1(I) chain | COL1A1 |
| Collagen a 2(I) chain | COL1A2 |
| Collagen a 1(III) chain | COL2A1 |
| Collagen a 2(IV) chain | COL4A2 |
| Collagen a 1(V) chain | COL5A1 |
| Collagen a 1(VI) chain | COL6A1 |
| Collagen a 2(VI) chain | COL6A2 |
| Collagen a 3(VI) chain | COL6A3 |
| Collagen a 1(XII) chain | COL12A1 |
| Collagen a 1(XIV) chain (undulin) | COL14A1 |
| Collagen a 1(XV) chain | COL15A1 |
| Collagen a 1(XVIII) chain | COL18A1 |
| Decorin (bone proteoglycan II) | DCN |
| Dermatopontin (tyrosine-rich acidic matrix protein; early quiescence protein 1) | DPT |
| Elastin microfibril interface-located protein 1 | EMILIN1 |
| Fibronectin (FN) (cold-insoluble globulin) | FN1 |
| Fibulin-1 | FBLN1 |
| Fibulin-3 (EGF-containing fibulin-like extracellular matrix protein 1) | FBLN3 |
| Fibulin-5 (developmental arteries and neural crest EGF-like protein | FBLN5 |
| Galectin-1 | LGALS1 |
| Galectin-3-binding protein (lectin galactoside-binding soluble 3-binding protein) | LGALS3BP |
| Glypican 1 | GPC1 |
| Laminin α-4 chain | LAMA4 |
| Laminin β-1 chain | LAMB1 |
| Laminin β-2 chain | LAMB2 |
| Laminin γ-1 chain | LAMC1 |
| Lumican (keratan sulfate proteoglycan lumican) | LUM |
| Matrilin-2 | MATN2 |
| Microfibril-associated glycoprotein 4 | MFAP4 |
| Mimecan (osteoglycin) | OGN |
| Nidogen 1 (entactin) | NID1 |
| Nidogen 2 (osteonidogen) | NID2 |
| Periostin | POSTN |
| Proteoglycan 4 | PRG4 |
| SPARC (osteonectin) | SPARC |
| Spondin-1 (F-spondin) (vascular smooth muscle | SPON1 |

TABLE 5-continued

| Core Proteins of Human Adipocyte ECM | |
|---|---|
| Protein | Symbol |
| cell growth-promoting factor) | |
| Spondin-2 (mindin) | SPON2 |
| Tenascin-C (TN) (hexabrachion) (cytotactin) (neuronectin) (GMEM) | TNC |
| Tenascin-X | TNXB |
| Thrombospondin-1 | THBS1 |
| Thrombospondin-2 | THBS2 |
| Transforming growth factor-b-induced protein IG-H3 (bIG-H3) | TGFB1 |
| Versican core protein (large fibroblast proteoglycan) | CSPG2 |
| Versican V3 isoform | VCAN |

Adipocyte ECM undergoes biphasic development during adipogenesis, the process of formation of mature adipose tissue compartments. There is an initial decrease in collagen I and III, whereas their levels come back to pre-differentiation state at later stages. Mature adipocyte ECM is maintained in a dynamic state with constant turnover of ECM components by a balance of activities of ECM constructive enzymes and ECM degradation enzymes. In early stages of differentiation, the balance is shifted towards the constructive factors. (Mariman et al., 2010, *Cell. Mol. Life Sci.,* 67:1277-1292). Maturation of newly synthesized ECM components is initiated in the ER lumen where ECM proteins undergo biochemical modifications and proteolytic processing prior to assembly. For collagen, such modifications include proline- and lysine-hydroxylation and glycosylation and clipping of N- and C-terminal peptides by respective procollagen-N- and -C-collagenase. Processed proteins are then assembled and secreted into the extracellular environment where they undergo further processing by secreted extracellular modification and processing enzymes. As the preadipocytes differentiate and begin to store fatty substances, including lipids, ECM assumes a basal laminar structure.

Adipose-Derived Stem Cells

Adipose also comprises a population of pluripotent stem cells that have the potential to give rise to cells of all three embryonic lineages: ectodermal, mesodermal and endodermal. Adipogenesis, which comprises the steps of differentiation of such pluripotent cells to mature adipocytes, is initiated by differentiation of these pluripotent cells to give rise to a population of mesenchymal precursor cells or mesenchymal stem cells (MSCs), which have the potential to differentiate into a variety of mesodermal cell lineages such as for example, myoblasts, chondroblasts, osteoblasts and adipocytes. In the presence of appropriate environmental and gene expression signals, the MSCs go through growth arrest and differentiate into precursors with a determined fate that undergo clonal expansion, become committed and terminally differentiate to give rise to mature cells. The population of MSCs and more committed adipose progenitors that are found along with the stroma of adipose tissue collectively are termed adipose-derived stem cells (ASCs). These cells have a characteristic CD45-CD31-CD34$^+$CD105$^+$ surface phenotype. In the case of adipocyte differentiation, ASCs differentiate to proadipocytes that undergo final differentiation to give rise to mature adipocytes. Mesenchymal progenitor cells with chondrogenic potential have also been identified in the infrapatellar fat pad in joints. (Lee et al., Tissue Engg. 2010, 16 (1): 317-325).

Table 6 lists cell lineages and respective inductive factors that can be derived from ASC lines. (Brown et. al., 2010, Plast. Reconstr. Surg., 126 (6): 1936-1946; Gregoire et al., 1998, Physiol. Rev. 78 (3): 783-809).

TABLE 6

| Inductive Factors and Cell Lineages from Adipose-derived Stem Cells | |
|---|---|
| Cell Lineage | Inductive Factors |
| Adipocyte | Dexamethasone; isobutyl methylxanthine,; indoxanthine; insulin; thiazolidinedione; nuclear hormone glucocorticoids, e.g., 3,3',5-triiodothyronine (T$_3$) and retinoic acid (RA); IGF-1; PGE2 |
| Cardiomyocyte | Transferrin; IL-3; IL-6; VEGF |
| Chondrocyte | Ascorbic acid; bone morphogenetic protein 6; dexamethasone; insulin; transforming growth factor-β (TGF-3) |
| Endothelial | EGM-2-MV medium (Cambrex, Walkersville, MD) containing ascorbate, epidermal growth factor, basic fibroblast growth factor, and hydrocortisone |
| Myocyte | Dexamethasone horse serum |
| Neuronal-like | Butylated hydroxianisole; valproic acid; insulin |
| Osteoblast | Ascorbic acid; bone morphogenetic protein-2; dexamethasone; 1,25-dihydroxyvitamin D |

Adipose Secreted Factors

Adipose is considered a secretory organ. The adipose secretome not only includes structural and soluble factors contributing to the formation of the adipose matrix, but also a horde of soluble factors with endocrine function, such as growth factors, hormones, chemokines and lipids, collectively termed adipokines. Exemplary adipokines include, without limitation, leptin, adiponectin, resistin, interleukin 6 (IL-6), monocyte chemoattractant protein 1 (MCP-1), tumor necrosis factor alpha (TNF-α); fibroblast growth factor (FGF), and vascular endothelial growth factor (VEGF). Exemplary immunogical adipokines, particularly involved in inflammatory pathways include, without limitation, serum amyloid A3 (SAA3), IL-6, adiponectin, TNF-α and haptoglobin. Exemplary adipokines involved in the production of new blood vessels include, without limitation, angiopoietin-1, angiopoietin-2, VEGF, transforming growth factor beta (TGF-β), hepatic growth factor (HGF), stromal derived growth factor 1 (SDF-1), TNF-α, resistin, leptin, tissue factor, placental growth factor (PGF), insulin like growth factor (IGF), and monobutyrin.

Adiponectin, a key metabolic factor secreted from adipocytes, is a 30-KDa protein that may exist as a trimer, low molecular weight hexamers or high molecular weight 18mers. Adiponectin circulates throughout the plasma and has a variety of metabolic effects including, but not limited to, glucose lowering and cardioprotection stimulation of smooth muscle proliferation. Adiponectin has been implicated in a number of pathological conditions including, but not limited to diabetes, obesity, metabolic syndrome, cardiovascular disease and wound healing.

Resistin, a member of the resistin-like (RELM) hormone family, is secreted by stromal vascular cells of adipose. Resistin is secreted in two multimeric isoforms and functions to counterbalance the insulin sensitizing effects of adiponectin. (Truillo, M. E. and Scherer P. E., Endocrine Rev. 2006, 27 (7): 762-778).

Secretions from resident adipocytes, macrophages and ASCs collectively contribute to the adipose secretome. Table 7 provides a reported adipokine profile of ASCs. (Kilroy et. al., 2007, J. Cell. Physiol. 212:702-709.)

TABLE 7

| Reported Adipokine Profile of Human ASCs | |
| --- | --- |
| Function | Adipokine |
| Angiogenic | HGF |
| | VEGF |
| Hematopoietic | Flt-3 ligand |
| | G-CSF |
| | GM-CSF |
| | IL-7 |
| | IL-12 |
| | M-CSF |
| | SCF |
| Proinflammatory | IL-1alpha |
| | IL-6 |
| | IL-8 |
| | IL-11 |
| | LIF |
| | TNF-alpha |

Transcription Factors Responsible for Adipogenesis

Adipocyte differentiation involves the crosstalk between external signals in the ECM environment with internal signals generated from the nucleus. The peroxisome prolif-erator-activated receptors (PPAR) and CCAAT-enhancer-binding proteins (C/EBP) family of transcription factors play an important role in adipogenesis. The PPARs, members of type II nuclear hormone receptor family, form heterodimers with the retinoid X receptor (RXR). They regulate transcription by binding of PPAR-RXR heteridi-mers to a response element characterized by a direct repeat of the nuclear receptor hexameric DNA recognition motif, PuGG-TCA. PPAR-γ is most adipose-specific of all PPARs and is activated prior to transcriptional up-regulation of most other adipocyte genes. The C/EBP family of transcription factors are also induced prior to activation of other adipocyte genes and plays a major role in adipocyte differentiation. Members of the basic helix-loop-helix (bHLH) family of transcription factors have also been implicated in adipogen-esis. (Gregoire et al., 1998, Physiol. Rev. 78 (3): 783-809).

2.2. Bone (Osseous) Tissue Compartment

Osseous tissue is a rigid form of connective tissue nor-mally organized into definite structures, the bones. These form the skeleton, serve for the attachment and protection of the soft parts, and, by their attachment to the muscles, act as levers that bring about body motion. Bone is also a storage place for calcium that can be withdrawn when needed to maintain a normal level of calcium in the blood.

Bones can be classified according to their shape. Examples of bone types include: long bones whose length is greater than their widths (e.g., femur (thigh bone), humerus (long bone of the upper limb), tibia (shin bone), fibula (calf bone), radius (the outer of the two bones of the forearm), and ulna (inner of two bones of the forearm)), short bones whose length and width is approximately equal (e.g., carpals bones (wrist bones in the hand)), flat bones (e.g., cranium (skull bones surrounding the brain), scapula (shoulder blade), and ilia (the uppermost and largest bone of the pelvis)), irregular bones (e.g., vertebra), and sesamoid bones, small bones present in the joints to protect tendons (fibrous connective tissues that connect muscles to the bones, e.g., patella bones (knee cap)).

Grossly, two types of bone may be distinguished: cancel-lous, trabecular or spongy bone, and cortical, compact, or dense bone.

Cortical bone, also referred to as compact bone or dense bone, is the tissue of the hard outer layer of bones, so-called due to its minimal gaps and spaces. This tissue gives bones their smooth, white, and solid appearance. Cortical bone consists of haversian sites (the canals through which blood vessels and connective tissue pass in bone) and osteons (the basic units of structure of cortical bone comprising a hav-ersian canal and its concentrically arranged lamellae), so that in cortical bone, bone surrounds the blood supply. Cortical bone has a porosity of about 5% to about 30%, and accounts for about 80% of the total bone mass of an adult skeleton.

Cancellous Bone (Trabecular or Spongy Bone)

Cancellous bone tissue, an open, cell-porous network also called trabecular or spongy bone, fills the interior of bone and is composed of a network of rod- and plate-like elements that make the overall structure lighter and allows room for blood vessels and marrow so that the blood supply surrounds bone. Cancellous bone accounts for the remaining 20% of total bone mass but has nearly ten times the surface area of cortical bone. It does not contain haversian sites and osteons and has a porosity of about 30% to about 90%.

The head of a bone, termed the epiphysis, has a spongy appearance and consists of slender irregular bone trabeculae, or bars, which anastomose to form a lattice work, the interstices of which contain the marrow, while the thin outer shell appears dense. The irregular marrow spaces of the epiphysis become continuous with the central medullary cavity of the bone shaft, termed the diaphysis, whose wall is formed by a thin plate of cortical bone.

Both cancellous and cortical bone have the same types of cells and intercellular substance, but they differ from each other in the arrangement of their components and in the ratio of marrow space to bone substance. In cancellous bone, the marrow spaces are relatively large and irregularly arranged, and the bone substance is in the form of slender anastomo-sing trabeculae and pointed spicules. In cortical bone, the spaces or channels are narrow and the bone substance is densely packed.

With very few exceptions, the cortical and cancellous forms are both present in every bone, but the amount and distribution of each type vary considerably. The diaphyses of the long bones consist mainly of cortical tissue; only the innermost layer immediately surrounding the medullary cavity is cancellous bone. The tabular bones of the head are composed of two plates of cortical bone enclosing marrow space bridged by irregular bars of cancellous bone. The epiphyses of the long bones and most of the short bones consist of cancellous bone covered by a thin outer shell of cortical bone.

Each bone, except at its articular end, is surrounded by a vascular fibroelastic coat, the periosteum. The so-called endosteum, or inner periosteum of the marrow cavity and marrow spaces, is not a well-demarcated layer; it consists of a variable concentration of medullary reticular connective tissue that contains osteogenic cells that are in immediate contact with the bone tissue.

Components of Bone

Bone is composed of cells and an intercellular matrix of organic and inorganic substances.

The organic fraction consists of collagen, glycosamino-glycans, proteoglycans, and glycoproteins. The protein matrix of bone largely is composed of collagen, a family of fibrous proteins that have the ability to form insoluble and rigid fibers. The main collagen in bone is type I collagen.

The inorganic component of bone, which is responsible for its rigidity and may constitute up to two-thirds of its fat-free dry weight, is composed chiefly of calcium phos-phate and calcium carbonate, in the form of calcium hydroxyapatite, with small amounts of magnesium hydrox-ide, fluoride, and sulfate. The composition varies with age and with a number of dietary factors. The bone minerals form long fine crystals that add strength and rigidity to the collagen fibers; the process by which it is laid down is termed mineralization.

Bone Cells

Four cell types in bone are involved in its formation and maintenance. These are 1) osteoprogenitor cells, 2) osteoblasts, 3) osteocytes, and 4) osteoclasts.

Osteoprogenitor Cells

Osteoprogenitor cells arise from mesenchymal cells, and occur in the inner portion of the periosteum and in the endosteum of mature bone. They are found in regions of the embryonic mesenchymal compartment where bone formation is beginning and in areas near the surfaces of growing bones. Structurally, osteoprogenitor cells differ from the mesenchymal cells from which they have arisen. They are irregularly shaped and elongated cells having pale-staining cytoplasm and pale-staining nuclei. Osteoprogenitor cells, which multiply by mitosis, are identified chiefly by their location and by their association with osteoblasts. Some osteoprogenitor cells differentiate into osteocytes. While osteoblasts and osteocytes are no longer mitotic, it has been shown that a population of osteoprogenitor cells persists throughout life.

Osteoblasts

Osteoblasts, which are located on the surface of osteoid seams (the narrow region on the surface of a bone of newly formed organic matrix not yet mineralized), are derived from osteoprogenitor cells. They are immature, mononucleate, bone-forming cells that synthesize collagen and control mineralization. Osteoblasts can be distinguished from osteoprogenitor cells morphologically; generally they are larger than osteoprogenitor cells, and have a more rounded nucleus, a more prominent nucleolus, and cytoplasm that is much more basophilic. Osteoblasts make a protein mixture known as osteoid, primarily composed of type I collagen, which mineralizes to become bone. Osteoblasts also manufacture hormones, such as prostaglandins, alkaline phosphatase, an enzyme that has a role in the mineralization of bone, and matrix proteins.

Osteocytes

Osteocytes, star-shaped mature bone cells derived from osteoblasts and the most abundant cell found in compact bone, maintain the structure of bone. Osteocytes, like osteoblasts, are not capable of mitotic division. They are actively involved in the routine turnover of bony matrix and reside in small spaces, cavities, gaps or depressions in the bone matrix called lacuna. Osteocytes maintain the bone matrix, regulate calcium homeostasis, and are thought to be part of the cellular feedback mechanism that directs bone to form in places where it is most needed. Bone adapts to applied forces by growing stronger in order to withstand them; osteocytes may detect mechanical deformation and mediate bone-formation by osteoblasts.

Osteoclasts

Osteoclasts, which are derived from a monocyte stem cell lineage and possess phagocytic-like mechanisms similar to macrophages, often are found in depressions in the bone referred to as Howship's lacunae. They are large multinucleated cells specialized in bone resorption. During resorption, osteoclasts seal off an area of bone surface; then, when activated, they pump out hydrogen ions to produce a very acid environment, which dissolves the hydroxyapatite component. The number and activity of osteoclasts increase when calcium resorption is stimulated by injection of parathyroid hormone (PTH), while osteoclastic activity is suppressed by injection of calcitonin, a hormone produced by thyroid parafollicular cells.

Bone Matrix

The bone matrix accounts for about 90% of the total weight of compact bone and is composed of microcrystalline calcium phosphate resembling hydroxyapatite (60%) and fibrillar type I collagen (27%). The remaining 3% consists of minor collagen types and other proteins including osteocalcin, osteonectin, osteopontin, bone sialoprotein, as well as proteoglycans, glycosaminoglycans, and lipids.

Bone matrix is also a major source of biological information that skeletal cells can receive and act upon. For example, extracellular matrix glycoproteins and proteoglycans in bone bind a variety of growth factors and cytokines, and serve as a repository of stored signals that act on osteoblasts and osteoclasts. Examples of growth factors and cytokines found in bone matrix include, but are not limited to, Bone Morphogenic Proteins (BMPs), Epidermal Growth Factors (EGFs), Fibroblast Growth Factors (FGFs), Platelet-Derived Growth Factors (PDGFs), Insulin-like Growth Factor-1 (IGF-1), Transforming Growth Factors (TGFs), Bone-Derived Growth Factors (BDGFs), Cartilage-Derived Growth Factor (CDGF), Skeletal Growth Factor (hSGF), Interleukin-1 (IL-1), and macrophage-derived factors.

There is an emerging understanding that extracellular matrix molecules themselves can serve regulatory roles, providing both direct biological effects on cells as well as key spatial and contextual information.

The Periosteum and Endosteum

The periosteum is a fibrous connective tissue investment of bone, except at the bone's articular surface. Its adherence to the bone varies by location and age. In young bone, the periosteum is stripped off easily. In adult bone, it is more firmly adherent, especially so at the insertion of tendons and ligaments, where more periosteal fibers penetrate into the bone as the perforating fibers of Sharpey (bundles of collagenous fibers that pass into the outer circumferential lamellae of bone). The periosteum consists of two layers, the outer of which is composed of coarse, fibrous connective tissue containing few cells but numerous blood vessels and nerves. The inner layer, which is less vascular but more cellular, contains many elastic fibers. During growth, an osteogenic layer of primitive connective tissue forms the inner layer of the periosteum. In the adult, this is represented only by a row of scattered, flattened cells closely applied to the bone. The periosteum serves as a supporting bed for the blood vessels and nerves going to the bone and for the anchorage of tendons and ligaments. The osteogenic layer, which is considered a part of the periosteum, is known to furnish osteoblasts for growth and repair, and acts as an important limiting layer controlling and restricting the extend of bone formation. Because both the periosteum and its contained bone are regions of the connective tissue compartment, they are not separated from each other or from other connective tissues by basal laminar material or basement membranes. Perosteal stem cells have been shown to be important in bone regeneration and repair. (Zhang et al., 2005, J. Musculoskelet. Neuronal. Interact. 5 (4): 360-362).

The endosteum lines the surface of cavities within a bone (marrow cavity and central canals) and also the surface of trabeculae in the marrow cavity. In growing bone, it consists of a delicate striatum of myelogenous reticular connective tissue, beneath which is a layer of osteoblasts. In the adult, the osteogenic cells become flattened and are indistinguishable as a separate layer. They are capable of transforming into osteogenic cells when there is a stimulus to bone formation, as after a fracture.

Marrow

The marrow is a soft connective tissue that occupies the medullary cavity of the long bones, the larger central canals, and all of the spaces between the trabeculae of spongy bone. It consists of a delicate reticular connective tissue, in the meshes of which lie various kinds of cells. Two varieties of marrow are recognized: red and yellow. Red marrow is the only type found in fetal and young bones, but in the adult it is restricted to the vertebrae, sternum, ribs, cranial bones, and epiphyses of long bones. It is the chief site for the genesis of blood cells in the adult body. Yellow marrow consists primarily of fat cells that gradually have replaced the other marrow elements. Under certain conditions, the yellow marrow of old or emaciated persons loses most of its fat and assumes a reddish color and gelatinous consistency, known as gelatinous marrow. With adequate stimulus, yellow marrow may resume the character of red marrow and play an active part in the process of blood development.

Osteogenesis or Ossification

Osteogenesis or ossification is a process by which the bones are formed. There are three distinct lineages that generate the skeleton. The somites generate the axial skeleton, the lateral plate mesoderm generates the limb skeleton, and the cranial neural crest gives rise to the branchial arch, craniofacial bones, and cartilage. There are two major modes of bone formation, or osteogenesis, and both involve the transformation of a preexisting mesenchymal tissue into bone tissue. The direct conversion of mesenchymal tissue into bone is called intramembranous ossification. This process occurs primarily in the bones of the skull. In other cases, mesenchymal cells differentiate into cartilage, which is later replaced by bone. The process by which a cartilage intermediate is formed and replaced by bone cells is called endochondral ossification.

Intramembranous Ossification

Intramembraneous ossification is the characteristic way in which the flat bones of the scapula, the skull and the turtle shell are formed. In intramembraneous ossification, bones develop sheets of fibrous connective tissue. During intramembranous ossification in the skull, neural crest-derived mesenchymal cells proliferate and condense into compact nodules. Some of these cells develop into capillaries; others change their shape to become osteoblasts, committed bone precursor cells. The osteoblasts secrete a collagen-proteoglycan matrix that is able to bind calcium salts. Through this binding, the prebone (osteoid) matrix becomes calcified. In most cases, osteoblasts are separated from the region of calcification by a layer of the osteoid matrix they secrete. Occasionally, osteoblasts become trapped in the calcified matrix and become osteocytes. As calcification proceeds, bony spicules radiate out from the region where ossification began, the entire region of calcified spicules becomes surrounded by compact mesenchymal cells that form the periosteum, and the cells on the inner surface of the periosteum also become osteoblasts and deposit osteoid matrix parallel to that of the existing spicules. In this manner, many layers of bone are formed.

Intramembraneous ossification is characterized by invasion of capillaries into the mesenchymal zone, and the emergence and differentiation of mesenchymal cells into mature osteoblasts, which constitutively deposit bone matrix leading to the formation of bone spicules, which grow and develop, eventually fusing with other spicules to form trabeculae. As the trabeculae increase in size and number they become interconnected forming woven bone (a disorganized weak structure with a high proportion of osteocytes), which eventually is replaced by more organized, stronger, lamellar bone.

The molecular mechanism of intramembranous ossification involves bone morphogenetic proteins (BMPs) and the activation of a transcription factor called CBFA1. Bone morphogenetic proteins, for example, BMP2, BMP4, and BMP7, from the head epidermis are thought to instruct the neural crest-derived mesenchymal cells to become bone cells directly. BMPs activate the Cbfa1 gene in mesenchymal cells. The CBFA1 transcription factor is known to transform mesenchymal cells into osteoblasts. Studies have shown that the mRNA for mouse CBFA1 is largely restricted to the mesenchymal condensations that form bone, and is limited to the osteoblast lineage. CBFA1 is known to activate the genes for osteocalcin, osteopontin, and other bone-specific extracellular matrix proteins.

Endochondral Ossification (Intracartilaginous Ossification)

Endochondral ossification, which involves the in vivo formation of cartilage tissue from aggregated mesenchymal cells, and the subsequent replacement of cartilage tissue by bone, can be divided into five stages. The skeletal components of the vertebral column, the pelvis, and the limbs are first formed of cartilage and later become bone.

First, the mesenchymal cells are committed to become cartilage cells. This commitment is caused by paracrine factors that induce the nearby mesodermal cells to express two transcription factors, Pax1 and Scleraxis. These transcription factors are known to activate cartilage-specific genes. For example, Scleraxis is expressed in the mesenchyme from the sclerotome, in the facial mesenchyme that forms cartilaginous precursors to bone, and in the limb mesenchyme.

During the second phase of endochondral ossification, the committed mesenchyme cells condense into compact nodules and differentiate into chondrocytes (cartilage cells that produce and maintain the cartilaginous matrix, which consists mainly of collagen and proteoglycans). Studies have shown that N-cadherin is important in the initiation of these condensations, and N-CAM is important for maintaining them. In humans, the SOX9 gene, which encodes a DNA-binding protein, is expressed in the precartilaginous condensations.

During the third phase of endochondral ossification, the chondrocytes proliferate rapidly to form the model for bone. As they divide, the chondrocytes secrete a cartilage-specific extracellular matrix.

In the fourth phase, the chondrocytes stop dividing and increase their volume dramatically, becoming hypertrophic chondrocytes. These large chondrocytes alter the matrix they produce (by adding collagen X and more fibronectin) to enable it to become mineralized by calcium carbonate.

The fifth phase involves the invasion of the cartilage model by blood vessels. The hypertrophic chondrocytes die by apoptosis, and this space becomes bone marrow. As the cartilage cells die, a group of cells that have surrounded the cartilage model differentiate into osteoblasts, which begin forming bone matrix on the partially degraded cartilage. Eventually, all the cartilage is replaced by bone. Thus, the cartilage tissue serves as a model for the bone that follows.

The replacement of chondrocytes by bone cells is dependent on the mineralization of the extracellular matrix. A number of events lead to the hypertrophy and mineralization of the chondrocytes, including an initial switch from aerobic to anaerobic respiration, which alters their cell metabolism and mitochondrial energy potential. Hypertrophic chondrocytes secrete numerous small membrane-bound vesicles into the extracellular matrix. These vesicles contain enzymes that are active in the generation of calcium and phosphate ions and initiate the mineralization process within the cartilaginous matrix. The hypertrophic chondrocytes, their metabolism and mitochondrial membranes altered, then die by apoptosis.

In the long bones of many mammals (including humans), endochondral ossification spreads outward in both directions from the center of the bone. As the ossification front nears the ends of the cartilage model, the chondrocytes near the ossification front proliferate prior to undergoing hypertrophy, pushing out the cartilaginous ends of the bone. The cartilaginous areas at the ends of the long bones are called epiphyseal growth plates. These plates contain three regions: a region of chondrocyte proliferation, a region of mature chondrocytes, and a region of hypertrophic chondrocytes. As the inner cartilage hypertrophies and the ossification front extends farther outward, the remaining cartilage in the epiphyseal growth plate proliferates. As long as the epiphyseal growth plates are able to produce chondrocytes, the bone continues to grow.

Bone Remodeling

Bone constantly is broken down by osteoclasts and re-formed by osteoblasts in the adult. It has been reported that as much as 18% of bone is recycled each year through the process of renewal, known as bone remodeling, which maintains bone's rigidity. The balance in this dynamic process shifts as people grow older: in youth, it favors the formation of bone, but in old age, it favors resorption.

As new bone material is added peripherally from the internal surface of the periosteum, there is a hollowing out of the internal region to form the bone marrow cavity. This destruction of bone tissue is due to osteoclasts that enter the bone through the blood vessels. Osteoclasts dissolve both the inorganic and the protein portions of the bone matrix. Each osteoclast extends numerous cellular processes into the matrix and pumps out hydrogen ions onto the surrounding material, thereby acidifying and solubilizing it. The blood vessels also import the blood-forming cells that will reside in the marrow for the duration of the organism's life.

The number and activity of osteoclasts must be tightly regulated. If there are too many active osteoclasts, too much bone will be dissolved, and osteoporosis will result. Conversely, if not enough osteoclasts are produced, the bones are not hollowed out for the marrow, and osteopetrosis (known as stone bone disease, a disorder whereby the bones harden and become denser) will result.

Bone Regeneration and Fracture Repair

A fracture, like any traumatic injury, causes hemorrhage and tissue destruction. The first reparative changes thus are characteristic of those occurring in any injury of soft tissue. Proliferating fibroblasts and capillary sprouts grow into the blood clot and injured area, thus forming granulation tissue. The area also is invaded by polymorphonuclear leukocytes and later by macrophages that phagocytize the tissue debris. The granulation tissue gradually becomes denser, and in parts of it, cartilage is formed. This newly formed connective tissue and cartilage is designated as a callus. It serves temporarily in stabilizing and binding together the fractured bone. As this process is taking place, the dormant osteogenic cells of the periosteum enlarge and become active osteoblasts. On the outside of the fractured bone, at first at some distance from the fracture, osseous tissue is deposited. This formation of new bone continues toward the fractured ends of the bone and finally forms a sheath-like layer of bone over the fibrocartilaginous callus. As the amount of bone increases, osteogenic buds invade the fibrous and cartilaginous callus and replace it with a bony one. The cartilage undergoes calcification and absorption in the replacement of the fibrocartilaginous callus and intramembraneous bone formation also takes place. The newly formed bone is at first a spongy and not a compact type, and the callus becomes reduced in diameter. At the time when this subperiosteal bone formation is taking place, bone also forms in the marrow cavity. The medullary bone growing centripetally from each side of the fracture unites, thus aiding the bony union.

The process of repair is, in general, an orderly process, but it varies greatly with the displacement of the fractured ends of the bone and the degree of trauma inflicted. Uneven or protruding surfaces gradually are removed, and the healed bone, especially, in young individuals, assumes its original contour.

Osteogenesis and Angiogenesis

Skeletal development and fracture repair includes the coordination of multiple events such as migration, differentiation, and activation of multiple cell types and tissues. The development of a microvasculature and microcirculation is important for the homeostasis and regeneration of living bone, without which the tissue would degenerate and die. Recent developments using in vitro and in vivo models of osteogenesis and fracture repair have provided a better understanding of the recruitment nature of the vasculature in skeletal development and repair.

The vasculature transports oxygen, nutrients, soluble factors and numerous cell types to all tissues in the body. The growth and development of a mature vascular structure is one of the earliest events in organogenesis. In mammalian embryonic development, the nascent vascular networks develop by aggregation of de novo forming angioblasts into a primitive vascular plexus (vasculogenesis). This undergoes a complex remodeling process in which sprouting, bridging and growth from existing vessels (angiogenesis) leads to the onset of a functional circulatory system.

The factors and events that lead to the normal development of the embryonic vasculature are recapitulated during situations of neoangiogenesis in the adult. There are a number of factors involved in neoangiogenesis; these include, but are not limited to, Vascular Endothelial Growth Factor (VEGF), basic Fibroblast Growth Factor (bFGF), various members of the Transforming Growth factor beta (TGFβ) family and Hypoxia-Inducible Transcription Factor (HIF). Other factors that have angiogenic properties include the Angiopoietins, (Ang-1); Hepatocyte Growth Factor (HGF); Platelet-Derived Growth Factor (PDGF); Insulin-like Growth Factor family (IGF-1, IGF-2) and the Neurotrophins (NGF).

The VEGFs and their corresponding receptors are key regulators in a cascade of molecular and cellular events that ultimately lead to the development of the vascular system, either by vasculogenesis, angiogenesis, or in the formation of the lymphatic vascular system. Although VEGF is a critical regulator in physiological angiogenesis, it also plays a significant role in skeletal growth and repair.

In the mature established vasculature, the endothelium plays an important role in the maintenance of homeostasis of the surrounding tissue by providing the communicative network to neighboring tissues to respond to requirements as needed. Furthermore, the vasculature provides growth factors, hormones, cytokines, chemokines and metabolites, and the like, needed by the surrounding tissue and acts as a barrier to limit the movement of molecules and cells. Signals and attractant factors expressed on the bone endothelium help recruit circulating cells, particularly hematopoietic cells, to the bone marrow and coordinate with metastatic cells to target them to skeletal regions. Thus, any alteration in the vascular supply to bone tissue can lead to skeletal pathologies, such as osteonecrosis (bone death caused by reduced blood flow to bones), osteomyelitis (infection of the bone or bone marrow by microorganism), and osteoporosis (loss of bone density). A number of factors have been found to have a prominent effect on the pathology of the vasculature and skeleton, including Osteoprotegerin (OPG), which inhibits Receptor Activator of NF-κB Ligand (RANKL)-induced osteoclastogenic bone resorption.

Both intramembraneous and endochondral bone ossification occur in close proximity to vascular ingrowth. In endochondral ossification, the coupling of chondrogenesis and osteogenesis to determine the rate of bone ossification is dependent on the level of vascularization of the growth plate. For example, vascular endothelial growth (VEGF) factor isoforms are essential in coordinating metaphyseal and epiphyseal vascularization, cartilage formation, and ossification during endochondral bone development. HIF-1 stimulates transcription of the VEGF gene (and of other genes whose products are needed when oxygen is in short supply). The VEGF protein is secreted, diffuses through the tissue, and acts on nearby endothelial cells.

The response of the endothelial cells includes at least four components. First, the cells produce proteases to digest their way through the basal lamina of the parent capillary or venule. Second, the endothelial cells migrate toward the source of the signal. Third, the cells proliferate. Fourth, the cells form tubes and differentiate. VEGF acts on endothelial cells selectively to stimulate this entire set of effects. Other growth factors, including some members of the fibroblast growth factor family, also can stimulate angiogenesis, but they influence other cell types besides endothelial cells. As the new vessels form, bringing blood to the tissue, the oxygen concentration rises, HIF-1 activity declines, VEGF production is shut off, and angiogenesis ceases.

The vascularization of cartilage regions in long bones occurs at different stages of development. In early embryonic development, blood vessels that originate from the perichondrium invaginate into the cartilage structures. During elevated postnatal growth, capillaries invade the growth plate of long bones. In adulthood, angiogenesis periodically can be switched on during bone remodeling in response to bone trauma or pathophysiological conditions such as rheumatoid arthritis (RA) and osteoarthritis (OA).

Bone has the unique capacity to regenerate without the development of a fibrous scar, which is symptomatic of soft tissue healing of wounds. This is achieved through the complex interdependent stages of the healing process, which mimic the tightly regulated development of the skeleton. Following trauma with damage to the musculoskeletal system, disruption of the vasculature leads to acute necrosis and hypoxia of the surrounding tissue. This disruption of the circulation leads to the activation of thrombotic factors in a coagulation cascade leading to the formation of a hematoma. The inflammatory response and tissue breakdown activate factors such as cytokines and growth factors that recruit osteoprogenitor and mesenchymal cells to the fracture site. The stimulation of the endosteal circulation in the fractured bone allows mesenchymal cells associated with growing capillaries to invade the wound region from the endosteum and bone marrow. At the edge of a bone fracture, the transiently formed granulation tissue is replaced by fibrocartilage. Concomitantly, the periosteum directly undergoes intramembranous bone formation leading to the formation of an external callus; while internally, the tissue is being mineralized to form woven bone. After stabilization of the bone tissue and vasculature in the bone fracture, the cell-mediated remodeling cascade is activated where osteoclastic removal of necrotic bone is followed by the replacement of the large fracture callus by lamellar bone, the callus size is reduced, and the normal vascular supply is restored.

A plurality of mediators associated with fetal and postnatal bone development plays a prominent role in the cascade response in bone fracture repair. These include but are not limited to BMP-2 and 4, VEGF, bFGF, TGF-β, and PDGF. VEGF expression is detected on chondroblasts, chondrocytes, osteoprogenitor cells and osteoblasts in the fracture callus where it is highly expressed in angioblasts, osteoprogenitor and osteoblast cells during the first seven days of healing but decreases after eleven days. Additionally, osteoclasts release heparinase that induces the release of the active form of VEGF from heparin, activating not only angiogenesis but also osteoclast recruitment, differentiation and activity leading to the remodeling of the fracture callus during endochondral ossification. Fractures in some cases fail to repair or unite resulting in fibrous filled pseudarthrosis. A number of contributing factors can lead to non-union or delayed union of bone fractures, such as, but not limited to, anti-inflammatory drugs, steroids, Vitamin C, Vitamin D and calcium deficiencies, tobacco smoking, diabetes, and other physiological disorders.

The absence of a functional vascular network is also an important factor in the lack of bone healing in non-union fractures. Studies have reported that angiogenic factors released from biomimetic scaffolds can enhance bone regeneration and that combination strategies that release both angiogenic and osteogenic factors can enhance the regenerative capacity of bone.

The critical sequential timing of osteoclast differentiation and activation, angiogenesis, recruitment of osteoprogenitor cells and the release of growth factors such as BMP-2 in osteogenesis and fracture repair may be enhanced by the synchronized endogenous production of angiogenic and osteogenic mediators. Studies in rat femoral drill-hole injury have shown differential expression of VEGF splicing isoforms along with its receptors, indicating an important role in the bone healing process. Other studies have demonstrated that angiogenesis occurs predominantly before the onset of osteogenesis in bone lengthening in an osteodistraction model.

Another angiogenic inducing growth factor, FGF-2, can accelerate fracture repair when added exogenously to the early healing stage of a bone. Although the mechanism has not been fully elucidated, it has the ability to stimulate angiogenesis and the proliferation and differentiation of osteoblasts to possibly aid the repair of bone fractures.

2.3. Cartilaginous Tissue Compartments

Cartilaginous tissue compartments are specialized connective tissue compartments comprising cartilage cells, known as chondrocytes, cartilage fibers and ground substance constituting the cartilage matrix, that collectively contribute to characteristic elastic firmness rendering cartilage capable of withstanding high levels of pressure or sheer. Cartilage is histologically classified into three types depending on its molecular composition: hyaline cartilage; fibrocartilage and elastic cartilage.

Hyaline cartilage is the predominant form of cartilage comprising an amorphous matrix surrounding chondrocytes embedded within spaces, known as lacunae. Hyaline cartilage, which is commonly associated with the skeletal system and found in the nose, trachea, bronchi and larynx, predominantly functions to provide support. Hyaline cartilage associated with the articular portions of bone, forming the major component of synovial joints, is termed articular cartilage. Hyaline cartilage is usually avascular except where vessels may pass through to supply other tissues and in ossification centers involved in intracartilaginous bone development.

Fibrocartilage, which is commonly found in intervertebral discs and pubic symphysis and functions to provide tensile strength and in shock absorption, is less firm than hyaline cartilage. It comprises a combination of dense collagenous fibers with cartilage cells and a scant cartilage matrix. Fibrocartilage is not usually circumscribed by a perichondrium. Proportions of cells, fibers and ECM components in fibrocartilage are variable.

Elastic cartilage, which is found in the external ear, the Eustachian tube, epiglottis and some of the laryngeal cartilages, is characterized by a large number of elastic fibers that branch and course in all directions to form a dense network of anastomosing and interlacing fibers.

Articular Cartilage Matrix

The chondrocytes in articular cartilage are surrounded by a narrow region of connective tissue ECM, termed the pericellular matrix (PCM), which together with the chondrocyte, is termed chondron. The PCM, which is very rich in fibronectin, proteoglycans (e.g., aggrecan, hyaluron and decorin) and collagen (types II, VI and IX), is particularly characterized by a high concentration of type VI collagen as compared to the surrounding ECM. In normal articular cartilage, type VI collagen is restricted to the chondrons, but in osteoarthritic cartilage, it is upregulated and found throughout the ECM. A proteomic analysis of articular cartilage revealed the presence of collagen $\alpha1$(II) C-propeptide, collagen $\alpha1$(XI) C-propeptide, collagen $\alpha2$(XI) C-propeptide, collagen $\alpha1$(VI), collagen $\alpha2$(VI), link protein, biglycan, .decorin, osteonectin, matrillin-1, annexin-V, lactadherin, and binding immunoglobulin protein (BiP), in addition to metabolic proteins. (Wilson et. al., 2008, Methods, 48:22-31).

Chondrocyte Differentiation

The specific structure of articular cartilage, with endogenous chondrocytes forming adult joints, is the result of endochondral ossification, as described above under the heading, Osseous Tissue Compartments Formation.

Chondrocyte differentiation and maintenance in articular cartilage is governed by interaction of multiple factors. Key players include, but are not limited to, ions (e.g., calcium); steroids (e.g., estrogens); terpenoids (e.g., retinoic acid); peptides (e.g., Parathyroid hormone (PTH), parathyroid hormone-related peptide (PTHrP)), insulin growth factors (e.g., TGF$\beta$ hormones, including, without limitation, BMPs, IGF-1, VEGF, PDGF, FGF); transcription factors (e.g., Wnt, SOX-9); eicosanoids (e.g., prostaglandins); catabolic interleukins (e.g., IL-1); and anabolic interleukins (e.g., IL-6, IL-4 and IL-10). (Gaissmaier et al., 2008, Int. J. Care Injured, 39S1: S88-S96).

Growth Plate

The epiphyseal plates or growth plates are a hyaline cartilage plate located in the metaphysis at the end of long bones. Whereas endochondral ossification is responsible for the formation of cartilage in utero and in infants, the growth plates are responsible for the longitudinal growth of long bones via a cartilage template. The ongoing developmental processes of proliferation and differentiation within the growth plates are mediated by a number of hormonal and paracrine factors secreted by the growth plate chondrocytes. The growth plate is a highly organized structure comprising a large number of chondrocytes in various stages of differentiation and proliferation embedded in a scaffold of ECM components.

The growth plate can be subdivided into four zones depending on the stage of differentiation and spatial distribution of collagen types. The resting zone is the smallest zone close to the epiphyseal cartilage comprising small monomorphic chondrocytes with a narrow rim of cytoplasm. The chondrocytes of the resting zone secrete growth plate orienting factor (GPOF) that aligns proliferating cells parallel to the long axis of the developing bone. Stem cell-like cells of the resting zone have a limited proliferative capacity, which eventually leads to fusion of the growth plate (epiphyseal fusion). The proliferative zone of the growth plate comprises chondrocytes that are arranged in characteristic columns parallel to the longitudinal axis of the bone and are separated by ECM with high type II collagen. The chondrocytes of the proliferative zone are mitotically active, have high oxygen and glycogen content, and exhibit increased mitochondrial ATP production. The hypertrophic zone refers to the zone farthest from the resting zone where prehypertrophic chondrocytes stop dividing and terminally differentiate into elongated hypertrophic chondrocytes embedded in ECM high in type X collagen. Hypertrophic chondrocytes have a high intracellular calcium concentration required for the production of release vesicles containing $Ca^{2+}$-binding annexins, that secrete calcium phosphate, hydroxyapatite, phosphatases (such as alkaline phosphatase), metalloproteinases, all instrumental in proteolytic remodeling and mineralization of the surrounding matrix. The hypertrophic chondrocytes produce factors, such as VEGF, that initiate vascularization of the mineralized matrix that is then degraded by invading phagocytic chondroclasts and osteoclasts constituting the invading zone.

The developmental processes involving chondrogenesis are regulated by an interplay of a large number of systemic hormones and paracrine factors, including growth factors, cytokines and transcription factors. Table 8 lists key factors involved in chondrocyte proliferation and differentiation in the growth plate. (Brochhausen et al., J. Tissue Eng. Regen. Med. 2009, 3:416-429).

TABLE 8

Summary of Key Factors involved in Chondrocyte Proliferation and Differentiation in the Growth Plate

| Name | Class | Expression | Effect |
|---|---|---|---|
| ATF-2 | Transcription factor | Resting chondrocytes; proliferative chondrocytes | Apoptosis |
| Bcl-2 | Inner mitochondrial membrane protein | Proliferative chondrocytes; prehypertrophic chondrocytes | Apoptosis |
| Ihh | Signaling molecule | Prehypertrophic chondrocytes | Proliferation |
| PTHrP | Peptide hormone | Perichondrium perarticular chondrocytes | Proliferation |
| BMP | TGF-$\beta$ superfamily growth factors | Prehypertrophic chondrocytes | Cartilage formation; proliferation |
| PGE$_2$ | Lipid mediator | All zones of growth plate | Proliferation matrix synthesis |
| MMP | Metalloproteinase | Hypertrophic chondrocytes; chondroclasts | Apoptosis; vascularization matrix degradation |

TABLE 8-continued

| Summary of Key Factors involved in Chondrocyte Proliferation and Differentiation in the Growth Plate | | | |
| --- | --- | --- | --- |
| Name | Class | Expression | Effect |
| Sox | Transcription factor | Resting and proliferative chondrocytes; hypertrophic chondrocytes | Differentiation; proliferation; |
| Runx 2 (Cbfa 1) | Transcription factor | Hypertrophic chondrocytes | Terminal differentiation; matrix mineralization |
| NOTCH | Single pass transmembrane protein | Prehypertrophic and hypertrophic chondrocytes | Inhibits terminal differentiation |
| HOX | Homeobox transcription factors | Hypertrophic chondrocytes | Activates osteogenic genes |
| FGF | Fibroblast growth factor | Proliferative chondrocytes | Antiproliferation |

Stem Cells of Cartilaginous Tissue Compartments

Multipotent mesenchymal progenitor cells with adipogenic, osteogenic and chondrogenic potential, and that are CD105+/CD166+ (corresponding to TGF-β type III receptor (endoglin) and ALCAM, respectively), have been identified in articular cartilage. (Asalameh et al., Arthritis 5 & Rheumatism, 2004, 50 (5): 1522-1532). The presence of CD34–/CD45–/CD44+/CD73+/CD90+ mesenchymal stem cells with adipogenic, chondrogenic and osteogenic potential also has been shown. (Peng et al., Stem Cells and Development (2008), 17:761-774). Similar to bone-derived MSCs, articular-derived MSCs are positive for surface expression of Notch-1. (Hiraoka et al., Biorheology, 2006, 43:447-454). A potential MSC niche positive for Stro-1, Jagged-1 and BMPr1a has also been identified in the perichondrial zone of Ranvier on the growth plate. (Karlsson et al., 2009, J. Anat. 215 (3): 355-63).

Differential expression of Notch-1, Stro-1 and VCAM-1/CD106 markers has been observed in normal articular cartilage versus osteoarthritic (OA) cartilage. In normal cartilage, expression of these markers is higher in the superficial zone (SZ) as compared to the middle zone (MZ) and deep zone (DZ). On the other hand, OA cartilage SZ has reduced Notch-1 and Sox-9 while MZ has increased Notch-1, Stro-1 and VCAM-1 positive cells. (Grogan et al., Arthritis Res. Ther. 2009, 11 (3): R85-R97).

Intervertebral Disc Fibrocartilage Tissue Compartments

The intervertebral discs (IVD) predominantly are comprised of fibrocartilage. The IVD fibrocartilage is continuous both with and below the articular cartilage of adjacent vertebrae as well as peripherally with spinal ligaments. The IVD is a unique structure containing annulus fibrosus (AF) and nucleus pulposus (NP), a gelatinous ellipsoidal remnant of the embryonic notochord, and is sandwiched between two adjacent cartilaginous endplates (EP). IVD rupture and herniation of the nucleus pulposus into the spinal cord may cause severe pain and other neurological symptoms. The NP and AF synergistically function to achieve the primary role of IVD in transferring load, dissipating energy and facilitating in joint mobility.

The adult IVD is essentially avascular; hence, endogenous cells survive in a low-nutrient and low-oxygen microenvironment. The major ECM components of IVD include but are not limited to aggrecan, collagen (e.g., types I, II and IX), leucine rich repeat (LRR) proteins and proteoglycans (e.g., fibromodulin, decorin, lumican), cartilage oligomatrix protein, and collagen VI beaded filament network. (Feng et al., 2006, J. Bone Joint Surg. Am. 88:25-29). The water content, GAG content, aggrecan levels and levels of type II collagen are significantly lower in older discs demonstrating the effects of IVD degeneration with age. (Murakami et al., 2010, Med. Biol. Eng. Comput. 48:469-474).

The central nucleus pulposus (NP) is rich in aggrecan and hyaluron. The developing NP is characterized by the presence of highly vacuolated chondrocytes and small chondroblasts inherited from the notochord. Primarily functioning as a primitive axial support, the integrity of the notochord is maintained by a proteoglycan (PG-) and laminin-rich sheath. As NP matures, the cellular composition becomes predominantly chondrocytic. Mature NP cells are small and have an aggrecan rich matrix, which is essential in maintaining requisite hydration levels for mechanical function. Their gene expression profile and metabolic activity are distinct from the chondrocytes of articular cartilage. The ECM of immature NP has high aggrecan levels and primarily contains type II collagen, with the type IIA isoform expressed by progenitor cells during chondrogenesis, not by mature chondrocytes. (Hsieh A. H. and Tworney J. D., J. Biomech., 2010, 43 (1): 137-156).

The AF surrounds the NP with layers of unidirectional sheets of collagen parallel to the circumference of a disc to form collagen lamellae. Alternating bidirectional collagen fibers intersperse the AF collagen lamellae. AF can be subdivided into three regions: inner AF, middle AF and outer AF. The inner AF arises along with endochondral formation of the vertebrae. The outer AF arises as a separate cell condensation with slower matrix formation. Lamellae of inner AF comprises predominantly of type II collagen and fibrochondrocytes, while those of outer AF are comprised of type I collagen and fibroblasts. A population of pancake shaped interlamellar cells as well as elastin fibers are also found within the lamellae, in vertebral attachments, and at the NP-AF interface. Large proteoglycans (PGs; for example aggrecan and versican) and type I and VI collagen permeate interlamellar and translamellar ECM. (Hsieh A. H. and Tworney J. D., J. Biomech., 2010, 43 (1): 137-156).

A large number of coordinated signals originating from the cells of the notochord and floor plate of the embryonal neural tube are instrumental in disc embryogenesis. Key signals include, but are not limited to, sonic hedgehog (Shh), Wnt, noggin, Pax family of transcription factors (e.g., Pax 1 and Pax 9), Sox family of transcription factors (Sox5, Sox6 and Sox) and TGF-β. (Smith et al., 2011, Dis Model Mech. 4 (1): 31-41). Herniation and IVD degeneration are associated with changes in inflammatory and immune cytokine profiles, including, but not limited to, the activation of Th1-related cytokines (e.g. IFNγ) as well as Th17-related cytokines (e.g., IL-4, IL-6, IL-12 and IL-17). (Shamji et al., 2010, Arthritis & Rheumatism, 62 (7): 1974-1982).

A potential stem cell niche comprised of progenitor cells that are positive for Notch1, Delta4, Jagged1, CD117, Stro-1 and Ki67 has been identified in intervertebral discs of a number of animals, including humans. It has been reported that the IVD tissue compartments comprise a slow growing zone in the AF as well as the NP regions. (Henriksson et al., 2009, SPINE, 34 (21): 2278-2287).

2.4. Dental Tissue Compartments

A tooth has three anatomical divisions (crown, root and neck), and four structural components (enamel, dentin, cementum and pulp).

Enamel is the hardest, most mineralized biological tissue in the human body. It is composed of elongated hydroxyapatite crystallites bundled into rods or prisms, interspersed with crystalline interrods filling the interstitial space. Enamel cells, known as ameloblasts, are responsible for enamel development. Ameloblastin, TRAP and enamelin are key proteins found in enamel tissue whereas the enamel matrix is devoid of collagen, composed primarily of amelogenin. An intricate orchestration of signaling factors, such as BMPs (e.g., BMP-2, BMP-4, BMP-7), FGFs (e.g., FGF-3, -4, -9, -20), Wnt-3, 10a, 10b and transcription factors, such as, p21, Msx2 and Lef1 is responsible for morphogenesis of enamel. Self-assembly of amelogens to form amelogenin nanospheres play a role in nucleation of hydroxyapatite crystallization and enamel mineralization. Matrix processing enzymes, such as MMP-20, kallikrein-4 (KLK4), also known as enamel matrix serine protease-1 (EMSP-1), are involved in the complete elimination of the protein matrix and replacement with a mineralized matrix. (Fong et al., 2005, J. Dent. Educ., 69 (5): 555-570). Ameloblasts arise from epithelial stem cells of ectodermal origin. They are lost after tooth eruption leaving no adult human ectodermal stem cells in the mature enamel. In contrast, rodent enamel retain a niche of epithelial stem cells, known as apical bud cells, for continuous enamel production. (Ulmer et al., 2010, Schweiz Monatsschr Zahnmed, 120:860-872).

Dentin is a hard, yellowish and elastic living connective tissue compartment with biomechanical properties similar to bone. The formation of dentin is driven by mesenchymally derived mature odontoblasts that are fully differentiated and nondividing and that form a single layer underneath the dentin in a mature tooth. A series of epithelial-mesenchymal interactions regulates odontoblast differentiation from neural crest cells in the first branchial arch and frontonasal processes. Mature dentin is comprised of a mantle, composed of intertubular and peritubular dentin made of a collagen fibril matrix, with odontoblast cell processes extending into dentin tubules. During dentinogenesis, odontoblasts secrete predentin, a mineralized tissue composed of type I collagen. Unlike osteogenesis, in dentinogenesis, as the predentin layer is formed, the odontoblasts recede instead of becoming embedded within the dentin matrix, leaving behind cells processes within dentinal tubules. Subsequently, the unmineralized predentin is converted to dentin by gradual mineralization of collagen. Dentinogenesis is directed by a series of highly controlled biochemical events that control the rates of collagen secretion, its maturation into thick fibrils, loss of proteoglycans, mineral formation including hydroxy apatite crystallization, and growth. The dentin matrix is primarily composed of collagens (e.g., types I, III and V) as well as other matrix proteins, including, but not limited to, phosphorylated and nonphosphorylated matrix proteins, proteoglycans, growth factors, metalloproteinases, alkaline phosphatase serum derived proteins, and phospholipids. (Fong et al., 2005, J. Dent. Educ., 69 (5): 555-570). No stem cells have been identified in mature dentin.

The dental pulp is the tooth's living tissue that responds to pain and damage and initiates tissue repair. An odontoblast cell layer forms the outer boundary of the pulp and is associated with an underlying network of dendritic cells. A cell-free zone underlying the odontoblast layer is rich in nerve fibers and blood vessels. Similar to dentin, dental pulp also differentiates from neural crest-derived ectomesenchyme during tooth development.

Several sources of stem cells have been identified associated with pulp tissue. In immature teeth, apical papilla, the embryonal organ responsible for pulp differentiation, is the source for stem cells of apical papilla (SCAP). Mature dental pulp is the source of dental pulp stem cells (DPSC) whereas stem cells are also extracted from exfoliated deciduous teeth (SHED). Additional cells of the dental pulp core that function in pulpal defense, include, but are not limited to, macrophages, lymphocytes and mast cells. Pulp matrix is composed of collagens (e.g., types I, III, V and VI), but lacks mineralization. Other noncollagenous proteins of the pulp matrix are similar in composition to dentin. The dental pulp is capable of responding to dentin tissue damage by secreting new dentin from old odontoblast populations or generation and secretion of dentin from new secondary odontoblast populations. (Fong et al., 2005, J. Dent. Educ., 69 (5): 555-570).

The periodontium consists of tissues supporting the tooth crown, including a nonmineralized periodontal ligament (PDL) sandwiched between layers of mineralized tissues, including the cementum, alveolar bone and dentin. Cementum is a thin mineralized layer covering the dentin. Cementoblasts are cells responsible for cementum matrix secretion and subsequent mineralization. When cementoblasts become entrapped within cementum matrix, they are termed cementocytes. Cementoblasts are ectomesenchymal, being derived from neural crest cells, similar to PDL and alveolar bone. Like bone and dentin, cementum is a collagenous mineralized tissue that hardens upon formation of carbonated hydroxyapatite. (Fong et al., 2005, J. Dent. Educ., 69 (5): 555-570).

PDL is a space between cementum and alveolar bone. It represents a replacement of the dental follicle region in immature developing teeth. Mature PDL contains mostly periodontal fibroblasts as well as stem cells, known as periodontal ligament stem cells (PDLSCs). The immature dental follicle is also a source of mesenchymal stem cells, known as dental follicle stem cells (DFSCs). (Fong et al., 2005, J. Dent. Educ., 69 (5): 555-570).

Table 9 shows the differentiation potential of dental mesenchymal cells. (Ulmer et al., 2010, Schweiz Monatsschr Zahnmed, 120:860-872).

TABLE 9

| Differentiation Potential Dental Mesenchymal Stem Cells | | | | |
| --- | --- | --- | --- | --- |
| | DPSC | SHED | PDLSC | DFSC | SCAP |
| Adipocytes | X | X | X | X | |
| Cementoblasts | | | X | X | |
| Chondrocytes | X | | X | | |
| Dental pulp | X | | | | |
| Dentin | X | | | | |
| Endothelocytes | X | X | | | |
| Musculature | X | | | | |
| Neuroblasts | | | | X | |
| Neurons | X | X | | | |
| Odontoblasts | X | X | X | | X |
| Osteoblasts | X | X | X | X | X |
| PDL | | | | X | |
| Progenitors | | | | | |
| Periodontium | | | X | | |

Several dental stem cell markers have been identified. Stro-1 and Stro-4 are commonly used dental stem cell markers for all dental mesenchymal stem cells. Dental stem cells originating from the neural crest have the neural marker, nestin. An osteoblast marker, osteocalcin, is also used as a stem cell marker for DPSCs. Similarly, SCAPs express Oct-4, Nanog, SSEA-3, SSEA-4, TRA-1-60 and TRA-1-81. (Ulmer et al., 2010, Schweiz Monatsschr Zahnmed, 120:860-872).

2.5. Fascial Tissue Compartment

Fascial tissue compartments form a layer of fibrous tissue found throughout the body surrounding softer and more delicate organs, including but not limited to muscles, groups of muscles, blood vessels, nerves, etc. Fascial tissue originates from the embryonic mesenchyme. Fasciae form during the development of bones, muscles and vessels from the mesodermal layer of the embryo. Fascial tissue can be categorized into three types depending on location: (1) superficial fascial tissue, which is found beneath the integument throughout the body, usually blending with the reticular layer of the dermis; (2) deep fascial tissue comprising dense fibroareolar connective tissue surrounding muscles, bones, nerves and blood vessels; and (3) visceral or subserous fascia, which suspends organs within their cavities and wraps them in layers of connective tissue membranes. (Chapter IV. Myology, Section 3. Tendons, Aponeuroses, and Fasciae, Gray's Anatomy of the Human Body, 20th Edition, Re-edited by Lewis, W. H., Lea & Febiger, Philadelphia, 1918, Bartleby.com, New York, 2000).

The fibroareolar connective tissue of fascia comprises four kinds of cells: (1) flattened lamellar cells, which may be branched or unbranched (branched lamellar cells contain clear cytoplasm and oval nuclei and project multidirectional processes that may unite to form an open network, such as in the cornea; unbranched lamellar cells are joined end to end. (2) Clasmatocytes, which are large irregular vacuolated or granulated cells with oval nuclei. (3) Granule cells, which are ovoid or spherical in shape. (4) Plasma cells of Waldeyer, usually spheroidal, characterized by vacuolated protoplasm.

2.6. Ligament Tissue Compartment

The term "ligaments" as used herein refers to dense regular connective tissue comprising attenuated collagenous fibers that connect bones at joints. Ligament ECM is composed of type I and type III collagens together with other proteoglycans and glycoproteins. Mesenchymal stem cells have been found in the human anterior cruciate ligament that exhibit multilineage differentiation potential, like bone-derived mesenchymal stem cells. (Cheng et al., 2010, Tissue Engg. A, 16 (7): 2237-2253).

2.7. Synovial Tissue Compartment

The synovial membrane is composed of fibrous connective tissue and lines the joint cavity of synovial joints. It is made up of a layer of macrophage (type A) and fibroblast-like (type B) synoviocytes and a loose sublining tissue. Synovial fluid is secreted by synovial cells lining the synovial membrane in the joint capsule. It is a viscid, mucoalbuminous fluid, rich in hyaluronic acid. It acts as a lubricating fluid, facilitating the smooth gliding of the articular surface. Functional mesenchymal stem cell niches have been identified as resident to synovial lining and subsynovial tissue. These cells are positive for the artificial nucleoside, iododeoxyuridine (IdU) as well as MSC markers such as PDGFRα, p75 and CD44 and have chondrogenic potential. (Kurth et al., Arthritis Rheum., 2011, 63 (5): 1289-1300). Synovial fluid-derived MSCs have also been identified, and these have higher chondrogenic potential as compared to bone marrow-derived and adipogenic MSCs. (Koga et al., 2008, Cell Tissue Res., 333:207-215). Synovial MSCs and MPCs have been shown to prevent degeneration due to intervertebral disc disease (IVD) and to be useful for cartilage tissue engineering. (Miyamoto et al., 2010, Arthritis Res. Ther., 12: R206-218; Lee et al., 2010, Tissue Engg. A, 16 (1): 317-325).

2.8. Tendon Tissue Compartment

Tendons are specialized connective tissue compartments that connect bone to muscle. Tendon cells are embedded amongst a parallel group of collagenous fibers that secrete a unique ECM containing collagens, large proteoglycans, and small leucine rich proteoglycans that function as lubricators and organizers of collagen fibril assembly. A unique tendon stem/progenitor cell (TSPC) niche has been identified amongst the parallel collagen fibrils surrounded by ECM. The TSPCs exhibit osteogenic and adipogenic potential. Biglycan and fibromodulin are key tendon ECM components that direct TSPC fate through BMP signaling. These TSPCs are positive for bone marrow derived stem cell markers such as Stro-1, CD146, CD90 and CD44 but not for CD18. TSPCs do not express hematopoietic markers, such as CD34, CD45 and CD117, or the endothelial marker CD106. (Bi et al., 2007, Nat. Med., 13 (10): 1219-1227).

2.9. Vasculature Tissue Compartment

The vascular wall is made of three concentric zones with distinct cellular composition, all mesodermal in origin: the tunica intima, containing predominantly mature differentiated endothelial cells (EC), the tunica media, containing mature and differentiated smooth muscle cells, and the tunica adventitia, containing mature fibroblasts. (Tilki et al., 2009, Trends Mol. Med. 15 (11): 501-509). Endothelial progenitor cells (EPCs), meaning cells that exhibit clonal expression, stemness characteristics, adherence to matrix molecules and an ability to differentiate into endothelial cells (ECs) have been implicated in the formation of new blood vessels through angiogenesis and postnatal vasculogenesis. EPCs have many characteristic cell surface markers, including, but not limited to, CD34, AC133, KDR (VEGFR-2), Tie-2 and ligand for UEA-1 lectin. (Tilki et al., 2009, Trends Mol. Med. 15 (11): 501-509; Melero-Martin and Dudley, 2011, Stem Cells, 29:163-168; Pascilli et al., 2008, Exp. Cell Res., 315:901-914).

EPC niches have been identified in the bone-marrow, peripheral cord blood and vascular wall matrix. Bone-marrow derived and cord blood EPCs essentially may be proangiogenic hematopoietic progenitor cells (HPCs), circulating in the blood and committed to myeloid lineage. (Tilki et al., 2009, Trends Mol. Med. 15 (11): 501-509). The vascular wall stem and progenitor cells (VW-EPCs) reside in distinct zones of the vessel wall within subendothelial space, known as avasculogenic zone, within the vascular adventitia, forming vascular wall-specific niches. Fetal and adult arterial and venous blood vessel walls have also been found to harbor resident niches for a variety of stem and progenitor cells, such as EPCs, smooth muscle progenitors, HSCs, MSCs, mesangial cells coexpressing myogenic and endothelial markers, neural stem cells (NSCs), etc. (Tilki et al., 2009, Trends Mol. Med. 15 (11): 501-509). The VW-EPCs are CD34 (+) VEGFR-2 (+) Tie-2 (+) CD31 (−) CD144 (−). Proliferating and differentiating VW-EPCs become CD144 (+).

During embryogenesis, there is evidence of the existence of a hemangioblast (giving rise to endothelial and hematopoietic cells) and hemogenic endothelium, originating from precursors resident in the vascular wall. However, whether adult VW also contains ancestral progenitor hemangioblasts giving rise to both VW-EPCs as well as VW-HSCs is not known. Vascular wall also contains resident pericyte-like cells in the subendothelial spaces. These pericyte-like cells serve as a cellular reservoir for VW-MSCs, which can differentiate into colonies with adipogenic, osteogenic and chondrogenic markers. (Tilki et al., 2009, Trends Mol. Med. 15 (11): 501-509).

3. Cells of the Epithelial Tissue Compartment 3.1. Placental Tissue Matrix

The placenta is considered one of the most important sources of stem cells, and has been studied extensively. It fulfills two main *desiderata* of cell therapy: a source of a high as possible number of cells and the use of non-invasive methods for their harvesting. Their high immunological tolerance supports their use as an adequate source in cell therapy (Mihu, C. et al., 2008, Romanian Journal of Morphology and Embryology, 2008, 49 (4): 441-446).

The fetal adnexa is composed of the placenta, fetal membranes, and umbilical cord. The term placenta is discoid in shape with a diameter of 15-20 cm and a thickness of 2-3 cm. The fetal membranes, amnion and chorion, which enclose the fetus in the amniotic cavity, and the endometrial decidua extend from the margins of the chorionic disc. The chorionic plate is a multilayered structure that faces the amniotic cavity. It consists of two different structures: the amniotic membrane (composed of epithelium, compact layer, amniotic mesoderm, and spongy layer) and the chorion (composed of mesenchyme and a region of extravillous proliferating trophoblast cells interposed in varying amounts of Langhans fibrinoid, either covered or not by syncytiotrophoblast).

Villi originate from the chorionic plate and anchor the placenta through the trophoblast of the basal plate and maternal endometrium. From the maternal side, protrusions of the basal plate within the chorionic villi produce the placental septa, which divide the parenchyma into irregular cotyledons (Parolini, O. et al., 2008, Stem Cell, 2008, 26:300-311).

Some villi anchor the placenta to the basal plate, whereas others terminate freely in the intervillous space. Chorionic villi present with different functions and structure. In the term placenta, the stem villi show an inner core of fetal vessels with a distinct muscular wall and connective tissue consisting of fibroblasts, myofibroblasts, and dispersed tissue macrophages (Hofbauer cells). Mature intermediate villi and term villi are composed of capillary vessels and thin mesenchyme. A basement membrane separates the stromal core from an uninterrupted multinucleated layer, called the syncytiotrophoblast. Between the syncytiotrophoblast and its basement membrane are single or aggregated Langhans cytotrophoblastic cells, commonly called cytotrophoblast cells (Parolini, O. et al., 2008, Stem Cell, 2008, 26:300-311).

Four regions of fetal placenta can be distinguished: an amniotic epithelial region, an amniotic mesenchymal region, a chorionic mesenchymal region, and a chorionic trophoblastic region.

Amniotic Membrane

Fetal membranes continue from the edge of the placenta and enclose the amniotic fluid and the fetus. The amnion is a thin, avascular membrane composed of an inner epithelial layer and an outer layer of connective tissue that, and is contiguous, over the umbilical cord, with the fetal skin. The amniotic epithelium (AE) is an uninterrupted, single layer of flat, cuboidal and columnar epithelial cells in contact with amniotic fluid. It is attached to a distinct basal lamina that is, in turn, connected to the amniotic mesoderm (AM). In the amniotic mesoderm closest to the epithelium, an acellular compact layer is distinguishable, composed of collagens I and III and fibronectin. Deeper in the AM, a network of dispersed fibroblast-like mesenchymal cells and rare macrophages are observed. It has been reported that the mesenchymal layer of amnion indeed contains two subfractions, one having a mesenchymal phenotype, also known as amniotic mesenchymal stromal cells, and the second containing monocyte-like cells.

Chorionic Membrane

A spongy layer of loosely arranged collagen fibers separates the amniotic and chorionic mesoderm. The chorionic membrane (chorion laeve) consists of mesodermal and trophoblastic regions. Chorionic and amniotic mesoderm are similar in composition. A large and incomplete basal lamina separates the chorionic mesoderm from the extravillous trophoblast cells. The latter, similar to trophoblast cells present in the basal plate, are dispersed within the fibrinoid layer and express immunohistochemical markers of proliferation. The Langhans fibrinoid layer usually increases during pregnancy and is composed of two different types of fibrinoid: a matrix type on the inner side (more compact) and a fibrin type on the outer side (more reticulate). At the edge of the placenta and in the basal plate, the trophoblast interdigitates extensively with the decidua (Cunningham, F. et al., The placenta and fetal membranes, Williams Obstetrics, 20th ed. Appleton and Lange, 1997, 95-125; Benirschke, K. and Kaufmann, P. Pathology of the human placenta. New York, Springer-Verlag, 2000, 42-46, 116, 281-297).

Amnion-Derived Stem Cells

The amniotic membrane itself contains multipotent cells that are able to differentiate in the various layers. Studies have reported their potential in neural and glial cells, cardiac repair and also hepatocyte cells. Studies have shown that human amniotic epithelial cells express stem cell markers and have the ability to differentiate toward all three germ layers. These properties, the ease of isolation of the cells, and the availability of placenta, make amnionic membrane a useful and noncontroversial source of cells for transplantation and regenerative medicine.

Amniotic epithelial cells can be isolated from the amniotic membrane by several methods that are known in the art. According to one such method, the aminiotic membrane is stripped from the underlying chorion and digested with trypsin or other digestive enzymes. The isolated cells readily attach to plastic or basement membrane-coated culture dishes. Culture is established commonly in a simple medium such as Dulbecco's Modified Eagle's Medium (DMEM) supplemented with 5%-10% serum and epidermal growth factor (EGF), in which the cells proliferate robustly and display typical cuboidal epithelial morphology. Normally, 2-6 passages are possible before proliferation ceases. Amniotic epithelial cells do not proliferate well at low densities.

Amniotic membrane contains epithelial cells with different surface markers, suggesting some heterogeneity of phenotype. Immediately after isolation, human amniotic epithelial cells express very low levels of human leukocyte antigen (HLA)-A, B, C; however, by passage 2, significant levels are observed. Additional cell surface antigens on human amniotic epithelial cells include, but are not limited to, ATP-binding cassette transporter G2 (ABCG2/BCRP), CD9, CD24, E-cadherin, integrins $\alpha6$ and $\beta1$, c-met (hepatocyte growth factor receptor), stage-specific embryonic antigens (SSEAs) 3 and 4, and tumor rejection antigens 1-60 and 1-81. Surface markers thought to be absent on human amniotic epithelial cells include SSEA-1, CD34, and CD133, whereas other markers, such as CD117 (c-kit) and CCR4 (CC chemokine receptor), are either negative or may be expressed on some cells at very low levels. Although initial cell isolates express very low levels of CD90 (Thy-1), the expression of this antigen increases rapidly in culture (Miki, T. et al., Stem Cells, 2005, 23:1549-1559; Miki, T. et al., Stem Cells, 2006, 2:133-142).

In addition to surface markers, human amniotic epithelial cells express molecular markers of pluripotent stem cells, including octamer-binding protein 4 (OCT-4) SRY-related HMG-box gene 2 (SOX-2), and Nanog (Miki, T. et al., Stem Cells, 2005, 23:1549-1559). Previous studies also have shown that human amnion cells in xenogeneic, chimeric aggregates, which contain mouse embryonic stem cells, can differentiate into all three germ layers and that cultured human amniotic epithelial cells express neural and glial markers, and can synthesize and release acetylcholine, catecholamines, and dopamine. Hepatic differentiation of human amniotic epithelial cells also has been reported. Studies have reported that cultured human amniotic epithelial cells produce albumin and α-fetroprotein and that albumin and α-fetroprotein-positive hepatocyte-like cells could be identified integrated into hepatic parenchyma following transplantation of human amniotic epithelial cells into the livers of severe combined inmmunodeficiency (SCID) mice. The hepatic potential of human amniotic epithelial cells was confirmed and extended, whereby in addition to albumin and α-fetroprotein production, other hepatic functions, such as glycogen storage and expression of liver-enriched transcription factors, such as hepatocyte nuclear factor (HNF) 3γ and HNF4α, CCAAT/enhancer-binding protein (CEBP α and β), and several of the drug metabolizing genes (cytochrome P450) were demonstrated. The wide range of hepatic genes and functions identified in human amniotic epithelial cells has suggested that these cells may be useful for liver-directed cell therapy (Parolini, O. et al., 2008, Stem Cell, 2008, 26:300-311).

Differentiation of human amniotic epithelial cells to another endodermal tissue, pancreas, also has been reported. For example, it was shown that human amniotic epithelial cells cultured for 2-4 weeks in the presence of nicotinamide to induce pancreatic differentiation, expressed insulin. Subsequent transplantation of the insulin-expressing human amniotic epithelial cells corrected the hyperglycemia of streptozotocin-induced diabetic mice. In the same setting, human amniotic mesenchymal stromal cells were ineffective, suggesting that human amniotic epithelial cells, but not human amniotic mesenchymal stromal cells, were capable of acquiring β-cell fate (Parolini, O. et al., 2008, Stem Cell, 2008, 26:300-311).

Mesenchymal Stromal Cells from Amnion and Chorion: HAMSC and hCMSC

Human amniotic mesenchymal cells (hAMSC) and human chorionic mesenchymal cells (hCMSC) are thought to be derived from extraembryonic mesoderm. hAMSC and hCMSC can be isolated from first-, second-, and third-trimester mesoderm of amnion and chorion, respectively. For hAMSC, isolations are usually performed with term amnion dissected from the deflected part of the fetal membranes to minimize the presence of maternal cells. For example, homogenous hAMSC populations can be obtained by a two-step procedure, whereby: minced amnion tissue is treated with trypsin to remove hAEC and the remaining mesenchymal cells are then released by digestion (e.g., with collagenase or collagenase and DNase). The yield from term amnion is about 1 million hAMSC and 10-fold more hAEC per gram of tissue (Casey, M. and MacDonald P., Biol Reprod, 1996, 55:1253-1260).

hCMSCs are isolated from both first- and third-trimester chorion after mechanical and enzymatic removal of the trophoblastic layer with dispase. Chorionic mesodermal tissue is then digested (e.g., with collagenase or collagenase plus DNase). Mesenchymal cells also have been isolated from chorionic fetal villi through explant culture, although maternal contamination is more likely (Zhang, X., et al., Biochem Biophys Res Commun, 2006, 340:944-952; Soncini, M. et al., J Tissue Eng Regen Med, 2007, 1:296-305; Zhang et al., Biochem Biophys Res Commun, 2006, 351: 853-859).

The surface marker profile of cultured hAMSC and hCMSC, and mesenchymal stromal cells (MSC) from adult bone marrow are similar. All express typical mesenchymal markers (Table 7) but are negative for hematopoietic (CD34 and CD45) and monocytic markers (CD14). Surface expression of SSEA-3 and SSEA-4 and RNA for OCT-4 has been reported (Wei J. et al., Cell Transplant, 2003, 12:545-552; Wolbank, S. et al., Tissue Eng, 2007, 13:1173-1183; Alviano, F. et al., BMC Dev Biol, 2007, 7:11; Zhao, P. et al, Transplantation, 2005, 79:528-535). Both first- and third trimester hAMSC and hCMSC express low levels of HLA-A, B, C but not HLA-DR, indicating an immunoprivileged status (Portmann-Lanz, C. et al, Am J Obstet Gynecol, 2006, 194:664-673; Wolbank, S. et al., Tissue Eng, 2007, 13:1173-1183).

Table 10 provides surface antigen expression profile at passages 2-4 for amniotic mesenchymal stromal and human chorionic mesenchymal stromal stem cells.

TABLE 10

Specific surface antigen expression for aminiotic mesenchymal stromal cells and human chorionic mesenchymal stromal cells

| Positive (≥95%) | Negative (≤2%) |
|---|---|
| CD90 | CD45 |
| CD73 | CD34 |
| CD105 | HLA-DR |

Both hAMSCs and hCMSCs differentiate toward "classic" mesodermal lineages (osteogenic, chondrogenic, and adipogenic) and differentiation of hAMSC to all three germ layers-ectoderm (neural), mesoderm (skeletal muscle, cardiomyocytic and endothelial), and endoderm (pancreatic) was reported (Int'Anker, P. et al., Stem Cells, 2004, 22:1338-1345; Portmann-Lanz, C. et al, Am J Obstet Gynecol, 2006, 194:664-673; Wolbank, S. et al., Tissue Eng, 2007, 13:1173-1183; Soncini, M. et al., J Tissue Eng Regen Med, 2007, 1:296-305; Alviano, F., BMC Dev Biol, 2007, 7:11).

Human amniotic and chorionic cells successfully and persistently engraft in multiple organs and tissues in vivo. Human chimerism detection in brain, lung, bone marrow, thymus, spleen, kidney, and liver after either intraperitoneal or intravenous transplantation of human amnion and chorion cells into neonatal swine and rats was indeed indicative of an active migration consistent with the expression of adhesion and migration molecules (L-selectin, VLA-5, CD29, and P-selectin ligand 1), as well as cellular matrix proteinase (MMP-2 and MMP-9) (Bailo, M. et al., Transplantation, 2004, 78:1439-1448).

Umbilical Cord

Two types of umbilical stem cells can be found, namely hematopoietic stem cells (UC-HS) and mesenchymal stem cells, which in turn can be found in umbilical cord blood (UC-MS) or in Wharton's jelly (UC-MM). The blood of the umbilical cord has long been in the focus of attention of researchers as an important source of stem cells for transplantation, for several reasons: (1) it contains a higher number of primitive hematopoietic stem cells (HSC) per volume unit, which proliferate more rapidly, than bone marrow; (2) there is a lower risk of rejection after transplantation; (3) transplantation does not require a perfect HLA antigen match (unlike in the case of bone marrow); (4) UC blood has already been successfully used in the treatment of inborn metabolic errors; and (5) there is no need for a new technology for collection and storage of the mononuclear cells from UC blood, since such methods are long established.

Umbilical cord (UC) vessels and the surrounding mesenchyma (including the connective tissue known as Wharton's jelly) derive from the embryonic and/or extraembryonic mesodermis. Thus, these tissues, as well as the primitive germ cells, are differentiated from the proximal epiblast, at the time of formation of the primitive line of the embryo, containing MSC and even some cells with pluripotent potential. The UC matrix material is speculated to be derived from a primitive mesenchyma, which is in a transition state towards the adult bone marrow mesenchyma (Mihu, C. et al., 2008, Romanian Journal of Morphology and Embryology, 2008, 49 (4): 441-446).

The blood from the placenta and the umbilical cord is relatively easy to collect in usual blood donation bags, which contain anticoagulant substances. Mononuclear cells are separated by centrifugation on Ficoll gradient, from which the two stem cell populations will be separated: (1) hematopoietic stem cells (HSC), which express certain characteristic markers (CD34, CD133); and (2) mesenchymal stem cells (MSC) that adhere to the culture surface under certain conditions (e.g., modified McCoy medium and lining of vessels with Fetal Bovine Serum (FBS) or Fetal Calf Serum (FCS)). (Munn, D. et al., Science, 1998, 281:1191-1193; Munn, D. et al., J Exp Med, 1999, 189:1363-1372). Umbilical cord blood MSCs (UC-MS) can produce cytokines, which facilitate grafting in the donor and in vitro HSC survival compared to bone marrow MSC. (Zhang, X et al., Biochem Biophys Res Commun, 2006, 351:853-859).

MSCs from the umbilical cord matrix (UC-MM) are obtained by different culture methods depending on the source of cells, e.g., MSCs from the connective matrix, from subendothelial cells from the umbilical vein or even from whole umbilical cord explant. They are generally well cultured in DMEM medium, supplemented with various nutritional and growth factors; in certain cases prior treatment of vessels with hyaluronic acid has proved beneficial (Baban, B. et al., J Reprod Immunol, 2004, 61:67-77).

3.2. Lung

The lungs, which are paired organs that fill up the thoracic cavity, constitute an efficient air-blood gaseous exchange mechanism, accomplished by the passage of air from the mouth or nose, sequentially through an oropharynx, nasopharynx, a larynx, a trachea and finally through a progressively subdividing system of bronchi and bronchioles until it finally reaches alveoli where the air-blood gaseous exchange takes place. A resident niche with characteristic multipotent stem cells with c-kit positive surface profiles recently has been identified localized in small bronchioles alveoli. These stem cells express the transcription factors, Nanog, Oct3/4, Sox2 and Klf4, that govern pluripotency in embryonic stem cells. (Kajstura, J. et al., 2011, New Engl. J. Med., 364 (19): 1795-1806)).

3.3. Mammary

The mammary gland is a hormone sensitive bilayered epithelial organ comprising an inner luminal epithelial layer and an outer myoepithelial layer surrounded by a basement membrane in a stromal fat pad. Mammary stem cells with myoepithelial potential have been identified in their niches in the terminal ducts of mammary gland. (LaBarge, 2007, Stem Cell Rev., 3 (2): 137-146).

3.4. Skin

The skin functions as the primary barrier imparting protection from environmental insults. Skin is composed of an outer epidermis and inner dermis separated by a basement membrane (BM), rich in ECM and growth factors. The BM of the epidermal-dermal junction is composed of collagens (e.g., type IV and XVII), laminins, nidogen, fibronectin and proteoglycans that provide storage sites for growth factors and nutrients supporting the proliferation and adhesion of epidermal keratinocytes.

The epidermis is a solid epithelial tissue comprising keratinocytes that are linked to each other via cellular junctions, such as desmosomes. Keratinocytes are organized into distinct layers, comprising the stratum corneum, stratum granulosum, stratum spinosum and stratum basale. The epidermal matrix is made up of hyaluronan and other proteoglycans, including but not limited to, desmosealin, glycipans, versican, perlecan, and syndecans. (Sandjeu and Haftek, 2009, J. Physiol. Pharmacol. 60 (S4): 23-30). Epidermal desmosomes are multimeric complexes of transmembrane glycoprotein and cytosolic proteins with the keratin cytoskeleton. Desmosal proteins of the epidermis predominantly belong to the cadherin, Armadillo and plakin superfamilies.

The underlying dermis is connective tissue comprised primarily of fibroblasts with occasional inflammatory cells. Embedded within the dermis are also epidermal appendages, such as hair follicles and sebaceous glands, as well as nerves and cutaneous vasculature. The dermal ECM is essentially made of type I, III and V collagens and elastin together with noncollagenous components such as glycoproteins, proteoglycans, GAGs, cytokines and growth factors. Dermal collagens help mediate fibroblast-matrix interactions through a number of cell surface receptors and proteoglycans, such as $\beta 1$-integrins. (Hodde and Johnson, 2007, Am. J. Clin. Dermatol. 8 (2): 61-66).

During embryonic development, the epidermis originates from the ectoderm, while the dermis differentiates from the mesoderm. Following gastrulation, as mesenchymal stem cells of mesodermal origin populate the skin, they send signals to the single epidermal layer for initiation of epidermal stratification and direct the positioning of outgrowths of epidermal appendages, such as the hair follicles and sebaceous glands. Along with the mesenchyme, the basal layer of the epidermis organizes into a basement membrane that is rich in ECM proteins and growth factors. A number of different signaling pathways have been implicated in skin morphogenesis, including but not limited to Notch, Wnt, mitogen activated protein kinase (MAPK), nuclear factor-$\kappa$B (NF-$\kappa$B), transcriptional regulator, p63, the AP2 family of transcription factors, CCAAT/enhancer binding protein (C/EBP) transcriptional regulators, interferon regulatory 6 (URF6), grainyhead-like 3 (GRHL3) and Kruppel-like factor (KLF4). (Blanpain and Fuchs, 2009, Nat. Rev. Mol. Cell. Biol., 10 (3): 207-217).

Adult skin undergoes constant cellular turnover whereby dead skin cells are shed and new cells are regenerated and replaced, by a process known as skin homeostasis. Several stem cell niches with distinct surface marker profiles and differentiation potentials have been identified. These include, but are not limited to, epidermal stem cells of interfollicular epidermis, bulge stem cells and epithelial stem cells of the hair follicle, dermal stem cells (e.g., multipotent dermal cells, skin-derived progenitor cells, dermis-derived multipotent stem cells and fibrocytes), dermal papilla stem cells, and sebaceous gland stem cells. Collectively, these skin stem cell niches partake in maintaining skin homeostasis with the help of growth factors and cytokines. (Zouboulis et al., 2008, Exp. Gerontol. 43:986-997; Blanpain, 2010, Nature, 464:686-687).

4. Cells of the Muscular Tissue Compartment

The muscular tissue compartments are comprised of contractile muscle tissue. These can be of three kinds: skeletal muscle associated with the skeletal system; cardiac muscle associated with the heart; and smooth muscle associated with the vasculature and gastrointestinal tract. Skeletal muscle tissue fibers are striated and are voluntary in function. Cardiac muscle fibers have characteristic intercalated discs and are involuntary in function. Smooth muscle tissue is comprised of spindle shaped cells and is involuntary in function.

Skeletal muscles are composed of a population of quiescent myogenic precursor cells known as satellite cells with muscle regenerating and self-renewal properties, as well as a population of multipotent muscle-derived stem cells (MDSC) with multilineage differentiation potential, such as mesodermal lineages including, but not limited to, myogenic lineages, adipogenic lineages, osteogenic lineages, chondrogenic lineages, endothelial and hematopoetic lineages, and ectodermal lineages, including not limited to neuron-like cells. (Xu et al., 2010, Cell Tissue Res., 340:549-567).

Skeletal muscle satellite cells are quiescent mononucleated cells that are resident in the muscle fiber membrane, beneath the basal lamina forming distinct stem cell niches. Similar to other stem cell niches, the skeletal muscle satellite cell niche is a dynamic structure, capable of altering between inactive (quiescent) and activated states in response to external signals. Once activated, satellite cells have the potential to proliferate, expand and differentiate along the myogenic lineage. The basal lamina, which serves to separate individual skeletal muscle fibers, known as myofibers, and their associated satellite cell and stem cell niches, from the cells of the interstitium, is rich in collagen type IV, perlecan, laminin, entactin, fibronectin and several other glycoproteins and proteoglycans, that may function as receptors to growth factors effectuating their activation by extracellular processing and modifications. In addition to these interactions provided by the ECM, neighboring cells, such as endothelial cells and multipotent stem cells derived from blood vessels, such as pericytes and mesoangioblasts, or neural components, all have the potential of affecting the niche microenvironment. (Gopinath et al., 2008, Aging Cell, 7:590-598).

Endogenous cardiac stem cells have also been identified in cardiac stem cell niches. (Mazhari and Hare, 2007, Nat. Clin. Pract. Cardiovasc. Med., 4 (S1): S21-S26).

Vascular smooth muscle cells are derived from embryonic cardiac neural crest stem cells, as well as proepicardial cells and endothelial progenitor cells. Smooth muscle differentiation is dependent on a combination of factors, including but not limited to Pax3, Tbx1, FoxC1 and serum response factor, interacting with microenvironment components of the ECM, such as BMPs, Wnts, endothelin (ET)-1, and FGF8. In the adult, vascular smooth muscle cells undergo constant degeneration, repair and regeneration by the concerted efforts of both multipotent bone-derived mesenchymal cells as well as smooth muscle stem cells resident within vascular smooth muscle tissue. (Hirschi and Majesky, 2004, The Anatomical Record, Part A, 276A: 22-33).

5. Cells of the Neural Tissue Compartment

The neural tissue compartments are comprised of neurons and the neuroglia, embedded with the neural matrix. Neural tissue is ectodermal in origin, derived from the embryonic neural plate. Neural tissue is primarily located within the brain, spinal cord and nerves.

Resident neural stem cell niches have been identified in the adult mammalian brain, restricted to the subventricular zone as well as to the lateral ventricle and dentate gyrus subgranular zone of the hippocampus. Astrocytes, which are star-shaped nerve cells, serve as both neural stem cells as well as supporting niche cells secreting essential growth factors that provide support for neurogenesis and vasculogenesis. The basal lamina and associated vasculogenesis are essential components of the niche. Embryonic molecular factors and signals persist within the neural stem cell niches and play critical role in neurogenesis. Neural stem cells have VEGFR2, doublecortin and Lex (CD15) markers. Major signaling pathways implicated in neurogenesis include but are not limited to Notch, Eph/ephrins, Shh, and BMPs. (Alvarez-Buylla and Lim, 2004, Neuron, 41:683-686).

6. Grafts—Grafts and Graft Rejection

A graft is a tissue or organ used for transplantation to a patient. A common strategy employed in tissue engineering involves the seeding of decellularized natural ECM or synthetic scaffolds with a variety of different stem or progenitor cells that are capable of regeneration (see, for example, Flynn and Woodhouse, 2008, Organogenesis, 4 (4): 228-235; Uriel et al., 2008, Biomaterials, 29:3712-3719; Flynn, 2010, Biomaterials, 31:4715-4724; Choi et al., Tissue Engg. C., 16 (3): 387-396; Brown et al., 2011, Tissue Engg. C., 17 (4): 411-421; Cheng et al., 2009, Tissue Engg. A, 15 (2): 231-241; Li et al., 2011, Biomaterials, doi: 10:1016/ j.biomaterials.2011.03.008; Butler et al., 2003, Connective Tissue Research, 44 (S1): 171-178); Mercuri et al., J. Biomed. Mater. Res. A., 96 (2): 422-435); Olson et al., 2011, Chonnam. Med. J. 47:1-13).

Transplanted grafts may be rejected by the recipient host via an orchestrated immune response against the histocompatibility antigens expressed by the grafted tissue, which the recipient host may see as foreign. Effectors primarily responsible for such rejections include type 1 helper CD4+ cells, cytotoxic CD8+ cells and antibodies. Alternative mechanisms of rejection include the involvement of type 2 helper CD4+ cells, memory CD8+ cells, and cells that belong to the innate immune system, such as natural killer cells, eosinophils, and neutrophils. In addition, local inflammation associated with rejection is tightly regulated at the graft level by regulatory T cells and mast cells.

Implants

Patients suffering from affected or injured organs may be treated with organ transplantation. However, current methods of organ transplantation are faced with challenges due, in part to the need to suppress immune rejection of the transplanted organ. Most methods rely on the use of immunosuppressive drugs that are associated with unwanted side effects.

It is estimated that more than one million patients need to be treated surgically for skeletal afflictions every year due to bony defects created during tumor surgery or caused by trauma, congenital skeletal abnormalities, fracture, scoliosis, spinal arthrodesis, or joint and tooth replacement. Surgical treatments, however, are not always effective to address these problems because of inadequate local bone conditions and impaired bone healing. For example, complicated fractures may fail to heal, resulting in delayed unions (a bone fracture that is taking an exceptionally long amount of time to heal) or non-unions (absence of healing in a fracture). In addition, the treatment of bone tumors or congenital syndromes often requires the artificial creation of large bony defects, which need to be filled, demanding suitable and biocompatible substitutes for bone grafts.

Bone healing around implants involves the activation of a sequence of osteogenic, vascular, and immunological events that are similar to those occurring during bone healing. Various cell types, growth factors and cytokines are involved and interact throughout the stages of osteointegration, including inflammation, vascularization, bone formation, and ultimately bone remodeling.

Bone Grafts

Fresh autologous bone grafts for the treatment of an osseous defect or fracture in a patient are derived from bone marrow freshly harvested from the iliac crest (the thick curved upper border of the ilium, the most prominent bone on the pelvis) and combined with other materials including osteoconductive substrates. Complications associated with autologous harvest include donor site morbidity as high as 25%, infection, malformation, pain, and loss of function.

Bone Matrix with Mesenchymal Stem Cells

Attempts have been made to repair osseous defects by implanting a bone matrix comprising autologous or allogeneic mesenchymal stem cells (MSCs). MSCs are considered immunologically neutral, meaning that the mesenchymal stem cells from the donor need not be tissue-matched to the recipient, thus allowing MSCs to be used effectively in allogeneic grafts. In addition, culture-expanded allogeneic MSCs have been implanted either directly or combined with a matrix, such as a gelatin-based or collagen-based matrix, or a bone matrix, in order to support differentiation of the MSCs in vivo.

In other instances, MSCs have been combined with a bone matrix from which bone marrow has been removed in order to remove undesirable cells, and the matrix then seeded with culture-expanded MSCs. Such compositions then are cryopreserved under standard cryopreservation procedures for later use. However, this method is not ideal for several reasons. First, because the MSCs have been removed from the original stem cell niche and seeded onto a new bone matrix, the MSCs in such a composition are not well-attached to the bone matrix and become merely suspended in the cryopreservation solution. As a result, many active cells can be lost during the process of removing the cryopreservation solution before transplantation into a subject. Secondly, since the cells are not attached to the stem cell niche or lacunae to which they were originally attached and in which they were nurtured, the expandability and osteogenic potential of the cells may be affected negatively by the separation and seeding procedures.

Tissue-derived implant materials replicate the biological and mechanical function of naturally occurring extracellular matrix found in body tissues. Such tissue-derived matrices provide the necessary support on which cells can adhere to, migrate and expand and allow the influx and efflux of cells, such as stem cells and progenitor cells, and other factors, such as growth factors and cytokines, capable of inducing and supporting growth and tissue repair.

Glossary

The term "ambient temperature" as used herein refers to the temperature of the immediate, unaltered surroundings. Ambient temperature is between about 18° C. and about 28° C. According to some embodiments, ambient temperature is room temperature.

The term "adherent" as used herein refers to the act of sticking to, clinging, or staying attached.

The term "adipokine" as used herein refers to a factor secreted by adipose tissue.

The term "adipocyte" as used herein refers to the functional cell type of fat, or adipose tissue, that is found throughout the body, particularly under the skin. Adipocytes store and synthesize fat (more specifically, triglycerides or lipids) for energy, thermal regulation and cushioning against mechanical shock. Although the lineage of adipocytes is still unclear, it appears that MSCs can differentiate into two types of lipoblasts, one that give rise to white adipocytes and the other to brown adipocytes. Both types of adipocytes store triglycerides and other lipids.

The term "adipogenic" as used herein refers to a potential of undifferentiated precursor cells to differentiate into fat-forming or adipocompetent cells.

The term "adipose stem cell" or "adipose-derived stem cell" (ASC) as used herein refers to pluripotent stem cells, MSCs and more committed adipose progenitors and stroma obtained from adipose tissue.

The term "administer" as used herein means to give or to apply.

The term "allogeneic" as used herein refers to being genetically different although belonging to or obtained from the same species.

The term "amniotic stem cells" as used herein refers to pluripotent stem cells, multipotent stem cells and progenitor cells derived from amniotic membrane, which can give rise to a limited number of cell types in vitro and/or in vivo under an appropriate condition, and expressly includes both amniotic epithelial cells and amniotic stromal cells.

The term "attached" as used herein refers to being fastened, fixed, joined, connected, bound, adhered to or assembled with.

The term "autologous" as used herein means derived from the same organism.

The term "autologous graft" or "autograft" as used herein refers to a tissue that is grafted into a new position in or on the body of the same individual.

The term "basic fibroblast growth factor" (bFGF, FGF2) as used herein refers to a multifunctional effector for many cells of mesenchymal and neuroectodermal origin that is a potent inducer of neovascularization and angiogenesis.

The term "biocompatible" as used herein refers to causing no clinically relevant tissue irritation, injury, toxic reaction, or immunological reaction to living tissue.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention.

The term "bone" as used herein refers to a hard connective tissue consisting of cells embedded in a matrix of mineralized ground substance and collagen fibers. The fibers are impregnated with a form of calcium phosphate similar to hydroxyapatite as well as with substantial quantities of carbonate, citrate and magnesium. Bone consists of a dense outer layer of compact substance or cortical substance covered by the periosteum and an inner loose, spongy substance; the central portion of a long bone is filled with marrow.

The terms "cancellous bone" or "trabecular bone" as used herein refer to the spongy bone found in the inner parts of compact bone in which the matrix forms a lattice of large plates and rods known as the trabeculae, which anastomose to form a latticework. This latticework partially encloses many intercommunicating spaces filled with bone marrow. The marrow spaces are relatively large and irregularly arranged, and the bone substance is in the form of slender anastomosing trabeculae and pointed spicules.

The terms "cortical bone" or "compact bone" as used herein refer to the dense outer layer of bone that consists largely of concentric lamellar osteons and interstitial lamellae. The spaces or channels are narrow and the bone substance is densely packed.

The term "bone morphogenetic protein (BMP) as used herein refers to a group of cytokines that are part of the transforming growth factor-ß (TGF-ß) superfamily. BMP ligands bind to a complex of the BMP receptor type II and a BMP receptor type I (Ia or Ib). This leads to the phosphorylation of the type I receptor that subsequently phosphorylates the BMP-specific Smads (Smad1, Smad5, and Smad8), allowing these receptor-associated Smads to form a complex with Smad4 and move into the nucleus where the Smad complex binds a DNA binding protein and acts as a transcriptional enhancer. BMPs have a significant role in bone and cartilage formation in vivo. It has been reported that most BMPs are able to stimulate osteogenesis in mature osteoblasts, while BMP-2, 6, and 9 may play an important role in inducing osteoblast differentiation of mesenchymal stem cells. Cheng, H. et al., J. Bone & Joint Surgery 85:1544-52 (2003).

The term "bound" or any of its grammatical forms as used herein refers to the capacity to hold onto, attract, interact with or combine with.

The term "buffer" or "buffer solution" as used herein refers to a compound, usually a salt, which, when dissolved in an aqueous medium, serves to maintain the free hydrogen ion concentration of the solution within a certain pH range when hydrogen ions are added or removed from the solution. A salt or solution is said to have a "buffering capacity" or to buffer the solution over such a range, when it provides this function. Generally a buffer will have adequate buffering capacity over a range that is within .±.1 pH unit of its pK.

The term "buffered isotonic solution" as used herein refers to any buffer that is commonly used in biological research or the commercial biotechnology field. Exemplary buffered isotonic solutions include but are not limited to balanced salt solution (BSS), Hank's Balanced Salt Solution, Gey's Balanced Salt Solution, Hank's Buffered Salt Solution, Phosphate Buffered Saline, Tris-Buffered Saline, etc. The term "isotonic solution" as used herein refers to a solution whose osmolarity and ion concentrations closely match those within normal cells of the body and the blood.

The term "carrier" as used herein refer to a pharmaceutically acceptable inert agent or vehicle for delivering one or more active agents to a subject, and often is referred to as "excipient." The carrier must be of sufficiently high purity and of sufficiently low toxicity to render it suitable for administration to the subject being treated. The carrier further should maintain the stability and bioavailability of an active agent The term "cell" is used herein to refer to the structural and functional unit of living organisms and is the smallest unit of an organism classified as living.

The term "chemokine" as used herein refers to a class of chemotactic cytokines that signal leukocytes to move in a specific direction.

The terms "chemotaxis" or "chemotactic" refer to the directed motion of a motile cell or part along a chemical concentration gradient towards environmental conditions it deems attractive and/or away from surroundings it finds repellent.

The term "chondrocytes" as used herein refers to cells found in cartilage that produce and maintain the cartilaginous matrix for, for example, joints, ear canals, trachea, epiglottis, larynx, the discs between vertebrae and the ends of ribs. From least to terminally differentiated, the chondrocytic lineage is (i) Colony-forming unit-fibroblast (CFU-F); (ii) mesenchymal stem cell/marrow stromal cell (MSC); (iii) chondrocyte.

The term "chondrogenesis" as used herein refers to the formation of new cartilage from cartilage forming or chondrocompetent cells.

The term "chondrogenic" as used herein refers to a potential of undifferentiated precursor cells to differentiate into cartilage forming or chondrocompetent cells.

The term "compatible" as used herein means that the components of a composition are capable of being combined with each other in a manner such that there is no interaction that would substantially reduce the efficacy of the composition under ordinary use conditions.

The term "component" as used herein refers to a constituent part, element or ingredient.

The term "condition", as used herein, refers to a variety of health states and is meant to include disorders or diseases caused by any underlying mechanism or disorder, injury, and the promotion of healthy tissues and organs.

The term "contact" and its various grammatical forms as used herein refers to a state or condition of touching or of immediate or local proximity. Contacting a composition to a target destination may occur by any means of administration known to the skilled artisan.

The term "cut section thickness" as used herein refers to thickness of a section as measured directly from the sectioning device (cryostat, microtome, etc.) prior to histological processing, which may cause shrinkage in the z-axis. Also known as the block advance of the microtome.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include e.g., IL-1.alpha., IL-.beta., IL-2, IL-3, IL-4, IL-5, IL-6, IL-7, IL-8, IL-9, IL-10, IL-11, IL-12/IL-23 P40, IL13, IL-17, IL-18, TGF-beta., IFN-gamma., GM-CSF, Gro.alpha., MCP-1 and TNF-alpha.

The term "cytometry" as used herein refers to a process in which physical and/or chemical characteristics of single cells, or by extension, of other biological or nonbiological particles in roughly the same size or stage, are measured. In flow cytometry, the measurements are made as the cells or particles pass through the measuring apparatus (a flow cytometer) in a fluid stream. A cell sorter, or flow sorter, is a flow cytometer that uses electrical and/or mechanical means to divert and collect cells (or other small particles) with measured characteristics that fall within a user-selected range of values.

"Decellularization", as used herein in all of its grammatical forms, is any process by which cells and cellular components (including DNA) are removed from a tissue, thereby leaving the extracellular matrix (ECM) essentially free of such cells and cellular components. When used to describe a degree of decellularization, "essentially free of cells and cellular components" means that the tissue, matrix, or composition contains less than 550 ng dsDNA per mg dry tissue, as determined by fluorescence emission intensity measurements on an appropriate reader such as the Biotek Syngery II Microplate Reader, after DNA isolation/purification using the QIAamp DNA Mini Kit (Qiagen) and staining using the Quant-iT™ PicoGreen™ dsDNA Assay Kit (Thermo-Fisher Scientific). Similarly, "entirely free of cells and cellular components" means that the tissue, matrix, or composition contains less than 50 ng dsDNA per mg dry tissue, as also determined by the aforesaid test method.

The terms "delipidization" and "delipidation", as used herein in all of their grammatical forms (such as "delipidized" and "delipidated," respectively), are any processes by which at least a portion of the lipids naturally present in a tissue are removed from the tissue, and are used interchangeably herein.

"Demineralized bone matrix" (DBM) refers to a bone-derived material that has osteoconductive and osteoinductive activity. DBM may be prepared by acid extraction of allograft bone, resulting in loss of most of the mineralized component but retention of collagen and noncollagenous proteins, including growth factors. Methods for preparing demineralized bone matrix from bone are known in the art, as disclosed, for example, in U.S. Pat. Nos. 5,073,373; 5,484,601; and 5,284,655, which are incorporated herein by reference. DBM may be prepared from autologous bone, allogeneic (or "allograft") bone, or xenogeneic bone. DBM may be prepared from cancellous bone, cortical bone, or combinations of cancellous and cortical bone. For the purpose of the present disclosure, demineralized bone includes bone matrix having a residual mineral content of 5% or less (w/w), 2% or less (w/w), 1% or less (w/w), 0.5% or less (w/w), or consisting essentially of collagen, non-collagen proteins such as growth factors, and other nonmineral substances found in the original bone, although not necessarily in their original quantities. The term "demineralized cortical bone" (DCB) as used herein refers to a demineralized allograft cortical bone.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by well-known chemical modification methods (see, e.g., Glazer et al., Chemical Modification of Proteins, Selected Methods and Analytical Procedures, Elsevier Biomedical Press, New York (1975)).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "devitalization", as used herein in all of its grammatical forms, is any process which renders a tissue substantially or essentially free from reproductively or metabolically viable cells, without necessarily leaving the tissue essentially free of such cells and cellular components.

The term "differential label" as used herein generally refers to a stain, dye, marker, or antibody used to characterize or contrast structures, components or proteins of a single cell or organism.

The term "differentiation" as used herein refers to the process of development with an increase in the level of organization or complexity of a cell or tissue, accompanied with a more specialized function.

The terms "disease" or "disorder" as used herein refer to an impairment of health or a condition of abnormal functioning.

The term "disinfection", as used herein in all of its grammatical forms, is any process which renders a tissue essentially free of viable pathogenic organisms and viruses by destroying them or otherwise inhibiting their growth or vital activity. For example, a "disinfected" acellular matrix has been subjected to a "disinfecting" step and is, therefore, essentially free of viable pathogenic organisms and viruses. When used to describe a degree of disinfection, "essentially free of pathogenic organisms and viruses" means the tissue matrix in its final configuration yields negative sterility results (zero evidence of microbial growth), as determined by USP <71> sterility test (2019 USP42-NF37, International Press Publication, Inc. of Richmond Hill, Ontario, Canada).

The term "dye" (also referred to as "fluorochrome" or "fluorophore") as used herein refers to a component of a molecule which causes the molecule to be fluorescent. The component is a functional group in the molecule that absorbs energy of a specific wavelength and re-emits energy at a different (but equally specific) wavelength. The amount and wavelength of the emitted energy depend on both the dye and the chemical environment of the dye. Many dyes are known, including, but not limited to, FITC, R-phycoerythrin (PE), PE-Texas Red Tandem, PE-Cy5 Tandem, propidium iodem, EGFP, EYGP, ECF, DsRed, allophycocyanin (APC), PerCp, SYTOX Green, courmarin, Alexa Fluors (350, 430, 488, 532, 546, 555, 568, 594, 633, 647, 660, 680, 700, 750), Cy2, Cy3, Cy3.5, Cy5, Cy5.5, Cy7, Hoechst 33342, DAPI, Hoechst 33258, SYTOX Blue, chromomycin A3, mithramy-cin, YOYO-1, SYTOX Orange, ethidium bromide, 7-AAD, acridine orange, TOTO-1, TO-PRO-1, thiazole orange, TOTO-3, TO-PRO-3, thiazole orange, propidium iodide (PI), LDS 751, Indo-1, Fluo-3, DCFH, DHR, SNARF, Y66F, Y66H, EBFP, GFPuv, ECFP, GFP, AmCyanl, Y77W, S65A, S65C, S65L, S65T, ZsGreenl, ZsYellowl, DsRed2, DsRed monomer, AsRed2, mRFP1, HcRedl, monochlorobimane, calcein, the DyLight Fluors, cyanine, hydroxycoumarin, aminocoumarin, methoxycoumarin, Cascade Blue, Lucifer Yellow, NBD, PE-Cy5 conjugates, PE-Cy7 conjugates, APC-Cy7 conjugates, Red 613, fluorescein, FluorX, BODIDY-FL, TRITC, X-rhodamine, Lissamine Rhodamine B, Texas Red, TruRed, and derivatives thereof.

The term "nonexpanded" as used herein refers to a cell population that has not been grown in culture (in vitro) to increase the number of cells in the cell population.

The term "endogenous" as used herein refers to that which is naturally occurring, incorporated within, housed within, adherent to, attached to or resident in.

The term "extracellular matrix" as used herein refers to a scaffold in a cell's external environment with which the cell interacts via specific cell surface receptors. The extracellular matrix serves many functions, including, but not limited to, providing support and anchorage for cells, segregating one tissue from another tissue, and regulating intracellular communication. The extracellular matrix is composed of an interlocking mesh of fibrous proteins and glycosaminogly-cans (GAGs). Examples of fibrous proteins found in the extracellular matrix include collagen, elastin, fibronectin, and laminin. Examples of GAGs found in the extracellular matrix include proteoglycans (e.g., heparin sulfate), chon-droitin sulfate, keratin sulfate, and non-proteoglycan poly-saccharide (e.g., hyaluronic acid). The term "proteoglycan" refers to a group of glycoproteins that contain a core protein to which is attached one or more glycosaminoglycans.

The term "factors" as used herein refers to nonliving components that have a chemical or physical effect. For example, a "paracrine factor" is a diffusible signaling mol-ecule that is secreted from one cell type that acts on another cell type in a tissue. A "transcription factor" is a protein that binds to specific DNA sequences and thereby controls the transfer of genetic information from DNA to mRNA.

The term "fluorescence" as used herein refers to the result of a three-state process that occurs in certain molecules, generally referred to as "fluorophores" or "fluorescent dyes," when a molecule or nanostructure relaxes to its ground state after being electrically excited. Stage 1 involves the excitation of a fluorophore through the absorp-tion of light energy; Stage 2 involves a transient excited lifetime with some loss of energy; and Stage 3 involves the return of the fluorophore to its ground state accompanied by the emission of light.

The term "fluorescent-activated cell sorting" (also referred to as "FACS") as used herein refers to a method for sorting a heterogeneous mixture of biological cells into one or more containers, one cell at a time, based upon the specific light scattering and fluorescent characteristics of each cell.

The term "fossa" as used herein means a small cavity or depression, as in a bone.

The term "fragment" as used herein refers to a small part, which may be, without exclusion, a particle, chip, or fiber, derived from, cut off, or broken from a larger unit which retains the desired biological activity of the larger unit.

The term "functional equivalent" or "functionally equiva-lent" are used interchangeably herein to refer to substances, molecules, polynucleotides, proteins, peptides, or polypep-tides having similar or identical effects or use.

The term "graft" as used herein refers to a tissue or organ transplanted from a donor to a recipient. It includes, but is not limited to, a self-tissue transferred from one body site to another in the same individual ("autologous graft"), a tissue transferred between genetically identical individuals or suf-ficiently immunologically compatible to allow tissue trans-plant ("syngeneic graft"), a tissue transferred between genetically different members of the same species ("alloge-neic graft" or "allograft"), and a tissue transferred between different species ("xenograft").

The term "growth" as used herein refers to a process of becoming larger, longer or more numerous, or an increase in size, number, or volume.

The term "growth conduction" as used herein refers to a process by which a tissue is directed to regenerate or grow so as to conform to a material's surface. A growth-conduc-tive surface is one that permits tissue growth on its surface or down into pores, channels or pipes. Growth-conductive material facilitates the spontaneous formation of a tissue by furnishing a microenvironment that supports deposition or adhesion of tissuegenic cells and optionally, vascularization. Examples of growth-conductive materials, include, but are not limited to, processed human bone (e.g., allograft bone, which may be an osteoconductive material), purified colla-gen, calcium phosphate ceramics, synthetic polymers, tis-sue-derived matrices, BMP-2 and 4, VEGF, bFGF, TGF-β, and PDGF.

The term "growth-conductive matrix" as used herein refers to a matrix that may be inert in and of itself but which supports three-dimensional tissue formation. For example, allograft bone tissue may be an osteoconductive matrix.

The term "growth factor" as used herein refers to extra-cellular polypeptide molecules that bind to a cell-surface receptor triggering an intracellular signaling pathway, lead-ing to proliferation, differentiation, or other cellular response. Growth factors include, but are not limited to, cytokines and hormones.

The term "growth induction" as used herein refers to a process by which primitive, undifferentiated and tissuegenic cells are stimulated to develop into an ensemble of cells, not necessarily identical, that together carry out a specific func-tion. This ensemble of cells is termed a tissue.

The term "growth-inductive matrix" as used herein refers to a matrix containing a substance or substances capable of recruiting or stimulating local tissuegenic cells so that the cells are induced (meaning to cause, bring about, bring about, or trigger) to differentiate and/or produce a tissue.

The terms "growth-inductive components" or "growth-inductive factors" or "tissuegenic factors" are used interchangeably to refer to the plethora of mediators associated with tissue development and repair.

For example, Table 11 lists exemplary growth-inductive factors secreted by adipose tissue classified according to metabolic, immunological or other function. (Halberg et. al., 2008, Endocrinol. Metab. Clin. North Am., 37 (3): 753-767). The subcutaneous adipose secretome includes adiponectin, leptin, IL-6, IL-7, IL-8, MCP-1, GRO, angiogenin, HGF, VEGF, TIMP-1, TIMP-2, etc. (Klimkakova et. al., 2007, Biochem. Biophys. Res. Commun., 358:897-902).

The term "implant" refers to any device or material inserted or placed, permanently or temporarily, into or onto a subject as well as those used for the administration or delivery of a therapeutic agent(s) or substance.

The term "improve" (or improving) as used herein refers to bring into a more desirable or excellent condition.

The terms "in the body", "void volume", "resection pocket", "excavation", "injection site", "deposition site" or "implant site" as used herein are meant to include all tissues of the body without limit, and may refer to spaces formed therein from injections, surgical incisions, tumor or tissue removal, tissue injuries, abscess formation, or any other

TABLE 11

| Secreted Soluble non-ECM Factors of Adipose Secretome | | |
| --- | --- | --- |
| Metabolic Factors | Immunological Factors | Other Factors |
| Adipsin | Alpha 1 acid glycoprotein | Angiogenin |
| Adiponectin | Colony stimulating factor-1 | Angiopoietin 1 |
| Apelin | Complement component inhibitor C1 | Angiopoietin 2 |
| ApoE | Complement C1 | Angiotensinogen |
| Cortisol | Complement C2 | Calcitonin |
| Insulin-like growth factor 1 (IGF-1) | Complement C3 | Chemerin |
| Insulin-like growth factor (IGF) | Complement C4 | Cyclophilin A |
| Binding protein 7 (Bp 7) | Complement C7 | Extracellular SOD |
| Lipoprotein lipase | Complement factor B | Galectin 1 |
| Leptin | Complement factor C | Growth related oncogene (GRO) |
| Fasting induced adipose factor | Complement factor D | Fibroblast growth factor (FGF) |
| Plasminogen activated inhibitor-1 | C reactive protein | Hepatic growth factor (GF) |
| Resistin | Haptoglobin | Mineralcorticoid releasing factor (MRF) |
| Retinol binding protein 4 | Interleukin 1 beta (IL-1) | Monocyte chemoattractant protein 1 (MCP-1) |
| Vaspin | Interleukin 4 (IL-4) | Nerve growth factor (NGF) |
| Vistafin | Interleukin 6 (IL-6) | Pigment epithelium derived factor (PEDF) |
| | Interleukin 7 (IL-7) | Prostaglandin E2 |
| | Interleukin 8 (IL-8) | Prostaglandin I2 |
| | Interleukin 10 (IL-10) | Prostaglandin 2alpha |
| | Interleukin 12 (IL-12) | Serum transferring |
| | Interleukin 18 (IL-18) | Stromal derived factor 1 |
| | Lipocalin 24p3 | TGF beta |
| | Macrophage migration inhibitory factor 1 | TIMP-1 |
| | Serum amyloid A3 (SAA3) | TIMP-2 |
| | Tumor necrosis factor alpha (TNF-α) | Tissue factor |
| | | Vascular endothelial growth factor (VEGF) |

The term "hematopoietic stem cell" refers to a cell isolated from the blood or from the bone marrow that can renew itself, differentiate to a variety of specialized cells, mobilize out of the bone marrow into the circulating blood, and undergo programmed cell death (apoptosis). According to some embodiments of the described invention, hematopoietic stem cells derived from human subjects express at least one type of cell surface marker, including, but not limited to, CD34, CD38, HLA-DR, c-kit, CD59, Sca-1, Thy-1, and/or CXCR-4, or a combination thereof.

"HLA-DR" refers to a human class II histocompatibility antigen present on several cell types, including antigen-presenting cells, B cells, monocytes, macrophages, and activated T cells.

The term "interleukin" as used herein refers to a cytokine secreted by white blood cells as a means of communication with other white blood cells.

similar cavity, space, or pocket formed thus by action of clinical assessment, treatment or physiologic response to disease or pathology as non-limiting examples thereof.

The term "indicator" as used herein refers to any substance, number or ratio derived from a series of observed facts that may reveal relative changes as a function of time; or a signal, sign, mark, note or symptom that is visible or evidence of the existence or presence thereof.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators.

Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents.

The term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity.

The term "injury," as used herein, refers to damage or harm to a structure or function of the body caused by an outside agent or force, which may be physical or chemical.

The term "isolate" and its various grammatical forms as used herein refers to placing, setting apart, or obtaining a protein, molecule, substance, nucleic acid, peptide, cell or particle, in a form essentially free from contaminants or other materials with which it is commonly associated, separate from its natural environment.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "labile" as used herein refers to subject to increased degradation.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The term "matrix" refers to a surrounding substance within which something is contained or embedded.

The term "mechanical agitation" as used herein refers to a process whereby tissue is physically shaken or churned via mechanical means. Such mechanical means include, but are not limited to, a mixer or other mechanical device.

The term "mesenchymal stem cells (MSCs)" as used herein refers to non-blood adult stem cells found in a variety of tissues. They are characterized by their spindle-shape morphologically; by the expression of specific markers on their cell surface; and by their ability under appropriate conditions, to differentiate along a minimum of three lineages (osteogenic, chondrogenic and adipogenic). When referring to bone or cartilage, MSCs commonly are known as osteochondrogenic, osteogenic, or chondrogenic, since a single MSC has shown the ability to differentiate into chondrocytes or osteoblasts, depending on the medium.

MSCs secrete many biologically important molecules, including interleukins 6, 7, 8, 11, 12, 14, and 15, M-CSF, Flt-3 ligand, SCF, LIF, bFGF, VEGF, PlGF and MCP1 (Majumdar, et al., J. Cell Physiol. 176:57-66 (1998), Kinnaird et al, Circulation 109:1543-49 (2004)). In 2004, it was reported that no single marker that definitively identifies MSCs in vivo had yet been identified, due to the lack of consensus from diverse documentations of the MSC phenotype. Baksh, et al., J. Cell. Mol. Med. 8 (3): 301-16, 305 (2004). There is general agreement that MSCs lack typical hematopoietic antigens, namely CD14, CD34, and CD45. (Id.; citing Pittenger, M. F. et al., Science 284:143-47 (1999)).

The term "mill," and its various grammatical forms, as used herein refers to operations performed to grind, to cut, to shred, to chip, or to pulverize a substance, or equipment for performing such operations on a substance. The term "freezer-mill" and its various grammatical forms, as used herein refers to mill a substance in a frozen state, or equipment for performing such operations.

The term "mounted section thickness" as used herein, refers to the thickness of tissue sections after histological processing.

The term "multipotent" as used herein refers to a cell capable of giving rise to a limited number of cell types of a particular cell line.

The term "myogenic" refers to a potential of undifferentiated precursor cells to differentiate into a muscle forming or myocompetent cells.

The term "Optical Disector" refers to a stereological probe for counting or selecting objects in a tissue section. This is an extension to the basic Disector method, which is applied to a thick section using a series, or stack, of Disectors. Rather than using pairs of physical sections (the basic Disector method), optical sectioning is used by creating focal planes with a thin depth-of-field through the section. The Optical Disector begins with a lookup section at the top of the optical disector and ends with a reference section at the bottom of the optical disector. The focal plane is the current reference section. The lookup section is immediately above the focal plane. A particle in focus at the top of the optical disector is therefore seen in the lookup section and not counted. A particle in focus at the bottom of the optical disector is in the reference section and therefore not in the lookup section, is counted. Counting frame rules are applied when the particle first comes into focus.

The term "osteoblasts" as used herein refers to cells that arise when osteoprogenitor cells or mesenchymal cells, which are located near all bony surfaces and within the bone marrow, differentiate under the influence of growth factors. Osteoblasts, which are responsible for bone matrix synthesis, secrete a collagen rich ground substance essential for later mineralization of hydroxyapatite and other crystals. The collagen strands to form osteoids (spiral fibers of bone matrix). Osteoblasts cause calcium salts and phosphorus to precipitate from the blood, which bond with the newly formed osteoid to mineralize the bone tissue. Once osteoblasts become trapped in the matrix they secrete, they become osteocytes. From least to terminally differentiated, the osteocyte lineage is (i) colony-forming unit-fibroblast (CFU-F); (ii) mesenchymal stem cell/marrow stromal cell (MSC); (iii) osteoblast; and (iv) osteocyte.

The term "osteocalcin" as used herein refers to a protein constituent of bone; circulating levels are used as a marker of increased bone turnover.

The term "osteoclast" as used herein refers to large multinucleate cells associated with areas of bone resorption (breakdown).

The term "osteoconduction" as used herein refers to a process by which bone is directed so as to conform to a material's surface. An osteoconductive surface is one that permits bone growth on its surface or down into pores, channels or pipes. Osteoconductive material facilitates the spontaneous formation of bone by furnishing a microenvironment that supports the ingrowth of blood vessels, perivascular tissue and osteoprogenitor cells into the site where it is deposited. Examples of osteoconductive materials, include, but not limited to, processed human bone (e.g., allograft bone), purified collagen, calcium phosphate ceramics, synthetic polymers, BMP-2 and 4, VEGF, bFGF, TGF-β, and PDGF.

The term "osteoconductive matrix" as used herein refers to a matrix that is inert in and of itself but on which cells can climb and grow bone.

The term "osteogenic" refers to a potential of undifferentiated precursor cells to differentiate into bone forming or osteocompetent cells.

The term "osteogenesis" as used herein refers to the development or formation of new bone by bone forming or osteocompetent cells.

The term "osteoinduction" as used herein refers to a process by which primitive, undifferentiated and pluripotent cells are stimulated to develop into a bone forming cell lineage thereby inducing osteogenesis. For example, the majority of bone healing in a fracture is dependent on osteoinduction. Osteoinductive materials can be generated by combining a porous scaffold with osteogenic cells and/or osteoinductive components, including, but not limited to, growth factors such as BMP-2 and 4, VEGF, bFGF, TGF-β, and PDGF.

The term "osteoinductive matrix" as used herein refers to a matrix containing a substance or substances that recruit local cells to induce (meaning to cause, bring about, bring about, or trigger) local cells to produce bone.

The terms "osteoinductive components" or "osteogenic factors" are used interchangeably to refer to the plethora of mediators associated with bone development and repair, including, but not limited to, bone morphogenic proteins (BMPs), vascular endothelial growth factor (VEGF), basic fibroblast growth factor (bFGF), transforming growth factor beta (TGFβ), and platelet-derived growth factor (PDGF).

The term "osteointegration" refers to an anchorage mechanism whereby nonvital components can be incorporated reliably into living bone and that persist under all normal conditions of loading.

The term "particle" as used herein refers to a chip, fragment, slice, fiber or other small constituent of a larger body (e.g., picoparticles, nanoparticles, microparticles, milliparticle, centiparticle, deciparticle; fractions thereof, or, in some instances, a larger segment or piece).

The term "piece" as used herein refers to a particle, section, strip, chip, fragment, slice, fiber or other part, derived from, cut off, or broken from a larger unit.

The term "peptide" is used herein to refer to two or more amino acids joined by a peptide bond.

The term "periosteum" as used herein refers to the normal investment of bone, consisting of a dense, fibrous outer layer, to which muscles attach, and a more delicate, inner layer capable of forming bone.

The term "Platelet Derived Growth Factor" (PDGF) as used herein refers to a major mitogen for connective tissue cells and certain other cell types. It is a dimeric molecule consisting of disulfide-bonded, structurally similar A and B-polypeptide chains, which combine to homo- and heterodimers. The PDGF isoforms exert their cellular effects by binding to and activating two structurally related protein tyrosine kinase receptors, the α-receptor and the β-receptor. Activation of PDGF receptors leads to stimulation of cell growth, but also to changes in cell shape and motility; PDGF induces reorganization of the actin filament system and stimulates chemotaxis, i.e., a directed cell movement toward a gradient of PDGF. In vivo, PDGF plays a role in embryonic development and during wound healing.

The term "pluripotent" as used herein refers to the ability to develop into multiple cells types, including all three embryonic lineages, forming the body organs, nervous system, skin, muscle and skeleton.

The term "progenitor cell" as used herein refers to an early descendant of a stem cell that can only differentiate, but can no longer renew itself. Progenitor cells mature into precursor cells that mature into mature phenotypes. Hematopoietic progenitor cells are referred to as colony-forming units (CFU) or colony-forming cells (CFC). The specific lineage of a progenitor cell is indicated by a suffix, such as, but not limited to, CFU-E (erythrocytic), CFU-F (fibroblastic), CFU-GM (granulocytic/macrophage), and CFU-GEMM (pluripotent hematopoietic progenitor). Osteoclasts arise from hematopoietic cells of the monocyte/neutrophil lineage (CFU-GM). Osteoprogenitor cells arise from mesenchymal stem cells and are committed to an osteocyte lineage.

The term "propagate" as used herein refers to reproduce, multiply, or to increase in number, amount or extent by any process.

The term "purification" as used herein refers to the process of isolating or freeing from foreign, extraneous, or objectionable elements.

The term "random" as used herein refers to unpredictable. There is some element of chance. This is the opposite of deterministic, in which the next number or event is knowable.

The term "reduced" or "to reduce", as used herein in all of its grammatical forms, refers to a diminishing, a decrease in, an attenuation or abatement of the degree, intensity, extent, size, amount, density or number of.

The term "regeneration" or "regenerate" as used herein refers to a process of recreation, reconstitution, renewal, revival, restoration, differentiation and growth to form a tissue with characteristics that conform with a natural counterpart of the tissue.

The term "relative" as used herein refers to something having, or standing in, some significant association to something else. The term "relative frequency" as used herein refers to the rate of occurrence of something having or standing in some significant association to the rate of occurrence of something else. For example, two cell types, X cells and Y cells occupy a given location. There are 5 X cells and 5 Y cells in that location. The relative frequency of cell type X is 5/10; the relative frequency of cell type Y is 5/10 in that location. Following processing, there are 5 X cells, but only 1 Y cell in that location. The relative frequency of cell type X following processing is 5/6, and the relative frequency of cell type Y following processing is 1/6 in that location.

The term "repair" as used herein as a noun refers to any correction, reinforcement, reconditioning, remedy, making up for, making sound, renewal, mending, patching, or the like that restores function. When used as a verb, it means to correct, to reinforce, to recondition, to remedy, to make up for, to make sound, to renew, to mend, to patch or to otherwise restore function. According to some embodiments "repair" includes full repair and partial repair.

The term "resident," and its various grammatical forms, as used herein refers to being present habitually, existing in or intrinsic to or incorporated therein.

The term "rinse," and its various grammatical forms, as used herein refers to wash, to douse with a liquid or liquids or to flow a liquid or liquids over the material being rinsed.

The term "scaffold" as used herein refers to a structure capable of supporting a three-dimensional tissue formation. A three-dimensional scaffold is believed to be critical to replicate the in vivo milieu and to allow the cells to influence their own microenvironment. Scaffolds may serve to promote cell attachment and migration, to deliver and retain cells and biochemical factors, to enable diffusion of vital cell nutrients and expressed products, and to exert certain mechanical and biological influences to modify the behavior of the cell phase. A scaffold utilized for tissue reconstruction has several requisites. Such a scaffold should have a high porosity and an adequate pore size to facilitate cell seeding and diffusion of both cells and nutrients throughout the whole structure. Biodegradability of the scaffold is also an essential requisite. The scaffold should be absorbed by the surrounding tissues without the necessity of a surgical removal, such that the rate at which degradation occurs coincides as closely as possible with the rate of tissue formation. As cells are fabricating their own natural matrix structure around themselves, the scaffold provides structural integrity within the body and eventually degrades leaving the neotissue (newly formed tissue) to assume the mechanical load.

The term "section" when used in the context of stereology refers to a cut through material that has effectively zero thickness compared to the size of the particles being studied. Biologists refer to sections as thick slices through tissue. The actual thickness of sections can leads to the Holmes effect.

The term "side-effect" as used herein refers to a result of a therapy in addition to, or in extension of, the desired therapeutic effect.

The term "similar" is used interchangeably with the terms analogous, comparable, or resembling, meaning having traits or characteristics in common.

The term "size reduction", as used herein in all of its grammatical forms, refers to a process by which an object, such as a tissue, is divided or reduced in size. Such processes include, without limitation, cutting, slicing, chopping, grinding, milling, freezer-milling, blending, homogenizing, tearing, shredding, fracturing, breaking, crushing, and morselizing.

A "solution" generally is considered as a homogeneous mixture of two or more substances. It is frequently, though not necessarily, a liquid. In a solution, the molecules of the solute (or dissolved substance) are uniformly distributed among those of the solvent. The term "solvent" as used herein refers to a substance capable of dissolving another substance (termed a "solute") to form a uniformly dispersed mixture (solution).

The term "stain" as used herein refers to a composition of a dye(s) or pigment(s) used to make a structure, a material, a cell, a cell component, a membrane, a granule, a nucleus, a cell surface receptor, a peptide, a microorganism, a nucleic acid, a protein or a tissue differentiable.

The term "Sca-1" or "stem cell antigen-1" refers to a surface protein component in a signaling pathway that affects the self-renewal ability of mesenchymal stem cells.

The term "stem cells" refers to undifferentiated cells having high proliferative potential with the ability to self-renew (make more stem cells by cell division) that can generate daughter cells that can undergo terminal differentiation into more than one distinct cell phenotype.

The term "stereology" as used herein refers to a method of quantifying 2D and 3D structures using estimation methods.

The term "sterilization", as used herein in all of its grammatical forms, is any process that renders an object (e.g., a tissue, a container for tissue, or an implement for processing tissue) essentially free from pathogenic organisms and/or viruses by destroying them or otherwise inhibiting their growth or vital activity. Such processes may include exposure of the object to one or more, without limitation, of gamma radiation, electron beam radiation, chemical agents (e.g., alcohol, phenol, ethylene oxide gas, acids, bases, or peroxides), heat, or ultraviolet radiation for sufficient duration and dosages. When sterilization is performed on a finished tissue product in its final packaging, the process may be referred to as "terminal sterilization".

The term "stimulate", as used herein in all of its grammatical forms, as used herein refers to activate, provoke, or spur. The term "stimulating agent" as used herein refers to a substance that exerts some force or effect.

The term "subcutaneous", as used herein with reference to tissues, refers to tissues that are beneath the dermis and not part of the dermis (i.e, the hypodermis), and may interchangeably used with the term "subdermal".

The phrase "subject in need thereof" as used herein refers to a patient that (i) will be administered at least one allograft, (ii) is receiving at least one allograft; or (iii) has received at least one allograft, unless the context and usage of the phrase indicates otherwise.

The term "substantially similar" as used herein means that a first value, aspect, trait, feature, number, or amount is of at least 70%, at least 75%, at least 80%, at least 85%, at least 90%, or at least 95% of a second value, aspect, trait, feature, number, or amount.

The term "surfactant", as used herein, refers to a surface-active agent that acts to reduce surface tension, which is the elastic like force existing in the surface of a body, e.g., a liquid, at an interface between two liquids, or that between a liquid and a solid, tending to minimize the area of the surface, caused by asymmetries in the intermolecular forces between surface molecules. Surfactants usually are organic compounds that contain both hydrophobic groups and hydrophilic groups, i.e., are amphiphilic. Surfactants can be anionic, cationic, nonionic, and zwitterionic. Exemplary surfactants include, but are not limited to, Triton®, Tween® 80, egg lecithin, vitamin E-t d-α-tocopheryl polyethylene glycol 1000 succinate (TPGS). Exemplary surfactants suitable for use in this invention are described in, for example, Becher, Emulsions Theory and Practice; Robert E. Krieger Publishing, Malabar, Fla. (1965), which is incorporated herein by reference.

The term "symptom" as used herein refers to a sign or an indication of disorder or disease, especially when experienced by an individual as a change from normal function, sensation, or appearance.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The term "tissuegenic" as used herein refers to a potential of a precursor cell to differentiate into a mature cell type and to regenerate a tissue. Exemplary tissuegenic cells include but are not limited to a stem cell, a progenitor cell, a precursor cell, a non-terminally differentiated cell, an immature cell anywhere along its maturation pathway up to the point of terminal differentiation, any cell type with differentiation potential or any combination thereof. The term "osteogenic" refers more specifically to cell differentiation and tissue regeneration with regard to bone. The term "adipogenic" refers more specifically to cell differentiation and tissue regeneration with regard to the adipose compartment. The term "chondrogenic" refers more specifically to cell differentiation and tissue regeneration with regard to cartilgae.

The term "transforming growth factor beta (TGFβ) signaling pathway" is used herein to refer to the signaling pathway is involved in many cellular processes in both the adult organism and the developing embryo including cell growth, cell differentiation, apoptosis, cellular homeostasis and other cellular functions. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vascularization" as used herein refers to a process of ingrowth of blood vessels and perivascular tissue within a growth-conductive matrix to support the deposition and adhesion of tissuegenic cells to effect tissue regeneration.

The terms "VEGF", "VEGF-1" or "vascular endothelial growth factor-1" are used interchangeably herein to refer to a cytokine that mediates numerous functions of endothelial cells including proliferation, migration, invasion, survival, and permeability. The term "VEGF-2" refers to a regulator for growth of vascular endothelial and smooth muscle cells. VEGF-2 stimulates the growth of human vascular endothelial cells but inhibits growth of human aortic smooth muscle cells induced by platelet-derived growth factor.

The term "viable" as used herein refers to having the ability to grow, expand, or develop; capable of living.

The term "% w/v" means concentration on a weight per volume basis.

The term "% w/w" means percent on a weight basis, i.e., a mass fraction.

The term "xenogeneic" as used herein refers to cells or tissues derived from individuals of different species, including, but not limited to, porcine, bovine, caprine, equine, canine, lapine, feline, and/or non-human mammals, such as, but not limited to, whale, and porpoise.

Implants Containing Decellularized Matrix

Embodiments of the present invention include implants having a soft tissue derived decelluarized (acellular) matrix, and, optionally, exogenous tissuegenic cells, growth factors, and a carrier. In some embodiments, the soft tissue comprises a single type of tissue. In some embodiments, the soft tissue comprises two or more types of tissue. According to some embodiments, the implant is in the form of a sheet. According to some embodiments, the implant is in particulate form. According to some embodiments, the implant is in the form of a paste, gel, or slurry. According to some embodiments, the implant is injectable. According to some embodiments, the implant is in a substantially dried, preformed shape. According to some embodiments, the implant is in a wet, pre-hydrated shape, which is a preformed shape that has not been dried or has been only partially dried. According to some embodiments, the implant is in a porous form. According to some embodiments, the implant is in a fibrous form. According to some embodiments, the implant fills a void in a tissue. According to some embodiments, the implant is in a bulking agent form.

According to some embodiments, the implant is a scaffold for the delivery of growth-inductive factors. According to some embodiments, the implant is growth-inductive. According to some embodiments, the implant is a scaffold for the delivery of cells. According to some embodiments, the implant is a scaffold for the migration of cells. According to some embodiments, the implant is a growth-conductive medium for the in-growth of tissue.

Shaped Acellular Tissue

According to some embodiments of the present invention, shaped decelluarized tissues (also referred to herein as "shaped acellular tissues") include three-dimensional shaped structures formed by a process in which acellular tissues are broken into smaller components (e.g., by milling or homogenization), then reformed into a three-dimensional structure that is different from the source tissue. All soft tissue types discussed in the present application may be used, either alone or in combination with one another. Tissue types can be allografts, autographs or xenografts. Suitable acellular tissues may be prepared using methods disclosed in the present application. Exemplary tissues suitable for forming shaped acellular tissues according to embodiments of the present invention include, without limitation, delipidated, decellularized adipose tissues, delipidated, decellularized fascia tissues, delipidated, decellularized dermal tissues, and combinations thereof.

According to some embodiments of the present invention, acellular tissues are mechanically or chemically manipulated into a particulate form, which can be resuspended in a liquid (e.g., water or a buffer solution) to form a flowable mass, such as a slurry. The flowable mass may be poured into a mold of a desired shape, in which it may form a porous or sponge-like shaped acellular tissue. According to some embodiments, the liquid and the acellular tissue particles are manipulated to form a putty, which can then be molded into a desired shape. According to some embodiments, the liquid and the acellular tissue particles are manipulated to form a paste. According to some embodiments, the liquid and the acellular tissue particles are manipulated to form a gel. According to some embodiments, the gel is formed during the process used to delipidize and decellularize the tissue.

According to some embodiments, the acellular tissue particles are mixed with a polymer to form a paste or a putty. According to some embodiments, the porous or sponge-like shaped acellular tissue is formed by drying the slurry, paste or gel. According to some embodiments, the porous or sponge-like shaped acellular tissue is formed by lyophilizing the slurry, paste or gel. According to some embodiments, the porous or sponge-like shaped acellular tissue is formed without drying or lyophilization, or with partial drying. According to some embodiments, the porosity of the shaped acellular tissue is controlled selecting the amount of liquid relative to the amount of particulate acellular tissue particles. According to some embodiments, the porous or sponge-like shaped acellular material is a solid piece that conforms to the shape of the mold after being dried.

According to some embodiments, the shaped acellular tissue is formed by one or more of the processes of molding a slurry, paste, or gel, machining a sponge-like shaped acellular tissue into a different shape, using three-dimensional ("3-D") printing to deposit a flowable slurry, paste, or gel into a three-dimensional shape, laminating pieces of shaped acellular tissue, and other technologies known for use in shaping three-dimensional objects from soft or flowable materials. According to some embodiments, shaped acellular materials may be provided in a pre-hydrated, lyophilized, cryopreserved, or frozen form.

According to some embodiments of the present invention, shaped acellular tissues may be used to surgically repair defects in a patient. According to some embodiments, shaped acellular tissues are used alone or after being seeded or cultured with appropriate exogenous tissuegenic cells. According to some such embodiments, the cells may be either autologous or allogeneic, or a mixture of autologous and allogeneic cells. According to some embodiments, the shaped acellular tissues are provided with substances such as growth factors, proteins, angiogenic factors and/or controlled-release nanotubes/nanoparticles that preferentially secrete factors for specific processes. According to some embodiments, the substances are added to the slurry, paste, or gel before the shaped acellular tissue is formed. According to some embodiments, the substances are added to the shaped acellular tissue after it is formed.

According to some embodiments of the present invention, the degradation profile of the shaped acellular tissue and a substance therein cause the substance to be released at an appropriate time for growth or healing of tissues to occur. An example of this would be to promote the formation of vasculature necessary to supply cells within or adjacent to a shaped acellular tissue with nutrients. In such an example, specific factors, cells, and other substances, if needed, may be provided at selected locations on the shaped acellular tissue to promote angiogenesis at the desired locations. Other factors may be included that do not promote angiogenesis, such that vasculature is formed only where is it desired. As a more specific example, the creation of a kidney using a shaped acellular tissue would include such factors and cells needed to preferentially create architecture for renal arteries, renal veins, a ureter, and other features of a functional kidney.

According to some embodiments of the present invention, the shaped acellular tissues have simple shapes. According to some embodiments, the shaped acellular tissues have complex shapes. According to some embodiments, the shaped acellular tissues have symmetrical shapes. According to some embodiments, the shaped acellular tissues have asymmetrical shapes. According to some embodiments, the shaped acellular tissues have shapes similar to the shapes of anatomical structures. According to some embodiments, the shaped acellular tissues have the shapes of anatomical organs. According to some embodiments, the shaped acellular tissues have an initial shape and can be reshaped prior to use.

According to some embodiments, the shaped acellular tissues are provided for ex vivo use. According to some embodiments, the shaped acellular tissues are provided for in vivo use (i.e., for implantation). According to some embodiments, the shaped acellular tissues have porosities customized for their intended use. According to some embodiments of the present invention, the shaped acellular tissues have pH customized for their intended use. According to some embodiments, the shaped acellular tissues include cross-linked collagen. According to some embodiments of the present invention, the shaped acellular tissues include cross-linked non-collagen components. According to some embodiments, the shaped acellular tissues have biological polymers that are cross-linked with non-biological (i.e., synthetic) polymers.

According to some embodiments of the present invention, a method of forming a shaped acellular tissue includes a step of scanning or imaging a portion of a patient's body (e.g., a portion of patient's face or other anatomical structure), then making shaped acellular tissues to replace those anatomical structures. In other embodiments, a shaped acellular tissue is made to restore the shape of an anatomical structure. In other embodiments, a shaped acellular tissue is made to provide a substitute for a missing anatomical structure.

According to some embodiments of the present invention, the shaped acellular tissue is formed, then cultured in vitro with exogenous cells. When the cells reach a sufficient number, the shaped acellular tissue is implanted for plastic, reconstructive or regenerative surgery or used in wound care procedures.

According to some embodiments of the present invention, the shaped acellular tissue is formed, then cultured in vitro with cells. When the cells reach a sufficient number, the composition is cryopreserved, and then reconstituted when needed for use.

According to an embodiment of the present invention, mesenchymal stem cells are harvested from a patient in need of a nasal graft, cultured onto a shaped acellular tissue resembling the patient's own nasal structure. After the cells have differentiated into a sufficient number of chondrocytes, the shaped acellular tissue can be provided to the patient as a viable graft.

According to an embodiment of the present invention, a shaped acellular tissue is provided in a lyophilized form. The lyophilized shaped acellular tissue is rehydrated in the operating room, where it may be combined with such substances as the patient's platelet-rich plasma (PRP), autologous cells such as those obtained from the patient's bone marrow or stromal vascular fraction (SVF) (e.g., SVF from adipose tissue obtained by liposuction), allogeneic cells such as those obtained from a cell bank (e.g., stem cells, progenitor cells or other cell types available from cell banks), or bone marrow and bone marrow components including bone marrow cells (both autologous and allogeneic).

According to an embodiment of the present invention, a shaped acellular tissue is provided in a pre-hydrated form. Such a pre-hydrated shaped acellular tissue does not require rehydration in the operating room. A pre-hydrated shaped acellular tissue may be combined with such substances as the patient's platelet-rich plasma (PRP), autologous cells such as those obtained from the patient's bone marrow or stromal vascular fraction (SVF) (e.g., SVF from adipose tissue obtained by liposuction), allogeneic cells such as those obtained from a cell bank (e.g., stem cells, progenitor cells or other cell types available from cell banks), or bone marrow and bone marrow components including bone marrow cells (both autologous and allogeneic).

Embodiments of the present invention include methods of making the various embodiments of shaped acellular tissues described above. Embodiments of such methods will be obvious to those having ordinary skill in the art and possession of the present disclosure.

Decellularized Matrix

According to one aspect, the described invention provides a decellularized matrix (also referred to herein as an "acellular matrix") derived from a biological tissue, and suitable for implantation into a patient. The decellularized matrix comprises ECM derived from one or more types of soft tissue from which unwanted cells and cell fragments have been removed. According to one embodiment, the acellular matrix is derived from a single type of soft tissue. According to one embodiment, the acellular matrix is derived from soft tissue comprising a first soft tissue and a second soft tissue which are different types of tissue which were attached when recovered from a donor and not intentionally separated before being subjected to process steps. According to one embodiment, the acellular matrix is derived from soft tissue comprising a first soft tissue and a second soft tissue which are different types of tissue which were attached when recovered from a donor and were separated from each other before being subjected to one or more process steps and recombined after being subjected to one or more process steps. According to one embodiment, the soft tissue is autologous to the patient. According to another embodiment, the soft tissue is allogeneic to the patient. According to yet another embodiment, the soft tissue is xenogeneic to the patient.

According to one embodiment, the tissue is selected from the group consisting of an adipose tissue, an amnion tissue, an artery tissue, a demineralized bone tissue, a cartilage tissue, a connective tissue, a chorion tissue, a colon tissue, a non-calcified dental tissue, a dermal tissue, a duodenal tissue, an endothelial tissue, an epithelial tissue, a fascial tissue, a gastrointestinal tissue, a gingival tissue, a growth plate tissue, an intervertebral disc tissue, an intestinal mucosal tissue, an intestinal serosal tissue, a ligament tissue, a liver tissue, a lung tissue, a mammary tissue, a membranous tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, other non-calcified tissues, and combinations thereof.

According to one embodiment, the source of the tissue is a mammalian donor. According to one embodiment, the source of the tissue is a human donor. According to one embodiment, the human donor is a living donor. According to another embodiment, is the human donor is a cadaveric donor. According to yet another embodiment, the tissue donor is the intended recipient of the acellular matrix.

Adipose Tissue

According to some embodiments, the tissue comprises an adipose tissue derived from an adipose-rich body region.

According to some embodiments, the adipose rich body region is selected from the group consisting of an abdomen, a hip, a hypodermal region of skin, an infrapatellar fat pad, a knee, a mammary organ, a thigh, and a combination thereof.

According to some embodiments, the tissue is an adipose tissue selected from the group consisting of a visceral adipose tissue, a hypodermal adipose tissue and, a combination thereof. According to some embodiments, the tissue is an adipose tissue comprising a visceral adipose tissue. According to some embodiments, the tissue is an adipose tissue comprising a subcutaneous adipose tissue.

According to one embodiment, the source of the tissue is a mammalian donor. According to some embodiments, the tissue is an adipose tissue derived from an adipose-rich body region of a human donor. According to some embodiments, the human donor is a cadaveric donor. According to some embodiments, the human donor is a living donor.

According to one embodiment, the tissue is an adipose tissue derived from an autologous adipose tissue. According to one embodiment, the tissue is an adipose tissue comprising an adipose tissue derived from an allogeneic adipose tissue. According to one embodiment, the tissue is an adipose tissue comprising an adipose tissue derived from a xenogeneic adipose tissue.

Cartilage Tissue

According to some embodiments, the tissue comprises a cartilage tissue selected from the group consisting of a hyaline cartilage tissue, a fibrocartilage tissue, an elastic cartilage tissue, and a combination thereof. According to some embodiments, the tissue comprises a hyaline cartilage tissue. According to some embodiments, the tissue comprises a fibrocartilage cartilage tissue. According to some embodiments, the tissue comprises an elastic cartilage tissue.

According to some embodiments, the tissue comprises a cartilage tissue derived from a cartilaginous organ or at least one fragment thereof.

According to some embodiments, the cartilaginous organ is selected from the group consisting of an articular cartilage organ, a bronchus, a growth plate, an intervertebral disc, a larynx, a meniscus, a nose, a trachea, and a combination thereof.

According to one embodiment, the source of the tissue is a mammalian donor. According to some embodiments, the tissue comprises a cartilage tissue derived from a human donor. According to some embodiments, the human donor is a cadaveric donor. According to some embodiments, the human donor is a living donor.

According to one embodiment, the tissue is a cartilage tissue derived from an autologous cartilage tissue. According to one embodiment, the tissue is a cartilage tissue derived from an allogeneic cartilage tissue. According to one embodiment, the tissue is a cartilage tissue derived from a xenogeneic cartilage tissue.

Non-Calcified Dental Tissue

According to some embodiments, the tissue comprises a non-calcified dental tissue. According to some such embodiments, the tissue comprises a dental pulp tissue.

According to some embodiments, the tissue comprises a dental pulp tissue derived from at least one tooth. According to some embodiments, the tissue comprises a dental pulp tissue derived from a plurality of teeth.

According to some embodiments, the tooth is selected from the group consisting of a deciduous tooth, a permanent tooth, and a combination thereof. According to some embodiments, the tooth is a deciduous tooth. According to some embodiments, the tooth is a permanent tooth.

According to one embodiment, the source of the tissue is a dental pulp tissue derived from a mammalian donor. According to some embodiments, the tissue is a dental pulp tissue derived from a human donor. According to some embodiments, the human donor is a cadaveric donor. According to some embodiments, the human donor is a living donor.

According to one embodiment, the tissue is an autologous dental pulp tissue. According to one embodiment, the tissue is an allogeneic dental pulp tissue. According to one embodiment, the tissue is a xenogeneic dental pulp tissue.

Epithelial Tissue

According to some embodiments, the tissue comprises an epithelial tissue selected from the group consisting of a cutaneous epithelial tissue, a mucous epithelial tissue, a serous epithelial tissue, and a combination thereof. According to some embodiments, the tissue comprises a basement membrane tissue.

According to some embodiments, the tissue comprises an epithelial tissue derived from an epithelial organ or at least one fragment thereof.

According to some embodiments, the epithelial tissue is selected from the group consisting of a gastrointestinal lining, an intestinal mucosal lining, an intestinal serosal lining, a pericardial lining, a peritoneal lining, a pleural lining, a reproductive lining, a respiratory lining, and a urinary lining.

According to some embodiments, the gastrointestinal lining is selected from the group consisting of a duodenum lining, an esophagus lining, an ileum lining, a jejunum lining, a large intestine lining, a mouth lining, a pharynx lining, a small intestine lining, a stomach lining, and a combination thereof.

According to some embodiments, the epithelial organ is selected from the group consisting of a gastrointestinal organ, a respiratory organ, a urological organ, and a combination thereof.

According to some embodiments, the gastrointestinal organ is selected from the group consisting of a duodenum, an esophagus, an ileum, a jejunum, a large intestine, a mouth, a gingiva, a small intestine, a stomach, and a combination thereof.

According to some embodiments, the respiratory organ is selected from the group consisting of a bronchii, a diaphragm, a heart, a larynx, a lung, a mouth, a nose, a pharynx, a trachea, and a combination thereof.

According to some embodiments, the urological organ is selected from the group consisting of an adrenal gland, an epididymis, a kidney, an ovary, a penis, a prostate gland, a seminal vesicle, a testes, a ureter, a urethra, a urinary bladder, a vas deferens, and a combination thereof.

According to some embodiments, the epithelial organ is selected from the group consisting of a duodenum, an esophagus, a heart, an ileum, a jejunum, a large intestine, a lung, a mouth, a gingiva, a pharynx, a small intestine, a skin, a stomach, and a combination thereof.

According to one embodiment, the source of the tissue is a mammalian donor. According to some embodiments, the tissue is an epithelial tissue derived from a human donor.

According to some embodiments, the human donor is a cadaveric donor. According to some embodiments, human donor is a living donor.

According to one embodiment, the tissue is an epithelial tissue derived from an autologous epithelial tissue. According to one embodiment, the tissue is an epithelial tissue derived from an allogeneic epithelial tissue. According to one embodiment, the tissue is an epithelial tissue derived from a xenogeneic epithelial tissue.

Fascial Tissue

According to some embodiments, the tissue comprises a fascial tissue selected from the group consisting of a superficial fascia, a deep fascia, a visceral fascia, and a combination thereof. The term "fascia" as used herein refers to a fibroareolar connective tissue lamellae distributed throughout the body surrounding delicate organs.

According to some embodiments, the tissue comprises a fascial tissue derived from a fascia-rich body part or at least one fragment thereof. According to some embodiments, the fascia-rich body part is selected from the group consisting of an arm, a back, an elbow, a foot, a hand, a head, a knee, a leg, a muscle, a neck, a skin, a thigh, a toe, a wrist, and a combination thereof.

According to some embodiments, the tissue comprises fascial tissue selected from the group consisting of a myofascia associated with a muscle, palmar fascia associated with a palm of a hand, plantar fascia associated with a sole of a foot, thoracolumbar fascia associated with a back, fascii lata associated with a thigh, tensor fascia lata associated with tendon tissue, and a combination thereof.

According to one embodiment, the source of the tissue is a mammalian donor. According to some embodiments, the tissue comprises a fascia tissue derived from a human donor. According to some embodiments, the human donor is a cadaveric donor. According to some embodiments, human donor is a living donor.

According to one embodiment, the tissue is a fascial tissue derived from an autologous fascia. According to one embodiment, the tissue is a fascial tissue derived from an allogeneic fascia. According to one embodiment, the tissue is a fascial tissue derived from a xenogeneic fascia.

Ligament Tissue

According to some embodiments, the tissue comprises a ligament tissue selected from the group consisting of a capsular ligament, an extra-capsular ligament, an intracapsular ligament, a cruciate ligament, and a combination thereof. The term "ligament" as used herein refers to a band or sheet of fibrous tissue connecting two or more bones, cartilages, or other structures, or serving as support for fasciae or muscles and a fold of peritoneum supporting any of the abdominal viscera According to some embodiments, the tissue comprises a ligament tissue derived from a ligament-rich body part or at least one fragment thereof. According to some embodiments, the ligament-rich body part is selected from the group consisting of an arm, an elbow, a foot, a hand, a head, a knee, a leg, a neck, a pelvis, a phalange, a thorax, a toe, a wrist, and a combination thereof.

According to some embodiments, the tissue comprises a ligament tissue derived from a ligament organ or a fragment thereof. According to some embodiments, the ligament organ is selected from the group consisting of a joint, a mouth, a patella, and a combination thereof.

According to one embodiment, the source of the tissue is a mammalian donor. According to some embodiments, the tissue comprises a ligament tissue derived from a human donor. According to some embodiments, the human donor is a cadaveric donor. According to some embodiments, the human donor is a living donor.

According to one embodiment, the tissue is a ligament tissue derived from an autologous ligament. According to one embodiment, the tissue is a ligament tissue derived from an allogeneic ligament tissue. According to one embodiment, the tissue is a ligament tissue derived from a xenogeneic ligament tissue.

Mammary Tissue

According to some embodiments, the tissue comprises a mammary tissue derived from a mammary organ or at least one fragment thereof.

According to one embodiment, the source of the tissue is a mammalian donor. According to some embodiments, the tissue is a mammary organ from a human donor. According to some embodiments, the human donor is a cadaveric donor. According to some embodiments, the human donor is a living donor.

According to one embodiment, the tissue is a mammary tissue derived from an autologous mammary organ. According to one embodiment, the tissue is a mammary tissue derived from an allogeneic mammary organ. According to one embodiment, the tissue is a mammary tissue derived from a xenogeneic mammary organ.

Muscle Tissue

According to some embodiments, the tissue comprises a muscle tissue selected from the group consisting of a cardiac muscle tissue, a skeletal muscle tissue, a smooth muscle tissue, and a combination thereof.

According to some embodiments, the tissue is a muscle tissue derived from a muscle tissue-rich organ or at least one fragment thereof.

According to some embodiments, the muscle tissue-rich organ is selected from the group consisting of a gastrointestinal organ, a skeletal organ, a heart, and a combination thereof.

According to one embodiment, the source of the tissue is a mammalian donor. According to some embodiments, the tissue comprises a muscle tissue derived from a human donor. According to some embodiments, the human donor is a cadaveric donor. According to some embodiments, human donor is a living donor.

According to one embodiment, the tissue comprises a muscle tissue derived from an autologous muscle tissue. According to one embodiment, the tissue comprises a muscle tissue derived from an allogeneic muscle tissue. According to one embodiment, the tissue comprises a muscle tissue derived from a xenogeneic muscle tissue.

Nerve Tissue

According to some embodiments, the tissue comprises a nerve tissue derived from a nerve tissue-rich organ or at least one fragment thereof.

According to some embodiments, the nerve tissue-rich organ is selected from the group consisting of a brain, a spinal cord, and a combination thereof.

According to one embodiment, the source of the tissue is a mammalian donor. According to some embodiments, the tissue is a nerve tissue derived from a human donor. According to some embodiments, the human donor is a cadaveric donor.

According to one embodiment, the tissue comprises a nerve tissue derived from an autologous nerve tissue. According to one embodiment, the tissue comprises a nerve tissue derived from an allogeneic nerve tissue. According to one embodiment, the tissue comprises a nerve tissue derived from a xenogeneic nerve tissue.

Placental Tissue

According to some embodiments, the tissue comprises a placental tissue selected from the group consisting of an amnion tissue, a chorion tissue, an umbilical cord tissue, and a combination thereof.

According to some embodiments, the tissue comprises a placental tissue derived from an isolated placental organ or at least one fragment thereof. According to some embodiments, the placental organ is selected from the group consisting of an amnion, a chorion, an umbilical cord, a placenta, and a combination thereof.

According to one embodiment, the tissue comprises a placental tissue derived from an autologous placental tissue. According to one embodiment, the tissue comprises a placental tissue derived from an allogeneic placental tissue. According to one embodiment, the tissue comprises a placental tissue derived from a xenogeneic placental tissue.

According to one embodiment, the tissue is an umbilical cord derived from an autologous umbilical cord. According to one embodiment, the tissue is an umbilical cord tissue derived from an allogeneic umbilical cord. According to one embodiment, the tissue is an umbilical cord tissue derived from a xenogeneic umbilical cord.

Skin Tissue

According to some embodiments, the tissue comprises a skin tissue selected from the group consisting of an epidermal tissue, a dermal tissue, a basement membrane tissue, and a combination thereof.

According to one embodiment, the source of the tissue is a mammalian donor. According to some embodiments, the skin tissue is derived from a human donor. According to some embodiments, the human donor is a cadaveric donor. According to some embodiments, the human donor is a living donor.

According to one embodiment, the tissue comprises a skin tissue derived from an autologous skin tissue. According to one embodiment, the tissue comprises a skin tissue derived from an allogeneic skin tissue. According to one embodiment, the tissue comprises a skin tissue derived from a xenogeneic skin tissue.

Vascular Tissue

The term "vasculature" or "vascular tissue" as used herein refers to the vascular network of a part of the body and its arrangement. The vascular network comprises blood vessels, i.e. any vessel conveying blood: arteries, arterioles, capillaries, venules, and veins. An artery is a relatively thick-walled, muscular pulsating vessel conveying blood away from the heart. A vein is a blood vessel carrying blood toward the heart. Both arteries and veins comprise three layers: the tunica intima, the tunica media and the tunica adventitia. Veins also contain valves that prevent blood backflow. The tunica intima, a single layer of simple squamous endothelial cells glued by a polysaccharide intercellular matrix, surrounded by a thin layer of subendothelial connective tissue interlaced with a number of circularly arranged elastic bands called the internal elastic lamina; a tunica media, comprising circularly arranged elastic fiber, connective tissue, polysaccharide substances, and a thick elastic band called the external elastic lamina, and the tunica adventitia, entirely made of connective tissue. Capillaries comprise a layer of endothelium and connective tissue.

According to some embodiments, the tissue comprises vascular tissue. According to some embodiments, the vascular tissue is derived from a mammalian donor. According to some embodiments, the vascular tissue is derived from a human donor. According to some embodiments, the vascular tissue is derived from a cadaveric donor. According to some embodiments, the vascular tissue is derived from a living donor.

According to one embodiment, the tissue is a vascular tissue derived from an autologous vascular tissue. According to one embodiment, the tissue is a vascular tissue derived from an allogeneic vascular tissue. According to one embodiment, the tissue is a vascular tissue derived from a xenogeneic vascular tissue.

Matrix Seeded with Tissuegenic Cells

According to some embodiments of the present invention, the matrix is seeded with at least one viable population of tissuegenic cells. The at least one viable population of tissuegenic cells may be derived from one or more of the tissue types from which the matrix may be derived. Such tissue types are identified above with respect to the discussion of the acellular matrix. According to some embodiments the source tissue type for the matrix and the viable population of tissuegenic cells is the same. According to some embodiments the source tissue type for the matrix and the viable population of tissuegenic cells is different. According to some embodiments the source donor for the matrix and the viable population of tissuegenic cells is the same. According to some embodiments the source donor for the matrix and the viable population of tissuegenic cells is different.

According to one embodiment, the at least one viable population of tissuegenic cells is selected from the group consisting of a viable population of pluripotent stem cells, a viable population of mesenchymal stem cells, a viable population of tissue-derived stem cells, a viable population of tissue-derived progenitor cells, a viable population of precursor cells, a viable population of non-terminally differentiated cells, a viable population of immature cells anywhere along the cell's maturation pathway up to the point of terminal differentiation, a viable population of any cell type with differentiation potential or any combination thereof.

According to one embodiment, the at least one viable population of tissuegenic cells secretes at least one growth-inductive factor.

According to one embodiment, the at least one viable population of tissuegenic cells can be reprogrammed to at least one viable induced pluripotent stem cell (iPSC) population.

According to one embodiment, the at least one viable population of tissuegenic cells is capable of differentiating into cells of at least one embryonic lineage. According to one embodiment, the embryonic lineage is selected from the group consisting of an ectodermal lineage, a mesodermal lineage and an endodermal lineage.

According to one embodiment, the at least one viable population of tissuegenic cells is capable of regenerating a target tissue. According to one embodiment, the target tissue is selected from the group consisting of an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a gastrointestinal tissue, a gingival tissue, a growth plate tissue, an intervertebral disc tissue, an intestinal mucosal tissue, an intestinal serosal tissue, a kidney tissue, a ligament tissue, a liver tissue, a lung tissue, a meniscal tissue, a muscle tissue, a nerve tissue, an ovarian tissue, a pancreatic tissue, a parenchymal organ tissue, a pericardial tissue, a periosteal tissue, a peritoneal tissue, a skin tissue, a spleen tissue, a synovial tissue, a tendon tissue, a testes tissue, a urological tissue, a vascular tissue, a vein tissue, and a combination thereof.

According to one embodiment, the at least one viable population of tissuegenic cells is capable of differentiating into a target tissue cell lineage. According to one embodiment, the target tissue cell lineage is selected from the group consisting of an adipose cell lineage, an amnion cell lineage, an artery cell lineage, a bone cell lineage, a cartilage cell lineage, a dental cell lineage, a dermal cell lineage, a duodenal cell lineage, an endothelial lineage, an epithelial cell lineage, a gastrointestinal cell lineage, a growth plate cell lineage, an intervertebral disc cell lineage, an intestinal mucosal cell lineage, an intestinal serosal cell lineage, a kidney cell lineage, a ligament cell lineage, a liver cell lineage, a lung cell lineage, a meniscal cell lineage, a muscle cell lineage, a nerve cell lineage, an ovarian cell lineage, a pancreatic cell lineage, a parenchymal organ cell lineage, a pericardial cell lineage, a periosteal cell lineage, a peritoneal cell lineage, a skin cell lineage, a spleen cell lineage, a synovial cell lineage, a tendon cell lineage, a testes cell lineage, a urological cell lineage, a vascular cell lineage, a vein cell lineage, and a combination thereof.

According to one embodiment, the at least one viable population of tissuegenic cells derived from adipose tissue differentiates along an osteogenic lineage. According to one embodiment, the at least one viable population of tissuegenic cells derived from adipose tissue differentiates along an adipogenic lineage. According to one embodiment, the at least one viable population of tissuegenic cells derived from adipose tissue differentiates along a chondrogenic lineage. According to one embodiment, the at least one viable population of tissuegenic cells derived from adipose tissue differentiates along a neurogenic lineage. According to one embodiment, the at least one viable population of tissuegenic cells derived from adipose tissue differentiates along a myogenic lineage.

According to one embodiment, the at least one viable population of tissuegenic cells is capable of migrating from or to the at least one growth-conductive matrix. According to one embodiment, the at least one viable population of tissuegenic cells comprises a viable nonexpanded population of tissuegenic cells. According to one embodiment, the at least one viable population of tissuegenic cells comprises a viable expanded population of tissuegenic cells. According to some embodiments, the at least one viable population of tissuegenic cells adherent to and resident in the endogenous milieu of the growth conductive matrix is immune privileged. The term "immune privileged" as used herein refers to the characteristic of tissuegenic cells by which there is no induction of an immune response upon transplantation of such cells.

Frequency of Tissuegenic Cells

According to some embodiments, the at least one viable population of tissuegenic cells comprise a relative frequency substantially similar to the total cell population of the growth-conductive matrix. According to some embodiments, the at least one viable population of tissuegenic cells comprise a relative frequency substantially higher than the total cell population of the growth-conductive matrix. According to some embodiments, the at least one viable population of tissuegenic cells comprise a relative frequency substantially less than the total cell population of the growth-conductive matrix.

According to some embodiments, the at least one viable population of tissuegenic cells comprise at least about at least about 1,000 tissuegenic cells per cubic centimeter (cc) of implant. According to some embodiments, the at least one viable population of tissuegenic cells comprise at least about at least about 5,000 tissuegenic cells per cc of implant. According to some embodiments, the at least one viable population of tissuegenic cells comprise at least about at least about 10,000 tissuegenic cells per cc of implant. According to some embodiments, the at least one viable population of tissuegenic cells comprise at least about at least about 20,000 tissuegenic cells per cc of implant. According to some embodiments, the at least one viable population of tissuegenic cells comprise at least about at least about 30,000 tissuegenic cells per cc of implant. According to some embodiments, the at least one viable population of tissuegenic cells comprise at least about at least about 40,000 tissuegenic cells per cc of implant. According to some embodiments, the at least one viable population of tissuegenic cells comprise at least about at least about 50,000 tissuegenic cells per cc of implant.

Growth-Inductive Component

According to some embodiments, the matrix further comprises at least one growth-inductive component. According to some such embodiments, the growth-inductive component is at least one cytokine. According to some such embodiments, the at least one growth-inductive component comprises at least one growth factor. According to some such embodiments, the at least one growth factor is fibroblast growth factor-2 (FGF-2). According to some such embodiments, the at least one growth factor is fibroblast growth factor-5 (FGF-5). According to some such embodiments, the at least one growth factor is insulin-like growth factor-1 (IGF-1). According to some such embodiments, the at least one growth factor is transdermal growth factor-beta (TGF-β). According to some such embodiments, the at least one growth factor is bone morphogenic protein-2 (BMP-2). According to some such embodiments, the at least one growth factor is bone morphogenic protein-7 (BMP-7). According to some such embodiments, the at least one growth factor is platelet derived growth factor (PDGF). According to some such embodiments, the at least one growth factor is vascular endothelial growth factor (VEGF). According to some such embodiments, the at least one growth factor is neural epidermal growth-factor-like 1 (NELL-1).

According to some such embodiments, the at least one growth-inductive component is a demineralized bone matrix (DBM). According to some such embodiments, the DBM is demineralized autologous bone. According to some such embodiments, the DBM is demineralized allogeneic bone. According to some such embodiments, the DBM is demineralized xenogenic bone. According to some such embodiments, the DBM is derived by demineralization of cancellous bone. According to some such embodiments the DBM is derived by demineralization of cortical bone (i.e., demineralized cortical bone or DCB). According to some such embodiments, DBM has a residual mineral content of 8% or less (w/w). According to some such embodiments, DBM has a residual mineral content of 5% or less (w/w). According to some such embodiments, DBM has a residual mineral content of 2% or less (w/w). According to some such embodiments, DBM has a residual mineral content of 1% or less (w/w). According to some such embodiments, DBM has a residual mineral content of 0.5% or less (w/w). According to some such embodiments, DBM consists essentially of collagen, non-collagen proteins such as growth factors, and other nonmineral substances found in the original bone, although not necessarily in the original quantities. According to some such embodiments, the demineralized bone is in the form of demineralized bone fibers (e.g., elongated particles of DBM having minimum dimensions on the order of one micron to hundreds of microns and a maximum dimension on the order of one millimeter to hundreds of millimeters).

According to some embodiments, the implant further comprises at least one cryopreservative. According to some such embodiments, the at least one cryopreservative is a solution. According to some such embodiments, the cryopreservative is dimethylsulfoxide (DMSO). According to some such embodiments, the cryopreservative is basal media solution comprising about 5% DMSO. According to some such embodiments, the cryopreservative is basal media solution comprising about 10% DMSO. According to some such embodiments, the cryopreservative is basal media solution comprising about 15% DMSO. According to some such embodiments, the cryopreservative is fetal bovine serum comprising about 5% DMSO. According to some such embodiments, the cryopreservative is fetal bovine serum comprising about 10% DMSO. According to some such embodiments, the cryopreservative is a human serum comprising about 15% DMSO. According to some such embodiments, the cryopreservative is human serum comprising about 5% DMSO. According to some such embodiments, the cryopreservative is human serum comprising about 10% DMSO. According to some such embodiments, the cryopreservative is ethylene glycol. According to some such embodiments, the cryopreservative is propylene glycol. According to some such embodiments, the cryopreservative is glycerol.

Method of Fabricating an Acellular Soft Tissue-Derived Matrix

Referring to FIG. 1, according to another aspect, the described invention provides a method of fabricating an implant, the method comprising one or more of the steps of:

(a) isolating a sample of a soft tissue from its source;

(b) pre-processing the soft tissue;

(c) delipidizing the soft tissue;

(d) decellularizing the soft tissue;

(e) disinfecting the soft tissue;

(f) post-processing the soft tissue; and (g) packaging the soft tissue.

In various embodiments of the disclosed method, some of the aforesaid steps may be omitted, the order of the steps may be varied, or additional steps may be provided. The "soft tissue" of the method may be the soft tissue in the form isolated from the source, the pre-processed soft tissue, the delipidized soft tissue, the decellularized (or acellular) soft tissue, the disinfected soft tissue, the post-processed soft tissue, or the packaged soft tissue. Furthermore, the sample of soft tissue may be a single type of soft tissue, or comprise two or more types of soft tissues. Embodiments of the disclosed method are discussed further hereinbelow, and exemplary embodiments are presented.

1. Isolating Step (a): Isolating a Sample of a Soft Tissue from its Source.

According to some embodiments, isolating step (a) comprises excising the sample of desired soft tissue from its source. According to some embodiments, isolating step (a) comprises removing the sample of desired soft tissue from its source. According to some embodiments, isolating step (a) comprises aspirating the sample of desired soft tissue from its source. According to some embodiments, isolating step (a) comprises recovering the sample of desired source tissue from its source.

According to some embodiments, isolating step (a) comprises separating the sample of desired soft tissue from adjacent or attached tissues of a different type than the desired soft tissue. According to some embodiments, isolating step (a) comprises cutting the adjacent tissues from the sample of desired soft tissue. According to some embodiments, isolating step (a) comprises pulling the adjacent tissues away from the sample of desired soft tissue. According to some embodiments, isolating step (a) comprises scraping the adjacent tissues from the sample of desired soft tissue. According to some embodiments, isolating step (a) comprises separating the adjacent tissues from the sample of desired soft tissue by differential settling of the desired soft tissue and adjacent tissues in a liquid medium.

According to some embodiments, the desired soft tissue is a non-calcified tissue from the mammalian body. According to some embodiments, the desired soft tissue includes one or more types of tissue such as, without limitation, an adipose tissue, an amnion tissue, an artery tissue, a cartilage tissue, a connective tissue, a chorion tissue, a colon tissue, a non-calcified dental tissue, a dermal tissue, a duodenal tissue, an endothelial tissue, an epithelial tissue, a fascial tissue, a gastrointestinal tissue, a gingival tissue, a growth plate tissue, an intervertebral disc tissue, an intestinal mucosal tissue, an intestinal serosal tissue, a ligament tissue, a liver tissue, a lung tissue, a mammary tissue, a membranous tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, other non-calcified tissues, and combinations thereof.

The sample of soft tissue may comprise a single type of soft tissue, or two or more types of soft tissues. According to some embodiments, the sample of soft tissue comprises a single type of tissue. According to some embodiments, the sample of soft tissue comprises a first soft tissue and a second soft tissue which are different types of tissue and which are attached to each other when recovered. In some embodiments wherein the sample of soft tissue comprises first and second soft tissues which are different types of tissue and which are attached to each other when recovered, the sample of soft tissue is subjected to process steps together without intentional separation of the first and second soft tissues from each other (see, e.g., FIG. 1).

According to one embodiment, the source of the desired soft tissue is a mammalian donor. According to one embodiment, the source of the desired soft tissue is a human donor. According to one embodiment, the human donor is a living donor. According to another embodiment, is the human donor is a cadaveric donor. According to yet another embodiment, the tissue donor is the intended recipient of the acellular matrix.

According to one embodiment, the source of the desired soft tissue is a frozen source and the isolating step (a) includes a step of thawing the source.

According to some embodiments, isolating step (a) is performed at a temperature of about 25° C. According to some embodiments, isolating step (a) is performed at a temperature of about 4° C. to about 10° C. According to some embodiments, isolating step (a) is performed at an ambient temperature.

According to some embodiments, isolating step (a) comprises reducing the bioburden of the soft tissue before it is isolated. According to some embodiments, isolating step (a) comprises rinsing with a liquid prior to reduce bioburden levels on the surface of the tissue. According to some embodiments, the liquid comprises phosphate buffered saline (PBS). According to some embodiments, the liquid comprises acetic acid. According to some embodiments, the liquid comprises peracetic acid.

2. Pre-Processing Step (b): Pre-Processing the Sample of Soft Tissue.

According to some embodiments, pre-processing step (b) includes size reduction of the sample of soft tissue. According to some embodiments, pre-processing step (b) comprises cutting the sample of soft tissue into strips. According to some embodiments, pre-processing step (b) comprises slicing the sample of soft tissue. According to some embodiments, pre-processing step (b) comprises cutting the sample of soft tissue into chunks. According to some embodiments, pre-processing step (b) comprises mincing the sample of soft tissue. According to some embodiments, pre-processing step (b) comprises grinding the sample of soft tissue. According to some embodiments, the sample of soft tissue is ground using a coarse plate. According to some embodiments, the sample of soft tissue is ground using a fine plate. According to some embodiments, separating step (b) comprises milling the sample of desired soft tissue. According to some embodiments, pre-processing step (b) comprises homogenizing the sample of soft tissue. According to some embodiments, pre-processing step (b) comprises homogenizing the sample of soft tissue. According to some embodiments, pre-processing step (b) comprises homogenizing the sample of soft tissue and centrifuging the homogenized sample of soft tissue. According to some embodiments, pre-processing step (b) comprises separating components of the sample of soft tissue by differential settling of the components of the soft tissue. According to some embodiments, multiple pre-processing steps are performed. For example, one, or two, or more cycles or stages of size reduction techniques may be employed, such as for example without limitation, cutting, slicing, mincing, grinding, or combinations thereof.

Figure 2:
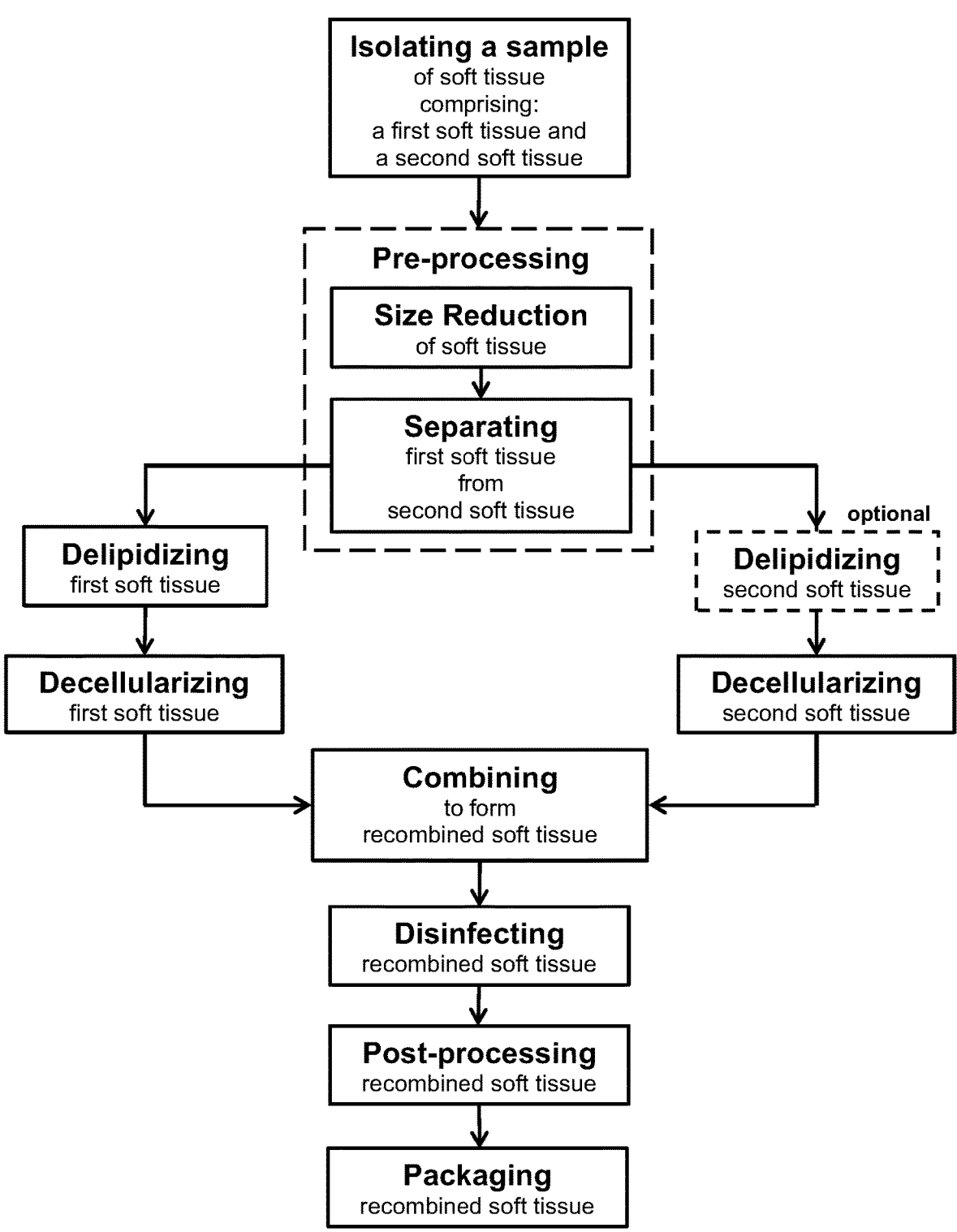
FIG. 2 is a schematic flowchart illustrating another exemplary embodiment of the process of preparing an acellular soft tissue-derived matrix in which the isolated soft tissue comprises two different types of tissue, and the process comprises separating the first and second soft tissues, decellularizing them independently, and then combining them for further processing together.
Figure 3:
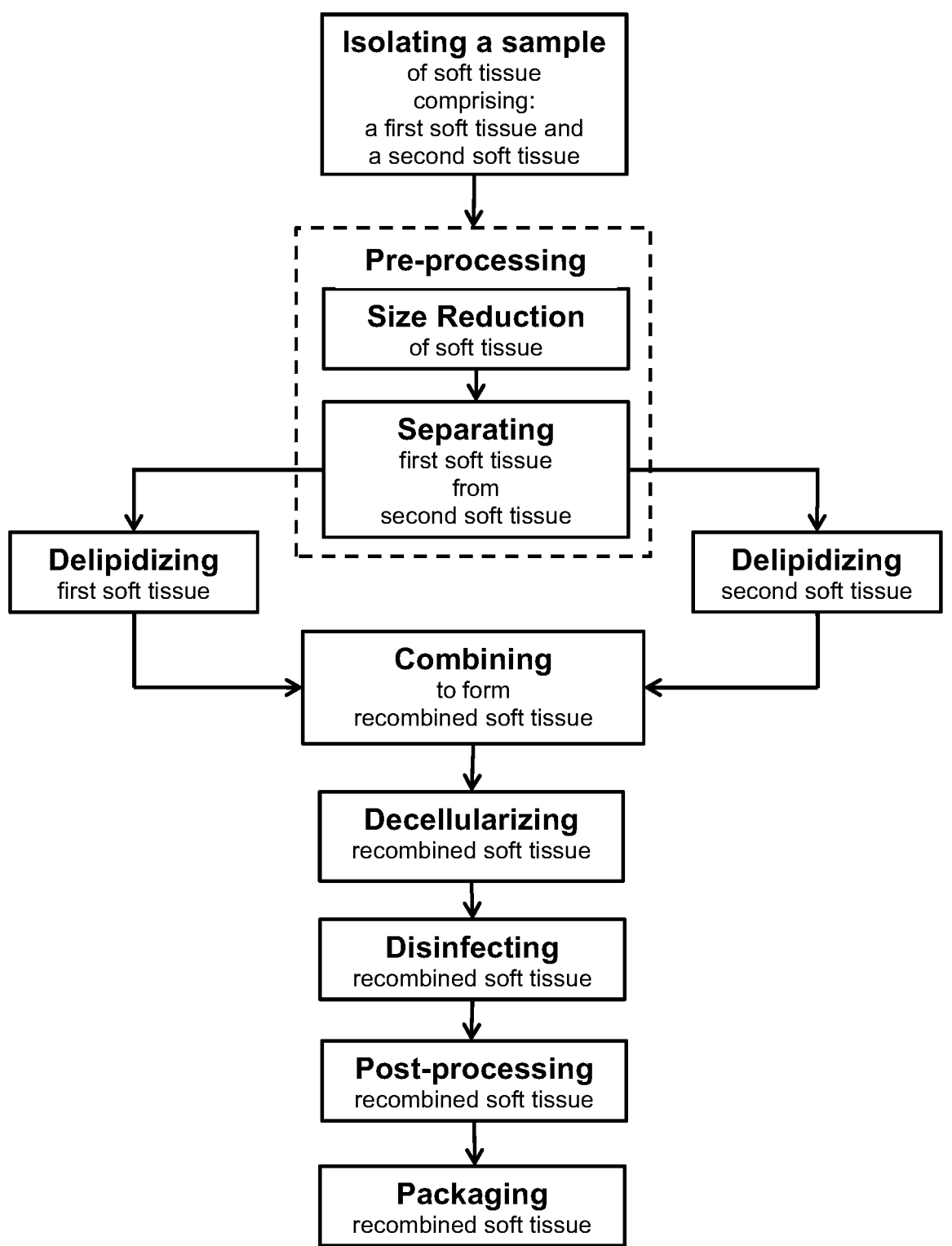
FIG. 3 is a schematic flowchart illustrating still another exemplary embodiment of the process of preparing an acellular soft tissue-derived matrix in which the isolated soft tissue comprises two different types of tissue, and the process comprises separating the first and second soft tissues, subjecting each of them independently to one or more process steps, combining the first and second soft tissues, and then decellularizing them together.

As shown schematically in FIGS. 2 and 3, in some embodiments in which the sample of soft tissue comprises first and second soft tissues which are different types of tissue and which are attached to each other when recovered, the step of pre-processing (b) may comprise separating the first and second soft tissues from each other. In some such embodiments, each of the first and second soft tissues are subjected separately and independently to further process steps, where "independently" means that the one or more process steps may be but are not necessarily the same type of process step. In some embodiments, in which first and second soft tissues of different types of tissue are separated from each other and subjected separately and independently to further process steps, the process further comprises the step of combining the first and second soft tissues to form a recombined soft tissue, and performing one or more process steps on the recombined soft tissue. Moreover, it should be understood that combining the first and second soft tissues may be performed at any time during the process, including before, during or after any of the process steps, including without limitation, delipidizing step (c), decellularizing step (d), or disinfecting step (e).

For example, as shown schematically in FIG. 2, in one exemplary embodiment, in which first and second soft tissues of different types of tissue are separated from each other, the process may comprise delipidizing and then decellularizing the first soft tissue, independently decellularizing the second soft tissue, then combining the first and second tissues to form a recombined soft tissue, followed by subjecting the recombined soft tissue to further process steps, such as without limitation disinfecting, post-processing, and packaging. As shown schematically in FIG. 3, in another exemplary embodiment, in which first and second soft tissues of different types of tissue are separated from each other, the process may comprise delipidizing the first soft tissue, independently homogenizing and centrifuging the second soft tissue, then combining the first and second tissues to form a recombined soft tissue, decellularizing the recombined soft tissue, and subjecting the recombined soft tissue to further process steps, such as without limitation disinfecting, post-processing, and packaging.

In some embodiments, the step of combining the first and second soft tissues comprises combining the first and second soft tissues in a predetermined ratio of first soft tissue: second soft tissue, based on the total weight of the first and second soft tissues (i.e., a predetermined weight ratio). Surprisingly and unexpectedly, it has been discovered that where the first soft tissue is adipose tissue and the second soft tissue is fascia tissue, the predetermined ratio may determine the degree of volume retention provided by the acellular matrix after passage of a minimum period of time from implantation of the acellular matrix in a subject. For example without limitation, the predetermined ratio of first soft tissue:second soft tissue may be at least about 4:1, or at least about 3:1, or at least about 2:1, or at least about 1:1, or at least about 1:2, or at least about 1:3, or at least about 1:4, or in a range of from about 99:1 to about 1:99, or in a range of from about 95:1 to about 1:95, or in a range of from about 90:1 to about 1:90, or in a range of from about 5:1 to about 1:5, or in a range of from about 4:1 to about 1:4, or in a range of from about 3:1 to about 1:4, or in a range of from about 1:1 to about 1:4, or in a range of from about 1:2 to about 1:4, or even in a range from about 1:3 to about 1:4, on a weight basis, based on the total weight of the first and second soft tissues. Additionally, for example without limitation, the minimum period of time from implantation may be at least 3 weeks, such as at least 6 weeks, such as at least 10 weeks, or such as at least 12 weeks. In some embodiments, the minimum period of time from implantation may be at least 3 months, or at least 6 months, or at least 12 months, or even greater.

More particularly, the greater the proportion of fascia tissue in the sample of soft tissue from which the acellular matrix is derived, the greater the degree of volume retention that will be achieved after the passage of time from implantation. For example, after passage of a particular period of time from implantation in a subject, an acellular matrix derived from a sample of soft tissue having a ratio of adipose tissue:fascia tissue of 1:4 (80 wt % fascia) will provide a greater degree of volume retention, than an acellular matrix derived from a sample of soft tissue having a ratio of adipose tissue:fascia tissue of 1:3 (75 wt % fascia), which will in turn provide a greater degree of volume retention than an acellular matrix derived from a sample of soft tissue having a ratio of adipose tissue:fascia tissue of 1:2, which will in turn provide a greater degree of volume retention than an acellular matrix derived from a sample of soft tissue having a ratio of adipose tissue:fascia tissue of 1:1. It is within the ability of persons of ordinary skill to select a desired degree of volume retention depending upon the subject and the particular treatment being applied to that subject using such an adipose-fascia acellular matrix for implantation.

Traditionally, it is understood that soft tissue derived acellular matrices degrade with the passage of time after implantation in a subject and are absorbed by the surrounding tissues of the subject. Implanting acellular matrices may be performed for any of various reasons as mentioned above, such as without limitation, to increase bulk, modify the shape or contour of body features, replace or supplement missing or damaged tissue, supplement existing tissue, provide a stimulus to host tissue, etc. In such cases, the beneficial effect of implanting the acellular matrix is temporary due to the degradation and absorption of the acellular matrix, which then requires repeated, periodic implantation of additional portions of acellular matrix. Where it is desired to maximize the volume retention over a 10 or 12 week period of time (or even longer such as 6 months, 12 months, or even longer), the adipose tissue and fascia tissue should be combined in a predetermined ratio in a range of from about 1:1 to about 1:99 for adipose tissue:fascia tissue and the resulting recombined soft tissue subjected to further processing steps such as disinfection, shaping and packaging. Additionally, it is noted that implantation of matrices derived from fascia tissue, without any adipose combined therewith (i.e., 100 wt % fascia matrices), will maximize the volume retention after passage of a minimum period of time after implantation, such as a 3, 10 or 12 week period or time, or even after 6 months, or after 12 months, or even longer. Of course, as will be understood by persons of ordinary skill in the relevant art, the benefits provided by the adipose tissue derived component of such acellular matrices (i.e., adipogenesis, providing growth factors, etc.) will be lessened as the proportion of adipose tissue is decreased. Accordingly, depending on the particular procedure and purpose (i.e., condition being treated or desired result), practitioners will need to balance and prioritize the desired effects and benefits provided by each of the adipose- and fascia-derived components of the acellular matrices when selecting the predetermined ratio. Thus, methods for increasing, enhancing, or improving volume retention comprise implanting, in, on or proximate to a region to be treated in a subject, an acellular soft tissue-derived matrix which comprises adipose derived matrix and fascia derived matrix, wherein the fascia derived matrix is present in a proportion of from about 1% to about 100%, by weight, based on the total weight of the adipose derived and fascia derived matrices, as compared to an acellular soft tissue-derived matrix comprising 0% fascia derived matrix. The region to be treated may be any tissue site at which replacement or augmented tissue volume is reasonably expected to be beneficial, such as, for example without limitation, a tissue site comprising a wound, atrophy, disease, loss, or other condition susceptible to healing, repair, reconstruction, etc., or a tissue site selected for cosmetic or reconstructive surgery.

Additionally, acellular fascia-derived matrices provide enhanced wound healing properties when implanted in, on or proximate to a wound site having wounded (e.g., damaged, diseased, or missing) tissue. Accordingly, in addition to 100 wt % fascia acellular matrices, combined adipose-fascia acellular matrices as described herein have increased wound healing benefits as the proportion of fascia increases in such adipose-fascia acellular matrices, the wound healing benefits increase (i.e., shortened healing time, more complete tissue repair and regeneration with less scaring and adhesions). Accordingly, methods for increasing, enhancing, or improving wound healing comprise implanting, in or proximate to a wound site in a subject, an acellular soft tissue-derived matrix which comprises adipose derived matrix and fascia derived matrix, wherein the fascia derived matrix is present in a proportion of from about 1% to about 100%, by weight, based on the total weight of the adipose derived and fascia derived matrices, as compared to an acellular soft tissue-derived matrix comprising 0% fascia derived matrix.

The ability to select a predetermined ratio of first and second soft tissues of different tissue types, such as adipose and fascia tissues, to include in the soft tissue derived acellular matrices and, thereby, select and control the degree of post implantation volume retention and/or improved wound healing is predicated upon the ability to successfully and sufficiently separate the first and second tissues, which has historically been difficult to accomplish. The techniques and processes disclosed herein, such as Examples 7, 8, 9 and 11, provide persons of ordinary skill with suitable processes for successfully and sufficiently accomplishing such separation of types of tissue normally recovered in a natural, attached state, thereby enabling the combination of such tissue types in particular, predetermined ratios as described above.

According to some embodiments, pre-processing step (b) is performed at a temperature of about 25° C. According to some embodiments, pre-processing step (b) is performed at a temperature of about 4° C. to about 10° C. According to some embodiments, pre-processing step (b) is performed at an ambient temperature. According to some embodiments, pre-processing step (b) is performed at a temperature greater than an ambient temperature. According to some embodiments, pre-processing step (b) is performed at a physiological temperature of a living mammal. According to some embodiments, pre-processing step (b) is performed at a temperature of about 37° C.

3. Delipidizing Step (c): Delipidizing the Sample of Soft Tissue.

According to some embodiments, delipidizing step (c) is a step of removing lipids from the sample of soft tissue. Some disruption of cellular membranes and removal of cells may also occur. According to some embodiments, delipidizing step (c) comprises removing some of the lipids native to the soft tissue. According to some embodiments, delipidizing step (c) comprises removing most (i.e., at least 51% (w/w), based on the total weight of the lipids naturally in the tissue) of the lipids native to the soft tissue. According to some embodiments, delipidizing step (c) comprises removing substantially all (i.e., at least 95% (w/w), based on the total weight of the lipids naturally in the tissue) of the lipids native to the soft tissue. According to some embodiments, delipidizing step (c) disrupts cellular membranes of cells resident in the soft tissue. According to some embodiments, delipidizing step (c) removes cellular components from the soft tissue. According to some embodiments, delipidizing step (c) is performed after decellularization step (d). According to some embodiments, multiple delipidizing steps are performed. According to some embodiments, delipidizing step (c) is not performed.

According to some embodiments, delipidizing step (c) comprises contacting the soft tissue with a liquid so as to separate lipids from the soft tissue. According to some embodiments, delipidizing step (c) comprises immersing the soft tissue in the liquid. According to some embodiments, delipidizing step (c) comprises soaking the soft tissue in the liquid. According to some embodiments, delipidizing step (c) comprises mechanically agitating the soft tissue in the liquid. According to some embodiments, delipidizing step (c) comprises blending the soft tissue in the liquid. According to some embodiments, blending includes a step of mixing the soft tissue in the liquid under conditions of high shear. According to some embodiments, blending includes a step of mixing the soft tissue in the liquid using at least one rotating blade rotating at a rate in the range of from about 1,000 rpm to about 20,000 rpm. According to some embodiments, delipidizing step (c) comprises homogenizing the soft tissue in the liquid. According to some embodiments, homogenization includes a step of mixing the soft tissue in the liquid such that the tissue is evenly distributed throughout the liquid.

According to some embodiments, the liquid is water. According to some embodiments, the liquid is an organic solvent. According to some embodiments, the liquid is a mixture of organic solvents. According to some embodiments, the liquid is a mixture of one or more organic solvents and water. According to some embodiments, the organic solvent is selected from a group consisting of a paraffin, an aromatic hydrocarbon, a cyclic hydrocarbon, a chlorinated hydrocarbon, a fluorinated hydrocarbon, a chlorinated methane, a fluorinated methane, an alcohol, an ether, a ketone, an organic acid, an aldehyde, an ester, and combinations thereof. According to some embodiments, the organic solvent has one carbon atom. According to some embodiments, the organic solvent has two carbon atoms. According to some embodiments, the organic solvent has three carbon atoms. According to some embodiments, the organic solvent has four carbon atoms. According to some embodiments, the organic solvent has five carbon atoms. According to some embodiments, the organic solvent has six carbon atoms.

According to some embodiments, the liquid includes an organic acid. According to some embodiments, the liquid includes a mineral acid. According to some embodiments, the liquid includes an organic base. According to some embodiments, the liquid includes a mineral base. According to some embodiments, the liquid includes an organic salt. According to some embodiments, the liquid contains a mineral salt.

According to some embodiments, delipidizing step (c) comprises recovering a lipid layer, which may be a mixture of lipid and the aforesaid liquid, from the soft tissue. According to some embodiments, delipidizing step (c) comprises recovering the lipid layer by differential settling. According to some embodiments, delipidizing step (c) comprises recovering the lipid layer by centrifugation. According to some embodiments, delipidizing step (c) comprises recovering the lipid layer by filtration. According to some embodiments, delipidizing step (c) comprises recovering the lipid layer by decantation.

According to some embodiments, delipidizing step (c) comprises recovering the delipidized tissue. According to some embodiments, delipidizing step (c) comprises recovering the delipidized tissue by differential settling. According to some embodiments, delipidizing step (c) comprises recovering the delipidized tissue by centrifugation. According to some embodiments, delipidizing step (c) comprises recovering the delipidized tissue by filtration. According to some embodiments, delipidizing step (c) comprises recovering the delipidized tissue by decantation.

According to some embodiments, delipidization step (c) comprises contacting the soft tissue with a supercritical fluid (e.g., supercritical carbon dioxide). According to some embodiments, delipidization step (c) comprises recovering the lipid by evaporation of the supercritical fluid.

According to some embodiments, delipidization step (c) is performed at a temperature of about 25° C. According to some embodiments, delipidization step (c) is performed at an ambient temperature. According to some embodiments, delipidization step (c) is performed at a temperature greater than an ambient temperature. According to some embodiments, delipidization step (c) is performed at a physiological temperature of a living mammal. According to some embodiments, delipidization step (c) is performed at a temperature of about 30° C. or higher, or about 40° C. or higher, or even about 50° C. or higher.

According to some embodiments, the delipidization step is performed under increased hydrostatic pressure. According to some embodiments, a portion of the delipidization step is performed under increased hydrostatic pressure. According to some embodiments, the increased hydrostatic pressure of the delipidization step could be as high as 30,000 psi, or a fluid beyond its critical point. According to some embodiments, the increased hydrostatic pressure could be achieved by performing the delipidization step in the presence of supercritical or non-supercritical gas or fluid. In some embodiments, the supercritical gas or fluid could be supercritical carbon dioxide, water or other gases or liquid beyond their critical point.

4. Decellularizing Step (d): Decellularizing the Sample of Soft Tissue.

According to some embodiments, decellularization step (d) comprises a step of removing cells and cell fragments from a sample of soft tissue. According to some embodiments, decellularization step (d) converts the soft tissue to an acellular matrix of ECM. According to some embodiments, the acellular matrix is essentially free of cell fragments. According to some embodiments, the acellular matrix is entirely free of cell fragments. According to some embodiments, the acellular matrix is free of native tissuegenic factors. According to some embodiments, the acellular matrix includes native tissuegenic factors.

According to some embodiments, decellularization step (d) comprises contacting the sample of soft tissue with a decellularizing solution. According to some embodiments, decellularization step (d) comprises contacting the soft tissue with a decellularizing solution so as to disrupt the cells and remove cells and cell fragments from the tissue. According to some embodiments, decellularization step (d) comprises immersing the soft tissue in the decellularizing solution. According to some embodiments, decellularization step (d) comprises soaking the soft tissue in the decellularizing solution. According to some embodiments, decellularization step (d) comprises mechanically agitating the soft tissue in the decellularization solution. According to some embodiments, decellularization step (d) comprises blending the soft tissue in the decellularization solution. According to some embodiments, blending includes a step of mixing the soft tissue in the decellularization solution under conditions of high shear. According to some embodiments, blending includes a step of mixing the soft tissue with the decellularization solution using at least one rotating blade rotating at a rate in the range of from about 1,000 rpm to about 20,000 rpm. According to some embodiments, decellularization step (d) comprises homogenizing the soft tissue in the decellularization solution. According to some embodiments, homogenization includes a step of mixing the soft tissue in the decellularization solution such that the tissue is evenly distributed throughout the liquid. According to some embodiments, decellularization step (d) comprises multiple decellularization steps. According to some embodiments, decellularization step (d) is performed before a delipidization step.

According to some embodiments, the decellularization step is performed under increased hydrostatic pressure. According to some embodiments, a portion of the decellularization step is performed under increased hydrostatic pressure. According to some embodiments, the increased hydrostatic pressure of the decellularization step could be as high as 30,000 psi, or that of a fluid beyond its critical point. According to some embodiments, the increased hydrostatic pressure could be achieved by performing the decellularization step in the presence of supercritical or non-supercritical gas or fluid. In some embodiments, the supercritical gas or fluid could be supercritical carbon dioxide, water or other gases or liquid beyond their critical point.

According to some embodiments, the decellularization solution is hypertonic relative to the interior of the cells. According to some embodiments, the decellularization solution is hypotonic relative to the interior of the cells. According to some embodiments, the decellularization solution includes a salt. According to some embodiments, the decellularization solution is a salt solution. According to some embodiments, the salt is sodium chloride. According to some embodiments, the decellularization solution is a pH-buffered solution. According to some embodiments, the pH-buffered solution has a physiological pH. According to some embodiments, the pH-buffered solution has a pH of about 7.4.

According to some embodiments, the decellularization solution includes a detergent, emulsifier, or surfactant. According to some embodiments, the detergent, emulsifier, or surfactant includes a derivative of a long chain fatty acid. According to some embodiments, the detergent, emulsifier, or surfactant includes sodium deoxycholate. According to some embodiments, the detergent, emulsifier, or surfactant includes sodium lauryl sulfate. According to some embodiments, the detergent, emulsifier, or surfactant includes sodium dodecyl sulfate. According to some embodiments, the detergent, emulsifier, or surfactant includes a non-ionic surfactant. According to some embodiments, the detergent, emulsifier, or surfactant includes a polyoxyethylene derivative of a long-chain fatty acid. According to some embodiments, the detergent, emulsifier, or surfactant includes a polyoxyethylene sorbitan monolaurate. According to some embodiments, the detergent, emulsifier, or surfactant includes a polyoxyethylene derivate of an aromatic hydrocarbon.

According to some embodiments, the concentration of the detergent, emulsifier, or surfactant is present in a solvent in a concentration in the range of from about 0.1% to about 5.0% (w/v). According to some embodiments, the solvent includes water. According to some embodiments, the solvent includes an organic solvent. According to some embodiments, the solvent includes a mixture of water and an organic solvent. According to some embodiments, the solvent includes less than 20% organic solvent by volume. According to some embodiments, the solvent includes from about 20% to about 40% organic solvent by volume. According to some embodiments, the solvent includes from about 40% to about 60% organic solvent by volume. According to some embodiments, the solvent includes from about 60% to about 80% organic solvent by volume. According to some embodiments, the solvent includes more than 80% organic solvent by volume.

According to some embodiments, the organic solvent is selected from a group consisting of a paraffin, an aromatic hydrocarbon, a cyclic hydrocarbon, a chlorinated hydrocarbon, a fluorinated hydrocarbon, a chlorinated methane, a fluorinated methane, an alcohol, an ether, a ketone, an aldehyde, an ester, an organic acid, and combinations thereof. According to some embodiments, the organic solvent has one carbon atom. According to some embodiments, the organic solvent has two carbon atoms. According to some embodiments, the organic solvent has three carbon atoms. According to some embodiments, the organic solvent has four carbon atoms. According to some embodiments, the organic solvent has five carbon atoms. According to some embodiments, the organic solvent has six carbon atoms.

According to some embodiments, the decellularization solution includes an enzyme. According to some embodiments, the decellularization solution includes a lipase. According to some embodiments, the decellularization solution includes a collagenase. According to some embodiments, the decellularization solution includes trypsin. According to some embodiments, the decellularization solution includes an endonuclease. According to some embodiments, the decellularization solution includes protease. According to some embodiments, the decellularization solution includes a protease inhibitor.

According to some embodiments, the decellularization solution is mildly alkaline. According to some embodiments, the decellularization solution is mildly acidic. In some embodiments, the decellularization solution has a pH that is less than 6. According to some embodiments, the decellularization solution has a pH in the range of about 6 to about 8. In some embodiments, the decellularization solution has a pH that is greater than 10. According to some embodiments, the decellularization solution includes per-acetic acid.

According to some embodiments, the soft tissue is in contact with the decellularization solution for at least 1 hour. According to some embodiments, the soft tissue is in contact with the decellularization solution for at least 2 hours. According to some embodiments, the soft tissue is in contact with the decellularization solution for at least 4 hours. According to some embodiments, the soft tissue is in contact with the decellularization solution for at least 6 hours. According to some embodiments, the soft tissue is in contact with the decellularization solution for at least 12 hours. According to some embodiments, the soft tissue is in contact with the decellularization solution for at least 18 hours. According to some embodiments, the soft tissue is in contact with the decellularization solution for at least 24 hours. According to some embodiments, the soft tissue is in contact with the decellularization solution for at least 36 hours. According to some embodiments, the soft tissue is in contact with the decellularization solution for at least 48 hours.

According to some embodiments, decellularization step (d) comprises a step of scraping a cellular layer from a basement membrane of the soft tissue.

According to some embodiments, decellularization step (d) is performed at a temperature of about 15° C. According to some embodiments, decellularization step (d) is performed at a temperature of about 20° C. According to some embodiments, decellularization step (d) is performed at a temperature of about 25° C. According to some embodiments, decellularization step (d) is performed at an ambient temperature. According to some embodiments, decellularization step (d) is performed at a temperature greater than an ambient temperature. According to some embodiments, decellularization step (d) is performed at a physiological temperature of a living mammal. According to some embodiments, decellularization step (d) is performed at a temperature of about 37° C.

5. Disinfection Step (e): Disinfecting the Soft Tissue.

According to some embodiments, disinfection step (e) comprises disrupting and/or removing micro-organisms in the soft tissue. According to some embodiments, disinfection step (e) comprises disrupting and/or removing viruses in the soft tissue.

According to some embodiments, disinfection step (e) comprises contacting the soft tissue with a disinfecting solution. According to some embodiments, disinfection step (e) comprises immersing the soft tissue in the disinfecting solution. According to some embodiments, disinfection step (e) comprises soaking the soft tissue in the disinfecting solution. According to some embodiments, disinfection step (e) comprises mechanically agitating the soft tissue in the disinfecting solution. According to some embodiments, disinfection step (e) comprises blending the soft tissue in the disinfecting solution. According to some embodiments, blending includes a step of mixing the soft tissue in the disinfecting solution under conditions of high shear. According to some embodiments, blending includes a step of mixing the soft tissue in the disinfecting solution using at least one rotating blade rotating at a rate in the range of from about 1,000 rpm to about 20,000 rpm.

According to some embodiments, the disinfecting solution includes an antibiotic. According to some embodiments, the disinfecting solution includes more than one antibiotic. According to some embodiments, the disinfecting solution includes an alcohol. According to some embodiments, the disinfecting solution includes a glycol. According to some embodiments the disinfecting solution includes a mixture or water with an alcohol and/or a glycol.

According to some embodiments, the disinfecting solution includes a peroxy compound. According to some embodiments, the disinfecting solution includes peracetic acid. According to some embodiments, the disinfecting solution includes chlorine dioxide. According to some embodiments, the disinfecting solution includes a detergent or surfactant. According to some embodiments, the disinfecting solution includes an ethylene diamine salt (e.g., ethylene diamine tetraacetic acid (EDTA)). According to some embodiments, the disinfecting solution includes a protein denaturant. According to some embodiments, the disinfecting solution includes a chaotropic salt (e.g., guanidine isothiocyanate).

According to some embodiments, the soft tissue is in contact with the disinfecting solution for at least 1 hour. According to some embodiments, the soft tissue is in contact with the disinfecting solution for at least 2 hours. According to some embodiments, the soft tissue is in contact with the disinfecting solution for at least 4 hours.

According to some embodiments, disinfection step (e) comprises exposing the soft tissue to ionizing radiation.

According to some embodiments, disinfection step (e) is performed at a temperature of about 15° C. According to some embodiments, disinfection step (e) is performed at a temperature of about 20° C. According to some embodiments, disinfection step (e) is performed at a temperature of about 25° C. According to some embodiments, disinfection step (e) is performed at an ambient temperature. According to some embodiments, disinfection step (e) is performed at a temperature greater than an ambient temperature. According to some embodiments, disinfection step (e) is performed at a physiological temperature of a living mammal. According to some embodiments, disinfection step (e) is performed at a temperature of about 37° C.

According to some embodiments, disinfection step (e) is performed at a pH in the range of from about 2 to about 8, such that said soft tissue forms a flowable gel. According to some embodiments, disinfection step (e) is performed at a pH in the range of about 4 to about 8 such that said soft tissue forms a flowable gel. According to some embodiments, disinfection step (e) is performed at a pH below the isoelectric point of collagen.

According to some embodiments, the disinfected soft tissue is washed with water to remove the disinfecting solution from the disinfected soft tissue. According to some embodiments, the disinfected soft tissue is washed with a buffer solution to remove the disinfecting solution from the disinfected soft tissue. According to some embodiments, the disinfected soft tissue is washed with a physiological buffer to remove the disinfecting solution from the disinfected soft tissue and bring the disinfected tissue to a physiological pH. According to some embodiments, the disinfected soft tissue is washed with a solution containing a volatile polar solvent to remove the disinfecting solution from the disinfected soft tissue.

According to some embodiments, the disinfection step is performed under increased hydrostatic pressure. According to some embodiments, a portion of the disinfection step is performed under increased hydrostatic pressure. According to some embodiments, the increased hydrostatic pressure of the disinfection step could be as high as 30,000 psi, or that of a fluid beyond its critical point. According to some embodiments, the increased hydrostatic pressure could be achieved by performing the disinfection step in the presence of supercritical or non-supercritical gas or fluid. In some embodiments, the supercritical gas or fluid could be supercritical carbon dioxide, water or other gases or liquid beyond their critical point.

6. Post-Processing Step (f): Post-Processing the Soft Tissue.

According to some embodiments, post-processing step (f) comprises forming the soft tissue into a final physical form, with or without a mold or other container. According to some embodiments, the final physical form of the soft tissue is a sheet. According to some embodiments, the final physical form of the soft tissue is particulate. According to some embodiments, the final physical form of the soft tissue is pieces or chunks. According to some embodiments, the final physical form of the soft tissue is a paste, gel, slurry, or suspension, or a combination thereof. According to some embodiments, the final physical form of the soft tissue is a layer or coating deposited on another scaffold. According to some embodiments, the final physical form of the soft tissue is a dried, pre-formed three dimensional shape such as, without limitation, a block, a sheet, a polyhedron, a strip, a cylinder, a rod, a sphere, a cone, a pyramid, and variations and combinations thereof. According to some embodiments, the final physical form of the soft tissue is a film, or membrane. According to some embodiments, the final physical form of the soft tissue is a layer or coating deposited on another scaffold. For example, the final physical form of the soft tissue may be a membrane having a thickness of about 100 microns or greater. According to some embodiments, the final physical form of the soft tissue is porous. According to some embodiments, the final physical form of the implant is fibrous. According to some embodiments, the final physical form of the soft tissue is a wet, pre-hydrated form that has not been dried and, therefore, is "ready to use" by practitioners without having to rehydrate the final acelluar matrix form.

According to some embodiments, post-processing step (f) comprises cutting the soft tissue to a final shape. According to some embodiments, post-processing step (f) comprises perforating the soft tissue. According to some embodiments, post-processing step (f) comprises centrifuging the soft tissue. According to some embodiments, post-processing step (f) comprises at least partially drying the soft tissue. According to some embodiments, post-processing step (f) comprises partially drying the soft tissue to a water content of at least about 20% by weight (wt %), based on the total weight of the soft tissue, for example, at least about 25 wt % or at least about 30 wt %, or at least about 40 wt %, or at least about 50 wt %, or at least about 60 wt %, or at least about 70 wt %, or at least about 80 wt %, or at least about 90 wt %, or at least about 95 wt %. According to some embodiments, post-processing step (f) comprises substantially drying the soft tissue to a water content of less than about 20 wt %, based on the total weight of the soft tissue, for example, less than about 18 wt %, or less than about 16 wt %, or less than about 15 wt %, or less than about 14 wt %, or less than about 12 wt %, or no more than 10 wt %, or less than about 8 wt %, or less than about 6 wt %, or no more than about 5 wt %, or less than about 3 wt %.

According to some embodiments, post-processing step (f) includes air-drying the soft tissue. According to some embodiments, post-processing step (f) includes drying the soft tissue while heating the soft tissue. According to some embodiments, post-processing step (f) includes at least partially drying the soft tissue by sublimation. According to some embodiments, post-processing step (f) includes at least partially drying the soft tissue by evaporation. According to some embodiments, post-processing step (f) includes lyophilizing the soft tissue. In some embodiments, post-processing step (f) does not involve any drying of the soft tissue.

According to some embodiments, post-processing step (f) includes performing one or more size reduction steps. According to some embodiments, post-processing step (f) includes milling the soft tissue. According to some embodiments, post-processing step (f) includes freezer-milling the soft tissue (i.e., milling the soft tissue while it is in a frozen state, for example, by impact milling). According to some embodiments, post-processing step (f) includes freeze-fracturing the soft tissue. According to some embodiments, post-processing step (f) includes compressing the soft tissue. According to some embodiments, such one or more additional size reduction steps may be performed, for example without limitation, after decellularizing step (d), or after disinfecting step (e), or even at both intervals.

According to some embodiments, post-processing step (f) comprises rehydrating the partially dried soft tissue. According to some embodiments, post-processing step (f) comprises rehydrating the substantially dried soft tissue. According to some embodiments, post-processing step (f) comprises combining particulate soft tissue with a carrier. According to some embodiments, the carrier includes at least one of an isotonic solution, a sodium chloride solution, lactated Ringer's solution, a phosphate-buffered saline solution (PBS), platelet rich plasma (PRP), hyaluronic acid (HA) or a derivative thereof such as sodium hyaluronate. According to some embodiments, the carrier is a sodium chloride solution at a concentration of about 0.1% to about 1%. According to some such embodiments, the sodium chloride solution is at a concentration of about 0.9%. According to some embodiments, the carrier is a mixture of sodium hydaluronate and an aqueous solution. In some embodiments, the sodium hyaluronate has a molecular weight of from about $5.0\times10^3$ to about $3.0\times10^6$ Daltons, such as from about $6.0\times10^5$ to about $3.0\times10^6$ Daltons and is mixed with an aqueous solution to form a matrix-carrier mixture having a viscosity ranging from about 1000 centipoise to about 275,000 centipoise, such as from about 6,000 to about 275,000 centipoise. In some embodiments, the aqueous solution of the carrier comprising sodium hyaluronate is, for example without limitation, one or more of water, saline, phosphate buffered solution (PBS), isotonic saline, and the like.

According to some embodiments, the carrier comprises thrombin. According to some embodiments, the carrier comprises fibrin. According to some embodiments, the carrier comprises glycerin. According to some embodiments, the carrier comprises collagen. According to some embodiments, the carrier comprises lecithin. According to some embodiments, the carrier comprises a sugar. According to some embodiments, the carrier comprises a polysaccharide. According to some embodiments, post-processing step (f) comprises mixing particulate soft tissue with a carrier on site for immediate administration to a patient.

According to some embodiments, the particulate soft tissue is mixed with a carrier such that the particulate soft tissue and carrier combine to form a flowable gel. According to some embodiments, the mixing step is performed at a pH in the range of from about 2 to about 8. According to some embodiments, the mixing step is performed at a pH in the range of about 4 to about 8. According to some embodiments, the mixing step is performed at a pH below the isoelectric point of collagen.

According to some embodiments, the particulate soft tissue is mixed with a carrier such that the particulate soft tissue and the carrier form a paste. According to some embodiments, the carrier includes a polymer such that the particulate soft tissue and the polymer form a paste. According to some embodiments, the polymer is selected from the group consisting of polysaccharides, nucleic acids, carbohydrates, proteins, polypeptides, poly($\alpha$-hydroxy acids), poly(lactones), poly(amino acids), poly(anhydrides), poly (orthoesters), poly(anhydride-co-imides), poly(orthocarbonates), poly($\alpha$-hydroxy alkanoates), poly(dioxanones), poly (phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\zeta$-caprolactone), poly(o-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly (vinyl alcohol), poly(vinylpyrrolidone), poly(ethyloxazoline), poly(ethylene oxide)-co-poly(propylene oxide) block copolymers, poly(ethylene terephthalate) polyamide, and copolymers thereof.

According to some embodiments the carrier includes a glycerin and/or glycerol. According to some embodiments the carrier includes gelatin. According to some embodiments the carrier includes alginates. According to some embodiments the carrier includes an isotonic solution, According to some embodiments the carrier includes a sodium chloride solution. According to some embodiments the carrier includes a lactated Ringer's solution. According to some embodiments the carrier includes a phosphate-buffered saline. According to some embodiments the carrier includes platelet rich plasma. According to some embodiments the carrier includes a hyaluronic salt. According to some embodiments the carrier includes a hyaluronic ester According to some embodiments the carrier includes fibrin. According to some embodiments the carrier includes thrombin. According to some embodiments the carrier includes a collagen. According to some embodiments the carrier includes lecithin. According to some embodiments the carrier includes a combination of two or more carrier components.

According to some embodiments, the post-processing step (f) includes diluting the acellular matrix with a biocompatible solvent, forming a protein solution. In some embodiments, the protein solution has a protein concentration that is about 5% w/v or less, or about 10% w/v or less, or about 15% w/v or less. In some embodiments, the biocompatible solvent is an aqueous buffer solution. In some embodiments, the biocompatible solvent is water. In some embodiments, the protein solution is suitable for application to a large wound area. In some embodiments, the protein solution is suitable for application to the surface of a device (e.g., a non-degradable mesh or a fracture plate) to increase the biocompatibility of the surface. In some embodiments, the protein solution is suitable for application within a device (e.g., a mesh cage or other containment device). In some embodiments, the protein solution is suitable for application as a spray.

According to some embodiments, post-processing step (f) includes forming the acellular matrix into a three-dimensional shaped acellular tissue. According to some embodiments, the shaped acellular tissue is formed by one or more of the processes of molding a slurry, paste, or gel, machining a sponge-like shaped acellular tissue into a different shape, using three-dimensional ("3-D") printing to deposit a flowable slurry, paste, or gel into a three-dimensional shape, laminating pieces of shaped acellular tissue, and other technologies known for use in shaping three-dimensional objects from soft or flowable materials. According to some embodiments, shaped acellular materials may be provided in a lyophilized, cryopreserved, or frozen form. In some embodiments, growth factors or other soluble proteins are applied to a surface of the shaped acellular tissue. In some embodiments, the growth factors or other soluble proteins are applied to a surface of the shaped acellular implant in a pattern.

According to some embodiments, post-processing step (f) comprises characterizing the acellular matrix. According to some embodiments, post-processing step (f) comprises characterizing the acellular matrix for DNA content using a PicoGreen® dsDNA assay available from Thermo Fisher Scientific, of Waltham, Massachusetts, U.S.A., as well as a Biotek Synergy II MicroPlate Reader for fluorescence measurement wherein absence of detectable amounts of DNA indicates the absence of intact cells and cellular components from the soft tissue. In some embodiments, post-processing step (f) comprises characterizing the acellular matrix for DNA content, wherein the amount of DNA detected by the characterizing is less than about 30%, such as less than about 25%, or less than about 20%, of the DNA content of the acellular matrix prior to decelluarizing step (d). According to some embodiments, post-processing step (f) comprises characterizing the acellular matrix for the presence of growth factors. According to some embodiments, post-processing step (f) comprises determining the particle size distribution of particulate acellular matrix. According to some embodiments, most of the particles have surface areas of 625 square microns or less. According to some embodiments, at least 80% of the particles have surface areas of 625 square microns or less.

7. Packaging Step (g): Packaging the Soft Tissue.

According to some embodiments, packaging step (g) comprises preparing the soft tissue for storage and subsequent use. According to some such embodiments, packaging step (g) comprises freezing the soft tissue for storage. According to some embodiments, packaging step (g) comprises packaging the soft tissue in a dried or lyophilized state.

According to some embodiments, packaging step (g) comprises contacting the soft tissue with a preservative solution. Suitable preservative solutions include, without limitation, solutions comprising salts or buffers (for example, sodium chloride, or a phosphate buffered saline), sugars (for example, glucose, dextrose, trehalose, and hyaluronic acid and its derivatives, including without limitation sodium hyaluronate), vitamins (for example, Vitamin C, Vitamin E), alcohols (for example, ethanol), antioxidants (for example, sodium benzoate, sodium erythorbate), and hormones (for example, dexamethasone). In some such embodiments, the preservative solution is aqueous ethanol. In some such embodiments, the preservative solution is a mixture of hyaluronic acid or a derivative thereof (e.g., sodium hyaluronate) and carrier, such as those described above in connection with suitable carriers which may be combined with the acellular matrices during post-processing (f). In some embodiments, the soft tissue is contacted with the preservative solution before the packaging step (g). In some embodiments, the packaging step (g) comprises immersing the soft tissue in the preservative solution. In some embodiments in which the sample of soft tissue from which the acellular matrices are derived comprises first and second soft tissues which are separated at some point during the process, one or both of the first and second soft tissues may be independently contacted with a preservative solution, after which they may or may not be combined to form a recombined soft tissue and subjected to process steps.

According to some embodiments, the soft tissue is in a dried or lyophilized particulate form, and packaging step (g) comprises packaging the dried or lyophilized tissue in a sterile container. According to some such embodiments, packaging step (g) comprises freezing the dried or lyophilized tissue for storage. According to some embodiments, packaging step (g) comprises storing the dried or lyophilized tissue at temperatures between 4° C. and an ambient temperature.

According to some embodiments, the soft tissue is packaged while in a frozen state. According to some embodiments, the soft tissue is provided in a frozen state, and then thawed before packaging. According to some embodiments, the soft tissue is not in a frozen state when provided, and is packaged while in the state in which it is provided.

According to some embodiments, the soft tissue is packaged as a sterile gel, paste, or protein solution. According to some embodiments, the sterile gel, paste, or protein solution is refrigerated for storage, but is not frozen. According to some embodiments, the sterile gel, paste, or protein solution is stored at room or ambient temperatures, but is not frozen or refrigerated.

8. Addition of Tissuegenic Cells

According to some embodiments, the method of fabricating an implant further comprises adding tissuegenic cells to the decellularized soft tissue. Implants with added tissuegenic cells are discussed elsewhere above. Such tissuegenic cells or implants with added tissuegenic cells may be cryopreserved.

Cryopreservation is used for the long-term preservation of various tissues and cells. According to some embodiments, tissuegenic cells derived from a tissue can be cryopreserved, reconstituted, and seeded onto an isolated matrix. According to some embodiments, tissuegenic cells derived from a tissue can be cryopreserved, reconstituted, and seeded onto an isolated matrix to promote tissuegenesis in vitro and in vivo.

Detrimental effects of ice crystal formation and increased solute concentration in cryopreserved cells can be reduced by using cryoprotective additives or chemicals that protect cells during freezing. Commonly used cryoprotective agents include, but are not limited to, dimethylsulfoxide (DMSO), ethylene glycol, propylene glycol, 2-Methyl-2.4-pentanediol (MPD), sucrose, and glycerol. Examples of cryopreservation solutions that can be used in preserving a tissue or a matrix include, but are not limited to, a commercially available basal media solution such as, Mesencult (Stem Cell Technologies), or Hyclone AdvanceStem, Fetal Bovine Serum with 5-15% DMSO, Bovine Serum Albumin with 5-15% DMSO, Human Serum Albumin with 5-15% DMSO, Aedesta (Cell Preservation Solutions), LiforCell (Lifeblood Medical), ethylene glycol, propylene glycol, and glycerol.

According to some embodiments, the packaged implant can be preserved for an extended period of time by slowly cooling the packaged implant in the presence of a cryoprotective agent and by storing at ultra-low temperatures. According to some embodiments, packaging step (g) comprises freezing the soft tissue implant to at least a temperature of −80° C. According to some such embodiments, packaging step (g) comprises freezing the soft tissue implant at a controlled freezing rate. According to some such embodiments, the controlled freezing rate is a controlled freezing rate of about 0.5° C. per minute to about 10° C. per minute. According to some such embodiments, the controlled freezing rate is a controlled freezing rate of about 1° C. per minute until about −100° C.

9. Addition of Growth-Inductive Components

According to some embodiments, the method of fabricating an implant further comprises supplementing the decellularized soft tissue with at least one growth-inductive component. According to some such embodiments, the at least one growth-inductive component includes one or more of a demineralized cortical bone, fibroblast growth factor-2 (FGF-2), fibroblast growth factor-5 (FGF-5), insulin-like growth factor 1 (IGF-1), transforming growth factor beta (TGF-β), bone morphogenic protein-2 (BMP-2), bone morphogenic protein-7 (BMP-7), platelet-derived growth factor (PDGF), vascular endothelial growth factor (VEGF), neural epidermal growth-factor-like 1 (NELL-1), epidermal growth factor (EGF), hepatocyte growth factor (HGF), and a cytokine.

According to one embodiment, the at least one growth-inductive component is tissue-derived. According to one embodiment, the at least one growth-inductive component comprises inducible pluripotent stem cells (iPSCs). According to one embodiment, the at least one growth-inductive component originates from a component of the tissue-derived growth-inductive component other than cells. According to one embodiment, tissuegenic cells added to the decellularized soft tissue secrete the at least one growth-inductive component. According to one embodiment, the growth-inductive component comprises a growth medium derived from expanded tissuegenic cells.

According to some embodiments, the tissue is rinsed with a liquid prior to being separated into pieces to reduce bioburden levels on the surface of the tissue. According to some embodiments, the liquid comprises phosphate buffered saline (PBS). According to some embodiments, the liquid comprises acetic acid. According to some embodiments, the liquid comprises peracetic acid.

Potential Uses of Acellular Soft Tissue-Derived Matrices

As will be recognized by persons of ordinary skill in the relevant art, many different uses for the acellular soft tissue-derived matrices and implants containing them are possible and contemplated herein. For example, in some embodiments the matrices or implants containing them may be injectable into autologous segments of the integument, where superficial fascia resides anatomically, to treat subcutaneous defects occurring naturally or from trauma. In other embodiments, the matrices or implants containing them may be pre-shaped for specific or non-specific applications in transplant engineering where grafts are either symmetrical or asymmetrical in the second, third, or fourth (i.e., time) dimension of the graft. In still other embodiments, the matrices or implants containing them may be combined with hyaluronic acid and/or elastomer for customized flow properties, which could be application specific, e.g., hypodermically warrants stiffer fluid and intradermal application warrants a more diffuse fluid. In some embodiments, the matrices or implants containing them may be combined with a heavily diluted protein scaffold (protein concentration≤5%) in some biocompatible carrier (saline, PBS) and pressurized for use as a spray for large wound coverings. In some embodiments, a coating of dilute protein matrix could be applied to the surface of an implant containing the matrices to increase biocompatibility, i.e. non-degradable meshes, fracture plates, etc. In still other embodiments, the matrices or implants containing them could have all soluble (growth) factors removed therefrom and then reseed the matrices or implants with specific growth factors in a known array for specific differentiation of infiltrating cells.

EXAMPLES

The following examples are put forth so as to provide those of ordinary skill in the art with a complete disclosure and description of exemplary embodiments of the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are parts by weight, molecular weight is weight average molecular weight, temperature is in degrees centigrade (° C.), and pressure is at or near atmospheric. Although the exemplary embodiments are adapted to specific soft tissues, it will be recognized by those skilled in the art that the methods described herein can be readily adapted to other soft tissues. Adipose, dermis, fascia, muscle, pericardium, and other connective or membranous tissues are among the soft tissues that may be processed according to the processes of the exemplary methods, or variations thereof.

I. Source Tissue: Adipose Tissue and Associated Superficial Fascia

Acellular matrices derived from adipose tissue, with or without its associated superficial fascia, may be in a bulk form, particulate form, or other forms. Such acellular matrices may be used as bulking agents for cosmetic, reconstructive or wound healing purposes. Some specific applications include use as a bulking agent for to restore natural contours where native adipose tissue has been removed, or damaged by injury or wasting, or to correct naturally-occuring asymmetries. In such instances, the acellular matrices may also be used to stimulate adipose regeneration and natural integration of the regenerated tissues. The acellular matrices may also be used to fill tunneling and complex wounds anywhere in the body. The acellular matrices may also be used for re-establishment of the fat pads in the foot. The acellular matrices may also be used to deliver precursor cells and/or tissuegenic factors for repair or regeneration of adipose tissue or other tissue types. The foregoing summary of uses is intended to be representative, and not to limit the range of uses for acellular adipose-derived matrices according to embodiments of the present invention.

According to other embodiments of the present invention, the superficial fascia are separated from the adipose tissue, and processed separately therefrom. The resulting acellular fascia-derived tissue may be in a bulk form, particulate form, or other forms, and may be used as bulking agents in a fashion similar to the use of adipose-derived acellular tissues. In some embodiments, tissuegenic cells, growth factors, chemokines, and/or soluble membrane proteins are extracted from untreated fascial tissue or other source tissue, and used to enrich processed acellular tissues. Since adipose-derived acellular tissues and fascia-derived acellular tissues differ from each other with respect to the amounts and types of structural proteins and other biochemical components, some embodiments of the present invention include the recombination of such processed tissues to provide a tissue mixture having desired biochemical and structural combinations.

Example 1: Decellularization with Sodium Deoxycholate

Adipose tissue is recovered aseptically from a cadaveric donor. Any muscle, fascia, or other tissues attached to the adipose tissue, if present, are cut away. Equal portions of the adipose tissue are measured into empty flasks and washed by agitation in deionized water, at a ratio of about 1000 ml of water to 500 gm of tissue. After a period of time sufficient to remove blood and loose tissue from the adipose tissue, the water is drained from the flask, while collecting the adipose tissue in a 212 μm to 300 μm sieve. After the water is drained, the adipose tissue is returned to the flask.

Following the washing step, the adipose tissue is soaked with mechanical agitation in a 4% solution of sodium deoxycholate, at a ratio of about 1000 ml deoxycholate solution to 500 gm of adipose tissue. After a period of time sufficient to disrupt and remove the adipocytes and other cells from the adipose tissue, the deoxycholate solution is drained from the flask, while collecting the adipose tissue in a 212 μm to 300 μm sieve. After the deoxycholate solution is drained, the adipose tissue is returned to the flask, and rinsed repeatedly in deionized water to remove any residual deoxycholate from the tissue. After each rinse, the water is drained from the flask, as described above, and the collected adipose tissue is returned to the flask.

Following the last water rinse, the adipose tissue is soaked in a disinfecting solution with mechanical agitation. One suitable disinfecting solution would be 0.5% to 1.0% peracetic acid in deionized water. One or more additional soaks in disinfecting solution may be needed to adequately disinfect the adipose tissue. After the final disinfecting soak, the adipose tissue is rinsed repeatedly in deionized water to remove any traces of disinfecting solution from the tissue.

Following the final water rinse, the adipose tissue is stored under refrigeration or frozen, or it is subjected to further processing steps, such as delipidization.

Example 2: Decellularization with a Hypertonic Solution

A sample of adipose tissue is measured into a flask and a hypertonic solution (e.g., 1M NaCl) is added in a 2:1 ratio. The mixture is agitated for at least 12 hours at an ambient temperature. After agitation, the hypertonic solution is decanted, and the adipose tissue is captured in a 212 μm to 300 μm sieve. The recovered adipose tissue is returned to the flask, and soaked in an 0.1% surfactant solution with agitation for at least 12 hours at ambient temperature.

Following the last water rinse, the adipose tissue is soaked in a disinfecting solution, with agitation. One suitable disinfecting solution would be 0.5% to 1.0% peracetic acid in a mixture of water, ethanol, and propylene glycol. One or more additional soaks in disinfecting solution may be needed to adequately disinfect the adipose tissue. After the final disinfecting soak, the adipose tissue is rinsed repeatedly in deionized water to remove any traces of disinfecting solution from the tissue.

Following the final water rinse, the adipose tissue is stored under refrigeration or frozen, or it is subjected to further processing steps, such as delipidization.

Example 3: Removal of Lipids from an Adipose Tissue

A sample of adipose tissue, which may be decellularized or untreated, is collected and a size reduction, such as grinding or mincing, is performed. At a temperature of ambient or greater, the adipose tissue is placed in a conical tube or beaker, and homogenized. The homogenized tissue is then centrifuged to separate lipid and water layers from the tissue, taking care not to lose the floating tissue layer.

Example 4: Delipidization of an Adipose Tissue

A sample of adipose tissue, which may be decellularized or untreated, is collected and a size reduction, such as grinding or mincing, is performed. After size reduction, the adipose tissue may be processed as described in Example 2, then delipidized as follows.

The adipose tissue is equally divided among a number of conical tubes, and an organic solvent (e.g., an alcohol) is added to the tube. Surfactants (e.g., Triton X-100 or Tween 80) may also be added to promote lipid removal. The alcohol/tissue mixture is rapidly homogenized at a temperature of ambient or greater, and the homogenized mixture is centrifuged to separate lipid, solvent, water and tissue layers. The lipid and solvent layers are removed from the tube, and the tissue is recovered. The solvent homogenization step is repeated for a number of times sufficient to remove all of the lipid from the tissue.

After the final solvent treatment, the tissue is homogenized with water, and the water is separated from the tissue by centrifugation. These steps may be repeated a number of times to remove the final traces of alcohol. The homogenate may be incubated before it is centrifuged. A final PBS wash may be performed. Removal of the lipids from the tissue can be verified by any of a number of well-known lipid assays.

Example 5: Fabrication of an Acellular Implant

A sample of adipose-rich soft tissue is obtained from a suitable donor. The tissue is inspected for muscle and dermis, which is then cut away from the adipose tissue. Size reduction is then performed by grinding or mincing the adipose tissue, or by another suitable method.

The adipose tissue is then delipidized by the method of Example 3, or by the method described herein. The adipose tissue is divided between a number of centrifuge tubes and a small amount of water is added to each tube to wet the tissue. The tissue is warmed to a temperature above ambient, and centrifuged to separate a lipid layer from the tissue. A lipid layer, a water layer, an adipose layer, and bottom pellet are formed.

The adipose layer is recovered and blended with an equal portion of an alcohol, or alcohol with surfactants or detergents (e.g., Triton X-100 or Tween 80), then returned to the centrifuge tube. The mixture of adipose tissue and alcohol is centrifuged to separate the mixture into layers of lipid, alcohol, and adipose tissue. The adipose tissue is then recovered. The alcohol treatment may be repeated a number of times to remove all of the lipid from the tissue.

After the final alcohol treatment, the adipose tissue is soaked in a hypertonic solution (e.g., 1M NaCl) with agitation for at least 6 hours at ambient temperature. The tissue and hypertonic solution may be blended before the soaking step begins. After soaking in hypertonic solution, the adipose tissue is recovered from the mixture by centrifugation at a temperature above ambient, and soaked in a dilute detergent or surfactant solution with agitation for at least 12 hours at ambient temperature. One suitable solution would have at least 0.1% of a surfactant in water. After soaking in the detergent, the adipose tissue is recovered by centrifugation, and rinsed at least twice in deionized water.

After the water rinse, the recovered adipose tissue is suspended in a disinfecting solution, and allowed to soak with agitation. One suitable disinfection solution would be between 0.5% and 1% peracetic acid in a mixture of water, ethanol, and propylene glycol. The adipose tissue is then recovered by centrifugation, and subjected to multiple water rinses to remove any remaining disinfecting solution.

The rinsed adipose tissue is then at least partially dried and milled to a particulate form. Drying may be performed by air-drying, drying with heat, sublimation, evaporation, lyophilization, or combinations thereof. The partially dried or substantially dried adipose tissue may be further milled in a frozen state (impact milling, or freezer-milling) to further reduce the particle sizes of the tissue, and produce a flowable particulate tissue. Suitable milling protocols are known in the art.

The particulate tissue may be packaged in a sterile container for later use, or thawed and rehydrated immediately. In one rehydration method, a desired amount of the thawed particulate tissue is added to a first syringe. The desired amount of fluid (e.g., a carrier) is added to a second syringe, and the syringes are attached to each other using a female-to-female locking cap. The fluid is ejected slowly into the tissue-filled syringe, while depressing the plungers of both syringes. The entirety of the mixture of tissue and fluid is transferred to one of the syringes, and the other is discarded. The syringe containing the mixture is stoppered and packaged in foil and/or a Kapak® pouch (Kapak Corporation, St. Louis Park, MN).

Example 6: Fabrication of an Implant by Reseeding Adipose-Derived Stem Cells on a Decellularized Matrix Adipose tissue with its endogenous stem cell niche is recovered aseptically from a cadaveric donor within 24 hours post mortem or from living donors undergoing elective liposuction surgery. For example, visceral fat can be excised from cadaveric donors or obtained with consent from living donors undergoing elective procedures, such as liposuction, from body regions rich in adipose, for example, hip, thigh and abdomen. Subcutaneous adipose can be procured from the hypodermis by dissecting it out from full thickness skin excised from cadaveric donor. Adipose tissue from infrapatellar fat pads can be dissected out during recovery of knee en-bloc from a cadaveric donor. The adipose tissue is stored at 4° C. until ready for processing. Generally, tissue processing commences within 72 hours post-mortem. The adipose tissue is exposed to a bioburden reducer to generate preprocessed adipose tissue. The preprocessed adipose tissue is subjected to a series of PBS soaks with agitation. The preprocessed agitated adipose tissue is then chopped into small pieces approximately 0.5×0.5×0.5 cm. The chopped adipose pieces are then subjected to a series of rinses with cold PBS. The pH of the rinseate is at or near physiological pH at the end of the rinse. The rinseate is divided into two batches for stem cell isolation and decellularized matrix preparation.

Isolation of ASCs

Viable adipose-derived stem cells (ASCs) are isolated according to established protocols (Young et al., 2011, Acta Biomaterialia, 7:1040-1049). Briefly, following rinses with a buffered saline solution (e.g., 0.01M PBS, pH 7.4), one batch of the rinsed tissue is digested with a dissociation agent (e.g., collagenase) in order to disperse the tissue while maintaining cell viability. The digest is subjected to centrifugation to separate the stromal vascular fraction (SVF) rich in adipose-derived stem cells from the supernatant rich in lipid filled adipocytes and matrix. The supernatant is aspirated and the aspirate is frozen at −80° C. until further use. The SVF pellet is resuspended in PBS washing solution and is subjected to a series of cold PBS washes with alternating steps of centrifugation. Following the final wash and resuspension in PBS, the resuspended solution is subjected to filtration to remove undigested tissue and to obtain isolated SVF enriched with ASCs for seeding. Alternatively, ASCs can be isolated from the other cells present in digested adipose tissue on the basis of cell size or immunohistochemically, for example, by using magnetic beads, affinity chromatography, fluorescence-activated cell sorting (FACS), flow cytometry, or with a suitable device.

Additionally, the isolated ASCs express antigens, including, but not limited to, CD73, CD90, CD29, CD44, CD105, and/or a combination thereof. Additionally or alternatively, the isolated ASCs do not express antigens, including, but not limited to CD33, CD34, CD45, CD4, CD31, CD62p CD14, HLA-DR, and/or combination thereof.

Additionally, a sample is set aside in order to evaluate the biological activity of the tissue using commercially available methods, including, but not limited to, for example, metabolic assays, such as involving luciferase, tetrazolium salts, e.g., 3-(4, 5-dimethyl-2-thiazolyl)-2, 5-diphenyl-2H-tetrazolium bromide (MTT), 3-(4,5-dimethylthiazol-2-yl)-5-(3-carboxymethoxyphenyl)-2-(4-sulfophenyl)-2H-tetrazolium (MTS), 2,3-bis-(2-methoxy-4-nitro-5-sulfophenyl)-2H-tetrazolium-5-carboxanilide (XTT), and other water soluble tetrazolium salts (e.g., WST-1, -3, -4, -5, -8, -9, -10, and -11), and dye exclusion assays such as Trypan Blue.

Alternatively, isolated ASCs can be cultured without differentiation using standard culture media typically supplemented with 5%-20% serum. For example, the ASCs are passaged at least 5 times in such medium without differentiating, while still retaining their multiplicity. Adipose-derived stem cells can be maintained in control medium until 80% confluent. Cells are harvested at confluence and population doubling calculated using the formula $\log N_1/\log N_2$, where $N_1$ is the number of cells at confluence prior to passaging and $N_2$ is the number of cells seeded after passaging. Cumulative population doubling is determined in cultures maintained until passage 13 (approximately 165 days). The mean cumulative population doubling obtained from 3 donors is expressed as a function of passage number. Confirmation of Multi-Lineage Differentiation of Adipose-Derived Stem Cells Adipose-derived stem cells at passage 1 can be analyzed for their capacity to differentiate toward the adipogenic, osteogenic, chondrogenic, and myogenic lineages. To induce differentiation, the stem cells are cultured with specific induction media as detailed in Table 12.

TABLE 12

| Lineage-specific differentiation induced by media supplementation | | | |
|---|---|---|---|
| Medium | Media | Serum | Supplementation |
| Control | DMEM | 10% FBS | None |
| Adipogenic (AM) | DMEM | 10% FBS | 0.5 mM isobutyl-methylxanthine (IBMX), 1 μM dexamethasone, 10 μM insulin, 200 μM indomethacin, 1% antibiotic/antimycotic |
| Osteogenic (OM) | DMEM | 10% FBS | 0.1 μM dexamethasone, 50 μM ascorbate-2-phosphate, 10 mM β-glycerophosphate, 1% antibiotic/antimycotic |
| Chondrogenic (CM) | DMEM | 1% FBS | 6.25 μg/ml insulin, 10 ng/ml TGFβ1, 50 nM ascorbate-2-phosphate, 1% antibiotic/antimycotic |
| Myogenic (MM) | DMEM | 10% FBS, 5% HS | 0.1 μM dexamethasone, 50 μM hydrocortisone, 1% antibiotic/antimycotic |

Each media has been previously described and shown to induce multi-lineage differentiation of MSCs (Pittenger, M. et al, 1999, Science 284:143-147; Grigoradis, A. et al., 1988, J. Cell. Biol., 106:2139-2151; Cheng, S-L. et al., 1994, Endo, 134:277-286; Loffler, G. et al., 1987, Klin. Wochenschr., 65:812-817; Hauner, H. et al., 1987, J. Clin. Endocrinol. Metabol. 64:832-835). Differentiation is confirmed using the histological and immunohistological assays outlined in Table 13 and compared to a commercial source of bone marrow-derived MSCs, lineage-specific precursors (positive controls), and human foreskin fibroblasts (HFFs) (negative controls)). The adipose-derived stem cells are maintained in Control Medium.

TABLE 13

| Differentiation Markers And Assays Of Lineage-Specific Differentiation. | | |
|---|---|---|
| Lineage | Lineage-specific Determinant | Histologic/Immuno-histochemical Assay |
| Adipogenic | 1. Lipid Accumulation | 1. Oil Red O stain |
| Osteogenic | 1. Alkaline phosphatase activity | 1. Alkaline phosphatase stain |
| | 2. Calcified matrix production | 2. Von Kossa stain |
| Chondrogenic | 1. Sulfated proteoglycan-rich matrix | 1. Alcian Blue (pH 1.0) stain |
| | 2. Collagen II synthesis | 2. Safranin O stain |
| | | 3. Collagen II-specific monoclonal antibody |
| Myogenic | 1. Multi-nucleation | 1. Phase contrast microscopy |
| | 2. Skeletal muscle myosin heavy chain and MyoD1 expression | 2. Myosin and MyoD1 specific monoclonal antibodies |

Adipogenesis

Adipogenic differentiation can be induced by culturing the stem cells for 2 weeks in Adipogenic Medium (AM) and assessed using an Oil Red O stain as an indicator of intracellular lipid accumulation (Preece, A. 1972 A Manual for Histologic Technicians, Boston, Mass.: Little, Brown, and Co.). Prior to staining, the cells are fixed for 60 minutes at room temperature in 4% formaldehyde/1% calcium and washed with 70% ethanol. The cells are incubated in 2% (w/v) Oil Red O reagent for 5 minutes at room temperature. Excess stain is removed by washing with 70% ethanol, followed by several changes of distilled water. The cells are counter-stained for 2 minutes with hematoxylin.

Preparation of Decellularized Adipose Matrix

Decellularized adipose matrix is obtained either using the original rinseate or the thawed and filtered aspirate obtained during the ASC isolation procedure. Following a series of thorough washes with cold PBS, the washed tissue is soaked in lysis buffer with continuous mechanical agitation. The soaked tissue then is subjected to cell lysis to yield a decellularized tissue. The sterile decellularized tissue can be subjected to alternate procedures. For example, (1) it can be lyophilized and milled using a freezer mill to yield a decellularized adipose-derived matrix powder; (2) it can be homogenized to obtain a decellularized adipose-derived matrix paste or slurry; (3) it can be homogenized and lyophilized to obtain a three-dimensional adipose-derived matrix; or (4) it can be lyophilized to obtain an adipose decellularized tissue matrix sheet. It can be delipidized and decellularized according to any of the methods in Examples 1 through 5.

Recellularization

Adipose-derived decellularized matrices in powder, paste/ slurry, three-dimensional or sheet form may be used to reseed isolated ASCs. Following the filtration step for isolating ASCs, the isolated stromal-vascular fraction (SVF) enriched with ASCs or otherwise purified ASCs are resuspended in basal or nutrient enriched medium. A portion of the resuspended SVF fraction or otherwise purified ASCs are then added to a sample of an adipose-derived decellularized matrix produced in any form (powder, paste/slurry, three dimensional or sheet). The decellularized adipose matrix containing the ASCs is incubated at 37° C. The incubation step is followed by static or dynamic seeding conditions for 24 hours, which are well known in the art. The re-cellularized adipose matrix is then subjected to a series of cold PBS rinses to wash away unwanted non-adherent cells.

Cryopreservation and Thawing

Additionally, prior to cryopreservation, one or more growth-inductive components optionally can be added. These include, but are not limited to, bone morphogenic proteins (BMPs), vascular endothelial growth factor (VEGF), basic fibroblast growth factor (bFGF), transforming growth factor beta (TGFβ), platelet-derived growth factor (PDGF), neural epidermal growth-factor-like 1 (NELL-1), insulin-like growth factor 1 (IGF-1), and a combination thereof. For cryopreservation, for example, mesencult basal media is prepared and sterile filtered. A cryoprotectant solution in basal or nutrient rich medium is added in order to assure full coverage of the tissue. Exemplary cryoprotectants include, but are not limited to, dimethyl sulfoxide (DMSO), glycerol, ethylene glycol, propylene glycol, 2-Methyl-2.4-pentanediol (MPD), and sucrose. The samples are packaged in cryoresistant containers. One sample as a probe sample is cryopreserved in a laboratory cryopreservation unit. The packaged tissue is then subjected to slow controlled rate freezing to at least −80° C. Once the program cycle is complete, the tissue is placed in liquid nitrogen.

Prior to implantation, a cryopreserved adipose implant is thawed. The thaw procedure warms the tissue preparing it for implantation. The vial containing cryopreservation solution and tissue is thawed at room temperature or alternatively warmed to 37° C. to expedite the thawing process. Alternatively, the thawing temperature can be at a temperature in the range of about 4° C. through 50° C. Alternatively, the freeze-thawing process can be repeated. Once the cryopreservation solution is free flowing, the cryopreservation solution is decanted from the vial and the tissue is implanted immediately, without any rinse. Prior to implantation, the tissue is optionally rinsed for 0-15 minutes with the other wash solutions including but not limited to saline, 5% dextrose in lactated ringers solution, phosphate buffered saline, and any additional isotonic solution.

The wash solution is added at room temperature or alternatively, prior to application to the tissue, the wash solution is warmed to a temperature not exceeding 37° C.-39° C. in order to minimize any damage to the cells contained in the tissue. The wash solution is exchanged throughout the rinse or alternatively the tissue is stored in the wash solution at 4° C. until ready for implantation. Any remaining tissue from the surgery is not re-frozen for future use. All remaining tissue is disposed of appropriately after surgery.

A strainer is used to contain the tissue during the decanting process. This allows the cryopreservation solution and rinseate to be removed from the tissue while minimizing any possible contamination of tissue during preparation (minimizes human contact). Gauze is optionally used to contain the tissue during the decant/thaw procedure.

As described in detail above, adipose-derived stem cells possess a potential to differentiate into a wide variety of cell types, including, but not limited to, nerve cells, astrocytes, fat cells, chondrogenic cells, osteogenic cells, or insulin-releasing pancreatic cells.

Example 7: Processing Superficial Fascia

A sample of adipose tissue with its associated superficial fascial tissue is obtained aseptically from a suitable donor, and a size reduction, such as grinding or mincing, is performed. At a temperature of ambient or greater, the tissue is placed in a conical tube or beaker, and homogenized. The homogenized tissue is then centrifuged to separate the sample into adipose tissue, which floats, one or more liquid layers, and fascial tissue, which forms below the liquid layers.

The fascial tissue is recovered and rinsed in water or buffer solution to remove undesired residual materials (e.g., blood cells or stromal cells). The fascial tissue is then soaked in a disinfecting solution, with agitation, as described in Example 2. Because of the relatively low number of cells in fascial tissues, the disinfection step in the present Example may be sufficient to produce an adequately decellularized or acellular tissue. The disinfected fascial tissue is then lyophilized and milled using a freezer mill to obtain a fascia-derived matrix powder.

Example 8: Processing Superficial Fascia with Surfactant Decellularization

A sample of adipose tissue with its associated superficial fascial tissue is obtained and processed as described in Example 7 above, except that the recovered fascial tissue is soaked with mechanical agitation in a sodium deoxycholate solution as described in Example 1 above prior to disinfection. Contact with the deoxycholate solution provides a complete decellularization of the recovered fascial tissue. Other suitable surfactants known to decellularize tissues may be used as an alternative to or in addition to sodium deoxycholate.

Example 9: Processing Superficial Fascia with Delipidization

A sample of adipose tissue with its associated superficial fascial tissue is obtained and processed as described in Example 7 above, except that the recovered tissue is delipidated using the process steps described in Example 4. Where less aggressive lipid removal is desired, the recovered fascial tissue may be processed according to the steps described in Example 3.

Example 10: Processing Superficial Fascia with Recovery of Soluble Proteins

A sample of adipose tissue with its associated superficial fascial tissue is obtained and processed as described in Example 7 above, except that a portion (e.g., 5 to 50 percent based on the total quantity of tissue being processed, not specific to structure or function) of the recovered fascial tissue is reserved prior to the decellularization step. Soluble proteins, which include, but are not necessarily limited to growth factors, chemokines, and soluble matrix proteins, are recovered from the reserved tissue by extraction. The resulting protein extract is concentrated, purified, and/or sterilized using techniques that are well-known in the art.

The remainder of the recovered fascial tissue is disinfected as discussed in Example 7, and the proteins recovered from the reserved fascial tissue are mixed into the disinfected tissue. The disinfected fascial tissue with the added proteins is then lyophilized and milled using a freezer mill to obtain a fascia-derived particulate matrix.

Example 11: Fabrication of an Acellular Matrix from Adipose and Fascial Tissues A sample of adipose tissue with its associated superficial fascia is obtained aseptically from a suitable donor, and the adipose tissue and fascia are separated as described in Example 7, and recovered separately. The recovered adipose tissue is processed as described in Example 5 to obtain a particulate adipose-derived acellular matrix. The recovered fascial tissue is processed as described in Example 7 to obtain a particulate fascia-derived acellular matrix. Portions of the particulate adipose-derived matrix and the particulate fascia-derived matrix are combined to produce the acellular implant. More particularly, particulate adipose-derived matrix and particulate fascia-derived matrix are combined in quantities that provide a desired ratio of adipose-derived protein to fascia-derived protein. For example, without limitation, the desired ratio of adipose-derived protein to fascia-derived protein may be from 1:1 to 1:4 of adipose to fascia, on a weight basis.

Two sample implants, Sample A and Sample B in Table 14, were produced in accordance with the foregoing method where Sample A had a ratio of adipose to fascia of 1:1 (by weight) and Sample B had a ratio of adipose to fascia of 1:4 (by weight). Comparative Samples C and D were also prepared where Comparative Sample C included only adipose derived material and Comparative Sample D included only fascia-derived material. All four of these samples were implanted into the bilateral flank of athymic (nude) mice after rehydration to 33% protein concentration in saline, on a weight of protein to volume of saline basis; injections into the subcutaneous space were performed in a fanning technique resulting in implantation of a total of 0.3 cc of material per implant. The mice were sacrificed in a sequence which allowed quantification of the remaining implant volume at 3 weeks after implantation and at 12 weeks after implantation. The Volume Retention for each implant was calculated as a percent compared to the original total volume of the implant when implanted (i.e., 0.3 cc). The following Table 14 provides the results of this experiment.

TABLE 14

| Adipose/Fascia Composite Implant Volume Retention in Mice | | |
|---|---|---|
| Sample ID | 3-Week Volume Retention Average | 12-Week Volume Retention Average |
| Comparative Sample C (Adipose) | 108.67 | 47.67 |
| Sample A (1:1) | 132.00 | 92.67 |
| Sample B (1:4) | 185.33 | 140.33 |
| Comparative Sample D (Fascia) | N/A | 230.67 |

With reference to Table 14, all 3-week explants are averages based on N=5 samples; all 12-week explants are averages based on N=10 except the Comparative Sample D (Fascial Scaffold Only condition), which is averaged based on N=5. The Volume Retention Averages reported in Table 14 above were the averages calculated using the Volume Retention results for the number, N, of recovered implant samples for each of the 3-week and 12-week experiments. Considering the volume retention trends, the data suggests that increasing volume is proportional to the fascial scaffold content contained within the graft; histologically, it was shown that adipogenesis, or the presence of adipocytes in the scaffold, was less prominent in scaffolds of higher fascial contents, suggesting an inversely proportional relationship.

In addition, each of Sample C (adipose only scaffold) and Sample D (fascia only scaffold) were tested for residual lipid content, using gas chromatography. Residual lipid in Sample C was approximately 39%, by weight. Residual lipid in Sample D was approximately 15%, by weight.

In some embodiments, decellularization of the size-reduced and delipidized matrices may be performed on each of the particulate adipose-derived matrix and particulate fascia-derived matrix separately before their combination with one another. In other embodiments, decellularization may be performed after their combination, i.e., the combined adipose/fascia matrix implant materal may be decellularized to produce the acellular matrix implant. In embodiments where decellularization is performed after combination of the adipose-derived matrix and fascia-derived matrix, one or more disinfection, micronization and lyophization processes may be performed on the combined implant material after decellularization.

Example 12: Fabrication of a Complex Acellular Matrix from Recombined Adipose and Fascial Tissues A sample of adipose tissue with its associated superficial fascia is obtained aseptically from a suitable donor, and the adipose tissue and fascia are separated as described in Example 7. The fascial tissue is rinsed and set aside, while the adipose tissue is delipidated as described in Example 5. The fascial tissue and delipidated adipose tissue are then recombined. The combined tissues are then decellularized and post-processed according to the processes described in Example 5 to obtain a complex particulate acellular matrix that is derived from the recombined adipose and fascial tissues.

The particulate acellular matrix is referred to as being "complex" because both the adipose-derived matrix and fascia-derived matrix may be present in the individual particles of the post-processed matrix. In a typical sample of adipose tissue with its associated superficial fascia, roughly 10 percent of the wet mass of the sample will be superficial fascia, roughly 80 percent of the wet mass of the sample will be adipose tissue, with the remainder comprising other types of cells and tissues. The complex acellular matrix derived from such a sample will have a ratio of fascia-derived matrix to adipose-derived matrix in the range of about 5:1 to about 25:1.

Example 13: Fabrication of a Complex Acellular Matrix from Unseparated Adipose and Fascial Tissues A sample of adipose tissue with its associated superficial fascia is obtained aseptically from a suitable donor, and processed as described in Example 5, without an initial separation of the adipose and fascial tissues. For a typical sample of adipose tissue with its associated superficial fascia, as described, for example, in Example 12, the post-processed matrix of the present Example is a complex matrix having a ratio of fascia-derived matrix to adipose-derived matrix in the range of about 5:1 to about 25:1.

Example 14: Delipidization of an Adipose Tissue Using Multiple Homogenizing Sequences at Higher RPM and Temperature A sample of adipose tissue is processed essentially as described in Example 4, with the following steps to homogenize and delipidize the adipose tissue. A first homogenizing sequence is performed which includes adding an organic alcolohol which comprises 1-propanol to the tubes, rapidly homogenizing the alcohol/tissue mixture by blending at from about 5,000 to about 20,000 revolutions per minute (RPM), such as from about 10,000 to about 15,000 RPM and centrifuging the homogenized mixture to separate lipid, solvent, water and tissue layers. A second homogenizing sequence is performed which comprises essentially the same steps as the first homogenizing sequence.

The homogenized adipose tissue is then delipidized by subjecting it to two soaks in an organic alcohol comprising 1-propanol, each of which administer intermittent 5-minute centrifugations performed at or near 40° C. or higher. It is believed that performing the homogenation at greater speed (i.e., about 10,000 RPM or greater) creates a more homogeneous hydrogel when the scaffold is blended with an acid-based disinfection solution and subsequently buffered to a neutral or near-neutral pH. Performing the delipidizing soaks with centrifuging at or near 40° C. or higher is believed to decrease the lipid viscosity, thereby facilitating a more proficient solubilization in the 1-propanol. The homogenized and delipidized adipose tissue is then subjected to further processing steps including decellularization, disinfection, and post-processing.

The following Table 15 provides the results of an evaluation of the performance of a process including the foregoing homogenizing and other processes (i.e., using multiple homogenizing sequences at greater RPM and delipidizing soaks at higher temperature) as compared to the performance of a delipidizing process that uses two sequences of homogenizing at reduced RPM and without any soaks. With reference to Table 15, adipose Samples 1-4, 6 and 8 were delipidized using the above-described increased RPM homogenizing sequences with the two higher temperature delipidizing soaks. Adipose Samples 5, 7 and 9 were delipidized using the comparative reduced RPM homogenizing and lower temperature delipidizing soaks.

TABLE 15

| Residual Lipid in Final Adipose Scaffold | |
| --- | --- |
| Sample # | Residual Lipid (%) |
| 1 | 4.12 |
| 2 | 5.21 |
| 3 | 2.97 |
| 4 | 2.19 |
| 5 (Comparative) | 38.8 |
| 6 | 2.37 |
| 7 (Comparative) | 43.7 |
| 8 | 1.21 |
| 9 (Comparative) | 70.1 |

The sources for the adipose tissue for each of Samples 1-3 were three different donors. The source for the adipose tissue of Samples 4 and 5 was the same donor, but different from the donors for Samples 1-3. The source for the adipose tissue of Samples 6 and 7 was the same donor, but different from the donors of any of Samples 1-5. The source for the adipose tissue of Samples 8 and 9 was the same donor, but different from the donors of any of Samples 1-7. Each of Samples 1-9 was tested to quantify the residual lipid content in the final adipose scaffold by gas chromatography, three of which were processed in a head-to-head fashion in an effort to directly compare the relative delipidation capacities of the two processes.

Based on the measured residual lipid values, the averages yielded from the two processes were 3.01% (by weight) for the greater RPM homogenizing and higher temperature delipidizing processes and 50.87% (by weight) for the comparative reduced RPM process without soaks. It should be noted that hydration with saline to approximately a 25% protein concentration (by weight) is recommended, which would dilute the lipid contents to 0.75% (greater RPM and higher temperature process) and 12.72% (comparative reduced RPM process without soaks).

In addition, analysis of the scaffolds including adipose tissue delipidized using the higher RPM and temperature process showed that such scaffolds contained the following factors after all processing was completed: IGF-1, EGF, angiopoietin-2, BMP-9, Endoglin, FGF-1, HB-EGF, PLGF, FGF-2, NGF, IL-6, IL-8, IL-1B, nidogen, and vitronectin. Typical and suitable extraction procedures for soluble factors are well known and understood by persons of ordinary skill in the art.

Example 15: Fabrication of an Acellular Matrix from Adipose and Fascial Tissues with Decellularizing after Combining Adipose and Fascial Matrices A sample of adipose tissue with its associated superficial fascia is obtained aseptically from a suitable donor, and the adipose tissue and fascial tissue are separated, as described in Example 7, and recovered separately. The recovered adipose tissue is homogenized and delipidized as described in Example 14 to obtain a delipidized adipose-derived matrix. The recovered fascial tissue is delipidized by performing at least one soak comprising extracting with an organic alcohol (e.g., 1-propanol) and centrifuging to obtain a delipidized fascia-derived matrix.

Portions of the delipidized adipose-derived matrix and the delipidized fascia-derived matrix are combined in a desired ratio to produce a combined delipidized adipose/fascial matrix. For example, without limitation, the desired ratio may be from 1:1 to 1:4 of adipose to fascia, on a weight basis. The combined adipose/fascial matrix is then subjected to further processing steps including decellularization, disinfection, and post-processing.

Example 16: Analyzing a Combined Adipose/Fascia Implant to Distinguish Adipose-Derived Matrix and Fascia-Derived Matrix Therein Collagen IV is present in adipose-derived tissue and matrices, but not in fascia-derived tissue and matrices. Both contain collagen I. Using counterstaining to investigate the collagen IV and collagen I content of a combined adipose/fascia implant, the counter-stained implant will provide semi-quantitative insight into the reunited mass of fascia relative to that of adipose. It is to be reasonably expected that a scaffold comprised of equal parts adipose and fascial protein would show approximately 50% the presence of collagen IV relative to the presence of collagen I. This method may, therefore, be employed to determine the resulting ratios of fascia and adipose in a combined adipose/fascia implant.

Example 17: Processing Superficial Fascia and Supplementing with Extracted Factors A sample of adipose tissue with its associated superficial fascia is obtained aseptically from a suitable donor, and the adipose tissue and fascial tissue are separated, as described in Example 7, and recovered separately. The recovered fascial tissue is subjected to one or more pre-processing steps to produce size-reduced fascial tissue. The recovered fascial tissue is delipidized by performing at least one soak comprising extracting with an organic alcohol (e.g., 1-propanol) and centrifuging to obtain a delipidized fascia-derived matrix. A portion of the delipidized facia-derived matrix which is in an amount of from about 5% to about 10% of the total delipidized fascia-derived matrix, by weight, is separated and subjected to an extraction process to separate extracted factors from the delipidized fascia-derived matrix. The remaining 90% to 95% of the delipidized fascia-derived matrix is subjected to a disinfection process and then combined with the extracted factors to produce a supplemented fascia-derived matrix. The supplemented fascia-derived matrix is lyophilized and then subjected to post-processing (e.g., milling) and packaging processes to produce a final fascia-derived matrix product.

Example 18: Fabrication of a Pre-Hydrated Acellular Implant Using Adipose Tissue A sample of adipose-rich soft tissue is obtained from a suitable donor. The tissue is inspected for muscle and dermis, which is then cut away from the adipose tissue. Size reduction is then performed by grinding or mincing the adipose tissue, or by another suitable method.

The adipose tissue is then delipidized by the method of either Example 3 or 4, or by the method described herein. The adipose tissue is divided between a number of centrifuge tubes and a small amount of water is added to each tube to wet the tissue. The tissue is warmed to a temperature above ambient, and centrifuged to separate a lipid layer from the tissue. A lipid layer, a water layer, an adipose layer, and bottom pellet are formed.

The adipose layer is recovered and blended with an equal portion of an alcohol, or alcohol with surfactants or detergents (e.g., Triton X-100 or Tween 80), then returned to the centrifuge tube. The mixture of adipose tissue and alcohol is centrifuged to separate the mixture into layers of lipid, alcohol, and adipose tissue. The adipose tissue is then recovered. The alcohol treatment may be repeated a number of times to remove all of the lipid from the tissue.

After the final alcohol treatment, the adipose tissue is decellularized by the method of either Example 1 or 2, or by the following method now described. The adipose tissue is soaked in a hypertonic solution (e.g., 1M NaCl) with agitation for at least 6 hours at ambient temperature. The tissue and hypertonic solution may be blended before the soaking step begins. After soaking in hypertonic solution, the adipose tissue is recovered from the mixture by centrifugation at a temperature above ambient, and soaked in a dilute detergent or surfactant solution with agitation for at least 12 hours at ambient temperature. One suitable solution would have at least 0.1% of a surfactant in water. After soaking in the detergent, the adipose tissue is recovered by centrifugation, and rinsed at least twice in deionized water.

After the water rinse, the recovered adipose tissue is suspended in a disinfecting solution, and allowed to soak with agitation. One suitable disinfection solution would be between 0.5% and 1% peracetic acid in a mixture of water, ethanol, and propylene glycol. The adipose tissue is then recovered by centrifugation, and subjected to multiple water rinses to remove any remaining disinfecting solution.

The resulting product is a pre-hydrated acellular soft-tissue-derived matrix which may be shaped or molded into an implant, or may be further treated as described herein above to adjust the flowability of the matrix for injection using a syringe or needle.

The pre-hydrated acellular soft tissue-derived matrix may be packaged in a sterile container for later use, or used immediately. Unlike the dry particulate acellular soft tissue-derived matrix, the pre-hydrated matrix does not need to be rehydrated prior to use. For example, the pre-hydrated matrix may be added to a syringe, which is then stoppered and packaged in foil and/or a Kapak® pouch (Kapak Corporation, St. Louis Park, MN).

Example 19: Fabrication of a Pre-Hydrated Acellular Matrix from Adipose and Fascial Tissues With Decellularizing After Combining Adipose and Fascial Matrices Similar to the general exemplary process shown in FIG. 3, a sample of adipose tissue with its associated superficial fascia is obtained aseptically from a suitable donor, and the adipose tissue and fascial tissue are separated, as described in Example 7, and recovered separately. The recovered adipose tissue is homogenized and delipidized as described in Example 14 to obtain a delipidized adipose-derived matrix. The recovered fascial tissue is delipidized by performing at least one soak comprising extracting with an organic alcohol and centrifuging to obtain a delipidized fascia-derived matrix.

Portions of the delipidized adipose-derived matrix and the delipidized fascia-derived matrix are combined in a desired ratio to produce a combined delipidized adipose/fascial matrix. For example, without limitation, the desired ratio may be from 4:1 to 1:4 of adipose to fascia, on a weight basis. The combined adipose/fascial matrix is then subjected to further processing steps including, for example without limitation, decellularization, disinfection and, optionally, centrifugation. The combined adipose/fascial matrix is not dried and, therefore, the resulting product is a pre-hydrated acellular soft tissue-derived matrix comprising both adipose-derived and fascia-derived material. This pre-hydrated acellular soft tissue-derived matrix may be used immediately or it may be packaged for later use.

Example 20: Fabrication of Pre-Hydrated Acellular Matrices from Adipose and Fascia Tissues—Adipose and Fascia Combined During Delipidating, Followed by Decellularizing Donor soft tissue matrix was recovered using standard aseptic recovery procedures and stored frozen (below 20° C.). The matrix, which contained adipose and (superficial) fascia tissue types, was transferred to the lab where it was thawed overnight on the counter. Following thawing, the tissue was cut into strips having a longest dimension of about 2 inches and then ground, using a 2 mm grinding plate in a modified Globe CC12 grinder available from Globe Food Equipment of Dayton, Ohio, U.S.A., and the ground soft tissue was collected in centrifuge bottles. 30-50 ml of purified USP water (i.e., United States Pharmacopeia standard for highly purified water containing less that 10 CFU/100 ml of aerobic bacteria) was added to each of the centrifuge bottles and the ground soft tissue was centrifuged at 4,600 rpm, at from 30° C. to 45° C., for 15 minutes.

The resulting centrifuged tissue in each bottle had four layers as follows: a bottommost layer of fascia tissue adhering to the bottle, a second layer comprising water in liquid phase on top of the bottommost fascia layer, a third layer comprising adipose floating on top of the water layer; and a topmost layer comprising lipids in liquid phase on top of the floating adipose layer. The adipose and fascia layers were separately recovered as follows. Using a spatula, or similar solids retention device to hold the adipose in the centrifuge bottle, the liquid phase water and lipids layers were poured (decanted) out of the bottle, leaving the adipose and fascia layers (fractions). Then the adipose was poured off the adhered fascia layer into a beaker, and the adhered fascia layer was manually scraped out of the bottle and into another beaker, using a spatula or similar collection device. Masses for both the recovered adipose and the recovered fascia were measured and recorded.

The recovered adipose fraction was then delipidated by subjecting it to two blend steps in 1-Proponal using a blender on high for 80 sec. First blend step with maximum concentration of 1000 g adipose/1.5 L 1-Propanol, and second blend step maximum concentration of 2000 g adipose in 2 L 1-Propanol. After each blend step, the adipose fraction was centrifuged (4,600 rpm, 30-45° C.) for 5 min, and the adipose fraction separated from the 1-Propanol and recovered (e.g., by decanting and using a spatula to retain the adipose in the container).

The recovered fascia fraction was then delipidated by blending it one time in 1-Proponal on high for 80 seconds with a maximum blend concentration of 200 g fascia/1.5 L 1-Propanol, followed by centrifugation (4,600 rpm, 30-45° C.) for 5 min, after which the fascia was separated from the 1-Propanol and recovered (e.g., by decanting the 1-Propanol off and scraping the adhered fascia out of the container). (Alternatively, the fascia may be soaked for 10-90 minutes in 1-Propanol at a maximum ratio of 350 g fascia/1 L 1-Propanol).

The adipose fraction and fascia fraction were then combined in amounts necessary to produce sample combined adipose/fascia complexes (i.e., matrices) having desired predetermined mass proportions (%) of adipose: fascia (i.e., mass ratios).

Each combined adipose/fascia complex was then further delipidized by blending with 1 L 1-Proponal (maximum concentration of 250 g of adipose/fascia complex/1 L 1-Propanol) for 80 seconds, followed by centrifugation at 4,600 rpm and 30-45° C. for 5 min. The resulting mass for each centrifuged complex was recorded.

To perform decellularization, 250 g (maximum) of each of adipose/fascia complexes were combined, separately, with 1 L 25% ethyl alcohol and 40 g sodium deoxycholate (SDC) and blended for 80 seconds on high speed. Each of the resulting mixtures were transferred to separate suitably sized flasks and soaked overnight (e.g., for about 18-24 hours) in an orbital shaker set at about 150 rpm, at room temperature (e.g., 20-25° C.).

Following the decellularization soak, each of the tissue-containing mixtures was poured directly into a blender and blended on high speed for 80 seconds, followed by three centrifugation steps (4,600 rpm, 15-30° C.) for 5 min each. For each mixture, the tissue was recovered and rinsed in 1 L 25% ethyl alcohol between the first and second centrifugation steps, and in 1 L USP water between the second and third centrifugation steps. Both rinses were performed in the flasks, at 150 rpm for 30 minutes at room temperature. The mass was recorded for each adipose/fascia complex and each complex was placed into a freezer bag pouch, each pouch was sealed and placed into a −70° C. freezer for storage.

Each adipose fascia complex was further processed as follows. Following storage for at least one day (i.e., approximately 22 to 26 hours) in the freezer, the adipose/fascia complex was thawed in the freezer bag, at room or in a refrigerator, with or without agitation. Alternatively, the complex may be removed from an outer layer of the freezer bag and placed in water.

The complex was then disinfected by combining from 200 g to 250 g of the complex with 1 L of disinfection solution (for example, 0.1-1.0 wt % peracetic acid in a mixture of water, ethanol and propylene glycol), and blended on high speed for 80 seconds. The complex in disinfection solution was then transferred to light-protected flasks and soaked for 2-4 hours, at room temperature, in an orbital shaker set at about 150 rpm.

After soaking, the complex in disinfection solution was transferred directly into a blender and blended for 80 seconds. Approximately 125 ml of 10× Dulbecco's phosphate buffered solution (DPBS) was added to the complex in disinfection solution in the blender, and the combination was blended on high for 10 seconds. The resulting solution was centrifuged (4,600 rpm, 10-30C) for 10 min. The disinfection solution was decanted and the tissue was recovered. The tissue was rinsed in 1 L 1×DPBS for 5 min, then centrifuged (4,600 rpm, 10-30C) for 5 minutes, followed by separation and recovery of the adipose/fascia complex. This rinsing-centrifuging process was repeated three more times using the same conditions. Then, the resulting complex was rinsed in USP water for 10 min and centrifuged (4,600 rpm 10-30C) for 5 minutes, at room temperature, followed by separation and recovery of the adipose/fascia complex. The water rinse-centrifugation step was repeated 1 more time at room temperature.

The resulting adipose/fascia complex was added to a clean container and 8% on a weight/weight basis of approximately 2 wt % hyaluronic acid paste (sodium hyaluronate powder in Sorenson's PBS) was added. The resulting combination was mixed thoroughly with a spatula until well-mixed (i.e., substantially homogenous). The resulting product was packaged into syringes (e.g., polymer syringes) which were sealed in a sterile manner. The tissue containing syringes were stored at ambient temperature (i.e., from about 15° C. to about 30° C.). All blending steps used a modified Waring blender, Model CB15.

Example 21: Pre-Hydrated Adipose-Fascia Acellular Matrices Having Varied Proportions of Fascia—Evaluation for Extrudability Several configurations of pre-hydrated adipose-fascia acellular matrices having varying adipose and fascia tissue proportions were prepared, generally as described in Example 20 above, in the proportions listed in Table 16 below. In particular, 100 wt % adipose matrix samples were produced by separating adipose from fascia tissue as described in Example 20, but without recombination with fascia matrix and subjected to the following further processing steps. Following delipidation blending of the recovered adipose fractionate as described in Example 20, the adipose tissue was additionally subjected to two soaks in 1-propanol solution for a duration of 10 minutes per soak (maximum concentration of 350 g of adipose/1 L 1-Propanol). Intermittent centrifugation for 5 minutes (4,600 rpm, 35-40C) had facilitated recovery of the tissue pellet.

To perform decellularization, 350 g (maximum) of adipose was combined with 1 L 25% ethyl alcohol and 40 g sodium deoxycholate (SDC), transferred to suitably sized flask, and soaked overnight (e.g., for about 18-24 hours) on an orbital shaker set at 150 rpm, at room temperature (e.g., 20-25° C.). Following decellularization, the tissue pellet had been recovered via centrifugation for 5 minutes (4,600 rpm, 10-30C). Subsequently, the tissue was rinsed in a tissue flask, first with 1 L 25% ethyl alcohol, and then with 1 L USP water, with agitation on an orbital shaker set to 150 rpm for a duration of 30 minutes per rinse (maximum tissue mass of 350 g/flask). Intermittent centrifugation for 5 minutes (4,600 rpm, 10-30C) had facilitated pellet recovery following each of the aforementioned rinses. The mass was recorded and the recovered pellet was placed into a freezer bag pouch, sealed, and placed into a −70° C. freezer for storage. Following storage for at least one day (i.e., approximately 22 to 26 hours) in the freezer, the adipose was thawed in the freezer bag, at room or in a refrigerator, with or without agitation. Alternatively, the complex may be removed from an outer layer of the freezer bag and placed in water.

The adipose was then disinfected by combining up to 350 g of the tissue matrix with 1 L of disinfection solution (for example, 0.1-1.0 wt % peracetic acid in a mixture of water, ethanol and propylene glycol), and blended on high speed for 80 seconds. The complex in disinfection solution was then transferred to light-protected flasks and soaked for 2-4 hours, at room temperature, in an orbital shaker set at about 150 rpm.

After soaking, approximately 110-120 ml of 10× Dulbecco's phosphate buffered solution (DPBS) was added to the adipose matrix in disinfection solution in the flask, and the suspension was agitated at 150 rpm for approximately 30 seconds. The resulting solution was centrifuged (4,600 rpm, 10-30C) for 10 min.

The tissue was rinsed in 1 L 1×DPBS for 5 min, then centrifuged (4,600 rpm, 10-30C) for 5 minutes, to facilitate the recovery of the adipose pellet. This rinsing-centrifuging process was repeated three more times, with rinse durations of 5 minutes, 10 minutes, and 10 minutes, for a total of four 1×DPBS rinses. Following the conclusion of the 1×DPBS rinses, the recovered adipose pellet was subsequently rinsed in USP water for 20 minutes and centrifuged (4,600 rpm 10-30C) for 5 minutes. This rinse was repeated, for a total of two twenty minute rinses in USP water.

The recovered adipose pellet was collected, mixed thoroughly with a spatula until well-mixed (i.e., substantially homogenous) and centrifuged using a high speed carbon fiber centrifuge rotor (Thermo Scientific F14-6×250 LE) at 15,000 RCF for a duration of 15 minutes at 10-30 C. The resulting pellet was collected, mixed thoroughly with a spatula until well-mixed (i.e., substantially homogenous) and packaged into syringes (e.g., polymer syringes) which were sealed in a sterile manner. The tissue containing syringes were stored at ambient temperature (i.e., from about 15° C. to about 30° C.).

The two adipose-fascia matrices (complexes), i.e., one having a mass proportion (%) of adipose: fascia of 50:50 (i.e., mass ratio of 1:1), and the other having a mass proportion (%) of 75:25 (i.e., mass ratio of 3:1), were prepared as described in Example 20 above, except that the 75:25 matrix samples tested were not combined with a 2% hyaluronic acid paste.

The 100% fascia matrix was produced as described in Example 20 above, but without recombining with adipose matrix and without addition of a 2% hyaluronic acid paste.

Multiple samples of each configuration (N=4) were tested for injectability by confirming each would pass through a 20 gauge needle and measuring the average injection force (Newtons, N) required to accomplish said passage. It has been demonstrated in published literature that an injection force less than about 30N is an acceptable injection force standard for practical human use by practitioners. The measured average injection force for all categories of acellular matrix compositions were well below 30N.

The method used to measure the average injection forces reported above in Table 16 was as follows:

Each sample matrix to be tested was packaged into 3 cc B-D Luer-Lok syringes, with 1.5 cc of sample matrix material per syringe. A single-use, transfer/female-female Luer-Lok adaptor for the samples comprising any amount of fascia or an emulsifier (0.5 mm ID) for the 100% adipose samples was attached to the sample syringe, and an empty 3-cc syringe was attached the adaptor or emulsifier. The sample was transferred back and forth slowly at least 10 times, the sample was then returned to the sample syringe and the syringe was disconnected from the adaptor or emulsifier. A hypodermic needle was then attached to the open end of the sample syringe. The syringe was loaded into a syringe collar which in turn was placed into a holding fixture affixed to an MTS 858 Bionix Testing System (MTS, Eden Prairie. MN). Samples were tested in compression by first applying a pre-load of 0.5 N (rate=63.5 mm/min) immediately followed by a constant extension rate of 25.4 mm/min until 31 mm extension was achieved. Average and maximum extrusion force was recorded, and the average extrusion forces required for each type of sample adipose-fascia matrix are listed in Table 16 below.

TABLE 16

| Adipose and Fascia Extrudability Tests | | |
|---|---|---|
| Acellular Matrix Composition (% adipose/% fascia) | Syringe Size (cc) | Avg $F_{inj}$ (N) |
| 50/50 in 8% hyaluronic acid paste* | 5 | 14.4 |

TABLE 16-continued

| Adipose and Fascia Extrudability Tests | | |
| --- | --- | --- |
| Acellular Matrix Composition (% adipose/% fascia) | Syringe Size (cc) | Avg $F_{inj}$ (N) |
| 75/25 | 3 | 6.0 |
| 100% adipose | 3 | 9.5 |
| 100% fascia* | 3 | 13.5 |

\*only 2 of the 4 samples passed through the 20 gauge needle
^the hyaluronic acid paste was 2 wt % HA in isotonic saline

Example 22: Adipose-Fascia Acellular Matrices Having Varied Proportion of Fascia—Evaluated for Volume Retention Several acellular matrices were prepared from adipose and fascia tissues, in varying predetermined ratios and evaluated with in vivo experiments for volume retention using normothymic rats over an eight (8) week period of time. The following procedure was followed for preparing the several sample matrices and evaluating the volume retention, with the results presented in Table 17 below.

A sample of adipose tissue with its associated superficial fascia was obtained aseptically from a suitable donor, and the adipose tissue and fascial tissue were separated, as follows to obtain recovered adipose tissue and recovered fascia tissue. Size reduction, such as grinding or mincing, is performed. At a temperature of ambient or greater, the tissue is placed in a conical tube or beaker, and homogenized. The homogenized tissue is then centrifuged to separate the sample into adipose tissue, which floats, one or more liquid layers, and fascial tissue, which forms below the liquid layers.

To prepare Comparative Sample Y (100% adipose), recovered adipose tissue was processed in the same manner as the 100 wt % adipose matrix samples described in Example 21, but without the high speed centrifugation process and instead performing a lyophilization treatment and subsequent hand and freezer milling steps. Specifically, post USP water rinses, the adipose tissue had been collected, mixed thoroughly with a spatula until well-mixed (i.e., substantially homogenous) and loaded into a stainless steel lyophilization mold. The mold had been packaged into a Tyvek pouch and subjected to an approximately 36 hour lyophilization cycle, resulting in the dehydration of the tissue matrix. The dehydrated discs were subsequently quartered using shears, and milled using a modified IKA Hand Mill A11 Basic to produce a coarse powder. This powder was then loaded into SPEX mid-size polycarbonate freezer mill vials (no more than 5.00 g of tissue/vial), along with a stainless steel impactor, and capped with stainless steel end plugs. All vials were then loaded into stainless steel housings and freezer milled using a SPEX Model 6870D with the following cycle parameters: 20 minute precool, 1:00 minute run time, 2 minute cool time, 15 cycles, rate of 15 CPS. Upon completion of the freezer milling cycles, all housings were allowed to thaw at ambient room temperature for minimally two hours. Thereafter, the resultant fine matrix powders had been collected, mixed thoroughly with a spatula until well-mixed (i.e., substantially homogenous) and packaged into syringes and subsequently sealed into foil pouches.

Comparative Sample Z (100% fascia) was prepared as described above, using the fascial tissue recovered following the grinding and initial layer separation. Additionally, during the delipidation of the fascial tissue, the aforementioned blending steps had been foregone, with only two 10 minute delipidation soaks using 1-propanol having taken place (no more than 350 g/flask with 1 L of solution/flask). Intermittent centrifugation (4,600 rpm, 35-40C) for 5 minutes had facilitated pellet recovery. In addition, during the disinfection of the facia tissue, a 2-4 hour disinfection soak, using 1 L of disinfection solution (for example, 0.1-1.0 wt % peracetic acid in a mixture of water, ethanol and propylene glycol) per flask, at 150 rpm had been utilized, in lieu of the aforementioned disinfection blending step. Following the conclusion of the disinfection soak, 110-120 mL of 10×DPBS had been added to the suspension, and centrifugation (4,600 rpm, 10-30C) for 10 minutes had facilitated recovery of the tissue pellet. 1×DPBS Buffer and USP water rinses, lyophilization, hand milling, freezer milling, and packaging of the dehydrated fascia-derived tissue powder had proceeded in the manner detailed above.

To prepare Samples V, W and X, (25 wt %, 50 wt % and 75 wt % fascia, respectively), processed adipose and fascia tissues (i.e. Samples Y and Z), as lyophilized, fine powders, were combined in an aseptic work environment in order to produce the aforementioned weighted ratios. Once the appropriate ratios of adipose-derived and fascia-derived powders had been weighed and verified, each sample had been mixed thoroughly with a spatula until well-mixed (i.e., substantially homogenous), packaged into syringes, and subsequently sealed into foil pouches.

All five of these Samples V-Z were implanted into the bilateral flank of normothymic rats after rehydration to 22.5 wt % protein concentration in saline, on a weight of protein to volume of saline basis; injections into the subcutaneous space were performed in a fanning technique resulting in implantation of a total of 1 cc of material per implant. The rats were sacrificed in a sequence which allowed quantification of the remaining implant volume at 8 weeks after implantation. The Volume Retention for each implant was calculated as a percent compared to the original total volume of the implant when implanted (i.e., 1 cc). The following Table 17 provides the results of this experiment.

TABLE 17

| Adipose/Fascia Composite Implant Volume Retention in Rats | | |
| --- | --- | --- |
| Sample ID | 8 Week Volume Retention Average | N= |
| Comparative Sample Y (100% Adipose) | 9% | 8* |
| Sample V (3:1, 25 wt % fascia) | 25% | 6 |
| Sample W (1:1, 50 wt % fascia) | 37.5% | 8 |
| Sample X (1:3, 75 wt % fascia) | 45% | 7 |
| Comparative Sample Z (100% Fascia) | 70% | 7 |

\*only 3 of the 8 explants of Sample V type were recovered, with the remaining 5 samples lacking sufficient tissue bulk for recovery and, therefore, entered as "zero" for calculation of the Volume Retention Average reported above With reference to Table 17, the Volume Retention Averages reported above are averages which were calculated using the Volume Retention results for the number, N, of recovered implant samples for each sample type. In particular, the Volume Retention Average values reported for the Sample V (25% fascia) 8-week explants were each based on N=6 samples. The Volume Retention Average values reported for the Sample W (50% fascia) 8-week explants were each based on N=8 samples. The Volume Retention Average values reported for the Sample X (75% fascia) and Sample Z (100% fascia) 8-week explants were each based on N=7. The values reported for the Comparative Sample Y (Adipose only) 8-week explants were averaged based on N=8 (see note above). Considering the volume retention trends, the data suggests that increasing volume is proportional to the proportion of fascial tissue-derived matrix contained within the graft.

Example 23: Fabrication of Acellular Matrices from Adipose and Fascia Tissues Mixed Earlier in the Process To facilitate upstream mixing of adipose and fascia derived tissue matrices, the adipose and fascia tissue layers were separated and isolated following mechanical reduction, homogenization, and centrifugation as previously described in Example 20.

Following tissue layer separation, the isolated adipose fractionate were delipidated in 1-propanol solution, via two-stage blending, as described in Example 20. Intermittent centrifugation (4,600 rpm, 35-40C) for 5 minutes had facilitated pellet recovery. Subsequently, the isolated fascia fractionate had undergone two 10-minute delipidation soaks in 1-propanol (1 L of solution/flask, with no more than 350 g of tissue/flask) on an orbital shaker set to 150 rpm. Intermittent centrifugation (4,600 rpm, 35-40C) for 5 minutes had facilitated pellet recovery. The partially delipidated adipose and partially delipidated fascia were combined at the desired 50:50 A:F ratio by weight, thereby creating an A:F Complex. This complex was then subjected to an additional two 10-minute delipidation soaks in 1-propanol (1 L of solution/flask, with no more than 350 g of tissue/flask) on an orbital shaker set to 150 rpm. Intermittent centrifugation (4,600 rpm, 35-40C) for 5 minutes had facilitated pellet recovery.

To perform decellularization, 350 g (maximum) of A:F complex was combined with 1 L 25% ethyl alcohol and 40 g sodium deoxycholate (SDC), transferred to suitably sized flask, and soaked overnight (e.g., for about 18-24 hours) on an orbital shaker set at 150 rpm, at room temperature (e.g., 20-25° C.). Following decellularization, the tissue pellet was recovered via centrifugation for 5 minutes (4,600 rpm, 10-30C). Subsequently, the tissue was rinsed in a tissue flask, first with 1 L 25% ethyl alcohol, and then with 1 L USP water, with agitation on an orbital shaker set to 150 rpm for a duration of approximately 30 minutes per rinse (maximum tissue mass of 350 g/flask). Intermittent centrifugation for 5 minutes (4,600 rpm, 10-30C) had facilitated pellet recovery following each of the aforementioned rinses. The mass was recorded and the recovered pellet was placed into a freezer bag pouch, sealed, and placed into a –70° C. freezer for storage. Following storage for at least one day (i.e., approximately 22 to 26 hours) in the freezer, the tissue complex was thawed in the freezer bag, at room or in a refrigerator. Alternatively, the complex may be removed from an outer layer of the freezer bag and placed in water.

The complex was then disinfected by combining up to 350 g of the tissue matrix with 1 L of disinfection solution (for example, 0.1-1.0 wt % peracetic acid in a mixture of water, ethanol and propylene glycol), in a tissue flask. The flask was then protected from ambient light and agitated for 2-4 hours, at room temperature, in an orbital shaker set at 150 rpm.

Following the conclusion of the disinfection soak, 110-120 mL of 10×DPBS was added to the suspension, and centrifugation (4,600 rpm, 10-30C) for 10 minutes had facilitated recovery of the tissue pellet. 1×DPBS Buffer and USP water rinses, lyophilization, hand milling, freezer milling, and packaging of the A:F tissue complex was performed as described in Example 22, above.

Adipose-fascia matrices (50:50 A:F Complexes) prepared as described above were implanted into the bilateral flank of normothymic rats after rehydration to 22.5 wt % protein concentration in saline, on a weight of protein to volume of saline basis. Injections into the subcutaneous space were performed in a fanning technique for a total of 1 cc of matrix material per implant. The rats were sacrificed in a sequence which allowed quantification of the remaining implant volume at 8 weeks after implantation. The following Table 18 provides the results of this experiment.

TABLE 18

| Adipose-Fascia Matrices Implant Volume Retention in Rats | |
| --- | --- |
| Sample Type | 8 Week Volume Retention Average |
| Adipose-Fascia (50:50) | 60% |

Example 24: Method for Improving Volume Retention at Implantation Site by Using Acellular Adipose-Fascia Matrix Treatment to improve tissue bulk (volume) in a region of skin tissue is performed by injecting an acellular adipose-fascia matrix, as prepared by any of the foregoing examples, into the subcutaneous region of skin using an appropriate gauge blunt tip cannula of desired length depending on the size of the region of interest. For example, for a region such as the wrist dorsum of a human patient, a 19 gauge blunt tip cannula can be used. The graft is prepared in a syringe to a total volume which depends on the size of the region of interest. For example, for an area of 1 cm×5 cm on the wrist dorsum, a total matrix volume of 5 cc would be suitable.

After administration of local anaesthetic, such as 0.5% lidocaine and 1:200,000 epinephrine, injection (implantation) of the implant can be performed using standard established surgical techniques such as the fanning/tunneling technique. The fanning/tunneling technique is executed by slowly depositing small volumes of the matrix implant (microdroplets) into the patient tissue while removing the needle along the length of the channel created by the injection. This implantation is then repeated using radiating paths from the same entry point (fan shape) until a visible raised weal of approximately 2-3 mm is observed on the region of interest. Upon completion, the injection point of entry(ies) may be covered with an appropriate wound dressing such as Tegaderm.

After the first injection, the patient is followed every two weeks at which time the physician assesses volume retention and the healing of the surgical site. A 100:0 adipose-fascia matrix composition (100% adipose) typically retains approximately 50% of original volume at week 16, while a 75:25 adipose-fascia (25% fascia) matrix composition would be expected to retain about 66% of original volume (16% more volume retention) during the same timeframe. Similarly, a 50:50 adipose-fascia (50% fascia) matrix composition would be expected to retain about 75% of original volume (25% more volume retention than the 100:0 adipose-fascia matrix) during the same timeframe.

II. Source Tissue: Dermis

Acellular matrices derived from the dermis may have forms such as sheets, meshes, particles, and other forms. As sheets or meshes, they may be used to repair or provide support for other membranous tissues. Some specific applications for sheets or meshes include use as slings for breast reconstruction, application to wounds or burns where skin has been destroyed or excised, application as a patch to repair perforations, as a support for weakened tissues, or to cover gaps in native tissues. In particulate forms, it may be injected as a bulking agent (e.g., to restore natural contours to damaged or wasted tissues), or applied to wounds in a paste, slurry, not dried, partially dried or substantially dried form to facilitate regeneration of damaged tissue. The acellular matrices may also be used to deliver precursor cells and/or tissuegenic factors for repair or regeneration of dermis or other tissue types. The foregoing summary of uses is intended to be representative, and not to limit the range of uses for acellular dermis-derived matrices according to embodiments of the present invention.

Example 25: Decellularization of Tissue Using a Hypertonic Solution

A sample of skin tissue is isolated from a suitable donor and inspected for damage (e.g., holes or tears), and distinctive features (e.g., moles, warts, tattoos), which are removed with a scalpel. Tissue is inspected for hair, and same is removed using forceps. Where the processed tissue is to be used in the form of strips or sheets, the tissue is inspected for a uniform thickness. Otherwise, the tissue may be reduced in size, (e.g., by grinding or mincing). The epidermis is removed before further processing of the dermis.

A sample of dermis is measured into a flask and a hypertonic solution (e.g., 1M NaCl) is added in a ratio in the range of from about 1:1 to about 5:1. The mixture is mechanically agitated for at least 12 hours at an ambient temperature. After agitation, the hypertonic solution is decanted, and the dermis is captured in a 212 μm to 300 μm sieve. The recovered dermis is returned to the flask, and soaked in an about 0.01%-0.50% surfactant solution with mechanical agitation for at least 1 hour at ambient temperature.

Following the last water rinse, the dermis is soaked in a disinfecting solution, with mechanical agitation. One suitable disinfecting solution would be 0.1% to 1.5% peracetic acid in a mixture of water, ethanol, and propylene glycol. One or more additional soaks in disinfecting solution may be needed to adequately disinfect the adipose tissue. After the final disinfecting soak, the dermis is rinsed repeatedly in deionized water to remove any traces of disinfecting solution from the tissue.

Following the final water rinse, the dermis is stored under refrigeration or frozen, or it is subjected to further processing steps, such as delipidization, which may be performed by the method of Example 3, the method of Example 4, the delipidization step of Example 5, or other methods disclosed herein.

Example 26: Particularization of a Decellularized Dermis

A sample of dermis is decellularized as in Example 7, above. The sample is then lyophilized according to a commercially-available process.

The lyophilized dermis is then milled to a particulate form. It may be further milled in a frozen state (e.g., impact milling or freezer-milling) to further reduce the particle size of the tissue, and produce a flowable particulate tissue. Suitable milling protocols are known in the art.

The particulate tissue may be packaged in a sterile container for later use, or thawed and rehydrated immediately. In one rehydration method, a desired amount of the thawed particulate tissue is added to a first syringe. The desired amount of fluid (e.g., a carrier) is added to a second syringe, and the syringes are attached to each other using a female-to-female locking cap. The fluid is ejected slowly into the tissue-filled syringe, while depressing the plungers of both syringes. The entirety of the mixture of tissue and fluid is transferred to one of the syringes, and the other is discarded. The syringe containing the mixture is stoppered and packaged in foil and/or a Kapak® pouch (Kapak Corporation, St. Louis Park, MN).

It will be understood that the embodiments described herein are merely exemplary and that a person of ordinary skill in the art may make many variations and modifications without departing from the spirit and scope of the invention. All such variations and modifications are intended to be included within the scope of the invention, as defined by the appended claims. Other exemplary embodiments may be described in co-owned U.S. Patent Application Publication No. US2015/0037436 A1, which is hereby incorporated by reference herein.

The invention claimed is:

1. A method for increasing, enhancing, or improving volume retention at a region to be treated in a patient, comprising a step of implanting a composition in, on, or proximate to the region to be treated in the patient, thereby forming an implantation site, wherein the composition comprises:

(a) an adipose component which is a delipidized, decellularized adipose tissue-derived matrix; and (b) a fascia component which is a decellularized fascial tissue-derived matrix;

wherein the adipose component and fascia component are present in the composition in a predetermined ratio of adipose component:fascia component in a range of from about 99:1 to about 1:99 on a weight basis;

whereby the composition provides greater volume retention at an implantation site after passage of a minimum period of time from implantation of the composition in a subject; and wherein volume retention is greater compared to a composition having a predetermined ratio of 100:0.

2. The method of claim 1, further comprising providing a ratio of adipose component:fascia component in the composition which will provide a particular degree of volume retention at the implantation site, wherein the implanted composition comprises the provided ratio of adipose component:fascia component.

3. The method of claim 2, wherein the degree of volume retention is provided based on one or more goals selected from: increasing bulk, modifying the shape or contour of a body feature, replacing or supplementing missing or damaged tissue, supplementing existing tissue, providing a stimulus to host tissue, and combinations thereof.

4. The method of claim 1, wherein implanting comprises inserting, placing, injecting, and combinations thereof.

5. The method of claim 1, wherein the composition further comprises a biocompatible carrier and wherein the step of implanting comprises injecting the composition to implant the composition proximate to the region to be treated.

6. The method of claim 1, wherein the step of implanting is performed as part of one or more treatments selected from: augmentation, volume restoration, and deficit management.

7. The method of claim 1, wherein the region to be treated comprises a wound, atrophied tissue, diseased tissue, tissue loss, and combinations thereof.

8. The method of claim 1, wherein the region to be treated comprises at least a portion of one or more body features selected from: a fat pad, a face, a lip, a joint, a musculoskeletal feature, a cheek, a temple, a nasolabial fold, a wrist, an eyelid, a jaw, and combinations thereof.

9. A method for cosmetic or reconstructive surgery on a patient having a region to be treated, comprising a step of implanting in, on, or proximate to the region to be treated, thereby forming an implantation site, a composition comprising:
    (a) an adipose component which is a delipidized, decellularized adipose tissue-derived matrix; and
    (b) a fascia component which is a decellularized fascial tissue-derived matrix;
    wherein the adipose component and fascia component are present in the composition in a predetermined ratio of adipose component:fascia component in a range of from about 99:1 to about 1:99 on a weight basis; and
    wherein improved volume retention is provided at the implantation site after passage of at least 3 weeks from implantation, as compared to a composition having a predetermined ratio of adipose component:fascia component of 100:0.

10. The method of claim 9, further comprising providing a ratio of adipose component:fascia component in the composition which will provide a particular degree of volume retention at the implantation site, wherein the implanted composition comprises the provided ratio of adipose component:fascia component.

11. The method of claim 10, wherein the degree of volume retention is provided based on one or more goals selected from: increasing bulk, modifying the shape or contour of a body feature, replacing or supplementing missing or damaged tissue, supplementing existing tissue, providing a stimulus to host tissue, and combinations thereof.

12. The method of claim 9, wherein implanting comprises inserting, placing, injecting, and combinations thereof.

13. The method of claim 9, wherein the composition further comprises a biocompatible carrier and wherein the step of implanting comprises injecting the composition to implant the composition proximate the region to be treated.

14. The method of claim 9, wherein the step of implanting is performed as part of one or more treatments selected from: augmentation, volume restoration, and deficit management.

15. The method of claim 9, wherein the region to be treated comprises a wound, atrophied tissue, diseased tissue, tissue loss, and combinations thereof.

16. The method of claim 9, wherein the region to be treated comprises at least a portion of one or more body features selected from: a fat pad, a face, a lip, a joint, a musculoskeletal feature, a cheek, a temple, a nasolabial fold, a wrist, an eyelid, a jaw, and combinations thereof.

17. A method for treatment of a wound site or tissue atrophy site of a patient, comprising a step of implanting, into, on, around, proximate to, or under the wound site or tissue atrophy site, a composition comprising:
    (a) an adipose component which is a delipidized, decellularized adipose tissue-derived matrix; and
    (b) a fascia component which is a decellularized fascial tissue-derived matrix;
    wherein the adipose component and fascia component are present in the composition in a predetermined ratio of adipose component:fascia component in a range of from about 99:1 to about 1:99 on a weight basis; and
    whereby tissue healing and reconstruction are facilitated and improved volume retention is provided at the wound site or the tissue atrophy site after passage of at least 3 weeks from implantation, as compared to a composition having a predetermined ratio of adipose component:fascia component of 100:0.

18. The method of claim 17, further comprising providing a ratio of adipose component:fascia component in the composition which will provide a particular degree of volume retention at the implantation site, wherein the implanted composition comprises the provided ratio of adipose component:fascia component.

19. The method of claim 18, wherein the degree of volume retention is provided based on one or more goals selected from: increasing bulk, modifying the shape or contour of a body feature, replacing or supplementing missing or damaged tissue, supplementing existing tissue, providing a stimulus to host tissue, and combinations thereof.

20. The method of claim 17, wherein implanting comprises inserting, placing, injecting, and combinations thereof.

21. The method of claim 17, wherein the composition further comprises a biocompatible carrier and wherein the step of implanting comprises injecting the composition to implant the composition proximate the region to be treated.

22. The method of claim 17, wherein the step of implanting is performed as part of one or more treatments selected from: augmentation, volume restoration, and deficit management.

23. The method of claim 17, wherein the wound site or tissue atrophy site comprises at least a portion of one or more body features selected from: a fat pad, a face, a lip, a joint, a musculoskeletal feature, a check, a temple, a nasolabial fold, a wrist, an eyelid, a jaw, and combinations thereof.

\* \* \* \* \*